(12) United States Patent
Mullican et al.

(10) Patent No.: US 11,713,345 B2
(45) Date of Patent: Aug. 1, 2023

(54) GLUCAGON LIKE PEPTIDE 1 (GLP1)-GROWTH DIFFERENTIATION FACTOR 15 (GDF15) FUSION PROTEINS AND USES THEREOF

(71) Applicant: Janssen Sciences Ireland Unlimited Company, Cork (IE)

(72) Inventors: Shannon Mullican, Spring House, PA (US); Matthew M. Rankin, Spring House, PA (US); Xiefan Lin-Schmidt, Spring House, PA (US); Chichi Huang, Spring House, PA (US); Jennifer Furman, San Diego, CA (US); Songmao Zheng, Spring House, PA (US); Shamina Rangwala, Spring House, PA (US); Serena Nelson, San Diego, CA (US)

(73) Assignee: Janssen Sciences Ireland Unlimited Company, Cork (IE)

(*) Notice: Subject to any disclaimer, the term of this patent is extended or adjusted under 35 U.S.C. 154(b) by 0 days.

(21) Appl. No.: 17/309,114

(22) PCT Filed: Oct. 22, 2019

(86) PCT No.: PCT/IB2019/059029
§ 371 (c)(1),
(2) Date: Apr. 26, 2021

(87) PCT Pub. No.: WO2020/084496
PCT Pub. Date: Apr. 30, 2020

(65) Prior Publication Data
US 2022/0089669 A1    Mar. 24, 2022

Related U.S. Application Data

(60) Provisional application No. 62/748,603, filed on Oct. 22, 2018.

(51) Int. Cl.
| | | |
|---|---|---|
| A61K 38/00 | (2006.01) | |
| C07K 14/605 | (2006.01) | |
| C07K 14/475 | (2006.01) | |
| C12N 15/63 | (2006.01) | |

(52) U.S. Cl.
CPC .......... *C07K 14/605* (2013.01); *C07K 14/475* (2013.01); *C12N 15/63* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 10,336,812 B2 | 7/2019 | Armstrong | |
| 2008/0044411 A1 | 2/2008 | O'Neil | |
| 2012/0030840 A1 | 2/2012 | Miles | |
| 2014/0120090 A1 | 5/2014 | Willemsen | |
| 2014/0141000 A1* | 5/2014 | Chiu | A61P 43/00 435/375 |
| 2014/0349929 A1 | 11/2014 | Camphausen | |
| 2016/0143998 A1 | 5/2016 | Reedtz-Runge | |
| 2016/0168213 A1 | 6/2016 | Xiong | |
| 2017/0204149 A1 | 7/2017 | Chopra | |
| 2017/0327560 A1 | 11/2017 | Armstrong | |

FOREIGN PATENT DOCUMENTS

| | | | | |
|---|---|---|---|---|
| WO | WO200246227 A2 * | 6/2002 | | A61K 38/18 |
| WO | WO-2014120619 A2 * | 8/2014 | | A61K 38/18 |
| WO | 2017147742 | 9/2017 | | |

OTHER PUBLICATIONS

Baek et al., "Nonsteroidal anti-inflammatory drug-activated gene-1 over expression in transgenic mice suppresses intestinal neoplasia," Gastroenterology 131:1553-60 (2006).
Bonaterra et al., "Growth differentiation factor-15 deficiency inhibits atheroscleoris progression by regulating interleukin-6-dependent inflammatory response to vascular injury," J. Amer. Heart Assoc. 1:e002550 (2012).
Casanovas et al., "The murine growth differentiation factor 15 is not essential for systemic iron homeostasis in phlebotomized mice," Haematologica 98:444-7 (2013).
Cheang and Moyle, "Glucagon-Like Peptide-1 (GLP-1)-based therapeutics: Current Status and Future Opportunities beyond Type 2 Diabetes," Chem Med Chern 13:662-71 (2018).
Chrysovergis et al., "NAG-1/GDF-15 prevents obesity by increasing thermogenesis, lipolysis and oxidative metabolism," Int. J. Obesity 38:1555-64 (2014).
Drucker et al., "Glucagon-like peptide I stimulates insulin gene expression and increases cyclic AMP levels in a rat islet cell line," PNAS 84:3434-8 (1987).
Drucker et al., "Mechanisms of Action and Therapeutic Application of Glucagon-like Peptide-1," Cell Met. 27:740-56 (2018).
Emmerson et al., "The metabolic effects of GDF15 are mediated by the orphan receptor GFRAL," Nat. Med. 23:1215-9 (2017).
Hallbrink et al., "Different domains in the third intracellular loop of the GLP-1 receptor are responsible for Galpha(s) and Galpha(i)/Galpha(o) activation," Biochim Biophys Acta 1546:79-86 (2001).
Holz et al., "Activation of a cAMP-regulated Ca(2+)-signaling pathway in pancreatic beta-cells by the insulinotropic hormone glucagon-like peptide-1," JBC 270:17749-57 (1995).
Hsu et al., "Non-homeostatic body weight regulation through a brainstem-restricted receptor for GDF15," Nature 550:255-9 (2017).
International Search Report dated Apr. 2, 2020 in International Application No. PCT/IB2019/59029 (5 pages).

(Continued)

*Primary Examiner* — Aradhana Sasan
*Assistant Examiner* — Mercy H Sabila
(74) *Attorney, Agent, or Firm* — Seed IP Law Group LLP

(57) ABSTRACT

Provided herein are GLP1-GDF15 fusion proteins comprising a GLP1 or GLP1 variant peptide, a first linker peptide, a serum albumin protein, a second linker peptide, and a GDF15 protein.

11 Claims, 22 Drawing Sheets

Specification includes a Sequence Listing.

(56) References Cited

OTHER PUBLICATIONS

Johnen et al., "Tumor-induced anorexia and weight loss are mediated by the TGF-beta superfamily cytokine MIC-1," Nat. Med. 13:1333-40 (2007).
Jones et al., "Supraphysiologic Administration of GDF11 Induces Cachexia in Part by Upregulating GDF15," Cell reports 22:1522-30 (2018).
Lim et al., "Glucagon-like Peptide-1 Receptor Agonists and Cardiovascular Events: Class Effects versus Individual Patterns," Trends Endocrinol Metab 29:238-48 (2018).
Macia et al., "Macrophage inhibitory cytokine 1 (MIC-1/GDF15) decreases food intake, body weight and improves glucose tolerance in mice on normal & obesogenic diets," PloS One 7:e34868 (2012).
Montrose-Rafizadeh et al., "Pancreatic glucagon-like peptide-1 receptor couples to multiple G proteins and activates mitogen-activated protein kinase pathways in Chinese hamster ovary cells," Endocrinology 140:1132-40 (1999).
Mullican and Rangwala, "Uniting GDF15 and GFRAL:Therapeutic Opportunities in Obesity and Beyond," Trends Endocrinol Metab 29(8):560-70 (2018).
Mullican et al., "GFRAL is the receptor for GDF15 and the ligand promotes weight loss in mice and nonhuman primates," Nat. Med. 23:1150-7 (2017).
Spahr et al., "O-glycosylation ofglycine-serine linkers in recombinant Fc-fusion proteins: attachment of glycosaminoglycans and other intermediates with phosphorylation at the xylose sugar subunit," mAbs6(4):904-914 (2014).
Strelau et al., "Progressive postnatal motoneuron loss in mice lacking GDF-15," J. Neurosci. 29:13640-8 (2009).
Taverna et al., "Specific antioxidant properties of human serum albumin," Ann. Intensive Care 3:4 (2013).
Thorens et al., "Cloning and Functional Expression of the Human Islet GLP-1 Receptor. Demonstration that exendin-4 is an agonist and exendin-(9-39) an antagonist of the receptor," Diabetes 42(11):1678-82 (1993).
Tsai et al., "Anorexia/cachexia of chronic diseases: a role for the TGF-b family cytokine MIC-1/GDF15," J. Cachexia Sarcopenia Muscle 3:239-43 (2012).
Tsai et al., "Antrodia cinnamomea reduces obesity and modulates the gut microbiota in high-fat diet-fed mice," Int. J. Obesity 42:561-71 (2018).
Tsai et al., "TGF-b superfamily cytokine MIC-1/GDF15 is a physiological appetite and body weight regulator," PloS One 8:e55174 (2013).
Vila et al., "The relationship between insulin resistance and the cardiovascular biomarker growth differentiation factor-15 in obese patients," Clin. Chem. 57:309-16 (2011).
Wheeler et al., "Functional expression of the rat glucagon-like peptide-1 receptor, evidence for coupling to both adenylyl cyclase and phospholipase-C," Endocrinology 133:57-62 (1993).
Xiong et al., "Long-acting MIC-1/GDF15 molecules to treat obesity: evidence from mice to monkeys," Sci. Trans. Med. 9:412 (2017).
Yang et al., "GFRAL is the receptor for GDF15 and is required for the anti-obesity effects of the ligand," Nat. Med. 23:1158-66 (2017).

* cited by examiner

Vehicle shown for reference only

Vehicle shown for reference only

Vehicle shown for reference only

SEQUENCE LISTING

<160> NUMBER OF SEQ ID NOS: 84

<210> SEQ ID NO 1
<211> LENGTH: 30
<212> TYPE: PRT
<213> ORGANISM: Artificial Sequence
<220> FEATURE:
<223> OTHER INFORMATION: (A8S, A30E) GLP-1(7-36)

<400> SEQUENCE: 1

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: (A8G, G22E, R36G) GLP1(7-36)

<400> SEQUENCE: 2

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 3
<211> LENGTH: 39
<212> TYPE: PRT
<213> ORGANISM: Artificial Sequence
<220> FEATURE:
<223> OTHER INFORMATION: Exendin 4 (1-39)

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 28
<212> TYPE: PRT
<213> ORGANISM: Artificial Sequence
<220> FEATURE:
<223> OTHER INFORMATION: Exendin 4 (1-28)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 5
<211> LENGTH: 10
<212> TYPE: PRT
<213> ORGANISM: Artificial Sequence
<220> FEATURE:
<223> OTHER INFORMATION: First linker peptide 1-1

<400> SEQUENCE: 5

Ala Pro Ala Pro Ala Pro Ala Pro Ala Pro
1               5                   10

<210> SEQ ID NO 6
<211> LENGTH: 20
<212> TYPE: PRT
<213> ORGANISM: Artificial Sequence
<220> FEATURE:
<223> OTHER INFORMATION: First linker peptide 1-2

<400> SEQUENCE: 6

Ala Pro Ala Pro Ala Pro Ala Pro Ala Pro Ala Pro Ala Pro Ala Pro
1               5                   10                  15

Ala Pro Ala Pro
            20

<210> SEQ ID NO 7
<211> LENGTH: 30
<212> TYPE: PRT
<213> ORGANISM: Artificial Sequence
<220> FEATURE:
<223> OTHER INFORMATION: First linker peptide 1-3

<400> SEQUENCE: 7

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro
            20                  25                  30

<210> SEQ ID NO 8
<211> LENGTH: 40
<212> TYPE: PRT
<213> ORGANISM: Artificial Sequence
<220> FEATURE:
<223> OTHER INFORMATION: First linker peptide 1-4

<400> SEQUENCE: 8

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 9
<211> LENGTH: 50
<212> TYPE: PRT
<213> ORGANISM: Artificial Sequence
<220> FEATURE:
<223> OTHER INFORMATION: First linker peptide 1-5

<400> SEQUENCE: 9

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro Ala Pro Ala Pro Ala Pro Ala Pro
        35                  40                  45

Ala Pro
    50

<210> SEQ ID NO 10
<211> LENGTH: 24

```
<212> TYPE: PRT
<213> ORGANISM: Artificial Sequence
<220> FEATURE:
<223> OTHER INFORMATION: First linker peptide 1-6

<400> SEQUENCE: 10

Ala Ser Ala Pro Ala Pro Ala Pro Ala Pro Ala Pro Ala Pro Ala Pro
1               5                   10                  15

Ala Pro Ala Pro Ala Pro Gly Ser
            20

<210> SEQ ID NO 11
<211> LENGTH: 14
<212> TYPE: PRT
<213> ORGANISM: Artificial Sequence
<220> FEATURE:
<223> OTHER INFORMATION: First linker peptide 1-7

<400> SEQUENCE: 11

Ala Ser Ala Pro Ala Pro Ala Pro Ala Pro Ala Pro Gly Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: First linker peptide 1-8

<400> SEQUENCE: 12

Ala Ser Gly Gly Gly Gly Ser Gly Gly Gly Gly Ser
1               5                   10

<210> SEQ ID NO 13
<211> LENGTH: 42
<212> TYPE: PRT
<213> ORGANISM: Artificial Sequence
<220> FEATURE:
<223> OTHER INFORMATION: First linker peptide 1-9

<400> SEQUENCE: 13

Ala Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40

<210> SEQ ID NO 14
<211> LENGTH: 12
<212> TYPE: PRT
<213> ORGANISM: Artificial Sequence
<220> FEATURE:
<223> OTHER INFORMATION: First linker peptide 1-10

<400> SEQUENCE: 14

Gly Ala Gly Gly Gly Gly Ala Gly Gly Gly Gly Ala
1               5                   10

<210> SEQ ID NO 15
<211> LENGTH: 42
<212> TYPE: PRT
<213> ORGANISM: Artificial Sequence
<220> FEATURE:
<223> OTHER INFORMATION: First linker peptide 1-11
```

```
<400> SEQUENCE: 15

Gly Ala Gly Gly Gly Gly Ala Gly Gly Gly Ala Gly Gly Gly
1               5                   10                  15

Ala Gly Gly Gly Gly Ala Gly Gly Gly Ala Gly Gly Gly Ala
            20                  25                  30

Gly Gly Gly Gly Ala Gly Gly Gly Gly Ala
            35                  40

<210> SEQ ID NO 16
<211> LENGTH: 15
<212> TYPE: PRT
<213> ORGANISM: Artificial Sequence
<220> FEATURE:
<223> OTHER INFORMATION: First linker peptide 1-12

<400> SEQUENCE: 16

Gly Gly Gly Gly Ala Gly Gly Gly Ala Gly Gly Gly Gly Ala
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: First linker peptide 1-13

<400> SEQUENCE: 17

Gly Gly Gly Gly Ala Gly Gly Gly Ala Gly Gly Gly Ala Gly
1               5                   10                  15

Gly Gly Gly Ala
            20

<210> SEQ ID NO 18
<211> LENGTH: 25
<212> TYPE: PRT
<213> ORGANISM: Artificial Sequence
<220> FEATURE:
<223> OTHER INFORMATION: First linker peptide 1-14

<400> SEQUENCE: 18

Gly Gly Gly Gly Ala Gly Gly Gly Ala Gly Gly Gly Ala Gly
1               5                   10                  15

Gly Gly Gly Ala Gly Gly Gly Gly Ala
            20                  25

<210> SEQ ID NO 19
<211> LENGTH: 30
<212> TYPE: PRT
<213> ORGANISM: Artificial Sequence
<220> FEATURE:
<223> OTHER INFORMATION: First linker peptide 1-15

<400> SEQUENCE: 19

Gly Gly Gly Gly Ala Gly Gly Gly Gly Ala Gly Gly Gly Ala Gly
1               5                   10                  15

Gly Gly Gly Ala Gly Gly Gly Gly Ala Gly Gly Gly Gly Ala
            20                  25                  30

<210> SEQ ID NO 20
<211> LENGTH: 40
<212> TYPE: PRT
<213> ORGANISM: Artificial Sequence
<220> FEATURE:
<223> OTHER INFORMATION: First linker peptide 1-16
```

```
<400> SEQUENCE: 20

Gly Gly Gly Gly Ala Gly Gly Gly Ala Gly Gly Gly Ala Gly
1               5                   10                  15

Gly Gly Gly Ala Gly Gly Gly Ala Gly Gly Gly Ala Gly Gly
                20                  25                  30

Gly Gly Ala Gly Gly Gly Gly Ala
        35                  40

<210> SEQ ID NO 21
<211> LENGTH: 20
<212> TYPE: PRT
<213> ORGANISM: Artificial Sequence
<220> FEATURE:
<223> OTHER INFORMATION: First linker peptide 1-17

<400> SEQUENCE: 21

Gly Gly Gly Gly Gly Gly Gly Gly Gly Gly Gly Gly Gly Gly Gly Gly
1               5                   10                  15

Gly Gly Gly Gly
            20

<210> SEQ ID NO 22
<211> LENGTH: 25
<212> TYPE: PRT
<213> ORGANISM: Artificial Sequence
<220> FEATURE:
<223> OTHER INFORMATION: First linker peptide 1-18

<400> SEQUENCE: 22

Gly Gly Gly Gly Gly Gly Gly Gly Gly Gly Gly Gly Gly Gly Gly Gly
1               5                   10                  15

Gly Gly Gly Gly Gly Gly Gly Gly Gly
            20                  25

<210> SEQ ID NO 23
<211> LENGTH: 15
<212> TYPE: PRT
<213> ORGANISM: Artificial Sequence
<220> FEATURE:
<223> OTHER INFORMATION: First linker peptide 1-19

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 25
<212> TYPE: PRT
<213> ORGANISM: Artificial Sequence
<220> FEATURE:
<223> OTHER INFORMATION: First linker peptide 1-20

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 25
<211> LENGTH: 30
<212> TYPE: PRT
<213> ORGANISM: Artificial Sequence
<220> FEATURE:
```

<223> OTHER INFORMATION: First linker peptide 1-21

<400> SEQUENCE: 25

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 26
<211> LENGTH: 585
<212> TYPE: PRT
<213> ORGANISM: Artificial Sequence
<220> FEATURE:
<223> OTHER INFORMATION: HSA(C34S)

<400> SEQUENCE: 26

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

```
Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 27
<211> LENGTH: 585
<212> TYPE: PRT
<213> ORGANISM: Artificial Sequence
<220> FEATURE:
<223> OTHER INFORMATION: GSA(C34S)

<400> SEQUENCE: 27

Asp Ala His Lys Ser Glu Val Ala His Arg Phe Lys Asp Leu Gly Glu
1               5                   10                  15

Glu Thr Phe Lys Ala Leu Val Leu Val Ala Phe Ala Gln Tyr Leu Gln
                20                  25                  30

Gln Ser Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Ala Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Leu Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

```
Ile Cys Thr Leu Ser Glu Lys Glu Arg Gln Ile Lys Lys Gln Thr Ala
            515                 520                 525

Leu Ala Glu Leu Val Lys His Lys Pro Lys Ala Thr Lys Glu Gln Leu
    530                 535                 540

Lys Thr Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 28
<211> LENGTH: 20
<212> TYPE: PRT
<213> ORGANISM: Artificial Sequence
<220> FEATURE:
<223> OTHER INFORMATION: Second linker peptide 2-1

<400> SEQUENCE: 28

Ala Pro Ala Pro Ala Pro Ala Pro Ala Pro Ala Pro Ala Pro Ala Pro
1               5                   10                  15

Ala Pro Ala Pro
            20

<210> SEQ ID NO 29
<211> LENGTH: 42
<212> TYPE: PRT
<213> ORGANISM: Artificial Sequence
<220> FEATURE:
<223> OTHER INFORMATION: Second linker peptide 2-2

<400> SEQUENCE: 29

Gly Ala Gly Gly Gly Gly Ala Gly Gly Gly Ala Gly Gly Gly Gly
1               5                   10                  15

Ala Gly Gly Gly Gly Ala Gly Gly Gly Gly Ala Gly Gly Gly Gly Ala
            20                  25                  30

Gly Gly Gly Gly Ala Gly Gly Gly Gly Ala
        35                  40

<210> SEQ ID NO 30
<211> LENGTH: 42
<212> TYPE: PRT
<213> ORGANISM: Artificial Sequence
<220> FEATURE:
<223> OTHER INFORMATION: Second linker peptide 2-3

<400> SEQUENCE: 30

Gly Ser Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser
        35                  40

<210> SEQ ID NO 31
<211> LENGTH: 108
<212> TYPE: PRT
<213> ORGANISM: Artificial Sequence
<220> FEATURE:
<223> OTHER INFORMATION: GDF15 variant 1

<400> SEQUENCE: 31
```

```
Asp His Cys Pro Leu Gly Pro Gly Arg Cys Cys Arg Leu His Thr Val
1               5                   10                  15
Arg Ala Ser Leu Glu Asp Leu Gly Trp Ala Asp Trp Val Leu Ser Pro
            20                  25                  30
Arg Glu Val Gln Val Thr Met Cys Ile Gly Ala Cys Pro Ser Gln Phe
        35                  40                  45
Arg Ala Ala Asn Met His Ala Gln Ile Lys Thr Ser Leu His Arg Leu
    50                  55                  60
Lys Pro Asp Thr Val Pro Ala Pro Cys Cys Val Pro Ala Ser Tyr Asn
65                  70                  75                  80
Pro Met Val Leu Ile Gln Lys Thr Asp Thr Gly Val Ser Leu Gln Thr
                85                  90                  95
Tyr Asp Asp Leu Leu Ala Lys Asp Cys His Cys Ile
            100                 105
```

<210> SEQ ID NO 32
<211> LENGTH: 112
<212> TYPE: PRT
<213> ORGANISM: Artificial Sequence
<220> FEATURE:
<223> OTHER INFORMATION: GDF15 WT mature

<400> SEQUENCE: 32

```
Ala Arg Asn Gly Asp His Cys Pro Leu Gly Pro Gly Arg Cys Cys Arg
1               5                   10                  15
Leu His Thr Val Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Asn Met His Ala Gln Ile Lys Thr Ser
    50                  55                  60
Leu His Arg Leu Lys Pro Asp Thr Val Pro Ala Pro Cys Cys Val Pro
65                  70                  75                  80
Ala Ser Tyr Asn Pro Met Val Leu Ile Gln Lys Thr Asp Thr Gly Val
                85                  90                  95
Ser Leu Gln Thr Tyr Asp Asp Leu Leu Ala Lys Asp Cys His Cys Ile
            100                 105                 110
```

<210> SEQ ID NO 33
<211> LENGTH: 768
<212> TYPE: PRT
<213> ORGANISM: Artificial Sequence
<220> FEATURE:
<223> OTHER INFORMATION: GLP1-GDF15 Fusion Protein 1

<400> SEQUENCE: 33

```
His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Gly Gly Gly
            20                  25                  30
Gly Gly Ala Gly Gly Gly Ala Gly Gly Gly Ala Gly Gly Gly Ala Gly
        35                  40                  45
Gly Ala Gly Gly Gly Gly Ala Asp Ala His Lys Ser Glu Val Ala His
    50                  55                  60
Arg Phe Lys Asp Leu Gly Glu Glu Asn Phe Lys Ala Leu Val Leu Ile
65                  70                  75                  80
Ala Phe Ala Gln Tyr Leu Gln Gln Ser Pro Phe Glu Asp His Val Lys
                85                  90                  95
```

```
Leu Val Asn Glu Val Thr Glu Phe Ala Lys Thr Cys Val Ala Asp Glu
            100                 105                 110

Ser Ala Glu Asn Cys Asp Lys Ser Leu His Thr Leu Phe Gly Asp Lys
            115                 120                 125

Leu Cys Thr Val Ala Thr Leu Arg Glu Thr Tyr Gly Glu Met Ala Asp
        130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
                180                 185                 190

Tyr Leu Tyr Glu Ile Ala Arg Arg His Pro Tyr Phe Tyr Ala Pro Glu
            195                 200                 205

Leu Leu Phe Phe Ala Lys Arg Tyr Lys Ala Ala Phe Thr Glu Cys Cys
        210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
        290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
        370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
                405                 410                 415

Ala Ala Ala Asp Pro His Glu Cys Tyr Ala Lys Val Phe Asp Glu Phe
            420                 425                 430

Lys Pro Leu Val Glu Glu Pro Gln Asn Leu Ile Lys Gln Asn Cys Glu
        435                 440                 445

Leu Phe Glu Gln Leu Gly Glu Tyr Lys Phe Gln Asn Ala Leu Leu Val
        450                 455                 460

Arg Tyr Thr Lys Lys Val Pro Gln Val Ser Thr Pro Thr Leu Val Glu
465                 470                 475                 480

Val Ser Arg Asn Leu Gly Lys Val Gly Ser Lys Cys Cys Lys His Pro
                485                 490                 495

Glu Ala Lys Arg Met Pro Cys Ala Glu Asp Tyr Leu Ser Val Val Leu
            500                 505                 510
```

Asn Gln Leu Cys Val Leu His Glu Lys Thr Pro Val Ser Asp Arg Val
            515                 520                 525

Thr Lys Cys Cys Thr Glu Ser Leu Val Asn Arg Arg Pro Cys Phe Ser
    530                 535                 540

Ala Leu Glu Val Asp Glu Thr Tyr Val Pro Lys Glu Phe Asn Ala Glu
545                 550                 555                 560

Thr Phe Thr Phe His Ala Asp Ile Cys Thr Leu Ser Glu Lys Glu Arg
                565                 570                 575

Gln Ile Lys Lys Gln Thr Ala Leu Val Glu Leu Val Lys His Lys Pro
                580                 585                 590

Lys Ala Thr Lys Glu Gln Leu Lys Ala Val Met Asp Asp Phe Ala Ala
            595                 600                 605

Phe Val Glu Lys Cys Cys Lys Ala Asp Asp Lys Glu Thr Cys Phe Ala
            610                 615                 620

Glu Glu Gly Lys Lys Leu Val Ala Ala Ser Gln Ala Ala Leu Gly Leu
625                 630                 635                 640

Ala Pro Ala Pro Ala Pro Ala Pro Ala Pro Ala Pro Ala Pro Ala Pro
                645                 650                 655

Ala Pro Ala Pro Asp His Cys Pro Leu Gly Pro Gly Arg Cys Cys Arg
                660                 665                 670

Leu His Thr Val Arg Ala Ser Leu Glu Asp Leu Gly Trp Ala Asp Trp
            675                 680                 685

Val Leu Ser Pro Arg Glu Val Gln Val Thr Met Cys Ile Gly Ala Cys
            690                 695                 700

Pro Ser Gln Phe Arg Ala Ala Asn Met His Ala Gln Ile Lys Thr Ser
705                 710                 715                 720

Leu His Arg Leu Lys Pro Asp Thr Val Pro Ala Pro Cys Cys Val Pro
                725                 730                 735

Ala Ser Tyr Asn Pro Met Val Leu Ile Gln Lys Thr Asp Thr Gly Val
            740                 745                 750

Ser Leu Gln Thr Tyr Asp Asp Leu Leu Ala Lys Asp Cys His Cys Ile
            755                 760                 765

<210> SEQ ID NO 34
<211> LENGTH: 758
<212> TYPE: PRT
<213> ORGANISM: Artificial Sequence
<220> FEATURE:
<223> OTHER INFORMATION: GLP1-GDF15 Fusion Protein 2

<400> SEQUENCE: 34

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ala Gly Gly Gly Gly Ala Gly Gly Gly Gly Ala Asp Ala His
        35                  40                  45

Lys Ser Glu Val Ala His Arg Phe Lys Asp Leu Gly Glu Glu Asn Phe
    50                  55                  60

Lys Ala Leu Val Leu Ile Ala Phe Ala Gln Tyr Leu Gln Gln Ser Pro
65                  70                  75                  80

Phe Glu Asp His Val Lys Leu Val Asn Glu Val Thr Glu Phe Ala Lys
                85                  90                  95

Thr Cys Val Ala Asp Glu Ser Ala Glu Asn Cys Asp Lys Ser Leu His
            100                 105                 110

```
Thr Leu Phe Gly Asp Lys Leu Cys Thr Val Ala Thr Leu Arg Glu Thr
            115                 120                 125

Tyr Gly Glu Met Ala Asp Cys Cys Ala Lys Gln Glu Pro Glu Arg Asn
        130                 135                 140

Glu Cys Phe Leu Gln His Lys Asp Asp Asn Pro Asn Leu Pro Arg Leu
145                 150                 155                 160

Val Arg Pro Glu Val Asp Val Met Cys Thr Ala Phe His Asp Asn Glu
                165                 170                 175

Glu Thr Phe Leu Lys Lys Tyr Leu Tyr Glu Ile Ala Arg Arg His Pro
                180                 185                 190

Tyr Phe Tyr Ala Pro Glu Leu Leu Phe Phe Ala Lys Arg Tyr Lys Ala
                195                 200                 205

Ala Phe Thr Glu Cys Cys Gln Ala Ala Asp Lys Ala Ala Cys Leu Leu
            210                 215                 220

Pro Lys Leu Asp Glu Leu Arg Asp Glu Gly Lys Ala Ser Ser Ala Lys
225                 230                 235                 240

Gln Arg Leu Lys Cys Ala Ser Leu Gln Lys Phe Gly Glu Arg Ala Phe
                245                 250                 255

Lys Ala Trp Ala Val Ala Arg Leu Ser Gln Arg Phe Pro Lys Ala Glu
            260                 265                 270

Phe Ala Glu Val Ser Lys Leu Val Thr Asp Leu Thr Lys Val His Thr
            275                 280                 285

Glu Cys Cys His Gly Asp Leu Leu Glu Cys Ala Asp Asp Arg Ala Asp
            290                 295                 300

Leu Ala Lys Tyr Ile Cys Glu Asn Gln Asp Ser Ile Ser Ser Lys Leu
305                 310                 315                 320

Lys Glu Cys Cys Glu Lys Pro Leu Leu Glu Lys Ser His Cys Ile Ala
                325                 330                 335

Glu Val Glu Asn Asp Glu Met Pro Ala Asp Leu Pro Ser Leu Ala Ala
                340                 345                 350

Asp Phe Val Glu Ser Lys Asp Val Cys Lys Asn Tyr Ala Glu Ala Lys
            355                 360                 365

Asp Val Phe Leu Gly Met Phe Leu Tyr Glu Tyr Ala Arg Arg His Pro
            370                 375                 380

Asp Tyr Ser Val Val Leu Leu Leu Arg Leu Ala Lys Thr Tyr Glu Thr
385                 390                 395                 400

Thr Leu Glu Lys Cys Cys Ala Ala Ala Asp Pro His Glu Cys Tyr Ala
                405                 410                 415

Lys Val Phe Asp Glu Phe Lys Pro Leu Val Glu Glu Pro Gln Asn Leu
            420                 425                 430

Ile Lys Gln Asn Cys Glu Leu Phe Glu Gln Leu Gly Glu Tyr Lys Phe
            435                 440                 445

Gln Asn Ala Leu Leu Val Arg Tyr Thr Lys Lys Val Pro Gln Val Ser
    450                 455                 460

Thr Pro Thr Leu Val Glu Val Ser Arg Asn Leu Gly Lys Val Gly Ser
465                 470                 475                 480

Lys Cys Cys Lys His Pro Glu Ala Lys Arg Met Pro Cys Ala Glu Asp
                485                 490                 495

Tyr Leu Ser Val Val Leu Asn Gln Leu Cys Val Leu His Glu Lys Thr
                500                 505                 510

Pro Val Ser Asp Arg Val Thr Lys Cys Cys Thr Glu Ser Leu Val Asn
            515                 520                 525

Arg Arg Pro Cys Phe Ser Ala Leu Glu Val Asp Glu Thr Tyr Val Pro
```

```
                530             535             540
Lys Glu Phe Asn Ala Glu Thr Phe Thr Phe His Ala Asp Ile Cys Thr
545                 550             555                 560

Leu Ser Glu Lys Glu Arg Gln Ile Lys Lys Gln Thr Ala Leu Val Glu
                565             570                 575

Leu Val Lys His Lys Pro Lys Ala Thr Lys Glu Gln Leu Lys Ala Val
            580                 585             590

Met Asp Asp Phe Ala Ala Phe Val Glu Lys Cys Cys Lys Ala Asp Asp
            595             600             605

Lys Glu Thr Cys Phe Ala Glu Glu Gly Lys Lys Leu Val Ala Ala Ser
            610             615             620

Gln Ala Ala Leu Gly Leu Ala Pro Ala Pro Ala Pro Ala Pro Ala Pro
625                 630             635                 640

Ala Pro Ala Pro Ala Pro Ala Pro Ala Pro Asp His Cys Pro Leu Gly
            645             650             655

Pro Gly Arg Cys Cys Arg Leu His Thr Val Arg Ala Ser Leu Glu Asp
            660             665             670

Leu Gly Trp Ala Asp Trp Val Leu Ser Pro Arg Glu Val Gln Val Thr
            675             680             685

Met Cys Ile Gly Ala Cys Pro Ser Gln Phe Arg Ala Ala Asn Met His
            690             695             700

Ala Gln Ile Lys Thr Ser Leu His Arg Leu Lys Pro Asp Thr Val Pro
705                 710             715                 720

Ala Pro Cys Cys Val Pro Ala Ser Tyr Asn Pro Met Val Leu Ile Gln
            725             730             735

Lys Thr Asp Thr Gly Val Ser Leu Gln Thr Tyr Asp Asp Leu Leu Ala
            740             745             750

Lys Asp Cys His Cys Ile
            755

<210> SEQ ID NO 35
<211> LENGTH: 793
<212> TYPE: PRT
<213> ORGANISM: Artificial Sequence
<220> FEATURE:
<223> OTHER INFORMATION: GLP1-GDF15 Fusion Protein 3

<400> SEQUENCE: 35

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Pro
            20                  25                  30

Ala Pro Ala Pro Ala Pro Ala Pro Ala Pro Ala Pro Ala Pro Ala Pro
            35                  40                  45

Ala Pro Ala Pro Ala Pro Ala Pro Ala Pro Ala Pro Ala Pro Ala Pro
            50                  55                  60

Ala Pro Ala Pro Ala Pro Ala Pro Ala Pro Ala Pro Ala Pro Ala Pro
65                  70                  75                  80

Asp Ala His Lys Ser Glu Val Ala His Arg Phe Lys Asp Leu Gly Glu
                85                  90                  95

Glu Asn Phe Lys Ala Leu Val Leu Ile Ala Phe Ala Gln Tyr Leu Gln
                100                 105                 110

Gln Ser Pro Phe Glu Asp His Val Lys Leu Val Asn Glu Val Thr Glu
            115                 120                 125

Phe Ala Lys Thr Cys Val Ala Asp Glu Ser Ala Glu Asn Cys Asp Lys
```

```
            130                 135                 140
Ser Leu His Thr Leu Phe Gly Asp Lys Leu Cys Thr Val Ala Thr Leu
145                 150                 155                 160

Arg Glu Thr Tyr Gly Glu Met Ala Asp Cys Cys Ala Lys Gln Glu Pro
                165                 170                 175

Glu Arg Asn Glu Cys Phe Leu Gln His Lys Asp Asp Asn Pro Asn Leu
            180                 185                 190

Pro Arg Leu Val Arg Pro Glu Val Asp Val Met Cys Thr Ala Phe His
        195                 200                 205

Asp Asn Glu Glu Thr Phe Leu Lys Lys Tyr Leu Tyr Glu Ile Ala Arg
210                 215                 220

Arg His Pro Tyr Phe Tyr Ala Pro Glu Leu Leu Phe Phe Ala Lys Arg
225                 230                 235                 240

Tyr Lys Ala Ala Phe Thr Glu Cys Cys Gln Ala Ala Asp Lys Ala Ala
                245                 250                 255

Cys Leu Leu Pro Lys Leu Asp Glu Leu Arg Asp Glu Gly Lys Ala Ser
            260                 265                 270

Ser Ala Lys Gln Arg Leu Lys Cys Ala Ser Leu Gln Lys Phe Gly Glu
        275                 280                 285

Arg Ala Phe Lys Ala Trp Ala Val Ala Arg Leu Ser Gln Arg Phe Pro
290                 295                 300

Lys Ala Glu Phe Ala Glu Val Ser Lys Leu Val Thr Asp Leu Thr Lys
305                 310                 315                 320

Val His Thr Glu Cys Cys His Gly Asp Leu Leu Glu Cys Ala Asp Asp
                325                 330                 335

Arg Ala Asp Leu Ala Lys Tyr Ile Cys Glu Asn Gln Asp Ser Ile Ser
            340                 345                 350

Ser Lys Leu Lys Glu Cys Cys Glu Lys Pro Leu Leu Glu Lys Ser His
        355                 360                 365

Cys Ile Ala Glu Val Glu Asn Asp Glu Met Pro Ala Asp Leu Pro Ser
370                 375                 380

Leu Ala Ala Asp Phe Val Glu Ser Lys Asp Val Cys Lys Asn Tyr Ala
385                 390                 395                 400

Glu Ala Lys Asp Val Phe Leu Gly Met Phe Leu Tyr Glu Tyr Ala Arg
                405                 410                 415

Arg His Pro Asp Tyr Ser Val Val Leu Leu Leu Arg Leu Ala Lys Thr
            420                 425                 430

Tyr Glu Thr Thr Leu Glu Lys Cys Cys Ala Ala Ala Asp Pro His Glu
        435                 440                 445

Cys Tyr Ala Lys Val Phe Asp Glu Phe Lys Pro Leu Val Glu Glu Pro
450                 455                 460

Gln Asn Leu Ile Lys Gln Asn Cys Glu Leu Phe Glu Gln Leu Gly Glu
465                 470                 475                 480

Tyr Lys Phe Gln Asn Ala Leu Leu Val Arg Tyr Thr Lys Lys Val Pro
                485                 490                 495

Gln Val Ser Thr Pro Thr Leu Val Glu Val Ser Arg Asn Leu Gly Lys
            500                 505                 510

Val Gly Ser Lys Cys Cys Lys His Pro Glu Ala Lys Arg Met Pro Cys
        515                 520                 525

Ala Glu Asp Tyr Leu Ser Val Val Leu Asn Gln Leu Cys Val Leu His
530                 535                 540

Glu Lys Thr Pro Val Ser Asp Arg Val Thr Lys Cys Cys Thr Glu Ser
545                 550                 555                 560
```

```
Leu Val Asn Arg Arg Pro Cys Phe Ser Ala Leu Glu Val Asp Glu Thr
                565                 570                 575

Tyr Val Pro Lys Glu Phe Asn Ala Glu Thr Phe Thr Phe His Ala Asp
            580                 585                 590

Ile Cys Thr Leu Ser Glu Lys Glu Arg Gln Ile Lys Lys Gln Thr Ala
        595                 600                 605

Leu Val Glu Leu Val Lys His Lys Pro Lys Ala Thr Lys Glu Gln Leu
    610                 615                 620

Lys Ala Val Met Asp Asp Phe Ala Ala Phe Val Glu Lys Cys Cys Lys
625                 630                 635                 640

Ala Asp Asp Lys Glu Thr Cys Phe Ala Glu Glu Gly Lys Lys Leu Val
                645                 650                 655

Ala Ala Ser Gln Ala Ala Leu Gly Leu Ala Pro Ala Pro Ala Pro Ala
            660                 665                 670

Pro Ala Pro Ala Pro Ala Pro Ala Pro Ala Pro Ala Pro Asp His Cys
        675                 680                 685

Pro Leu Gly Pro Gly Arg Cys Cys Arg Leu His Thr Val Arg Ala Ser
    690                 695                 700

Leu Glu Asp Leu Gly Trp Ala Asp Trp Val Leu Ser Pro Arg Glu Val
705                 710                 715                 720

Gln Val Thr Met Cys Ile Gly Ala Cys Pro Ser Gln Phe Arg Ala Ala
                725                 730                 735

Asn Met His Ala Gln Ile Lys Thr Ser Leu His Arg Leu Lys Pro Asp
            740                 745                 750

Thr Val Pro Ala Pro Cys Cys Val Pro Ala Ser Tyr Asn Pro Met Val
        755                 760                 765

Leu Ile Gln Lys Thr Asp Thr Gly Val Ser Leu Gln Thr Tyr Asp Asp
    770                 775                 780

Leu Leu Ala Lys Asp Cys His Cys Ile
785                 790

<210> SEQ ID NO 36
<211> LENGTH: 783
<212> TYPE: PRT
<213> ORGANISM: Artificial Sequence
<220> FEATURE:
<223> OTHER INFORMATION: GLP1-GDF15 Fusion Protein 4

<400> SEQUENCE: 36

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Pro
            20                  25                  30

Ala Pro Ala Pro Ala Pro Ala Pro Ala Pro Ala Pro Ala Pro Ala Pro
        35                  40                  45

Ala Pro Ala Pro Ala Pro Ala Pro Ala Pro Ala Pro Ala Pro Ala Pro
    50                  55                  60

Ala Pro Ala Pro Ala Pro Asp Ala His Lys Ser Glu Val Ala His Arg
65                  70                  75                  80

Phe Lys Asp Leu Gly Glu Glu Asn Phe Lys Ala Leu Val Leu Ile Ala
                85                  90                  95

Phe Ala Gln Tyr Leu Gln Gln Ser Pro Phe Glu Asp His Val Lys Leu
            100                 105                 110

Val Asn Glu Val Thr Glu Phe Ala Lys Thr Cys Val Ala Asp Glu Ser
        115                 120                 125
```

```
Ala Glu Asn Cys Asp Lys Ser Leu His Thr Leu Phe Gly Asp Lys Leu
    130                 135                 140
Cys Thr Val Ala Thr Leu Arg Glu Thr Tyr Gly Glu Met Ala Asp Cys
145                 150                 155                 160
Cys Ala Lys Gln Glu Pro Glu Arg Asn Glu Cys Phe Leu Gln His Lys
                165                 170                 175
Asp Asp Asn Pro Asn Leu Pro Arg Leu Val Arg Pro Glu Val Asp Val
            180                 185                 190
Met Cys Thr Ala Phe His Asp Asn Glu Glu Thr Phe Leu Lys Lys Tyr
        195                 200                 205
Leu Tyr Glu Ile Ala Arg Arg His Pro Tyr Phe Tyr Ala Pro Glu Leu
    210                 215                 220
Leu Phe Phe Ala Lys Arg Tyr Lys Ala Ala Phe Thr Glu Cys Cys Gln
225                 230                 235                 240
Ala Ala Asp Lys Ala Ala Cys Leu Leu Pro Lys Leu Asp Glu Leu Arg
                245                 250                 255
Asp Glu Gly Lys Ala Ser Ser Ala Lys Gln Arg Leu Lys Cys Ala Ser
            260                 265                 270
Leu Gln Lys Phe Gly Glu Arg Ala Phe Lys Ala Trp Ala Val Ala Arg
        275                 280                 285
Leu Ser Gln Arg Phe Pro Lys Ala Glu Phe Ala Glu Val Ser Lys Leu
    290                 295                 300
Val Thr Asp Leu Thr Lys Val His Thr Glu Cys Cys His Gly Asp Leu
305                 310                 315                 320
Leu Glu Cys Ala Asp Asp Arg Ala Asp Leu Ala Lys Tyr Ile Cys Glu
                325                 330                 335
Asn Gln Asp Ser Ile Ser Ser Lys Leu Lys Glu Cys Cys Glu Lys Pro
            340                 345                 350
Leu Leu Glu Lys Ser His Cys Ile Ala Glu Val Glu Asn Asp Glu Met
        355                 360                 365
Pro Ala Asp Leu Pro Ser Leu Ala Ala Asp Phe Val Glu Ser Lys Asp
    370                 375                 380
Val Cys Lys Asn Tyr Ala Glu Ala Lys Asp Val Phe Leu Gly Met Phe
385                 390                 395                 400
Leu Tyr Glu Tyr Ala Arg Arg His Pro Asp Tyr Ser Val Val Leu Leu
                405                 410                 415
Leu Arg Leu Ala Lys Thr Tyr Glu Thr Thr Leu Glu Lys Cys Cys Ala
            420                 425                 430
Ala Ala Asp Pro His Glu Cys Tyr Ala Lys Val Phe Asp Glu Phe Lys
        435                 440                 445
Pro Leu Val Glu Glu Pro Gln Asn Leu Ile Lys Gln Asn Cys Glu Leu
    450                 455                 460
Phe Glu Gln Leu Gly Glu Tyr Lys Phe Gln Asn Ala Leu Leu Val Arg
465                 470                 475                 480
Tyr Thr Lys Lys Val Pro Gln Val Ser Thr Pro Thr Leu Val Glu Val
                485                 490                 495
Ser Arg Asn Leu Gly Lys Val Gly Ser Lys Cys Cys Lys His Pro Glu
            500                 505                 510
Ala Lys Arg Met Pro Cys Ala Glu Asp Tyr Leu Ser Val Val Leu Asn
        515                 520                 525
Gln Leu Cys Val Leu His Glu Lys Thr Pro Val Ser Asp Arg Val Thr
    530                 535                 540
```

```
Lys Cys Cys Thr Glu Ser Leu Val Asn Arg Arg Pro Cys Phe Ser Ala
545                 550                 555                 560

Leu Glu Val Asp Glu Thr Tyr Val Pro Lys Glu Phe Asn Ala Glu Thr
                565                 570                 575

Phe Thr Phe His Ala Asp Ile Cys Thr Leu Ser Glu Lys Glu Arg Gln
            580                 585                 590

Ile Lys Lys Gln Thr Ala Leu Val Glu Leu Val Lys His Lys Pro Lys
        595                 600                 605

Ala Thr Lys Glu Gln Leu Lys Ala Val Met Asp Asp Phe Ala Ala Phe
    610                 615                 620

Val Glu Lys Cys Cys Lys Ala Asp Asp Lys Glu Thr Cys Phe Ala Glu
625                 630                 635                 640

Glu Gly Lys Lys Leu Val Ala Ala Ser Gln Ala Ala Leu Gly Leu Ala
                645                 650                 655

Pro Ala Pro Ala Pro Ala Pro Ala Pro Ala Pro Ala Pro Ala Pro Ala
                660                 665                 670

Pro Ala Pro Asp His Cys Pro Leu Gly Pro Gly Arg Cys Cys Arg Leu
            675                 680                 685

His Thr Val Arg Ala Ser Leu Glu Asp Leu Gly Trp Ala Asp Trp Val
        690                 695                 700

Leu Ser Pro Arg Glu Val Gln Val Thr Met Cys Ile Gly Ala Cys Pro
705                 710                 715                 720

Ser Gln Phe Arg Ala Ala Asn Met His Ala Gln Ile Lys Thr Ser Leu
                725                 730                 735

His Arg Leu Lys Pro Asp Thr Val Pro Ala Pro Cys Cys Val Pro Ala
            740                 745                 750

Ser Tyr Asn Pro Met Val Leu Ile Gln Lys Thr Asp Thr Gly Val Ser
        755                 760                 765

Leu Gln Thr Tyr Asp Asp Leu Leu Ala Lys Asp Cys His Cys Ile
    770                 775                 780

<210> SEQ ID NO 37
<211> LENGTH: 773
<212> TYPE: PRT
<213> ORGANISM: Artificial Sequence
<220> FEATURE:
<223> OTHER INFORMATION: GLP1-GDF15 Fusion Protein 5

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Pro
            20                  25                  30

Ala Pro Ala Pro Ala Pro Ala Pro Ala Pro Ala Pro Ala Pro Ala Pro
        35                  40                  45

Ala Pro Ala Pro Ala Pro Ala Pro Ala Pro Ala Pro Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Ser Pro Phe
                85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125
```

```
Leu Phe Gly Asp Lys Leu Cys Thr Val Ala Thr Leu Arg Glu Thr Tyr
        130                 135                 140
Gly Glu Met Ala Asp Cys Cys Ala Lys Gln Glu Pro Glu Arg Asn Glu
145                 150                 155                 160
Cys Phe Leu Gln His Lys Asp Asp Asn Pro Asn Leu Pro Arg Leu Val
                165                 170                 175
Arg Pro Glu Val Asp Val Met Cys Thr Ala Phe His Asp Asn Glu Glu
            180                 185                 190
Thr Phe Leu Lys Lys Tyr Leu Tyr Glu Ile Ala Arg Arg His Pro Tyr
        195                 200                 205
Phe Tyr Ala Pro Glu Leu Leu Phe Phe Ala Lys Arg Tyr Lys Ala Ala
    210                 215                 220
Phe Thr Glu Cys Cys Gln Ala Ala Asp Lys Ala Ala Cys Leu Leu Pro
225                 230                 235                 240
Lys Leu Asp Glu Leu Arg Asp Glu Gly Lys Ala Ser Ser Ala Lys Gln
                245                 250                 255
Arg Leu Lys Cys Ala Ser Leu Gln Lys Phe Gly Glu Arg Ala Phe Lys
            260                 265                 270
Ala Trp Ala Val Ala Arg Leu Ser Gln Arg Phe Pro Lys Ala Glu Phe
        275                 280                 285
Ala Glu Val Ser Lys Leu Val Thr Asp Leu Thr Lys Val His Thr Glu
    290                 295                 300
Cys Cys His Gly Asp Leu Leu Glu Cys Ala Asp Asp Arg Ala Asp Leu
305                 310                 315                 320
Ala Lys Tyr Ile Cys Glu Asn Gln Asp Ser Ile Ser Ser Lys Leu Lys
                325                 330                 335
Glu Cys Cys Glu Lys Pro Leu Leu Glu Lys Ser His Cys Ile Ala Glu
            340                 345                 350
Val Glu Asn Asp Glu Met Pro Ala Asp Leu Pro Ser Leu Ala Ala Asp
        355                 360                 365
Phe Val Glu Ser Lys Asp Val Cys Lys Asn Tyr Ala Glu Ala Lys Asp
    370                 375                 380
Val Phe Leu Gly Met Phe Leu Tyr Glu Tyr Ala Arg Arg His Pro Asp
385                 390                 395                 400
Tyr Ser Val Val Leu Leu Leu Arg Leu Ala Lys Thr Tyr Glu Thr Thr
                405                 410                 415
Leu Glu Lys Cys Cys Ala Ala Ala Asp Pro His Glu Cys Tyr Ala Lys
            420                 425                 430
Val Phe Asp Glu Phe Lys Pro Leu Val Glu Glu Pro Gln Asn Leu Ile
        435                 440                 445
Lys Gln Asn Cys Glu Leu Phe Glu Gln Leu Gly Glu Tyr Lys Phe Gln
    450                 455                 460
Asn Ala Leu Leu Val Arg Tyr Thr Lys Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
            500                 505                 510
Leu Ser Val Val Leu Asn Gln Leu Cys Val Leu His Glu Lys Thr Pro
        515                 520                 525
Val Ser Asp Arg Val Thr Lys Cys Cys Thr Glu Ser Leu Val Asn Arg
    530                 535                 540
Arg Pro Cys Phe Ser Ala Leu Glu Val Asp Glu Thr Tyr Val Pro Lys
```

```
                545                 550                 555                 560
Glu Phe Asn Ala Glu Thr Phe Thr Phe His Ala Asp Ile Cys Thr Leu
                565                 570                 575

Ser Glu Lys Glu Arg Gln Ile Lys Lys Gln Thr Ala Leu Val Glu Leu
                580                 585                 590

Val Lys His Lys Pro Lys Ala Thr Lys Glu Gln Leu Lys Ala Val Met
                595                 600                 605

Asp Asp Phe Ala Ala Phe Val Glu Lys Cys Cys Lys Ala Asp Asp Lys
    610                 615                 620

Glu Thr Cys Phe Ala Glu Glu Gly Lys Lys Leu Val Ala Ala Ser Gln
625                 630                 635                 640

Ala Ala Leu Gly Leu Ala Pro Ala Pro Ala Pro Ala Pro Ala Pro Ala
                645                 650                 655

Pro Ala Pro Ala Pro Ala Pro Ala Pro Asp His Cys Pro Leu Gly Pro
                660                 665                 670

Gly Arg Cys Cys Arg Leu His Thr Val Arg Ala Ser Leu Glu Asp Leu
                675                 680                 685

Gly Trp Ala Asp Trp Val Leu Ser Pro Arg Glu Val Gln Val Thr Met
        690                 695                 700

Cys Ile Gly Ala Cys Pro Ser Gln Phe Arg Ala Ala Asn Met His Ala
705                 710                 715                 720

Gln Ile Lys Thr Ser Leu His Arg Leu Lys Pro Asp Thr Val Pro Ala
                725                 730                 735

Pro Cys Cys Val Pro Ala Ser Tyr Asn Pro Met Val Leu Ile Gln Lys
                740                 745                 750

Thr Asp Thr Gly Val Ser Leu Gln Thr Tyr Asp Asp Leu Leu Ala Lys
                755                 760                 765

Asp Cys His Cys Ile
                770

<210> SEQ ID NO 38
<211> LENGTH: 783
<212> TYPE: PRT
<213> ORGANISM: Artificial Sequence
<220> FEATURE:
<223> OTHER INFORMATION: GLP1-GDF15 Fusion Protein 6

<400> SEQUENCE: 38

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Ala Gly Gly Gly Ala Gly Gly Gly Ala Gly Gly Gly Ala Gly Gly
            35                  40                  45

Gly Ala Gly Gly Gly Ala Gly Gly Gly Ala Gly Gly Gly
        50                  55                  60

Ala Gly Gly Gly Gly Ala Asp Ala His Lys Ser Glu Val Ala His Arg
65                  70                  75                  80

Phe Lys Asp Leu Gly Glu Glu Asn Phe Lys Ala Leu Val Leu Ile Ala
                85                  90                  95

Phe Ala Gln Tyr Leu Gln Gln Ser Pro Phe Glu Asp His Val Lys Leu
                100                 105                 110

Val Asn Glu Val Thr Glu Phe Ala Lys Thr Cys Val Ala Asp Glu Ser
                115                 120                 125

Ala Glu Asn Cys Asp Lys Ser Leu His Thr Leu Phe Gly Asp Lys Leu
```

```
            130                 135                 140
Cys Thr Val Ala Thr Leu Arg Glu Thr Tyr Gly Glu Met Ala Asp Cys
145                 150                 155                 160

Cys Ala Lys Gln Glu Pro Glu Arg Asn Glu Cys Phe Leu Gln His Lys
                165                 170                 175

Asp Asp Asn Pro Asn Leu Pro Arg Leu Val Arg Pro Glu Val Asp Val
            180                 185                 190

Met Cys Thr Ala Phe His Asp Asn Glu Glu Thr Phe Leu Lys Lys Tyr
                195                 200                 205

Leu Tyr Glu Ile Ala Arg Arg His Pro Tyr Phe Tyr Ala Pro Glu Leu
            210                 215                 220

Leu Phe Phe Ala Lys Arg Tyr Lys Ala Ala Phe Thr Glu Cys Cys Gln
225                 230                 235                 240

Ala Ala Asp Lys Ala Ala Cys Leu Leu Pro Lys Leu Asp Glu Leu Arg
                245                 250                 255

Asp Glu Gly Lys Ala Ser Ser Ala Lys Gln Arg Leu Lys Cys Ala Ser
                260                 265                 270

Leu Gln Lys Phe Gly Glu Arg Ala Phe Lys Ala Trp Ala Val Ala Arg
                275                 280                 285

Leu Ser Gln Arg Phe Pro Lys Ala Glu Phe Ala Glu Val Ser Lys Leu
            290                 295                 300

Val Thr Asp Leu Thr Lys Val His Thr Glu Cys Cys His Gly Asp Leu
305                 310                 315                 320

Leu Glu Cys Ala Asp Asp Arg Ala Asp Leu Ala Lys Tyr Ile Cys Glu
                325                 330                 335

Asn Gln Asp Ser Ile Ser Ser Lys Leu Lys Glu Cys Cys Glu Lys Pro
                340                 345                 350

Leu Leu Glu Lys Ser His Cys Ile Ala Glu Val Glu Asn Asp Glu Met
            355                 360                 365

Pro Ala Asp Leu Pro Ser Leu Ala Ala Asp Phe Val Glu Ser Lys Asp
            370                 375                 380

Val Cys Lys Asn Tyr Ala Glu Ala Lys Asp Val Phe Leu Gly Met Phe
385                 390                 395                 400

Leu Tyr Glu Tyr Ala Arg Arg His Pro Asp Tyr Ser Val Val Leu Leu
                405                 410                 415

Leu Arg Leu Ala Lys Thr Tyr Glu Thr Thr Leu Glu Lys Cys Cys Ala
                420                 425                 430

Ala Ala Asp Pro His Glu Cys Tyr Ala Lys Val Phe Asp Glu Phe Lys
                435                 440                 445

Pro Leu Val Glu Glu Pro Gln Asn Leu Ile Lys Gln Asn Cys Glu Leu
450                 455                 460

Phe Glu Gln Leu Gly Glu Tyr Lys Phe Gln Asn Ala Leu Leu Val Arg
465                 470                 475                 480

Tyr Thr Lys Lys Val Pro Gln Val Ser Thr Pro Thr Leu Val Glu Val
                485                 490                 495

Ser Arg Asn Leu Gly Lys Val Gly Ser Lys Cys Cys Lys His Pro Glu
                500                 505                 510

Ala Lys Arg Met Pro Cys Ala Glu Asp Tyr Leu Ser Val Val Leu Asn
                515                 520                 525

Gln Leu Cys Val Leu His Glu Lys Thr Pro Val Ser Asp Arg Val Thr
            530                 535                 540

Lys Cys Cys Thr Glu Ser Leu Val Asn Arg Arg Pro Cys Phe Ser Ala
545                 550                 555                 560
```

```
Leu Glu Val Asp Glu Thr Tyr Val Pro Lys Glu Phe Asn Ala Glu Thr
                565                 570                 575
Phe Thr Phe His Ala Asp Ile Cys Thr Leu Ser Glu Lys Glu Arg Gln
            580                 585                 590
Ile Lys Lys Gln Thr Ala Leu Val Glu Leu Val Lys His Lys Pro Lys
        595                 600                 605
Ala Thr Lys Glu Gln Leu Lys Ala Val Met Asp Asp Phe Ala Ala Phe
    610                 615                 620
Val Glu Lys Cys Cys Lys Ala Asp Asp Lys Glu Thr Cys Phe Ala Glu
625                 630                 635                 640
Glu Gly Lys Lys Leu Val Ala Ala Ser Gln Ala Ala Leu Gly Leu Ala
                645                 650                 655
Pro Ala Pro Ala Pro Ala Pro Ala Pro Ala Pro Ala Pro Ala Pro Ala
            660                 665                 670
Pro Ala Pro Asp His Cys Pro Leu Gly Pro Gly Arg Cys Cys Arg Leu
        675                 680                 685
His Thr Val Arg Ala Ser Leu Glu Asp Leu Gly Trp Ala Asp Trp Val
    690                 695                 700
Leu Ser Pro Arg Glu Val Gln Val Thr Met Cys Ile Gly Ala Cys Pro
705                 710                 715                 720
Ser Gln Phe Arg Ala Ala Asn Met His Ala Gln Ile Lys Thr Ser Leu
                725                 730                 735
His Arg Leu Lys Pro Asp Thr Val Pro Ala Pro Cys Cys Val Pro Ala
            740                 745                 750
Ser Tyr Asn Pro Met Val Leu Ile Gln Lys Thr Asp Thr Gly Val Ser
        755                 760                 765
Leu Gln Thr Tyr Asp Asp Leu Leu Ala Lys Asp Cys His Cys Ile
    770                 775                 780

<210> SEQ ID NO 39
<211> LENGTH: 802
<212> TYPE: PRT
<213> ORGANISM: Artificial Sequence
<220> FEATURE:
<223> OTHER INFORMATION: GLP1-GDF15 Fusion Protein 7

<400> SEQUENCE: 39

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Ser Ala Pro Ala Pro Ala Pro Ala Pro Ala Pro
            35                  40                  45
Pro Ala Pro Ala Pro Ala Pro Ala Pro Ala Pro Ala Pro Ala Pro Ala
        50                  55                  60
Pro Ala Pro Ala Pro Ala Pro Ala Pro Ala Pro Ala Pro Ala Pro Ala
65                  70                  75                  80
Pro Ala Pro Ala Pro Ala Pro Ala Pro Asp Ala His Lys Ser Glu Val
                85                  90                  95
Ala His Arg Phe Lys Asp Leu Gly Glu Glu Asn Phe Lys Ala Leu Val
            100                 105                 110
Leu Ile Ala Phe Ala Gln Tyr Leu Gln Gln Ser Pro Phe Glu Asp His
        115                 120                 125
Val Lys Leu Val Asn Glu Val Thr Glu Phe Ala Lys Thr Cys Val Ala
    130                 135                 140
```

```
Asp Glu Ser Ala Glu Asn Cys Asp Lys Ser Leu His Thr Leu Phe Gly
145                 150                 155                 160

Asp Lys Leu Cys Thr Val Ala Thr Leu Arg Glu Thr Tyr Gly Glu Met
            165                 170                 175

Ala Asp Cys Cys Ala Lys Gln Glu Pro Glu Arg Asn Glu Cys Phe Leu
        180                 185                 190

Gln His Lys Asp Asp Asn Pro Asn Leu Pro Arg Leu Val Arg Pro Glu
    195                 200                 205

Val Asp Val Met Cys Thr Ala Phe His Asp Asn Glu Glu Thr Phe Leu
210                 215                 220

Lys Lys Tyr Leu Tyr Glu Ile Ala Arg Arg His Pro Tyr Phe Tyr Ala
225                 230                 235                 240

Pro Glu Leu Leu Phe Phe Ala Lys Arg Tyr Lys Ala Ala Phe Thr Glu
                245                 250                 255

Cys Cys Gln Ala Ala Asp Lys Ala Ala Cys Leu Leu Pro Lys Leu Asp
            260                 265                 270

Glu Leu Arg Asp Glu Gly Lys Ala Ser Ser Ala Lys Gln Arg Leu Lys
        275                 280                 285

Cys Ala Ser Leu Gln Lys Phe Gly Glu Arg Ala Phe Lys Ala Trp Ala
    290                 295                 300

Val Ala Arg Leu Ser Gln Arg Phe Pro Lys Ala Glu Phe Ala Glu Val
305                 310                 315                 320

Ser Lys Leu Val Thr Asp Leu Thr Lys Val His Thr Glu Cys Cys His
                325                 330                 335

Gly Asp Leu Leu Glu Cys Ala Asp Asp Arg Ala Asp Leu Ala Lys Tyr
            340                 345                 350

Ile Cys Glu Asn Gln Asp Ser Ile Ser Ser Lys Leu Lys Glu Cys Cys
        355                 360                 365

Glu Lys Pro Leu Leu Glu Lys Ser His Cys Ile Ala Glu Val Glu Asn
    370                 375                 380

Asp Glu Met Pro Ala Asp Leu Pro Ser Leu Ala Ala Asp Phe Val Glu
385                 390                 395                 400

Ser Lys Asp Val Cys Lys Asn Tyr Ala Glu Ala Lys Asp Val Phe Leu
                405                 410                 415

Gly Met Phe Leu Tyr Glu Tyr Ala Arg Arg His Pro Asp Tyr Ser Val
            420                 425                 430

Val Leu Leu Leu Arg Leu Ala Lys Thr Tyr Glu Thr Thr Leu Glu Lys
        435                 440                 445

Cys Cys Ala Ala Ala Asp Pro His Glu Cys Tyr Ala Lys Val Phe Asp
    450                 455                 460

Glu Phe Lys Pro Leu Val Glu Glu Pro Gln Asn Leu Ile Lys Gln Asn
465                 470                 475                 480

Cys Glu Leu Phe Glu Gln Leu Gly Glu Tyr Lys Phe Gln Asn Ala Leu
                485                 490                 495

Leu Val Arg Tyr Thr Lys Lys Val Pro Gln Val Ser Thr Pro Thr Leu
            500                 505                 510

Val Glu Val Ser Arg Asn Leu Gly Lys Val Gly Ser Lys Cys Cys Lys
        515                 520                 525

His Pro Glu Ala Lys Arg Met Pro Cys Ala Glu Asp Tyr Leu Ser Val
    530                 535                 540

Val Leu Asn Gln Leu Cys Val Leu His Glu Lys Thr Pro Val Ser Asp
545                 550                 555                 560
```

```
Arg Val Thr Lys Cys Cys Thr Glu Ser Leu Val Asn Arg Arg Pro Cys
            565                 570                 575

Phe Ser Ala Leu Glu Val Asp Gly Thr Tyr Val Pro Lys Glu Phe Asn
        580                 585                 590

Ala Glu Thr Phe Thr Phe His Ala Asp Ile Cys Thr Leu Ser Glu Lys
            595                 600                 605

Glu Arg Gln Ile Lys Lys Gln Thr Ala Leu Val Glu Leu Val Lys His
610                 615                 620

Lys Pro Lys Ala Thr Lys Glu Gln Leu Lys Ala Val Met Asp Asp Phe
625                 630                 635                 640

Ala Ala Phe Val Glu Lys Cys Cys Lys Ala Asp Asp Lys Glu Thr Cys
            645                 650                 655

Phe Ala Glu Glu Gly Lys Lys Leu Val Ala Ala Ser Gln Ala Ala Leu
            660                 665                 670

Gly Leu Ala Pro Ala Pro Ala Pro Ala Pro Ala Pro Ala Pro Ala Pro
        675                 680                 685

Ala Pro Ala Pro Ala Pro Asp His Cys Pro Leu Gly Pro Gly Arg Cys
        690                 695                 700

Cys Arg Leu His Thr Val Arg Ala Ser Leu Glu Asp Leu Gly Trp Ala
705                 710                 715                 720

Asp Trp Val Leu Ser Pro Arg Glu Val Gln Val Thr Met Cys Ile Gly
            725                 730                 735

Ala Cys Pro Ser Gln Phe Arg Ala Ala Asn Met His Ala Gln Ile Lys
            740                 745                 750

Thr Ser Leu His Arg Leu Lys Pro Asp Thr Val Pro Ala Pro Cys Cys
            755                 760                 765

Val Pro Ala Ser Tyr Asn Pro Met Val Leu Ile Gln Lys Thr Asp Thr
        770                 775                 780

Gly Val Ser Leu Gln Thr Tyr Asp Asp Leu Leu Ala Lys Asp Cys His
785                 790                 795                 800

Cys Ile

<210> SEQ ID NO 40
<211> LENGTH: 782
<212> TYPE: PRT
<213> ORGANISM: Artificial Sequence
<220> FEATURE:
<223> OTHER INFORMATION: GLP1-GDF15 Fusion Protein 8

<400> SEQUENCE: 40

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Ala Pro Ala Pro Ala Pro
        35                  40                  45

Pro Ala Pro Ala Pro Ala Pro Ala Pro Ala Pro Ala Pro Ala Pro Ala
    50                  55                  60

Pro Ala Pro Ala Pro Asp Ala His Lys Ser Glu Val Ala His Arg Phe
65                  70                  75                  80

Lys Asp Leu Gly Glu Glu Asn Phe Lys Ala Leu Val Leu Ile Ala Phe
                85                  90                  95

Ala Gln Tyr Leu Gln Gln Ser Pro Phe Glu Asp His Val Lys Leu Val
            100                 105                 110

Asn Glu Val Thr Glu Phe Ala Lys Thr Cys Val Ala Asp Glu Ser Ala
```

```
            115                 120                 125
Glu Asn Cys Asp Lys Ser Leu His Thr Leu Phe Gly Asp Lys Leu Cys
130                 135                 140

Thr Val Ala Thr Leu Arg Glu Thr Tyr Gly Glu Met Ala Asp Cys Cys
145                 150                 155                 160

Ala Lys Gln Glu Pro Glu Arg Asn Glu Cys Phe Leu Gln His Lys Asp
                165                 170                 175

Asp Asn Pro Asn Leu Pro Arg Leu Val Arg Pro Glu Val Asp Val Met
            180                 185                 190

Cys Thr Ala Phe His Asp Asn Glu Glu Thr Phe Leu Lys Lys Tyr Leu
        195                 200                 205

Tyr Glu Ile Ala Arg Arg His Pro Tyr Phe Tyr Ala Pro Glu Leu Leu
    210                 215                 220

Phe Phe Ala Lys Arg Tyr Lys Ala Ala Phe Thr Glu Cys Cys Gln Ala
225                 230                 235                 240

Ala Asp Lys Ala Ala Cys Leu Leu Pro Lys Leu Asp Glu Leu Arg Asp
                245                 250                 255

Glu Gly Lys Ala Ser Ser Ala Lys Gln Arg Leu Lys Cys Ala Ser Leu
            260                 265                 270

Gln Lys Phe Gly Glu Arg Ala Phe Lys Ala Trp Ala Val Ala Arg Leu
        275                 280                 285

Ser Gln Arg Phe Pro Lys Ala Glu Phe Ala Glu Val Ser Lys Leu Val
    290                 295                 300

Thr Asp Leu Thr Lys Val His Thr Glu Cys Cys His Gly Asp Leu Leu
305                 310                 315                 320

Glu Cys Ala Asp Asp Arg Ala Asp Leu Ala Lys Tyr Ile Cys Glu Asn
                325                 330                 335

Gln Asp Ser Ile Ser Ser Lys Leu Lys Glu Cys Cys Glu Lys Pro Leu
            340                 345                 350

Leu Glu Lys Ser His Cys Ile Ala Glu Val Glu Asn Asp Glu Met Pro
        355                 360                 365

Ala Asp Leu Pro Ser Leu Ala Ala Asp Phe Val Glu Ser Lys Asp Val
    370                 375                 380

Cys Lys Asn Tyr Ala Glu Ala Lys Asp Val Phe Leu Gly Met Phe Leu
385                 390                 395                 400

Tyr Glu Tyr Ala Arg Arg His Pro Asp Tyr Ser Val Val Leu Leu Leu
                405                 410                 415

Arg Leu Ala Lys Thr Tyr Glu Thr Thr Leu Glu Lys Cys Cys Ala Ala
            420                 425                 430

Ala Asp Pro His Glu Cys Tyr Ala Lys Val Phe Asp Glu Phe Lys Pro
        435                 440                 445

Leu Val Glu Glu Pro Gln Asn Leu Ile Lys Gln Asn Cys Glu Leu Phe
    450                 455                 460

Glu Gln Leu Gly Glu Tyr Lys Phe Gln Asn Ala Leu Leu Val Arg Tyr
465                 470                 475                 480

Thr Lys Lys Val Pro Gln Val Ser Thr Pro Thr Leu Val Glu Val Ser
                485                 490                 495

Arg Asn Leu Gly Lys Val Gly Ser Lys Cys Cys Lys His Pro Glu Ala
            500                 505                 510

Lys Arg Met Pro Cys Ala Glu Asp Tyr Leu Ser Val Val Leu Asn Gln
        515                 520                 525

Leu Cys Val Leu His Glu Lys Thr Pro Val Ser Asp Arg Val Thr Lys
    530                 535                 540
```

Cys Cys Thr Glu Ser Leu Val Asn Arg Arg Pro Cys Phe Ser Ala Leu
545                 550                 555                 560

Glu Val Asp Glu Thr Tyr Val Pro Lys Glu Phe Asn Ala Glu Thr Phe
                565                 570                 575

Thr Phe His Ala Asp Ile Cys Thr Leu Ser Glu Lys Glu Arg Gln Ile
            580                 585                 590

Lys Lys Gln Thr Ala Leu Val Glu Leu Val Lys His Lys Pro Lys Ala
        595                 600                 605

Thr Lys Glu Gln Leu Lys Ala Val Met Asp Asp Phe Ala Ala Phe Val
    610                 615                 620

Glu Lys Cys Cys Lys Ala Asp Asp Lys Glu Thr Cys Phe Ala Glu Glu
625                 630                 635                 640

Gly Lys Lys Leu Val Ala Ala Ser Gln Ala Ala Leu Gly Leu Ala Pro
                645                 650                 655

Ala Pro Ala Pro Ala Pro Ala Pro Ala Pro Ala Pro Ala Pro Ala Pro
                660                 665                 670

Ala Pro Asp His Cys Pro Leu Gly Pro Gly Arg Cys Cys Arg Leu His
            675                 680                 685

Thr Val Arg Ala Ser Leu Glu Asp Leu Gly Trp Ala Asp Trp Val Leu
        690                 695                 700

Ser Pro Arg Glu Val Gln Val Thr Met Cys Ile Gly Ala Cys Pro Ser
705                 710                 715                 720

Gln Phe Arg Ala Ala Asn Met His Ala Gln Ile Lys Thr Ser Leu His
                725                 730                 735

Arg Leu Lys Pro Asp Thr Val Pro Ala Pro Cys Cys Val Pro Ala Ser
            740                 745                 750

Tyr Asn Pro Met Val Leu Ile Gln Lys Thr Asp Thr Gly Val Ser Leu
        755                 760                 765

Gln Thr Tyr Asp Asp Leu Leu Ala Lys Asp Cys His Cys Ile
    770                 775                 780

<210> SEQ ID NO 41
<211> LENGTH: 772
<212> TYPE: PRT
<213> ORGANISM: Artificial Sequence
<220> FEATURE:
<223> OTHER INFORMATION: GLP1-GDF15 Fusion Protein 9

<400> SEQUENCE: 41

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Ala Pro Ala Pro Ala Pro
        35                  40                  45

Pro Ala Pro Ala Pro Ala Pro Ala Pro Asp Ala His Lys Ser
    50                  55                  60

Glu Val Ala His Arg Phe Lys Asp Leu Gly Glu Glu Asn Phe Lys Ala
65                  70                  75                  80

Leu Val Leu Ile Ala Phe Ala Gln Tyr Leu Gln Gln Ser Pro Phe Glu
                85                  90                  95

Asp His Val Lys Leu Val Asn Glu Val Thr Glu Phe Ala Lys Thr Cys
            100                 105                 110

Val Ala Asp Glu Ser Ala Glu Asn Cys Asp Lys Ser Leu His Thr Leu
        115                 120                 125

```
Phe Gly Asp Lys Leu Cys Thr Val Ala Thr Leu Arg Glu Thr Tyr Gly
    130                 135                 140

Glu Met Ala Asp Cys Cys Ala Lys Gln Glu Pro Glu Arg Asn Glu Cys
145                 150                 155                 160

Phe Leu Gln His Lys Asp Asp Asn Pro Asn Leu Pro Arg Leu Val Arg
                165                 170                 175

Pro Glu Val Asp Val Met Cys Thr Ala Phe His Asp Asn Glu Glu Thr
            180                 185                 190

Phe Leu Lys Lys Tyr Leu Tyr Glu Ile Ala Arg Arg His Pro Tyr Phe
        195                 200                 205

Tyr Ala Pro Glu Leu Leu Phe Phe Ala Lys Arg Tyr Lys Ala Ala Phe
    210                 215                 220

Thr Glu Cys Cys Gln Ala Ala Asp Lys Ala Ala Cys Leu Leu Pro Lys
225                 230                 235                 240

Leu Asp Glu Leu Arg Asp Glu Gly Lys Ala Ser Ser Ala Lys Gln Arg
                245                 250                 255

Leu Lys Cys Ala Ser Leu Gln Lys Phe Gly Glu Arg Ala Phe Lys Ala
            260                 265                 270

Trp Ala Val Ala Arg Leu Ser Gln Arg Phe Pro Lys Ala Glu Phe Ala
        275                 280                 285

Glu Val Ser Lys Leu Val Thr Asp Leu Thr Lys Val His Thr Glu Cys
    290                 295                 300

Cys His Gly Asp Leu Leu Glu Cys Ala Asp Asp Arg Ala Asp Leu Ala
305                 310                 315                 320

Lys Tyr Ile Cys Glu Asn Gln Asp Ser Ile Ser Ser Lys Leu Lys Glu
                325                 330                 335

Cys Cys Glu Lys Pro Leu Leu Glu Lys Ser His Cys Ile Ala Glu Val
            340                 345                 350

Glu Asn Asp Glu Met Pro Ala Asp Leu Pro Ser Leu Ala Ala Asp Phe
        355                 360                 365

Val Glu Ser Lys Asp Val Cys Lys Asn Tyr Ala Glu Ala Lys Asp Val
    370                 375                 380

Phe Leu Gly Met Phe Leu Tyr Glu Tyr Ala Arg Arg His Pro Asp Tyr
385                 390                 395                 400

Ser Val Val Leu Leu Leu Arg Leu Ala Lys Thr Tyr Glu Thr Thr Leu
                405                 410                 415

Glu Lys Cys Cys Ala Ala Ala Asp Pro His Glu Cys Tyr Ala Lys Val
            420                 425                 430

Phe Asp Glu Phe Lys Pro Leu Val Glu Glu Pro Gln Asn Leu Ile Lys
        435                 440                 445

Gln Asn Cys Glu Leu Phe Glu Gln Leu Gly Glu Tyr Lys Phe Gln Asn
    450                 455                 460

Ala Leu Leu Val Arg Tyr Thr Lys Lys Val Pro Gln Val Ser Thr Pro
465                 470                 475                 480

Thr Leu Val Glu Val Ser Arg Asn Leu Gly Lys Val Gly Ser Lys Cys
                485                 490                 495

Cys Lys His Pro Glu Ala Lys Arg Met Pro Cys Ala Glu Asp Tyr Leu
            500                 505                 510

Ser Val Val Leu Asn Gln Leu Cys Val Leu His Glu Lys Thr Pro Val
        515                 520                 525

Ser Asp Arg Val Thr Lys Cys Cys Thr Glu Ser Leu Val Asn Arg Arg
530                 535                 540
```

-continued

```
Pro Cys Phe Ser Ala Leu Glu Val Asp Glu Thr Tyr Val Pro Lys Glu
545                 550                 555                 560

Phe Asn Ala Glu Thr Phe Thr Phe His Ala Asp Ile Cys Thr Leu Ser
                565                 570                 575

Glu Lys Glu Arg Gln Ile Lys Lys Gln Thr Ala Leu Val Glu Leu Val
            580                 585                 590

Lys His Lys Pro Lys Ala Thr Lys Glu Gln Leu Lys Ala Val Met Asp
        595                 600                 605

Asp Phe Ala Ala Phe Val Glu Lys Cys Cys Lys Ala Asp Asp Lys Glu
    610                 615                 620

Thr Cys Phe Ala Glu Glu Gly Lys Lys Leu Val Ala Ala Ser Gln Ala
625                 630                 635                 640

Ala Leu Gly Leu Ala Pro Ala Pro Ala Pro Ala Pro Ala Pro Ala Pro
                645                 650                 655

Ala Pro Ala Pro Ala Pro Ala Pro Asp His Cys Pro Leu Gly Pro Gly
                660                 665                 670

Arg Cys Cys Arg Leu His Thr Val Arg Ala Ser Leu Glu Asp Leu Gly
            675                 680                 685

Trp Ala Asp Trp Val Leu Ser Pro Arg Glu Val Gln Val Thr Met Cys
        690                 695                 700

Ile Gly Ala Cys Pro Ser Gln Phe Arg Ala Ala Asn Met His Ala Gln
705                 710                 715                 720

Ile Lys Thr Ser Leu His Arg Leu Lys Pro Asp Thr Val Pro Ala Pro
                725                 730                 735

Cys Cys Val Pro Ala Ser Tyr Asn Pro Met Val Leu Ile Gln Lys Thr
                740                 745                 750

Asp Thr Gly Val Ser Leu Gln Thr Tyr Asp Asp Leu Leu Ala Lys Asp
            755                 760                 765

Cys His Cys Ile
        770

<210> SEQ ID NO 42
<211> LENGTH: 792
<212> TYPE: PRT
<213> ORGANISM: Artificial Sequence
<220> FEATURE:
<223> OTHER INFORMATION: GLP1-GDF15 Fusion Protein 10

<400> SEQUENCE: 42

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ala Gly Gly Gly Gly Gly Gly
        35                  40                  45

Ala Gly Gly Gly Ala Gly Gly Gly Ala Gly Gly Gly Ala Gly Gly Ala
    50                  55                  60

Gly Gly Gly Ala Gly Gly Gly Ala Gly Gly Gly Ala Gly Gly Gly Ala Asp
65                  70                  75                  80

Ala His Lys Ser Glu Val Ala His Arg Phe Lys Asp Leu Gly Glu Glu
                85                  90                  95

Asn Phe Lys Ala Leu Val Leu Ile Ala Phe Ala Gln Tyr Leu Gln Gln
            100                 105                 110

Ser Pro Phe Glu Asp His Val Lys Leu Val Asn Glu Val Thr Glu Phe
        115                 120                 125
```

```
Ala Lys Thr Cys Val Ala Asp Glu Ser Ala Glu Asn Cys Asp Lys Ser
    130                 135                 140
Leu His Thr Leu Phe Gly Asp Lys Leu Cys Thr Val Ala Thr Leu Arg
145                 150                 155                 160
Glu Thr Tyr Gly Glu Met Ala Asp Cys Cys Ala Lys Gln Pro Glu
                165                 170                 175
Arg Asn Glu Cys Phe Leu Gln His Lys Asp Asp Asn Pro Asn Leu Pro
                180                 185                 190
Arg Leu Val Arg Pro Glu Val Asp Val Met Cys Thr Ala Phe His Asp
            195                 200                 205
Asn Glu Glu Thr Phe Leu Lys Lys Tyr Leu Tyr Glu Ile Ala Arg Arg
210                 215                 220
His Pro Tyr Phe Tyr Ala Pro Glu Leu Leu Phe Phe Ala Lys Arg Tyr
225                 230                 235                 240
Lys Ala Ala Phe Thr Glu Cys Cys Gln Ala Ala Asp Lys Ala Ala Cys
                245                 250                 255
Leu Leu Pro Lys Leu Asp Glu Leu Arg Asp Glu Gly Lys Ala Ser Ser
            260                 265                 270
Ala Lys Gln Arg Leu Lys Cys Ala Ser Leu Gln Lys Phe Gly Glu Arg
    275                 280                 285
Ala Phe Lys Ala Trp Ala Val Ala Arg Leu Ser Gln Arg Phe Pro Lys
290                 295                 300
Ala Glu Phe Ala Glu Val Ser Lys Leu Val Thr Asp Leu Thr Lys Val
305                 310                 315                 320
His Thr Glu Cys Cys His Gly Asp Leu Leu Glu Cys Ala Asp Asp Arg
                325                 330                 335
Ala Asp Leu Ala Lys Tyr Ile Cys Glu Asn Gln Asp Ser Ile Ser Ser
            340                 345                 350
Lys Leu Lys Glu Cys Cys Glu Lys Pro Leu Leu Glu Lys Ser His Cys
    355                 360                 365
Ile Ala Glu Val Glu Asn Asp Glu Met Pro Ala Asp Leu Pro Ser Leu
370                 375                 380
Ala Ala Asp Phe Val Glu Ser Lys Asp Val Cys Lys Asn Tyr Ala Glu
385                 390                 395                 400
Ala Lys Asp Val Phe Leu Gly Met Phe Leu Tyr Glu Tyr Ala Arg Arg
                405                 410                 415
His Pro Asp Tyr Ser Val Val Leu Leu Leu Arg Leu Ala Lys Thr Tyr
            420                 425                 430
Glu Thr Thr Leu Glu Lys Cys Cys Ala Ala Ala Asp Pro His Glu Cys
    435                 440                 445
Tyr Ala Lys Val Phe Asp Glu Phe Lys Pro Leu Val Glu Glu Pro Gln
450                 455                 460
Asn Leu Ile Lys Gln Asn Cys Glu Leu Phe Glu Gln Leu Gly Glu Tyr
465                 470                 475                 480
Lys Phe Gln Asn Ala Leu Leu Val Arg Tyr Thr Lys Lys Val Pro Gln
                485                 490                 495
Val Ser Thr Pro Thr Leu Val Glu Val Ser Arg Asn Leu Gly Lys Val
            500                 505                 510
Gly Ser Lys Cys Cys Lys His Pro Glu Ala Lys Arg Met Pro Cys Ala
    515                 520                 525
Glu Asp Tyr Leu Ser Val Val Leu Asn Gln Leu Cys Val Leu His Glu
530                 535                 540
Lys Thr Pro Val Ser Asp Arg Val Thr Lys Cys Cys Thr Glu Ser Leu
```

```
545                 550                 555                 560
Val Asn Arg Arg Pro Cys Phe Ser Ala Leu Glu Val Asp Glu Thr Tyr
                565                 570                 575

Val Pro Lys Glu Phe Asn Ala Glu Thr Phe Thr Phe His Ala Asp Ile
                580                 585                 590

Cys Thr Leu Ser Glu Lys Glu Arg Gln Ile Lys Lys Gln Thr Ala Leu
                595                 600                 605

Val Glu Leu Val Lys His Lys Pro Lys Ala Thr Lys Glu Gln Leu Lys
                610                 615                 620

Ala Val Met Asp Asp Phe Ala Ala Phe Val Glu Lys Cys Cys Lys Ala
625                 630                 635                 640

Asp Asp Lys Glu Thr Cys Phe Ala Glu Gly Lys Lys Leu Val Ala
                    645                 650                 655

Ala Ser Gln Ala Ala Leu Gly Leu Ala Pro Ala Pro Ala Pro Ala Pro
                660                 665                 670

Ala Pro Ala Pro Ala Pro Ala Pro Ala Pro Ala Pro Asp His Cys Pro
                675                 680                 685

Leu Gly Pro Gly Arg Cys Cys Arg Leu His Thr Val Arg Ala Ser Leu
                690                 695                 700

Glu Asp Leu Gly Trp Ala Asp Trp Val Leu Ser Pro Arg Glu Val Gln
705                 710                 715                 720

Val Thr Met Cys Ile Gly Ala Cys Pro Ser Gln Phe Arg Ala Ala Asn
                725                 730                 735

Met His Ala Gln Ile Lys Thr Ser Leu His Arg Leu Lys Pro Asp Thr
                740                 745                 750

Val Pro Ala Pro Cys Cys Val Pro Ala Ser Tyr Asn Pro Met Val Leu
                755                 760                 765

Ile Gln Lys Thr Asp Thr Gly Val Ser Leu Gln Thr Tyr Asp Asp Leu
                770                 775                 780

Leu Ala Lys Asp Cys His Cys Ile
785                 790

<210> SEQ ID NO 43
<211> LENGTH: 777
<212> TYPE: PRT
<213> ORGANISM: Artificial Sequence
<220> FEATURE:
<223> OTHER INFORMATION: GLP1-GDF15 Fusion Protein 11

<400> SEQUENCE: 43

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Ala Gly Gly Gly Gly
                35                  40                  45

Ala Gly Gly Gly Ala Gly Gly Gly Ala Gly Gly Gly Ala
        50                  55                  60

Asp Ala His Lys Ser Glu Val Ala His Arg Phe Lys Asp Leu Gly Glu
65                  70                  75                  80

Glu Asn Phe Lys Ala Leu Val Leu Ile Ala Phe Ala Gln Tyr Leu Gln
                85                  90                  95

Gln Ser Pro Phe Glu Asp His Val Lys Leu Val Asn Glu Val Thr Glu
                100                 105                 110

Phe Ala Lys Thr Cys Val Ala Asp Glu Ser Ala Glu Asn Cys Asp Lys
```

-continued

```
            115                 120                 125
Ser Leu His Thr Leu Phe Gly Asp Lys Leu Cys Thr Val Ala Thr Leu
        130                 135                 140
Arg Glu Thr Tyr Gly Glu Met Ala Asp Cys Cys Ala Lys Gln Glu Pro
145                 150                 155                 160
Glu Arg Asn Glu Cys Phe Leu Gln His Lys Asp Asp Asn Pro Asn Leu
                165                 170                 175
Pro Arg Leu Val Arg Pro Glu Val Asp Val Met Cys Thr Ala Phe His
                180                 185                 190
Asp Asn Glu Glu Thr Phe Leu Lys Lys Tyr Leu Tyr Glu Ile Ala Arg
                195                 200                 205
Arg His Pro Tyr Phe Tyr Ala Pro Glu Leu Leu Phe Phe Ala Lys Arg
        210                 215                 220
Tyr Lys Ala Ala Phe Thr Glu Cys Cys Gln Ala Ala Asp Lys Ala Ala
225                 230                 235                 240
Cys Leu Leu Pro Lys Leu Asp Glu Leu Arg Asp Glu Gly Lys Ala Ser
                245                 250                 255
Ser Ala Lys Gln Arg Leu Lys Cys Ala Ser Leu Gln Lys Phe Gly Glu
                260                 265                 270
Arg Ala Phe Lys Ala Trp Ala Val Ala Arg Leu Ser Gln Arg Phe Pro
        275                 280                 285
Lys Ala Glu Phe Ala Glu Val Ser Lys Leu Val Thr Asp Leu Thr Lys
        290                 295                 300
Val His Thr Glu Cys Cys His Gly Asp Leu Leu Glu Cys Ala Asp Asp
305                 310                 315                 320
Arg Ala Asp Leu Ala Lys Tyr Ile Cys Glu Asn Gln Asp Ser Ile Ser
                325                 330                 335
Ser Lys Leu Lys Glu Cys Cys Glu Lys Pro Leu Leu Glu Lys Ser His
                340                 345                 350
Cys Ile Ala Glu Val Glu Asn Asp Glu Met Pro Ala Asp Leu Pro Ser
        355                 360                 365
Leu Ala Ala Asp Phe Val Glu Ser Lys Asp Val Cys Lys Asn Tyr Ala
        370                 375                 380
Glu Ala Lys Asp Val Phe Leu Gly Met Phe Leu Tyr Glu Tyr Ala Arg
385                 390                 395                 400
Arg His Pro Asp Tyr Ser Val Val Leu Leu Leu Arg Leu Ala Lys Thr
                405                 410                 415
Tyr Glu Thr Thr Leu Glu Lys Cys Cys Ala Ala Ala Asp Pro His Glu
                420                 425                 430
Cys Tyr Ala Lys Val Phe Asp Glu Phe Lys Pro Leu Val Glu Glu Pro
        435                 440                 445
Gln Asn Leu Ile Lys Gln Asn Cys Glu Leu Phe Glu Gln Leu Gly Glu
        450                 455                 460
Tyr Lys Phe Gln Asn Ala Leu Leu Val Arg Tyr Thr Lys Lys Val Pro
465                 470                 475                 480
Gln Val Ser Thr Pro Thr Leu Val Glu Val Ser Arg Asn Leu Gly Lys
                485                 490                 495
Val Gly Ser Lys Cys Cys Lys His Pro Glu Ala Lys Arg Met Pro Cys
                500                 505                 510
Ala Glu Asp Tyr Leu Ser Val Val Leu Asn Gln Leu Cys Val Leu His
        515                 520                 525
Glu Lys Thr Pro Val Ser Asp Arg Val Thr Lys Cys Cys Thr Glu Ser
        530                 535                 540
```

```
Leu Val Asn Arg Arg Pro Cys Phe Ser Ala Leu Glu Val Asp Glu Thr
545                 550                 555                 560

Tyr Val Pro Lys Glu Phe Asn Ala Glu Thr Phe Thr Phe His Ala Asp
                565                 570                 575

Ile Cys Thr Leu Ser Glu Lys Glu Arg Gln Ile Lys Lys Gln Thr Ala
            580                 585                 590

Leu Val Glu Leu Val Lys His Lys Pro Lys Ala Thr Lys Glu Gln Leu
        595                 600                 605

Lys Ala Val Met Asp Asp Phe Ala Ala Phe Val Glu Lys Cys Cys Lys
    610                 615                 620

Ala Asp Asp Lys Glu Thr Cys Phe Ala Glu Glu Gly Lys Lys Leu Val
625                 630                 635                 640

Ala Ala Ser Gln Ala Ala Leu Gly Leu Ala Pro Ala Pro Ala Pro Ala
                645                 650                 655

Pro Ala Pro Ala Pro Ala Pro Ala Pro Ala Pro Ala Pro Asp His Cys
                660                 665                 670

Pro Leu Gly Pro Gly Arg Cys Cys Arg Leu His Thr Val Arg Ala Ser
            675                 680                 685

Leu Glu Asp Leu Gly Trp Ala Asp Trp Val Leu Ser Pro Arg Glu Val
        690                 695                 700

Gln Val Thr Met Cys Ile Gly Ala Cys Pro Ser Gln Phe Arg Ala Ala
705                 710                 715                 720

Asn Met His Ala Gln Ile Lys Thr Ser Leu His Arg Leu Lys Pro Asp
                725                 730                 735

Thr Val Pro Ala Pro Cys Cys Val Pro Ala Ser Tyr Asn Pro Met Val
                740                 745                 750

Leu Ile Gln Lys Thr Asp Thr Gly Val Ser Leu Gln Thr Tyr Asp Asp
            755                 760                 765

Leu Leu Ala Lys Asp Cys His Cys Ile
        770                 775

<210> SEQ ID NO 44
<211> LENGTH: 762
<212> TYPE: PRT
<213> ORGANISM: Artificial Sequence
<220> FEATURE:
<223> OTHER INFORMATION: GLP1-GDF15 Fusion Protein 12

<400> SEQUENCE: 44

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Ala Pro Ala Pro Ala Pro
        35                  40                  45

Pro Asp Ala His Lys Ser Glu Val Ala His Arg Phe Lys Asp Leu Gly
    50                  55                  60

Glu Glu Asn Phe Lys Ala Leu Val Leu Ile Ala Phe Ala Gln Tyr Leu
65                  70                  75                  80

Gln Gln Ser Pro Phe Glu Asp His Val Lys Leu Val Asn Glu Val Thr
                85                  90                  95

Glu Phe Ala Lys Thr Cys Val Ala Asp Glu Ser Ala Glu Asn Cys Asp
            100                 105                 110

Lys Ser Leu His Thr Leu Phe Gly Asp Lys Leu Cys Thr Val Ala Thr
        115                 120                 125
```

```
Leu Arg Glu Thr Tyr Gly Glu Met Ala Asp Cys Cys Ala Lys Gln Glu
            130                 135                 140

Pro Glu Arg Asn Glu Cys Phe Leu Gln His Lys Asp Asp Asn Pro Asn
145                 150                 155                 160

Leu Pro Arg Leu Val Arg Pro Glu Val Asp Val Met Cys Thr Ala Phe
                165                 170                 175

His Asp Asn Glu Glu Thr Phe Leu Lys Lys Tyr Leu Tyr Glu Ile Ala
            180                 185                 190

Arg Arg His Pro Tyr Phe Tyr Ala Pro Glu Leu Leu Phe Phe Ala Lys
            195                 200                 205

Arg Tyr Lys Ala Ala Phe Thr Glu Cys Cys Gln Ala Ala Asp Lys Ala
            210                 215                 220

Ala Cys Leu Leu Pro Lys Leu Asp Glu Leu Arg Asp Glu Gly Lys Ala
225                 230                 235                 240

Ser Ser Ala Lys Gln Arg Leu Lys Cys Ala Ser Leu Gln Lys Phe Gly
                245                 250                 255

Glu Arg Ala Phe Lys Ala Trp Ala Val Ala Arg Leu Ser Gln Arg Phe
            260                 265                 270

Pro Lys Ala Glu Phe Ala Glu Val Ser Lys Leu Val Thr Asp Leu Thr
            275                 280                 285

Lys Val His Thr Glu Cys Cys His Gly Asp Leu Leu Glu Cys Ala Asp
290                 295                 300

Asp Arg Ala Asp Leu Ala Lys Tyr Ile Cys Glu Asn Gln Asp Ser Ile
305                 310                 315                 320

Ser Ser Lys Leu Lys Glu Cys Cys Glu Lys Pro Leu Leu Glu Lys Ser
                325                 330                 335

His Cys Ile Ala Glu Val Glu Asn Asp Glu Met Pro Ala Asp Leu Pro
            340                 345                 350

Ser Leu Ala Ala Asp Phe Val Glu Ser Lys Asp Val Cys Lys Asn Tyr
            355                 360                 365

Ala Glu Ala Lys Asp Val Phe Leu Gly Met Phe Leu Tyr Glu Tyr Ala
            370                 375                 380

Arg Arg His Pro Asp Tyr Ser Val Val Leu Leu Leu Arg Leu Ala Lys
385                 390                 395                 400

Thr Tyr Glu Thr Thr Leu Glu Lys Cys Cys Ala Ala Ala Asp Pro His
                405                 410                 415

Glu Cys Tyr Ala Lys Val Phe Asp Glu Phe Lys Pro Leu Val Glu Glu
            420                 425                 430

Pro Gln Asn Leu Ile Lys Gln Asn Cys Glu Leu Phe Glu Gln Leu Gly
            435                 440                 445

Glu Tyr Lys Phe Gln Asn Ala Leu Leu Val Arg Tyr Thr Lys Lys Val
            450                 455                 460

Pro Gln Val Ser Thr Pro Thr Leu Val Glu Val Ser Arg Asn Leu Gly
465                 470                 475                 480

Lys Val Gly Ser Lys Cys Cys Lys His Pro Glu Ala Lys Arg Met Pro
                485                 490                 495

Cys Ala Glu Asp Tyr Leu Ser Val Val Leu Asn Gln Leu Cys Val Leu
            500                 505                 510

His Glu Lys Thr Pro Val Ser Asp Arg Val Thr Lys Cys Cys Thr Glu
            515                 520                 525

Ser Leu Val Asn Arg Arg Pro Cys Phe Ser Ala Leu Glu Val Asp Glu
530                 535                 540
```

```
Thr Tyr Val Pro Lys Glu Phe Asn Ala Glu Thr Phe Thr Phe His Ala
545                 550                 555                 560

Asp Ile Cys Thr Leu Ser Glu Lys Glu Arg Gln Ile Lys Lys Gln Thr
            565                 570                 575

Ala Leu Val Glu Leu Val Lys His Lys Pro Lys Ala Thr Lys Glu Gln
        580                 585                 590

Leu Lys Ala Val Met Asp Asp Phe Ala Ala Phe Val Glu Lys Cys Cys
    595                 600                 605

Lys Ala Asp Asp Lys Glu Thr Cys Phe Ala Glu Glu Gly Lys Lys Leu
610                 615                 620

Val Ala Ala Ser Gln Ala Ala Leu Gly Leu Ala Pro Ala Pro Ala Pro
625                 630                 635                 640

Ala Pro Ala Pro Ala Pro Ala Pro Ala Pro Ala Pro Ala Pro Asp His
            645                 650                 655

Cys Pro Leu Gly Pro Gly Arg Cys Cys Arg Leu His Thr Val Arg Ala
        660                 665                 670

Ser Leu Glu Asp Leu Gly Trp Ala Asp Trp Val Leu Ser Pro Arg Glu
    675                 680                 685

Val Gln Val Thr Met Cys Ile Gly Ala Cys Pro Ser Gln Phe Arg Ala
690                 695                 700

Ala Asn Met His Ala Gln Ile Lys Thr Ser Leu His Arg Leu Lys Pro
705                 710                 715                 720

Asp Thr Val Pro Ala Pro Cys Cys Val Pro Ala Ser Tyr Asn Pro Met
            725                 730                 735

Val Leu Ile Gln Lys Thr Asp Thr Gly Val Ser Leu Gln Thr Tyr Asp
        740                 745                 750

Asp Leu Leu Ala Lys Asp Cys His Cys Ile
    755                 760

<210> SEQ ID NO 45
<211> LENGTH: 763
<212> TYPE: PRT
<213> ORGANISM: Artificial Sequence
<220> FEATURE:
<223> OTHER INFORMATION: GLP1-GDF15 Fusion Protein 13

<400> SEQUENCE: 45

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Pro
            20                  25                  30

Ala Pro Ala Pro Ala Pro Ala Pro Ala Pro Ala Pro Ala Pro Ala Pro
        35                  40                  45

Ala Pro Asp Ala His Lys Ser Glu Val Ala His Arg Phe Lys Asp Leu
    50                  55                  60

Gly Glu Glu Asn Phe Lys Ala Leu Val Leu Ile Ala Phe Ala Gln Tyr
65                  70                  75                  80

Leu Gln Gln Ser Pro Phe Glu Asp His Val Lys Leu Val Asn Glu Val
            85                  90                  95

Thr Glu Phe Ala Lys Thr Cys Val Ala Asp Glu Ser Ala Glu Asn Cys
        100                 105                 110

Asp Lys Ser Leu His Thr Leu Phe Gly Asp Lys Leu Cys Thr Val Ala
    115                 120                 125

Thr Leu Arg Glu Thr Tyr Gly Glu Met Ala Asp Cys Cys Ala Lys Gln
130                 135                 140
```

```
Glu Pro Glu Arg Asn Glu Cys Phe Leu Gln His Lys Asp Asp Asn Pro
145                 150                 155                 160

Asn Leu Pro Arg Leu Val Arg Pro Glu Val Asp Val Met Cys Thr Ala
            165                 170                 175

Phe His Asp Asn Glu Glu Thr Phe Leu Lys Lys Tyr Leu Tyr Glu Ile
            180                 185                 190

Ala Arg Arg His Pro Tyr Phe Tyr Ala Pro Glu Leu Leu Phe Phe Ala
    195                 200                 205

Lys Arg Tyr Lys Ala Ala Phe Thr Glu Cys Cys Gln Ala Ala Asp Lys
    210                 215                 220

Ala Ala Cys Leu Leu Pro Lys Leu Asp Glu Leu Arg Asp Glu Gly Lys
225                 230                 235                 240

Ala Ser Ser Ala Lys Gln Arg Leu Lys Cys Ala Ser Leu Gln Lys Phe
            245                 250                 255

Gly Glu Arg Ala Phe Lys Ala Trp Ala Val Ala Arg Leu Ser Gln Arg
            260                 265                 270

Phe Pro Lys Ala Glu Phe Ala Glu Val Ser Lys Leu Val Thr Asp Leu
    275                 280                 285

Thr Lys Val His Thr Glu Cys Cys His Gly Asp Leu Leu Glu Cys Ala
290                 295                 300

Asp Asp Arg Ala Asp Leu Ala Lys Tyr Ile Cys Glu Asn Gln Asp Ser
305                 310                 315                 320

Ile Ser Ser Lys Leu Lys Glu Cys Cys Glu Lys Pro Leu Leu Glu Lys
            325                 330                 335

Ser His Cys Ile Ala Glu Val Glu Asn Asp Glu Met Pro Ala Asp Leu
            340                 345                 350

Pro Ser Leu Ala Ala Asp Phe Val Glu Ser Lys Asp Val Cys Lys Asn
    355                 360                 365

Tyr Ala Glu Ala Lys Asp Val Phe Leu Gly Met Phe Leu Tyr Glu Tyr
    370                 375                 380

Ala Arg Arg His Pro Asp Tyr Ser Val Val Leu Leu Leu Arg Leu Ala
385                 390                 395                 400

Lys Thr Tyr Glu Thr Thr Leu Glu Lys Cys Cys Ala Ala Ala Asp Pro
            405                 410                 415

His Glu Cys Tyr Ala Lys Val Phe Asp Glu Phe Lys Pro Leu Val Glu
            420                 425                 430

Glu Pro Gln Asn Leu Ile Lys Gln Asn Cys Glu Leu Phe Glu Gln Leu
    435                 440                 445

Gly Glu Tyr Lys Phe Gln Asn Ala Leu Leu Val Arg Tyr Thr Lys Lys
    450                 455                 460

Val Pro Gln Val Ser Thr Pro Thr Leu Val Glu Val Ser Arg Asn Leu
465                 470                 475                 480

Gly Lys Val Gly Ser Lys Cys Cys Lys His Pro Glu Ala Lys Arg Met
            485                 490                 495

Pro Cys Ala Glu Asp Tyr Leu Ser Val Val Leu Asn Gln Leu Cys Val
            500                 505                 510

Leu His Glu Lys Thr Pro Val Ser Asp Arg Val Thr Lys Cys Cys Thr
    515                 520                 525

Glu Ser Leu Val Asn Arg Arg Pro Cys Phe Ser Ala Leu Glu Val Asp
    530                 535                 540

Glu Thr Tyr Val Pro Lys Glu Phe Asn Ala Glu Thr Phe Thr Phe His
545                 550                 555                 560

Ala Asp Ile Cys Thr Leu Ser Glu Lys Glu Arg Gln Ile Lys Lys Gln
```

```
                565                 570                 575
Thr Ala Leu Val Glu Leu Val Lys His Lys Pro Lys Ala Thr Lys Glu
            580                 585                 590

Gln Leu Lys Ala Val Met Asp Asp Phe Ala Ala Phe Val Glu Lys Cys
            595                 600                 605

Cys Lys Ala Asp Asp Lys Glu Thr Cys Phe Ala Glu Glu Gly Lys Lys
            610                 615                 620

Leu Val Ala Ala Ser Gln Ala Ala Leu Gly Leu Ala Pro Ala Pro Ala
625                 630                 635                 640

Pro Ala Pro Ala Pro Ala Pro Ala Pro Ala Pro Ala Pro Ala Pro Asp
                645                 650                 655

His Cys Pro Leu Gly Pro Gly Arg Cys Cys Arg Leu His Thr Val Arg
                660                 665                 670

Ala Ser Leu Glu Asp Leu Gly Trp Ala Asp Trp Val Leu Ser Pro Arg
                675                 680                 685

Glu Val Gln Val Thr Met Cys Ile Gly Ala Cys Pro Ser Gln Phe Arg
            690                 695                 700

Ala Ala Asn Met His Ala Gln Ile Lys Thr Ser Leu His Arg Leu Lys
705                 710                 715                 720

Pro Asp Thr Val Pro Ala Pro Cys Cys Val Pro Ala Ser Tyr Asn Pro
                725                 730                 735

Met Val Leu Ile Gln Lys Thr Asp Thr Gly Val Ser Leu Gln Thr Tyr
                740                 745                 750

Asp Asp Leu Leu Ala Lys Asp Cys His Cys Ile
            755                 760
```

<210> SEQ ID NO 46
<211> LENGTH: 784
<212> TYPE: PRT
<213> ORGANISM: Artificial Sequence
<220> FEATURE:
<223> OTHER INFORMATION: GLP1-GDF15 Fusion Protein 14

<400> SEQUENCE: 46

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Ala Pro Ala Pro Ala Pro
            35                  40                  45

Pro Asp Ala His Lys Ser Glu Val Ala His Arg Phe Lys Asp Leu Gly
    50                  55                  60

Glu Glu Asn Phe Lys Ala Leu Val Leu Ile Ala Phe Ala Gln Tyr Leu
65                  70                  75                  80

Gln Gln Ser Pro Phe Glu Asp His Val Lys Leu Val Asn Glu Val Thr
                85                  90                  95

Glu Phe Ala Lys Thr Cys Val Ala Asp Glu Ser Ala Glu Asn Cys Asp
            100                 105                 110

Lys Ser Leu His Thr Leu Phe Gly Asp Lys Leu Cys Thr Val Ala Thr
            115                 120                 125

Leu Arg Glu Thr Tyr Gly Glu Met Ala Asp Cys Cys Ala Lys Gln Glu
        130                 135                 140

Pro Glu Arg Asn Glu Cys Phe Leu Gln His Lys Asp Asp Asn Pro Asn
145                 150                 155                 160

Leu Pro Arg Leu Val Arg Pro Glu Val Asp Val Met Cys Thr Ala Phe
```

```
              165                 170                 175
His Asp Asn Glu Glu Thr Phe Leu Lys Lys Tyr Leu Tyr Glu Ile Ala
                180                 185                 190

Arg Arg His Pro Tyr Phe Tyr Ala Pro Glu Leu Leu Phe Phe Ala Lys
            195                 200                 205

Arg Tyr Lys Ala Ala Phe Thr Glu Cys Cys Gln Ala Ala Asp Lys Ala
        210                 215                 220

Ala Cys Leu Leu Pro Lys Leu Asp Glu Leu Arg Asp Glu Gly Lys Ala
225                 230                 235                 240

Ser Ser Ala Lys Gln Arg Leu Lys Cys Ala Ser Leu Gln Lys Phe Gly
                245                 250                 255

Glu Arg Ala Phe Lys Ala Trp Ala Val Ala Arg Leu Ser Gln Arg Phe
            260                 265                 270

Pro Lys Ala Glu Phe Ala Glu Val Ser Lys Leu Val Thr Asp Leu Thr
        275                 280                 285

Lys Val His Thr Glu Cys Cys His Gly Asp Leu Leu Glu Cys Ala Asp
    290                 295                 300

Asp Arg Ala Asp Leu Ala Lys Tyr Ile Cys Glu Asn Gln Asp Ser Ile
305                 310                 315                 320

Ser Ser Lys Leu Lys Glu Cys Cys Glu Lys Pro Leu Leu Glu Lys Ser
                325                 330                 335

His Cys Ile Ala Glu Val Glu Asn Asp Glu Met Pro Ala Asp Leu Pro
            340                 345                 350

Ser Leu Ala Ala Asp Phe Val Glu Ser Lys Asp Val Cys Lys Asn Tyr
        355                 360                 365

Ala Glu Ala Lys Asp Val Phe Leu Gly Met Phe Leu Tyr Glu Tyr Ala
    370                 375                 380

Arg Arg His Pro Asp Tyr Ser Val Val Leu Leu Leu Arg Leu Ala Lys
385                 390                 395                 400

Thr Tyr Glu Thr Thr Leu Glu Lys Cys Cys Ala Ala Ala Asp Pro His
                405                 410                 415

Glu Cys Tyr Ala Lys Val Phe Asp Glu Phe Lys Pro Leu Val Glu Glu
            420                 425                 430

Pro Gln Asn Leu Ile Lys Gln Asn Cys Glu Leu Phe Glu Gln Leu Gly
        435                 440                 445

Glu Tyr Lys Phe Gln Asn Ala Leu Leu Val Arg Tyr Thr Lys Lys Val
    450                 455                 460

Pro Gln Val Ser Thr Pro Thr Leu Val Glu Val Ser Arg Asn Leu Gly
465                 470                 475                 480

Lys Val Gly Ser Lys Cys Cys Lys His Pro Glu Ala Lys Arg Met Pro
                485                 490                 495

Cys Ala Glu Asp Tyr Leu Ser Val Val Leu Asn Gln Leu Cys Val Leu
            500                 505                 510

His Glu Lys Thr Pro Val Ser Asp Arg Val Thr Lys Cys Cys Thr Glu
        515                 520                 525

Ser Leu Val Asn Arg Arg Pro Cys Phe Ser Ala Leu Glu Val Asp Glu
    530                 535                 540

Thr Tyr Val Pro Lys Glu Phe Asn Ala Glu Thr Phe Thr Phe His Ala
545                 550                 555                 560

Asp Ile Cys Thr Leu Ser Glu Lys Glu Arg Gln Ile Lys Lys Gln Thr
                565                 570                 575

Ala Leu Val Glu Leu Val Lys His Lys Pro Lys Ala Thr Lys Glu Gln
            580                 585                 590
```

```
Leu Lys Ala Val Met Asp Asp Phe Ala Ala Phe Val Glu Lys Cys Cys
        595                 600                 605

Lys Ala Asp Asp Lys Glu Thr Cys Phe Ala Glu Glu Gly Lys Lys Leu
    610                 615                 620

Val Ala Ala Ser Gln Ala Ala Leu Gly Leu Gly Ala Gly Gly Gly Gly
625                 630                 635                 640

Ala Gly Gly Gly Ala Gly Gly Gly Ala Gly Gly Gly Ala Gly Gly Ala
                645                 650                 655

Gly Gly Gly Gly Ala Gly Gly Gly Ala Gly Gly Gly Ala Gly Gly Gly
                660                 665                 670

Gly Gly Gly Ala Asp His Cys Pro Leu Gly Pro Gly Arg Cys Cys Arg
            675                 680                 685

Leu His Thr Val Arg Ala Ser Leu Glu Asp Leu Gly Trp Ala Asp Trp
        690                 695                 700

Val Leu Ser Pro Arg Glu Val Gln Val Thr Met Cys Ile Gly Ala Cys
705                 710                 715                 720

Pro Ser Gln Phe Arg Ala Ala Asn Met His Ala Gln Ile Lys Thr Ser
                725                 730                 735

Leu His Arg Leu Lys Pro Asp Thr Val Pro Ala Pro Cys Cys Val Pro
                740                 745                 750

Ala Ser Tyr Asn Pro Met Val Leu Ile Gln Lys Thr Asp Thr Gly Val
            755                 760                 765

Ser Leu Gln Thr Tyr Asp Asp Leu Leu Ala Lys Asp Cys His Cys Ile
        770                 775                 780

<210> SEQ ID NO 47
<211> LENGTH: 790
<212> TYPE: PRT
<213> ORGANISM: Artificial Sequence
<220> FEATURE:
<223> OTHER INFORMATION: GLP1-GDF15 Fusion Protein 15

<400> SEQUENCE: 47

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Gly Gly Gly Gly Gly Gly Gly Gly Gly Gly Gly Gly Gly
            35                  40                  45

Gly Gly Gly Gly Gly Gly Asp Ala His Lys Ser Glu Val Ala His
    50                  55                  60

Arg Phe Lys Asp Leu Gly Glu Glu Asn Phe Lys Ala Leu Val Leu Ile
65                  70                  75                  80

Ala Phe Ala Gln Tyr Leu Gln Gln Ser Pro Phe Glu Asp His Val Lys
                85                  90                  95

Leu Val Asn Glu Val Thr Glu Phe Ala Lys Thr Cys Val Ala Asp Glu
                100                 105                 110

Ser Ala Glu Asn Cys Asp Lys Ser Leu His Thr Leu Phe Gly Asp Lys
            115                 120                 125

Leu Cys Thr Val Ala Thr Leu Arg Glu Thr Tyr Gly Glu Met Ala Asp
        130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175
```

```
Val Met Cys Thr Ala Phe His Asp Asn Glu Glu Thr Phe Leu Lys Lys
            180                 185                 190

Tyr Leu Tyr Glu Ile Ala Arg Arg His Pro Tyr Phe Tyr Ala Pro Glu
            195                 200                 205

Leu Leu Phe Phe Ala Lys Arg Tyr Lys Ala Ala Phe Thr Glu Cys Cys
            210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
            245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
            275                 280                 285

Leu Val Thr Asp Leu Thr Lys Val His Thr Glu Cys Cys His Gly Asp
            290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
            325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
            355                 360                 365

Asp Val Cys Lys Asn Tyr Ala Glu Ala Lys Asp Val Phe Leu Gly Met
            370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
            405                 410                 415

Ala Ala Ala Asp Pro His Glu Cys Tyr Ala Lys Val Phe Asp Glu Phe
            420                 425                 430

Lys Pro Leu Val Glu Glu Pro Gln Asn Leu Ile Lys Gln Asn Cys Glu
            435                 440                 445

Leu Phe Glu Gln Leu Gly Glu Tyr Lys Phe Gln Asn Ala Leu Leu Val
            450                 455                 460

Arg Tyr Thr Lys Lys Val Pro Gln Val Ser Thr Pro Thr Leu Val Glu
465                 470                 475                 480

Val Ser Arg Asn Leu Gly Lys Val Gly Ser Lys Cys Cys Lys His Pro
            485                 490                 495

Glu Ala Lys Arg Met Pro Cys Ala Glu Asp Tyr Leu Ser Val Val Leu
            500                 505                 510

Asn Gln Leu Cys Val Leu His Glu Lys Thr Pro Val Ser Asp Arg Val
            515                 520                 525

Thr Lys Cys Cys Thr Glu Ser Leu Val Asn Arg Arg Pro Cys Phe Ser
            530                 535                 540

Ala Leu Glu Val Asp Glu Thr Tyr Val Pro Lys Glu Phe Asn Ala Glu
545                 550                 555                 560

Thr Phe Thr Phe His Ala Asp Ile Cys Thr Leu Ser Glu Lys Glu Arg
            565                 570                 575

Gln Ile Lys Lys Gln Thr Ala Leu Val Glu Leu Val Lys His Lys Pro
            580                 585                 590
```

```
Lys Ala Thr Lys Glu Gln Leu Lys Ala Val Met Asp Asp Phe Ala Ala
            595                 600                 605

Phe Val Glu Lys Cys Cys Lys Ala Asp Asp Lys Glu Thr Cys Phe Ala
610                 615                 620

Glu Glu Gly Lys Lys Leu Val Ala Ala Ser Gln Ala Ala Leu Gly Leu
625                 630                 635                 640

Gly Ala Gly Gly Gly Ala Gly Gly Gly Ala Gly Gly Gly
                645                 650                 655

Ala Gly Gly Gly Ala Gly Gly Gly Ala Gly Gly Gly Ala
            660                 665                 670

Gly Gly Gly Ala Gly Gly Gly Ala Asp His Cys Pro Leu Gly
            675                 680                 685

Pro Gly Arg Cys Cys Arg Leu His Thr Val Arg Ala Ser Leu Glu Asp
690                 695                 700

Leu Gly Trp Ala Asp Trp Val Leu Ser Pro Arg Glu Val Gln Val Thr
705                 710                 715                 720

Met Cys Ile Gly Ala Cys Pro Ser Gln Phe Arg Ala Ala Asn Met His
                725                 730                 735

Ala Gln Ile Lys Thr Ser Leu His Arg Leu Lys Pro Asp Thr Val Pro
            740                 745                 750

Ala Pro Cys Cys Val Pro Ala Ser Tyr Asn Pro Met Val Leu Ile Gln
        755                 760                 765

Lys Thr Asp Thr Gly Val Ser Leu Gln Thr Tyr Asp Asp Leu Leu Ala
        770                 775                 780

Lys Asp Cys His Cys Ile
785                 790

<210> SEQ ID NO 48
<211> LENGTH: 785
<212> TYPE: PRT
<213> ORGANISM: Artificial Sequence
<220> FEATURE:
<223> OTHER INFORMATION: GLP1-GDF15 Fusion Protein 16

<400> SEQUENCE: 48

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Gly Gly Gly Gly Gly Gly Gly Gly Gly
        35                  40                  45

Gly Gly Asp Ala His Lys Ser Glu Val Ala His Arg Phe Lys Asp Leu
    50                  55                  60

Gly Glu Glu Asn Phe Lys Ala Leu Val Leu Ile Ala Phe Ala Gln Tyr
65                  70                  75                  80

Leu Gln Gln Ser Pro Phe Glu Asp His Val Lys Leu Val Asn Glu Val
                85                  90                  95

Thr Glu Phe Ala Lys Thr Cys Val Ala Asp Glu Ser Ala Glu Asn Cys
            100                 105                 110

Asp Lys Ser Leu His Thr Leu Phe Gly Asp Lys Leu Cys Thr Val Ala
        115                 120                 125

Thr Leu Arg Glu Thr Tyr Gly Glu Met Ala Asp Cys Cys Ala Lys Gln
    130                 135                 140

Glu Pro Glu Arg Asn Glu Cys Phe Leu Gln His Lys Asp Asp Asn Pro
145                 150                 155                 160
```

```
Asn Leu Pro Arg Leu Val Arg Pro Glu Val Asp Val Met Cys Thr Ala
            165                 170                 175
Phe His Asp Asn Glu Glu Thr Phe Leu Lys Lys Tyr Leu Tyr Glu Ile
            180                 185                 190
Ala Arg Arg His Pro Tyr Phe Tyr Ala Pro Glu Leu Leu Phe Phe Ala
            195                 200                 205
Lys Arg Tyr Lys Ala Ala Phe Thr Glu Cys Cys Gln Ala Ala Asp Lys
            210                 215                 220
Ala Ala Cys Leu Leu Pro Lys Leu Asp Glu Leu Arg Asp Glu Gly Lys
225                 230                 235                 240
Ala Ser Ser Ala Lys Gln Arg Leu Lys Cys Ala Ser Leu Gln Lys Phe
            245                 250                 255
Gly Glu Arg Ala Phe Lys Ala Trp Ala Val Ala Arg Leu Ser Gln Arg
            260                 265                 270
Phe Pro Lys Ala Glu Phe Ala Glu Val Ser Lys Leu Val Thr Asp Leu
            275                 280                 285
Thr Lys Val His Thr Glu Cys Cys His Gly Asp Leu Leu Glu Cys Ala
            290                 295                 300
Asp Asp Arg Ala Asp Leu Ala Lys Tyr Ile Cys Glu Asn Gln Asp Ser
305                 310                 315                 320
Ile Ser Ser Lys Leu Lys Glu Cys Cys Glu Lys Pro Leu Leu Glu Lys
            325                 330                 335
Ser His Cys Ile Ala Glu Val Glu Asn Asp Glu Met Pro Ala Asp Leu
            340                 345                 350
Pro Ser Leu Ala Ala Asp Phe Val Glu Ser Lys Asp Val Cys Lys Asn
            355                 360                 365
Tyr Ala Glu Ala Lys Asp Val Phe Leu Gly Met Phe Leu Tyr Glu Tyr
            370                 375                 380
Ala Arg Arg His Pro Asp Tyr Ser Val Val Leu Leu Leu Arg Leu Ala
385                 390                 395                 400
Lys Thr Tyr Glu Thr Thr Leu Glu Lys Cys Cys Ala Ala Ala Asp Pro
            405                 410                 415
His Glu Cys Tyr Ala Lys Val Phe Asp Glu Phe Lys Pro Leu Val Glu
            420                 425                 430
Glu Pro Gln Asn Leu Ile Lys Gln Asn Cys Glu Leu Phe Glu Gln Leu
            435                 440                 445
Gly Glu Tyr Lys Phe Gln Asn Ala Leu Leu Val Arg Tyr Thr Lys Lys
            450                 455                 460
Val Pro Gln Val Ser Thr Pro Thr Leu Val Glu Val Ser Arg Asn Leu
465                 470                 475                 480
Gly Lys Val Gly Ser Lys Cys Cys Lys His Pro Glu Ala Lys Arg Met
            485                 490                 495
Pro Cys Ala Glu Asp Tyr Leu Ser Val Val Leu Asn Gln Leu Cys Val
            500                 505                 510
Leu His Glu Lys Thr Pro Val Ser Asp Arg Val Thr Lys Cys Cys Thr
            515                 520                 525
Glu Ser Leu Val Asn Arg Arg Pro Cys Phe Ser Ala Leu Glu Val Asp
            530                 535                 540
Glu Thr Tyr Val Pro Lys Glu Phe Asn Ala Glu Thr Phe Thr Phe His
545                 550                 555                 560
Ala Asp Ile Cys Thr Leu Ser Glu Lys Glu Arg Gln Ile Lys Lys Gln
            565                 570                 575
Thr Ala Leu Val Glu Leu Val Lys His Lys Pro Lys Ala Thr Lys Glu
```

```
                580                 585                 590
Gln Leu Lys Ala Val Met Asp Asp Phe Ala Ala Phe Val Glu Lys Cys
        595                 600                 605
Cys Lys Ala Asp Asp Lys Glu Thr Cys Phe Ala Glu Glu Gly Lys Lys
        610                 615                 620
Leu Val Ala Ala Ser Gln Ala Ala Leu Gly Leu Gly Ala Gly Gly Gly
625                 630                 635                 640
Gly Ala Gly Gly Gly Ala Gly Gly Gly Ala Gly Gly Gly
                645                 650                 655
Ala Gly Gly Gly Ala Gly Gly Gly Ala Gly Gly Gly Ala
        660                 665                 670
Gly Gly Gly Ala Asp His Cys Pro Leu Gly Pro Gly Arg Cys Cys
        675                 680                 685
Arg Leu His Thr Val Arg Ala Ser Leu Glu Asp Leu Gly Trp Ala Asp
        690                 695                 700
Trp Val Leu Ser Pro Arg Glu Val Gln Val Thr Met Cys Ile Gly Ala
705                 710                 715                 720
Cys Pro Ser Gln Phe Arg Ala Ala Asn Met His Ala Gln Ile Lys Thr
                725                 730                 735
Ser Leu His Arg Leu Lys Pro Asp Thr Val Pro Ala Pro Cys Cys Val
                740                 745                 750
Pro Ala Ser Tyr Asn Pro Met Val Leu Ile Gln Lys Thr Asp Thr Gly
                755                 760                 765
Val Ser Leu Gln Thr Tyr Asp Asp Leu Leu Ala Lys Asp Cys His Cys
        770                 775                 780
Ile
785

<210> SEQ ID NO 49
<211> LENGTH: 785
<212> TYPE: PRT
<213> ORGANISM: Artificial Sequence
<220> FEATURE:
<223> OTHER INFORMATION: GLP1-GDF15 Fusion Protein 17

<400> SEQUENCE: 49

His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Gly Gly Gly
                20                  25                  30
Gly Gly Ala Gly Gly Gly Ala Gly Gly Gly Ala Gly Gly Gly
        35                  40                  45
Gly Ala Asp Ala His Lys Ser Glu Val Ala His Arg Phe Lys Asp Leu
        50                  55                  60
Gly Glu Glu Asn Phe Lys Ala Leu Val Leu Ile Ala Phe Ala Gln Tyr
65              70                  75                  80
Leu Gln Gln Ser Pro Phe Glu Asp His Val Lys Leu Val Asn Glu Val
                85                  90                  95
Thr Glu Phe Ala Lys Thr Cys Val Ala Asp Glu Ser Ala Glu Asn Cys
                100                 105                 110
Asp Lys Ser Leu His Thr Leu Phe Gly Asp Lys Leu Cys Thr Val Ala
                115                 120                 125
Thr Leu Arg Glu Thr Tyr Gly Glu Met Ala Asp Cys Cys Ala Lys Gln
        130                 135                 140
Glu Pro Glu Arg Asn Glu Cys Phe Leu Gln His Lys Asp Asp Asn Pro
```

```
            145                 150                 155                 160
Asn Leu Pro Arg Leu Val Arg Pro Glu Val Asp Val Met Cys Thr Ala
                165                 170                 175

Phe His Asp Asn Glu Glu Thr Phe Leu Lys Lys Tyr Leu Tyr Glu Ile
                180                 185                 190

Ala Arg Arg His Pro Tyr Phe Tyr Ala Pro Glu Leu Leu Phe Phe Ala
                195                 200                 205

Lys Arg Tyr Lys Ala Ala Phe Thr Glu Cys Cys Gln Ala Ala Asp Lys
    210                 215                 220

Ala Ala Cys Leu Leu Pro Lys Leu Asp Glu Leu Arg Asp Glu Gly Lys
225                 230                 235                 240

Ala Ser Ser Ala Lys Gln Arg Leu Lys Cys Ala Ser Leu Gln Lys Phe
                245                 250                 255

Gly Glu Arg Ala Phe Lys Ala Trp Ala Val Ala Arg Leu Ser Gln Arg
                260                 265                 270

Phe Pro Lys Ala Glu Phe Ala Glu Val Ser Lys Leu Val Thr Asp Leu
                275                 280                 285

Thr Lys Val His Thr Glu Cys Cys His Gly Asp Leu Leu Glu Cys Ala
                290                 295                 300

Asp Asp Arg Ala Asp Leu Ala Lys Tyr Ile Cys Glu Asn Gln Asp Ser
305                 310                 315                 320

Ile Ser Ser Lys Leu Lys Glu Cys Cys Glu Lys Pro Leu Leu Glu Lys
                325                 330                 335

Ser His Cys Ile Ala Glu Val Glu Asn Asp Glu Met Pro Ala Asp Leu
                340                 345                 350

Pro Ser Leu Ala Ala Asp Phe Val Glu Ser Lys Asp Val Cys Lys Asn
                355                 360                 365

Tyr Ala Glu Ala Lys Asp Val Phe Leu Gly Met Phe Leu Tyr Glu Tyr
                370                 375                 380

Ala Arg Arg His Pro Asp Tyr Ser Val Val Leu Leu Leu Arg Leu Ala
385                 390                 395                 400

Lys Thr Tyr Glu Thr Thr Leu Glu Lys Cys Cys Ala Ala Ala Asp Pro
                405                 410                 415

His Glu Cys Tyr Ala Lys Val Phe Asp Glu Phe Lys Pro Leu Val Glu
                420                 425                 430

Glu Pro Gln Asn Leu Ile Lys Gln Asn Cys Glu Leu Phe Glu Gln Leu
                435                 440                 445

Gly Glu Tyr Lys Phe Gln Asn Ala Leu Leu Val Arg Tyr Thr Lys Lys
                450                 455                 460

Val Pro Gln Val Ser Thr Pro Thr Leu Val Glu Val Ser Arg Asn Leu
465                 470                 475                 480

Gly Lys Val Gly Ser Lys Cys Cys Lys His Pro Glu Ala Lys Arg Met
                485                 490                 495

Pro Cys Ala Glu Asp Tyr Leu Ser Val Val Leu Asn Gln Leu Cys Val
                500                 505                 510

Leu His Glu Lys Thr Pro Val Ser Asp Arg Val Thr Lys Cys Cys Thr
                515                 520                 525

Glu Ser Leu Val Asn Arg Arg Pro Cys Phe Ser Ala Leu Glu Val Asp
                530                 535                 540

Glu Thr Tyr Val Pro Lys Glu Phe Asn Ala Glu Thr Phe Thr Phe His
545                 550                 555                 560

Ala Asp Ile Cys Thr Leu Ser Glu Lys Glu Arg Gln Ile Lys Lys Gln
                565                 570                 575
```

```
Thr Ala Leu Val Glu Leu Val Lys His Lys Pro Lys Ala Thr Lys Glu
            580                 585                 590

Gln Leu Lys Ala Val Met Asp Asp Phe Ala Ala Phe Val Glu Lys Cys
        595                 600                 605

Cys Lys Ala Asp Asp Lys Glu Thr Cys Phe Ala Glu Glu Gly Lys Lys
    610                 615                 620

Leu Val Ala Ala Ser Gln Ala Ala Leu Gly Leu Gly Ala Gly Gly Gly
625                 630                 635                 640

Gly Ala Gly Gly Gly Ala Gly Gly Gly Ala Gly Gly Gly Gly
            645                 650                 655

Ala Gly Gly Gly Ala Gly Gly Gly Ala Gly Gly Gly Ala
            660                 665                 670

Gly Gly Gly Gly Ala Asp His Cys Pro Leu Gly Pro Gly Arg Cys Cys
            675                 680                 685

Arg Leu His Thr Val Arg Ala Ser Leu Glu Asp Leu Gly Trp Ala Asp
            690                 695                 700

Trp Val Leu Ser Pro Arg Glu Val Gln Val Thr Met Cys Ile Gly Ala
705                 710                 715                 720

Cys Pro Ser Gln Phe Arg Ala Ala Asn Met His Ala Gln Ile Lys Thr
                725                 730                 735

Ser Leu His Arg Leu Lys Pro Asp Thr Val Pro Ala Pro Cys Cys Val
            740                 745                 750

Pro Ala Ser Tyr Asn Pro Met Val Leu Ile Gln Lys Thr Asp Thr Gly
                755                 760                 765

Val Ser Leu Gln Thr Tyr Asp Asp Leu Leu Ala Lys Asp Cys His Cys
    770                 775                 780

Ile
785

<210> SEQ ID NO 50
<211> LENGTH: 790
<212> TYPE: PRT
<213> ORGANISM: Artificial Sequence
<220> FEATURE:
<223> OTHER INFORMATION: GLP1-GDF15 Fusion Protein 18

<400> SEQUENCE: 50

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ala Gly Gly Gly Ala Gly Gly Gly Ala Gly Gly Gly
        35                  40                  45

Gly Ala Gly Gly Gly Ala Asp Ala His Lys Ser Glu Val Ala His
    50                  55                  60

Arg Phe Lys Asp Leu Gly Glu Glu Asn Phe Lys Ala Leu Val Leu Ile
65                  70                  75                  80

Ala Phe Ala Gln Tyr Leu Gln Gln Ser Pro Phe Glu Asp His Val Lys
                85                  90                  95

Leu Val Asn Glu Val Thr Glu Phe Ala Lys Thr Cys Val Ala Asp Glu
            100                 105                 110

Ser Ala Glu Asn Cys Asp Lys Ser Leu His Thr Leu Phe Gly Asp Lys
        115                 120                 125

Leu Cys Thr Val Ala Thr Leu Arg Glu Thr Tyr Gly Glu Met Ala Asp
    130                 135                 140
```

```
Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
            180                 185                 190

Tyr Leu Tyr Glu Ile Ala Arg Arg His Pro Tyr Phe Tyr Ala Pro Glu
        195                 200                 205

Leu Leu Phe Phe Ala Lys Arg Tyr Lys Ala Ala Phe Thr Glu Cys Cys
    210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
                260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
    290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
                340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
    370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
                405                 410                 415

Ala Ala Ala Asp Pro His Glu Cys Tyr Ala Lys Val Phe Asp Glu Phe
                420                 425                 430

Lys Pro Leu Val Glu Glu Pro Gln Asn Leu Ile Lys Gln Asn Cys Glu
        435                 440                 445

Leu Phe Glu Gln Leu Gly Glu Tyr Lys Phe Gln Asn Ala Leu Leu Val
    450                 455                 460

Arg Tyr Thr Lys Lys Val Pro Gln Val Ser Thr Pro Thr Leu Val Glu
465                 470                 475                 480

Val Ser Arg Asn Leu Gly Lys Val Gly Ser Lys Cys Cys Lys His Pro
                485                 490                 495

Glu Ala Lys Arg Met Pro Cys Ala Glu Asp Tyr Leu Ser Val Val Leu
                500                 505                 510

Asn Gln Leu Cys Val Leu His Glu Lys Thr Pro Val Ser Asp Arg Val
        515                 520                 525

Thr Lys Cys Cys Thr Glu Ser Leu Val Asn Arg Arg Pro Cys Phe Ser
    530                 535                 540

Ala Leu Glu Val Asp Glu Thr Tyr Val Pro Lys Glu Phe Asn Ala Glu
545                 550                 555                 560
```

Thr Phe Thr Phe His Ala Asp Ile Cys Thr Leu Ser Glu Lys Glu Arg
                565                 570                 575

Gln Ile Lys Lys Gln Thr Ala Leu Val Glu Leu Val Lys His Lys Pro
            580                 585                 590

Lys Ala Thr Lys Glu Gln Leu Lys Ala Val Met Asp Asp Phe Ala Ala
            595                 600                 605

Phe Val Glu Lys Cys Cys Lys Ala Asp Asp Lys Glu Thr Cys Phe Ala
        610                 615                 620

Glu Glu Gly Lys Lys Leu Val Ala Ala Ser Gln Ala Ala Leu Gly Leu
625                 630                 635                 640

Gly Ala Gly Gly Gly Gly Ala Gly Gly Gly Ala Gly Gly Gly Gly
            645                 650                 655

Ala Gly Gly Gly Ala Gly Gly Gly Ala Gly Gly Gly Ala
            660                 665                 670

Gly Gly Gly Ala Gly Gly Gly Ala Asp His Cys Pro Leu Gly
        675                 680                 685

Pro Gly Arg Cys Cys Arg Leu His Thr Val Arg Ala Ser Leu Glu Asp
        690                 695                 700

Leu Gly Trp Ala Asp Trp Val Leu Ser Pro Arg Glu Val Gln Val Thr
705                 710                 715                 720

Met Cys Ile Gly Ala Cys Pro Ser Gln Phe Arg Ala Ala Asn Met His
            725                 730                 735

Ala Gln Ile Lys Thr Ser Leu His Arg Leu Lys Pro Asp Thr Val Pro
            740                 745                 750

Ala Pro Cys Cys Val Pro Ala Ser Tyr Asn Pro Met Val Leu Ile Gln
        755                 760                 765

Lys Thr Asp Thr Gly Val Ser Leu Gln Thr Tyr Asp Asp Leu Leu Ala
770                 775                 780

Lys Asp Cys His Cys Ile
785                 790

<210> SEQ ID NO 51
<211> LENGTH: 807
<212> TYPE: PRT
<213> ORGANISM: Artificial Sequence
<220> FEATURE:
<223> OTHER INFORMATION: GLP1-GDF15 Fusion Protein 19

<400> SEQUENCE: 51

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ala
            20                  25                  30

Gly Gly Gly Gly Ala Gly Gly Gly Gly Ala Gly Gly Gly Gly Ala Gly
        35                  40                  45

Gly Gly Gly Ala Gly Gly Gly Gly Ala Gly Gly Gly Gly Ala Gly Gly
    50                  55                  60

Gly Gly Ala Gly Gly Gly Ala Asp Ala His Lys Ser Glu Val Ala
65                  70                  75                  80

His Arg Phe Lys Asp Leu Gly Glu Glu Asn Phe Lys Ala Leu Val Leu
                85                  90                  95

Ile Ala Phe Ala Gln Tyr Leu Gln Gln Ser Pro Phe Glu Asp His Val
            100                 105                 110

Lys Leu Val Asn Glu Val Thr Glu Phe Ala Lys Thr Cys Val Ala Asp
        115                 120                 125

```
Glu Ser Ala Glu Asn Cys Asp Lys Ser Leu His Thr Leu Phe Gly Asp
        130                 135                 140
Lys Leu Cys Thr Val Ala Thr Leu Arg Glu Thr Tyr Gly Glu Met Ala
145                 150                 155                 160
Asp Cys Cys Ala Lys Gln Glu Pro Glu Arg Asn Glu Cys Phe Leu Gln
                    165                 170                 175
His Lys Asp Asp Asn Pro Asn Leu Pro Arg Leu Val Arg Pro Glu Val
                180                 185                 190
Asp Val Met Cys Thr Ala Phe His Asp Asn Glu Glu Thr Phe Leu Lys
            195                 200                 205
Lys Tyr Leu Tyr Glu Ile Ala Arg Arg His Pro Tyr Phe Tyr Ala Pro
        210                 215                 220
Glu Leu Leu Phe Phe Ala Lys Arg Tyr Lys Ala Ala Phe Thr Glu Cys
225                 230                 235                 240
Cys Gln Ala Ala Asp Lys Ala Ala Cys Leu Leu Pro Lys Leu Asp Glu
                    245                 250                 255
Leu Arg Asp Glu Gly Lys Ala Ser Ser Ala Lys Gln Arg Leu Lys Cys
                260                 265                 270
Ala Ser Leu Gln Lys Phe Gly Glu Arg Ala Phe Lys Ala Trp Ala Val
            275                 280                 285
Ala Arg Leu Ser Gln Arg Phe Pro Lys Ala Glu Phe Ala Glu Val Ser
        290                 295                 300
Lys Leu Val Thr Asp Leu Thr Lys Val His Thr Glu Cys Cys His Gly
305                 310                 315                 320
Asp Leu Leu Glu Cys Ala Asp Asp Arg Ala Asp Leu Ala Lys Tyr Ile
                    325                 330                 335
Cys Glu Asn Gln Asp Ser Ile Ser Ser Lys Leu Lys Glu Cys Cys Glu
                340                 345                 350
Lys Pro Leu Leu Glu Lys Ser His Cys Ile Ala Glu Val Glu Asn Asp
            355                 360                 365
Glu Met Pro Ala Asp Leu Pro Ser Leu Ala Ala Asp Phe Val Glu Ser
        370                 375                 380
Lys Asp Val Cys Lys Asn Tyr Ala Glu Ala Lys Asp Val Phe Leu Gly
385                 390                 395                 400
Met Phe Leu Tyr Glu Tyr Ala Arg Arg His Pro Asp Tyr Ser Val Val
                    405                 410                 415
Leu Leu Leu Arg Leu Ala Lys Thr Tyr Glu Thr Thr Leu Glu Lys Cys
                420                 425                 430
Cys Ala Ala Ala Asp Pro His Glu Cys Tyr Ala Lys Val Phe Asp Glu
            435                 440                 445
Phe Lys Pro Leu Val Glu Glu Pro Gln Asn Leu Ile Lys Gln Asn Cys
        450                 455                 460
Glu Leu Phe Glu Gln Leu Gly Glu Tyr Lys Phe Gln Asn Ala Leu Leu
465                 470                 475                 480
Val Arg Tyr Thr Lys Lys Val Pro Gln Val Ser Thr Pro Thr Leu Val
                    485                 490                 495
Glu Val Ser Arg Asn Leu Gly Lys Val Gly Ser Lys Cys Cys Lys His
                500                 505                 510
Pro Glu Ala Lys Arg Met Pro Cys Ala Glu Asp Tyr Leu Ser Val Val
            515                 520                 525
Leu Asn Gln Leu Cys Val Leu His Glu Lys Thr Pro Val Ser Asp Arg
        530                 535                 540
Val Thr Lys Cys Cys Thr Glu Ser Leu Val Asn Arg Arg Pro Cys Phe
```

```
                    545                 550                 555                 560

Ser Ala Leu Glu Val Asp Glu Thr Tyr Val Pro Lys Glu Phe Asn Ala
                565                 570                 575

Glu Thr Phe Thr Phe His Ala Asp Ile Cys Thr Leu Ser Glu Lys Glu
                580                 585                 590

Arg Gln Ile Lys Lys Gln Thr Ala Leu Val Glu Leu Val Lys His Lys
                595                 600                 605

Pro Lys Ala Thr Lys Glu Gln Leu Lys Ala Val Met Asp Asp Phe Ala
                610                 615                 620

Ala Phe Val Glu Lys Cys Cys Lys Ala Asp Asp Lys Glu Thr Cys Phe
625                 630                 635                 640

Ala Glu Glu Gly Lys Lys Leu Val Ala Ala Ser Gln Ala Ala Leu Gly
                645                 650                 655

Leu Gly Ser Gly Gly Gly Gly Ser Gly Gly Gly Gly Ser Gly Gly Gly
                660                 665                 670

Gly Ser Gly Gly Gly Gly Ser Gly Gly Gly Gly Ser Gly Gly Gly Gly
                675                 680                 685

Ser Gly Gly Gly Gly Ser Gly Gly Gly Ser Asp His Cys Pro Leu
                690                 695                 700

Gly Pro Gly Arg Cys Cys Arg Leu His Thr Val Arg Ala Ser Leu Glu
705                 710                 715                 720

Asp Leu Gly Trp Ala Asp Trp Val Leu Ser Pro Arg Glu Val Gln Val
                725                 730                 735

Thr Met Cys Ile Gly Ala Cys Pro Ser Gln Phe Arg Ala Ala Asn Met
                740                 745                 750

His Ala Gln Ile Lys Thr Ser Leu His Arg Leu Lys Pro Asp Thr Val
                755                 760                 765

Pro Ala Pro Cys Cys Val Pro Ala Ser Tyr Asn Pro Met Val Leu Ile
                770                 775                 780

Gln Lys Thr Asp Thr Gly Val Ser Leu Gln Thr Tyr Asp Asp Leu Leu
785                 790                 795                 800

Ala Lys Asp Cys His Cys Ile
                805

<210> SEQ ID NO 52
<211> LENGTH: 786
<212> TYPE: PRT
<213> ORGANISM: Artificial Sequence
<220> FEATURE:
<223> OTHER INFORMATION: GLP1-GDF15 Fusion Protein 20

<400> SEQUENCE: 52

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Ala Gly Gly Gly Ala Gly Gly
                35                  40                  45

Gly Gly Ala Asp Ala His Lys Ser Glu Val Ala His Arg Phe Lys Asp
            50                  55                  60

Leu Gly Glu Glu Asn Phe Lys Ala Leu Val Leu Ile Ala Phe Ala Gln
65                  70                  75                  80

Tyr Leu Gln Gln Ser Pro Phe Glu Asp His Val Lys Leu Val Asn Glu
                85                  90                  95

Val Thr Glu Phe Ala Lys Thr Cys Val Ala Asp Glu Ser Ala Glu Asn
```

```
            100                 105                 110
Cys Asp Lys Ser Leu His Thr Leu Phe Gly Asp Lys Leu Cys Thr Val
            115                 120                 125
Ala Thr Leu Arg Glu Thr Tyr Gly Glu Met Ala Asp Cys Cys Ala Lys
            130                 135             140
Gln Glu Pro Glu Arg Asn Glu Cys Phe Leu Gln His Lys Asp Asp Asn
145                 150                 155                 160
Pro Asn Leu Pro Arg Leu Val Arg Pro Glu Val Asp Val Met Cys Thr
                165                 170                 175
Ala Phe His Asp Asn Glu Glu Thr Phe Leu Lys Lys Tyr Leu Tyr Glu
            180                 185                 190
Ile Ala Arg Arg His Pro Tyr Phe Tyr Ala Pro Glu Leu Leu Phe Phe
            195                 200             205
Ala Lys Arg Tyr Lys Ala Ala Phe Thr Glu Cys Cys Gln Ala Ala Asp
            210                 215             220
Lys Ala Ala Cys Leu Leu Pro Lys Leu Asp Glu Leu Arg Asp Glu Gly
225                 230                 235                 240
Lys Ala Ser Ser Ala Lys Gln Arg Leu Lys Cys Ala Ser Leu Gln Lys
                245                 250                 255
Phe Gly Glu Arg Ala Phe Lys Ala Trp Ala Val Ala Arg Leu Ser Gln
            260                 265                 270
Arg Phe Pro Lys Ala Glu Phe Ala Glu Val Ser Lys Leu Val Thr Asp
            275                 280                 285
Leu Thr Lys Val His Thr Glu Cys Cys His Gly Asp Leu Leu Glu Cys
            290                 295             300
Ala Asp Asp Arg Ala Asp Leu Ala Lys Tyr Ile Cys Glu Asn Gln Asp
305                 310                 315                 320
Ser Ile Ser Ser Lys Leu Lys Glu Cys Cys Glu Lys Pro Leu Leu Glu
                325                 330                 335
Lys Ser His Cys Ile Ala Glu Val Glu Asn Asp Glu Met Pro Ala Asp
            340                 345                 350
Leu Pro Ser Leu Ala Ala Asp Phe Val Glu Ser Lys Asp Val Cys Lys
            355                 360             365
Asn Tyr Ala Glu Ala Lys Asp Val Phe Leu Gly Met Phe Leu Tyr Glu
            370                 375             380
Tyr Ala Arg Arg His Pro Asp Tyr Ser Val Val Leu Leu Leu Arg Leu
385                 390                 395                 400
Ala Lys Thr Tyr Glu Thr Thr Leu Glu Lys Cys Cys Ala Ala Ala Asp
                405                 410                 415
Pro His Glu Cys Tyr Ala Lys Val Phe Asp Glu Phe Lys Pro Leu Val
            420                 425                 430
Glu Glu Pro Gln Asn Leu Ile Lys Gln Asn Cys Glu Leu Phe Glu Gln
            435                 440             445
Leu Gly Glu Tyr Lys Phe Gln Asn Ala Leu Leu Val Arg Tyr Thr Lys
            450                 455             460
Lys Val Pro Gln Val Ser Thr Pro Thr Leu Val Glu Val Ser Arg Asn
465                 470                 475                 480
Leu Gly Lys Val Gly Ser Lys Cys Cys Lys His Pro Glu Ala Lys Arg
                485                 490                 495
Met Pro Cys Ala Glu Asp Tyr Leu Ser Val Val Leu Asn Gln Leu Cys
            500                 505                 510
Val Leu His Glu Lys Thr Pro Val Ser Asp Arg Val Thr Lys Cys Cys
            515                 520                 525
```

```
Thr Glu Ser Leu Val Asn Arg Arg Pro Cys Phe Ser Ala Leu Glu Val
        530                 535                 540

Asp Glu Thr Tyr Val Pro Lys Glu Phe Asn Ala Glu Thr Phe Thr Phe
545                 550                 555                 560

His Ala Asp Ile Cys Thr Leu Ser Glu Lys Glu Arg Gln Ile Lys Lys
                565                 570                 575

Gln Thr Ala Leu Val Glu Leu Val Lys His Lys Pro Lys Ala Thr Lys
            580                 585                 590

Glu Gln Leu Lys Ala Val Met Asp Asp Phe Ala Ala Phe Val Glu Lys
        595                 600                 605

Cys Cys Lys Ala Asp Asp Lys Glu Thr Cys Phe Ala Glu Glu Gly Lys
    610                 615                 620

Lys Leu Val Ala Ala Ser Gln Ala Ala Leu Gly Leu Ser Gly Gly
625                 630                 635                 640

Gly Gly Ser Gly Gly Gly Ser Gly Gly Gly Ser Gly Gly Gly
                645                 650                 655

Gly Ser Gly Gly Gly Ser Gly Gly Gly Ser Gly Gly Gly Gly
            660                 665                 670

Ser Gly Gly Gly Ser Asp His Cys Pro Leu Gly Pro Gly Arg Cys
        675                 680                 685

Cys Arg Leu His Thr Val Arg Ala Ser Leu Glu Asp Leu Gly Trp Ala
    690                 695                 700

Asp Trp Val Leu Ser Pro Arg Glu Val Gln Val Thr Met Cys Ile Gly
705                 710                 715                 720

Ala Cys Pro Ser Gln Phe Arg Ala Ala Asn Met His Ala Gln Ile Lys
                725                 730                 735

Thr Ser Leu His Arg Leu Lys Pro Asp Thr Val Pro Ala Pro Cys Cys
            740                 745                 750

Val Pro Ala Ser Tyr Asn Pro Met Val Leu Ile Gln Lys Thr Asp Thr
        755                 760                 765

Gly Val Ser Leu Gln Thr Tyr Asp Asp Leu Leu Ala Lys Asp Cys His
    770                 775                 780

Cys Ile
785
```

<210> SEQ ID NO 53
<211> LENGTH: 795
<212> TYPE: PRT
<213> ORGANISM: Artificial Sequence
<220> FEATURE:
<223> OTHER INFORMATION: GLP1-GDF15 Fusion Protein 21

<400> SEQUENCE: 53

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ala Gly Gly Gly Ala Gly Gly Gly Ala Gly Gly Gly
        35                  40                  45

Gly Ala Gly Gly Gly Gly Ala Gly Gly Gly Ala Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Ser Pro Phe
                85                  90                  95
```

-continued

```
Glu Asp His Val Lys Leu Val Asn Glu Val Thr Glu Phe Ala Lys Thr
            100                 105                 110
Cys Val Ala Asp Glu Ser Ala Glu Asn Cys Asp Lys Ser Leu His Thr
            115                 120                 125
Leu Phe Gly Asp Lys Leu Cys Thr Val Ala Thr Leu Arg Glu Thr Tyr
        130                 135                 140
Gly Glu Met Ala Asp Cys Cys Ala Lys Gln Glu Pro Glu Arg Asn Glu
145                 150                 155                 160
Cys Phe Leu Gln His Lys Asp Asp Asn Pro Asn Leu Pro Arg Leu Val
                165                 170                 175
Arg Pro Glu Val Asp Val Met Cys Thr Ala Phe His Asp Asn Glu Glu
            180                 185                 190
Thr Phe Leu Lys Lys Tyr Leu Tyr Glu Ile Ala Arg Arg His Pro Tyr
        195                 200                 205
Phe Tyr Ala Pro Glu Leu Leu Phe Phe Ala Lys Arg Tyr Lys Ala Ala
    210                 215                 220
Phe Thr Glu Cys Cys Gln Ala Ala Asp Lys Ala Ala Cys Leu Leu Pro
225                 230                 235                 240
Lys Leu Asp Glu Leu Arg Asp Glu Gly Lys Ala Ser Ser Ala Lys Gln
                245                 250                 255
Arg Leu Lys Cys Ala Ser Leu Gln Lys Phe Gly Glu Arg Ala Phe Lys
            260                 265                 270
Ala Trp Ala Val Ala Arg Leu Ser Gln Arg Phe Pro Lys Ala Glu Phe
        275                 280                 285
Ala Glu Val Ser Lys Leu Val Thr Asp Leu Thr Lys Val His Thr Glu
    290                 295                 300
Cys Cys His Gly Asp Leu Leu Glu Cys Ala Asp Asp Arg Ala Asp Leu
305                 310                 315                 320
Ala Lys Tyr Ile Cys Glu Asn Gln Asp Ser Ile Ser Ser Lys Leu Lys
                325                 330                 335
Glu Cys Cys Glu Lys Pro Leu Leu Glu Lys Ser His Cys Ile Ala Glu
            340                 345                 350
Val Glu Asn Asp Glu Met Pro Ala Asp Leu Pro Ser Leu Ala Ala Asp
        355                 360                 365
Phe Val Glu Ser Lys Asp Val Cys Lys Asn Tyr Ala Glu Ala Lys Asp
    370                 375                 380
Val Phe Leu Gly Met Phe Leu Tyr Glu Tyr Ala Arg Arg His Pro Asp
385                 390                 395                 400
Tyr Ser Val Val Leu Leu Leu Arg Leu Ala Lys Thr Tyr Glu Thr Thr
                405                 410                 415
Leu Glu Lys Cys Cys Ala Ala Ala Asp Pro His Glu Cys Tyr Ala Lys
            420                 425                 430
Val Phe Asp Glu Phe Lys Pro Leu Val Glu Glu Pro Gln Asn Leu Ile
        435                 440                 445
Lys Gln Asn Cys Glu Leu Phe Glu Gln Leu Gly Glu Tyr Lys Phe Gln
    450                 455                 460
Asn Ala Leu Leu Val Arg Tyr Thr Lys Lys Val Pro Gln Val Ser Thr
465                 470                 475                 480
Pro Thr Leu Val Glu Val Ser Arg Asn Leu Gly Lys Val Gly Ser Lys
                485                 490                 495
Cys Cys Lys His Pro Glu Ala Lys Arg Met Pro Cys Ala Glu Asp Tyr
            500                 505                 510
```

Leu Ser Val Val Leu Asn Gln Leu Cys Val Leu His Glu Lys Thr Pro
            515                 520                 525

Val Ser Asp Arg Val Thr Lys Cys Cys Thr Glu Ser Leu Val Asn Arg
        530                 535                 540

Arg Pro Cys Phe Ser Ala Leu Glu Val Asp Glu Thr Tyr Val Pro Lys
545                 550                 555                 560

Glu Phe Asn Ala Glu Thr Phe Thr Phe His Ala Asp Ile Cys Thr Leu
                565                 570                 575

Ser Glu Lys Glu Arg Gln Ile Lys Lys Gln Thr Ala Leu Val Glu Leu
            580                 585                 590

Val Lys His Lys Pro Lys Ala Thr Lys Glu Gln Leu Lys Ala Val Met
        595                 600                 605

Asp Asp Phe Ala Ala Phe Val Glu Lys Cys Cys Lys Ala Asp Asp Lys
610                 615                 620

Glu Thr Cys Phe Ala Glu Glu Gly Lys Lys Leu Val Ala Ala Ser Gln
625                 630                 635                 640

Ala Ala Leu Gly Leu Gly Ser Gly Gly Gly Ser Gly Gly Gly Gly
                645                 650                 655

Ser Gly Gly Gly Gly Ser Gly Gly Gly Ser Gly Gly Gly Ser
            660                 665                 670

Gly Gly Gly Gly Ser Gly Gly Gly Ser Gly Gly Gly Gly Ser Asp
        675                 680                 685

His Cys Pro Leu Gly Pro Gly Arg Cys Cys Arg Leu His Thr Val Arg
            690                 695                 700

Ala Ser Leu Glu Asp Leu Gly Trp Ala Asp Trp Val Leu Ser Pro Arg
705                 710                 715                 720

Glu Val Gln Val Thr Met Cys Ile Gly Ala Cys Pro Ser Gln Phe Arg
                725                 730                 735

Ala Ala Asn Met His Ala Gln Ile Lys Thr Ser Leu His Arg Leu Lys
            740                 745                 750

Pro Asp Thr Val Pro Ala Pro Cys Cys Val Pro Ala Ser Tyr Asn Pro
        755                 760                 765

Met Val Leu Ile Gln Lys Thr Asp Thr Gly Val Ser Leu Gln Thr Tyr
770                 775                 780

Asp Asp Leu Leu Ala Lys Asp Cys His Cys Ile
785                 790                 795

<210> SEQ ID NO 54
<211> LENGTH: 790
<212> TYPE: PRT
<213> ORGANISM: Artificial Sequence
<220> FEATURE:
<223> OTHER INFORMATION: GLP1-GDF15 Fusion Protein 22

<400> SEQUENCE: 54

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ala Gly Gly Gly Gly Ala Gly Gly Gly Gly Ala Gly Gly Gly
        35                  40                  45

Gly Ala Gly Gly Gly Gly Ala Asp Ala His Lys Ser Glu Val Ala His
    50                  55                  60

Arg Phe Lys Asp Leu Gly Glu Glu Asn Phe Lys Ala Leu Val Leu Ile
65                  70                  75                  80

-continued

```
Ala Phe Ala Gln Tyr Leu Gln Gln Ser Pro Phe Glu Asp His Val Lys
                85                  90                  95

Leu Val Asn Glu Val Thr Glu Phe Ala Lys Thr Cys Val Ala Asp Glu
            100                 105                 110

Ser Ala Glu Asn Cys Asp Lys Ser Leu His Thr Leu Phe Gly Asp Lys
        115                 120                 125

Leu Cys Thr Val Ala Thr Leu Arg Glu Thr Tyr Gly Glu Met Ala Asp
    130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
            180                 185                 190

Tyr Leu Tyr Glu Ile Ala Arg Arg His Pro Tyr Phe Tyr Ala Pro Glu
        195                 200                 205

Leu Leu Phe Phe Ala Lys Arg Tyr Lys Ala Ala Phe Thr Glu Cys Cys
    210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
    290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
    370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
                405                 410                 415

Ala Ala Ala Asp Pro His Glu Cys Tyr Ala Lys Val Phe Asp Glu Phe
            420                 425                 430

Lys Pro Leu Val Glu Glu Pro Gln Asn Leu Ile Lys Gln Asn Cys Glu
        435                 440                 445

Leu Phe Glu Gln Leu Gly Glu Tyr Lys Phe Gln Asn Ala Leu Leu Val
    450                 455                 460

Arg Tyr Thr Lys Lys Val Pro Gln Val Ser Thr Pro Thr Leu Val Glu
465                 470                 475                 480

Val Ser Arg Asn Leu Gly Lys Val Gly Ser Lys Cys Cys Lys His Pro
                485                 490                 495

Glu Ala Lys Arg Met Pro Cys Ala Glu Asp Tyr Leu Ser Val Val Leu
```

-continued

```
                500                 505                 510
Asn Gln Leu Cys Val Leu His Glu Lys Thr Pro Val Ser Asp Arg Val
            515                 520                 525

Thr Lys Cys Cys Thr Glu Ser Leu Val Asn Arg Arg Pro Cys Phe Ser
        530                 535                 540

Ala Leu Glu Val Asp Glu Thr Tyr Val Pro Lys Glu Phe Asn Ala Glu
545                 550                 555                 560

Thr Phe Thr Phe His Ala Asp Ile Cys Thr Leu Ser Glu Lys Glu Arg
                565                 570                 575

Gln Ile Lys Lys Gln Thr Ala Leu Val Glu Leu Val Lys His Lys Pro
            580                 585                 590

Lys Ala Thr Lys Glu Gln Leu Lys Ala Val Met Asp Asp Phe Ala Ala
        595                 600                 605

Phe Val Glu Lys Cys Cys Lys Ala Asp Asp Lys Glu Thr Cys Phe Ala
610                 615                 620

Glu Glu Gly Lys Lys Leu Val Ala Ala Ser Gln Ala Ala Leu Gly Leu
625                 630                 635                 640

Gly Ser Gly Gly Gly Gly Ser Gly Gly Gly Gly Ser Gly Gly Gly Gly
            645                 650                 655

Ser Gly Gly Gly Gly Ser Gly Gly Gly Gly Ser Gly Gly Gly Gly Ser
        660                 665                 670

Gly Gly Gly Gly Ser Gly Gly Gly Ser Asp His Cys Pro Leu Gly
            675                 680                 685

Pro Gly Arg Cys Cys Arg Leu His Thr Val Arg Ala Ser Leu Glu Asp
        690                 695                 700

Leu Gly Trp Ala Asp Trp Val Leu Ser Pro Arg Glu Val Gln Val Thr
705                 710                 715                 720

Met Cys Ile Gly Ala Cys Pro Ser Gln Phe Arg Ala Ala Asn Met His
                725                 730                 735

Ala Gln Ile Lys Thr Ser Leu His Arg Leu Lys Pro Asp Thr Val Pro
            740                 745                 750

Ala Pro Cys Cys Val Pro Ala Ser Tyr Asn Pro Met Val Leu Ile Gln
        755                 760                 765

Lys Thr Asp Thr Gly Val Ser Leu Gln Thr Tyr Asp Asp Leu Leu Ala
        770                 775                 780

Lys Asp Cys His Cys Ile
785                 790

<210> SEQ ID NO 55
<211> LENGTH: 795
<212> TYPE: PRT
<213> ORGANISM: Artificial Sequence
<220> FEATURE:
<223> OTHER INFORMATION: GLP1-GDF15 Fusion Protein 23

<400> SEQUENCE: 55

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Asp Ala His Lys
    50                  55                  60

Ser Glu Val Ala His Arg Phe Lys Asp Leu Gly Glu Glu Asn Phe Lys
```

```
                65                  70                  75                  80
Ala Leu Val Leu Ile Ala Phe Ala Gln Tyr Leu Gln Gln Ser Pro Phe
                        85                  90                  95

Glu Asp His Val Lys Leu Val Asn Glu Val Thr Glu Phe Ala Lys Thr
                        100                 105                 110

Cys Val Ala Asp Glu Ser Ala Glu Asn Cys Asp Lys Ser Leu His Thr
                        115                 120                 125

Leu Phe Gly Asp Lys Leu Cys Thr Val Ala Thr Leu Arg Glu Thr Tyr
            130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                    165                 170                 175

Arg Pro Glu Val Asp Val Met Cys Thr Ala Phe His Asp Asn Glu Glu
                180                 185                 190

Thr Phe Leu Lys Lys Tyr Leu Tyr Glu Ile Ala Arg Arg His Pro Tyr
                195                 200                 205

Phe Tyr Ala Pro Glu Leu Leu Phe Phe Ala Lys Arg Tyr Lys Ala Ala
            210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                    245                 250                 255

Arg Leu Lys Cys Ala Ser Leu Gln Lys Phe Gly Glu Arg Ala Phe Lys
                260                 265                 270

Ala Trp Ala Val Ala Arg Leu Ser Gln Arg Phe Pro Lys Ala Glu Phe
            275                 280                 285

Ala Glu Val Ser Lys Leu Val Thr Asp Leu Thr Lys Val His Thr Glu
290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
                340                 345                 350

Val Glu Asn Asp Glu Met Pro Ala Asp Leu Pro Ser Leu Ala Ala Asp
            355                 360                 365

Phe Val Glu Ser Lys Asp Val Cys Lys Asn Tyr Ala Glu Ala Lys Asp
370                 375                 380

Val Phe Leu Gly Met Phe Leu Tyr Glu Tyr Ala Arg Arg His Pro Asp
385                 390                 395                 400

Tyr Ser Val Val Leu Leu Leu Arg Leu Ala Lys Thr Tyr Glu Thr Thr
                405                 410                 415

Leu Glu Lys Cys Cys Ala Ala Ala Asp Pro His Glu Cys Tyr Ala Lys
                420                 425                 430

Val Phe Asp Glu Phe Lys Pro Leu Val Glu Glu Pro Gln Asn Leu Ile
            435                 440                 445

Lys Gln Asn Cys Glu Leu Phe Glu Gln Leu Gly Glu Tyr Lys Phe Gln
            450                 455                 460

Asn Ala Leu Leu Val Arg Tyr Thr Lys Lys Val Pro Gln Val Ser Thr
465                 470                 475                 480

Pro Thr Leu Val Glu Val Ser Arg Asn Leu Gly Lys Val Gly Ser Lys
                485                 490                 495
```

```
Cys Cys Lys His Pro Glu Ala Lys Arg Met Pro Cys Ala Glu Asp Tyr
            500                 505                 510

Leu Ser Val Val Leu Asn Gln Leu Cys Val Leu His Glu Lys Thr Pro
            515                 520                 525

Val Ser Asp Arg Val Thr Lys Cys Cys Thr Glu Ser Leu Val Asn Arg
            530                 535                 540

Arg Pro Cys Phe Ser Ala Leu Glu Val Asp Glu Thr Tyr Val Pro Lys
545                 550                 555                 560

Glu Phe Asn Ala Glu Thr Phe Thr Phe His Ala Asp Ile Cys Thr Leu
            565                 570                 575

Ser Glu Lys Glu Arg Gln Ile Lys Lys Gln Thr Ala Leu Val Glu Leu
            580                 585                 590

Val Lys His Lys Pro Lys Ala Thr Lys Glu Gln Leu Lys Ala Val Met
            595                 600                 605

Asp Asp Phe Ala Ala Phe Val Glu Lys Cys Cys Lys Ala Asp Asp Lys
            610                 615                 620

Glu Thr Cys Phe Ala Glu Glu Gly Lys Lys Leu Val Ala Ala Ser Gln
625                 630                 635                 640

Ala Ala Leu Gly Leu Gly Ser Gly Gly Gly Ser Gly Gly Gly Gly
            645                 650                 655

Ser Gly Gly Gly Gly Ser Gly Gly Gly Gly Ser Gly Gly Gly Ser
            660                 665                 670

Gly Gly Gly Gly Ser Gly Gly Gly Gly Ser Gly Gly Gly Gly Ser Asp
            675                 680                 685

His Cys Pro Leu Gly Pro Gly Arg Cys Cys Arg Leu His Thr Val Arg
            690                 695                 700

Ala Ser Leu Glu Asp Leu Gly Trp Ala Asp Trp Val Leu Ser Pro Arg
705                 710                 715                 720

Glu Val Gln Val Thr Met Cys Ile Gly Ala Cys Pro Ser Gln Phe Arg
            725                 730                 735

Ala Ala Asn Met His Ala Gln Ile Lys Thr Ser Leu His Arg Leu Lys
            740                 745                 750

Pro Asp Thr Val Pro Ala Pro Cys Cys Val Pro Ala Ser Tyr Asn Pro
            755                 760                 765

Met Val Leu Ile Gln Lys Thr Asp Thr Gly Val Ser Leu Gln Thr Tyr
            770                 775                 780

Asp Asp Leu Leu Ala Lys Asp Cys His Cys Ile
785                 790                 795

<210> SEQ ID NO 56
<211> LENGTH: 790
<212> TYPE: PRT
<213> ORGANISM: Artificial Sequence
<220> FEATURE:
<223> OTHER INFORMATION: GLP1-GDF15 Fusion Protein 24

<400> SEQUENCE: 56

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Gly Ser Gly Gly Gly Ser Gly Gly Gly
            35                  40                  45

Gly Ser Gly Gly Gly Gly Ser Asp Ala His Lys Ser Glu Val Ala His
            50                  55                  60
```

```
Arg Phe Lys Asp Leu Gly Glu Glu Asn Phe Lys Ala Leu Val Leu Ile
 65                  70                  75                  80

Ala Phe Ala Gln Tyr Leu Gln Gln Ser Pro Phe Glu Asp His Val Lys
                 85                  90                  95

Leu Val Asn Glu Val Thr Glu Phe Ala Lys Thr Cys Val Ala Asp Glu
            100                 105                 110

Ser Ala Glu Asn Cys Asp Lys Ser Leu His Thr Leu Phe Gly Asp Lys
            115                 120                 125

Leu Cys Thr Val Ala Thr Leu Arg Glu Thr Tyr Gly Glu Met Ala Asp
        130                 135                 140

Cys Cys Ala Lys Gln Glu Pro Glu Arg Asn Glu Cys Phe Leu Gln His
145                 150                 155                 160

Lys Asp Asp Asn Pro Asn Leu Pro Arg Leu Val Arg Pro Glu Val Asp
                165                 170                 175

Val Met Cys Thr Ala Phe His Asp Asn Glu Glu Thr Phe Leu Lys Lys
            180                 185                 190

Tyr Leu Tyr Glu Ile Ala Arg Arg His Pro Tyr Phe Tyr Ala Pro Glu
        195                 200                 205

Leu Leu Phe Phe Ala Lys Arg Tyr Lys Ala Ala Phe Thr Glu Cys Cys
210                 215                 220

Gln Ala Ala Asp Lys Ala Ala Cys Leu Leu Pro Lys Leu Asp Glu Leu
225                 230                 235                 240

Arg Asp Glu Gly Lys Ala Ser Ser Ala Lys Gln Arg Leu Lys Cys Ala
                245                 250                 255

Ser Leu Gln Lys Phe Gly Glu Arg Ala Phe Lys Ala Trp Ala Val Ala
            260                 265                 270

Arg Leu Ser Gln Arg Phe Pro Lys Ala Glu Phe Ala Glu Val Ser Lys
        275                 280                 285

Leu Val Thr Asp Leu Thr Lys Val His Thr Glu Cys Cys His Gly Asp
290                 295                 300

Leu Leu Glu Cys Ala Asp Asp Arg Ala Asp Leu Ala Lys Tyr Ile Cys
305                 310                 315                 320

Glu Asn Gln Asp Ser Ile Ser Ser Lys Leu Lys Glu Cys Cys Glu Lys
                325                 330                 335

Pro Leu Leu Glu Lys Ser His Cys Ile Ala Glu Val Glu Asn Asp Glu
            340                 345                 350

Met Pro Ala Asp Leu Pro Ser Leu Ala Ala Asp Phe Val Glu Ser Lys
        355                 360                 365

Asp Val Cys Lys Asn Tyr Ala Glu Ala Lys Asp Val Phe Leu Gly Met
        370                 375                 380

Phe Leu Tyr Glu Tyr Ala Arg Arg His Pro Asp Tyr Ser Val Val Leu
385                 390                 395                 400

Leu Leu Arg Leu Ala Lys Thr Tyr Glu Thr Thr Leu Glu Lys Cys Cys
                405                 410                 415

Ala Ala Ala Asp Pro His Glu Cys Tyr Ala Lys Val Phe Asp Glu Phe
            420                 425                 430

Lys Pro Leu Val Glu Glu Pro Gln Asn Leu Ile Lys Gln Asn Cys Glu
        435                 440                 445

Leu Phe Glu Gln Leu Gly Glu Tyr Lys Phe Gln Asn Ala Leu Leu Val
        450                 455                 460

Arg Tyr Thr Lys Lys Val Pro Gln Val Ser Thr Pro Thr Leu Val Glu
465                 470                 475                 480
```

Val Ser Arg Asn Leu Gly Lys Val Gly Ser Lys Cys Cys Lys His Pro
            485                 490                 495

Glu Ala Lys Arg Met Pro Cys Ala Glu Asp Tyr Leu Ser Val Val Leu
            500                 505                 510

Asn Gln Leu Cys Val Leu His Glu Lys Thr Pro Val Ser Asp Arg Val
            515                 520                 525

Thr Lys Cys Cys Thr Glu Ser Leu Val Asn Arg Arg Pro Cys Phe Ser
            530                 535                 540

Ala Leu Glu Val Asp Glu Thr Tyr Val Pro Lys Glu Phe Asn Ala Glu
545                 550                 555                 560

Thr Phe Thr Phe His Ala Asp Ile Cys Thr Leu Ser Glu Lys Glu Arg
            565                 570                 575

Gln Ile Lys Lys Gln Thr Ala Leu Val Glu Leu Val Lys His Lys Pro
            580                 585                 590

Lys Ala Thr Lys Glu Gln Leu Lys Ala Val Met Asp Asp Phe Ala Ala
            595                 600                 605

Phe Val Glu Lys Cys Cys Lys Ala Asp Asp Lys Glu Thr Cys Phe Ala
            610                 615                 620

Glu Glu Gly Lys Lys Leu Val Ala Ala Ser Gln Ala Ala Leu Gly Leu
625                 630                 635                 640

Gly Ser Gly Gly Gly Gly Ser Gly Gly Gly Gly Ser Gly Gly Gly Gly
            645                 650                 655

Ser Gly Gly Gly Gly Ser Gly Gly Gly Gly Ser Gly Gly Gly Gly Ser
            660                 665                 670

Gly Gly Gly Gly Ser Gly Gly Gly Ser Asp His Cys Pro Leu Gly
            675                 680                 685

Pro Gly Arg Cys Cys Arg Leu His Thr Val Arg Ala Ser Leu Glu Asp
690                 695                 700

Leu Gly Trp Ala Asp Trp Val Leu Ser Pro Arg Glu Val Gln Val Thr
705                 710                 715                 720

Met Cys Ile Gly Ala Cys Pro Ser Gln Phe Arg Ala Ala Asn Met His
            725                 730                 735

Ala Gln Ile Lys Thr Ser Leu His Arg Leu Lys Pro Asp Thr Val Pro
            740                 745                 750

Ala Pro Cys Cys Val Pro Ala Ser Tyr Asn Pro Met Val Leu Ile Gln
            755                 760                 765

Lys Thr Asp Thr Gly Val Ser Leu Gln Thr Tyr Asp Asp Leu Leu Ala
            770                 775                 780

Lys Asp Cys His Cys Ile
785                 790

<210> SEQ ID NO 57
<211> LENGTH: 789
<212> TYPE: PRT
<213> ORGANISM: Artificial Sequence
<220> FEATURE:
<223> OTHER INFORMATION: GLP1-GDF15 Fusion Protein 25

<400> SEQUENCE: 57

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Ser
                20                  25                  30

Ala Pro Ala Pro Ala Pro Ala Pro Ala Pro Ala Pro Ala Pro Ala Pro
            35                  40                  45

Ala Pro Ala Pro Gly Ser Asp Ala His Lys Ser Glu Val Ala His Arg
 50                  55                  60

Phe Lys Asp Leu Gly Glu Glu Asn Phe Lys Ala Leu Val Leu Ile Ala
 65                  70                  75                  80

Phe Ala Gln Tyr Leu Gln Gln Ser Pro Phe Glu Asp His Val Lys Leu
                 85                  90                  95

Val Asn Glu Val Thr Glu Phe Ala Lys Thr Cys Val Ala Asp Glu Ser
                100                 105                 110

Ala Glu Asn Cys Asp Lys Ser Leu His Thr Leu Phe Gly Asp Lys Leu
            115                 120                 125

Cys Thr Val Ala Thr Leu Arg Glu Thr Tyr Gly Glu Met Ala Asp Cys
130                 135                 140

Cys Ala Lys Gln Glu Pro Glu Arg Asn Glu Cys Phe Leu Gln His Lys
145                 150                 155                 160

Asp Asp Asn Pro Asn Leu Pro Arg Leu Val Arg Pro Glu Val Asp Val
                165                 170                 175

Met Cys Thr Ala Phe His Asp Asn Glu Glu Thr Phe Leu Lys Lys Tyr
            180                 185                 190

Leu Tyr Glu Ile Ala Arg Arg His Pro Tyr Phe Tyr Ala Pro Glu Leu
            195                 200                 205

Leu Phe Phe Ala Lys Arg Tyr Lys Ala Ala Phe Thr Glu Cys Cys Gln
210                 215                 220

Ala Ala Asp Lys Ala Ala Cys Leu Leu Pro Lys Leu Asp Glu Leu Arg
225                 230                 235                 240

Asp Glu Gly Lys Ala Ser Ser Ala Lys Gln Arg Leu Lys Cys Ala Ser
                245                 250                 255

Leu Gln Lys Phe Gly Glu Arg Ala Phe Lys Ala Trp Ala Val Ala Arg
            260                 265                 270

Leu Ser Gln Arg Phe Pro Lys Ala Glu Phe Ala Glu Val Ser Lys Leu
            275                 280                 285

Val Thr Asp Leu Thr Lys Val His Thr Glu Cys Cys His Gly Asp Leu
290                 295                 300

Leu Glu Cys Ala Asp Asp Arg Ala Asp Leu Ala Lys Tyr Ile Cys Glu
305                 310                 315                 320

Asn Gln Asp Ser Ile Ser Ser Lys Leu Lys Glu Cys Cys Glu Lys Pro
                325                 330                 335

Leu Leu Glu Lys Ser His Cys Ile Ala Glu Val Glu Asn Asp Glu Met
            340                 345                 350

Pro Ala Asp Leu Pro Ser Leu Ala Ala Asp Phe Val Glu Ser Lys Asp
            355                 360                 365

Val Cys Lys Asn Tyr Ala Glu Ala Lys Asp Val Phe Leu Gly Met Phe
370                 375                 380

Leu Tyr Glu Tyr Ala Arg Arg His Pro Asp Tyr Ser Val Val Leu Leu
385                 390                 395                 400

Leu Arg Leu Ala Lys Thr Tyr Glu Thr Thr Leu Glu Lys Cys Cys Ala
                405                 410                 415

Ala Ala Asp Pro His Glu Cys Tyr Ala Lys Val Phe Asp Glu Phe Lys
            420                 425                 430

Pro Leu Val Glu Glu Pro Gln Asn Leu Ile Lys Gln Asn Cys Glu Leu
            435                 440                 445

Phe Glu Gln Leu Gly Glu Tyr Lys Phe Gln Asn Ala Leu Leu Val Arg
450                 455                 460

Tyr Thr Lys Lys Val Pro Gln Val Ser Thr Pro Thr Leu Val Glu Val

```
            465                 470                 475                 480
Ser Arg Asn Leu Gly Lys Val Gly Ser Lys Cys Cys Lys His Pro Glu
                485                 490                 495

Ala Lys Arg Met Pro Cys Ala Glu Asp Tyr Leu Ser Val Val Leu Asn
                500                 505                 510

Gln Leu Cys Val Leu His Glu Lys Thr Pro Val Ser Asp Arg Val Thr
                515                 520                 525

Lys Cys Cys Thr Glu Ser Leu Val Asn Arg Arg Pro Cys Phe Ser Ala
                530                 535                 540

Leu Glu Val Asp Glu Thr Tyr Val Pro Lys Glu Phe Asn Ala Glu Thr
545                 550                 555                 560

Phe Thr Phe His Ala Asp Ile Cys Thr Leu Ser Glu Lys Glu Arg Gln
                565                 570                 575

Ile Lys Lys Gln Thr Ala Leu Val Glu Leu Val Lys His Lys Pro Lys
                580                 585                 590

Ala Thr Lys Glu Gln Leu Lys Ala Val Met Asp Asp Phe Ala Ala Phe
                595                 600                 605

Val Glu Lys Cys Cys Lys Ala Asp Asp Lys Glu Thr Cys Phe Ala Glu
                610                 615                 620

Glu Gly Lys Lys Leu Val Ala Ala Ser Gln Ala Ala Leu Gly Leu Gly
625                 630                 635                 640

Ser Gly Gly Gly Ser Gly Gly Gly Ser Gly Gly Gly Gly Gly Gly Ser
                645                 650                 655

Gly Gly Gly Gly Ser Gly Gly Gly Ser Gly Gly Gly Gly Gly Gly Ser Gly
                660                 665                 670

Gly Gly Ser Gly Gly Gly Ser Asp His Cys Pro Leu Gly Pro
                675                 680                 685

Gly Arg Cys Cys Arg Leu His Thr Val Arg Ala Ser Leu Glu Asp Leu
                690                 695                 700

Gly Trp Ala Asp Trp Val Leu Ser Pro Arg Glu Val Gln Val Thr Met
705                 710                 715                 720

Cys Ile Gly Ala Cys Pro Ser Gln Phe Arg Ala Ala Asn Met His Ala
                725                 730                 735

Gln Ile Lys Thr Ser Leu His Arg Leu Lys Pro Asp Thr Val Pro Ala
                740                 745                 750

Pro Cys Cys Val Pro Ala Ser Tyr Asn Pro Met Val Leu Ile Gln Lys
                755                 760                 765

Thr Asp Thr Gly Val Ser Leu Gln Thr Tyr Asp Asp Leu Leu Ala Lys
770                 775                 780

Asp Cys His Cys Ile
785

<210> SEQ ID NO 58
<211> LENGTH: 807
<212> TYPE: PRT
<213> ORGANISM: Artificial Sequence
<220> FEATURE:
<223> OTHER INFORMATION: GLP1-GDF15 Fusion Protein 26

<400> SEQUENCE: 58

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Ser
                20                  25                  30

Gly Gly Gly Gly Ser Gly Gly Gly Ser Gly Gly Gly Gly Ser Gly
```

-continued

```
                35                  40                  45
Gly Gly Gly Ser Gly Gly Gly Ser Gly Gly Gly Ser Gly Gly
 50                  55                  60
Gly Gly Ser Gly Gly Gly Ser Asp Ala His Lys Ser Glu Val Ala
 65                  70                  75                  80
His Arg Phe Lys Asp Leu Gly Glu Glu Asn Phe Lys Ala Leu Val Leu
                 85                  90                  95
Ile Ala Phe Ala Gln Tyr Leu Gln Gln Ser Pro Phe Glu Asp His Val
                100                 105                 110
Lys Leu Val Asn Glu Val Thr Glu Phe Ala Lys Thr Cys Val Ala Asp
                115                 120                 125
Glu Ser Ala Glu Asn Cys Asp Lys Ser Leu His Thr Leu Phe Gly Asp
            130                 135                 140
Lys Leu Cys Thr Val Ala Thr Leu Arg Glu Thr Tyr Gly Glu Met Ala
145                 150                 155                 160
Asp Cys Cys Ala Lys Gln Glu Pro Glu Arg Asn Glu Cys Phe Leu Gln
                165                 170                 175
His Lys Asp Asp Asn Pro Asn Leu Pro Arg Leu Val Arg Pro Glu Val
            180                 185                 190
Asp Val Met Cys Thr Ala Phe His Asp Asn Glu Glu Thr Phe Leu Lys
        195                 200                 205
Lys Tyr Leu Tyr Glu Ile Ala Arg Arg His Pro Tyr Phe Tyr Ala Pro
    210                 215                 220
Glu Leu Leu Phe Phe Ala Lys Arg Tyr Lys Ala Ala Phe Thr Glu Cys
225                 230                 235                 240
Cys Gln Ala Ala Asp Lys Ala Ala Cys Leu Leu Pro Lys Leu Asp Glu
                245                 250                 255
Leu Arg Asp Glu Gly Lys Ala Ser Ser Ala Lys Gln Arg Leu Lys Cys
            260                 265                 270
Ala Ser Leu Gln Lys Phe Gly Glu Arg Ala Phe Lys Ala Trp Ala Val
        275                 280                 285
Ala Arg Leu Ser Gln Arg Phe Pro Lys Ala Glu Phe Ala Glu Val Ser
    290                 295                 300
Lys Leu Val Thr Asp Leu Thr Lys Val His Thr Glu Cys Cys His Gly
305                 310                 315                 320
Asp Leu Leu Glu Cys Ala Asp Asp Arg Ala Asp Leu Ala Lys Tyr Ile
                325                 330                 335
Cys Glu Asn Gln Asp Ser Ile Ser Ser Lys Leu Lys Glu Cys Cys Glu
            340                 345                 350
Lys Pro Leu Leu Glu Lys Ser His Cys Ile Ala Glu Val Glu Asn Asp
        355                 360                 365
Glu Met Pro Ala Asp Leu Pro Ser Leu Ala Ala Asp Phe Val Glu Ser
    370                 375                 380
Lys Asp Val Cys Lys Asn Tyr Ala Glu Ala Lys Asp Val Phe Leu Gly
385                 390                 395                 400
Met Phe Leu Tyr Glu Tyr Ala Arg Arg His Pro Asp Tyr Ser Val Val
                405                 410                 415
Leu Leu Leu Arg Leu Ala Lys Thr Tyr Glu Thr Thr Leu Glu Lys Cys
            420                 425                 430
Cys Ala Ala Ala Asp Pro His Glu Cys Tyr Ala Lys Val Phe Asp Glu
        435                 440                 445
Phe Lys Pro Leu Val Glu Glu Pro Gln Asn Leu Ile Lys Gln Asn Cys
    450                 455                 460
```

| | | | | | | | | | | | | | | |
|---|---|---|---|---|---|---|---|---|---|---|---|---|---|---|
| Glu | Leu | Phe | Glu | Gln | Leu | Gly | Glu | Tyr | Lys | Phe | Gln | Asn | Ala | Leu | Leu |
| 465 | | | | 470 | | | | 475 | | | | 480 | | | |

Val Arg Tyr Thr Lys Val Pro Gln Val Ser Pro Thr Leu Val
485 490 495

Glu Val Ser Arg Asn Leu Gly Lys Val Gly Ser Lys Cys Cys Lys His
500 505 510

Pro Glu Ala Lys Arg Met Pro Cys Ala Glu Asp Tyr Leu Ser Val Val
515 520 525

Leu Asn Gln Leu Cys Val Leu His Glu Lys Thr Pro Val Ser Asp Arg
530 535 540

Val Thr Lys Cys Cys Thr Glu Ser Leu Val Asn Arg Arg Pro Cys Phe
545 550 555 560

Ser Ala Leu Glu Val Asp Glu Thr Tyr Val Pro Lys Glu Phe Asn Ala
565 570 575

Glu Thr Phe Thr Phe His Ala Asp Ile Cys Thr Leu Ser Glu Lys Glu
580 585 590

Arg Gln Ile Lys Lys Gln Thr Ala Leu Val Glu Leu Val Lys His Lys
595 600 605

Pro Lys Ala Thr Lys Glu Gln Leu Lys Ala Val Met Asp Asp Phe Ala
610 615 620

Ala Phe Val Glu Lys Cys Cys Lys Ala Asp Asp Lys Glu Thr Cys Phe
625 630 635 640

Ala Glu Glu Gly Lys Lys Leu Val Ala Ala Ser Gln Ala Ala Leu Gly
645 650 655

Leu Gly Ser Gly Gly Gly Gly Ser Gly Gly Gly Gly Ser Gly Gly Gly
660 665 670

Gly Ser Gly Gly Gly Gly Ser Gly Gly Gly Ser Gly Gly Gly Gly
675 680 685

Ser Gly Gly Gly Gly Ser Gly Gly Gly Ser Asp His Cys Pro Leu
690 695 700

Gly Pro Gly Arg Cys Cys Arg Leu His Thr Val Arg Ala Ser Leu Glu
705 710 715 720

Asp Leu Gly Trp Ala Asp Trp Val Leu Ser Pro Arg Glu Val Gln Val
725 730 735

Thr Met Cys Ile Gly Ala Cys Pro Ser Gln Phe Arg Ala Ala Asn Met
740 745 750

His Ala Gln Ile Lys Thr Ser Leu His Arg Leu Lys Pro Asp Thr Val
755 760 765

Pro Ala Pro Cys Cys Val Pro Ala Ser Tyr Asn Pro Met Val Leu Ile
770 775 780

Gln Lys Thr Asp Thr Gly Val Ser Leu Gln Thr Tyr Asp Asp Leu Leu
785 790 795 800

Ala Lys Asp Cys His Cys Ile
805

<210> SEQ ID NO 59
<211> LENGTH: 816
<212> TYPE: PRT
<213> ORGANISM: Artificial Sequence
<220> FEATURE:
<223> OTHER INFORMATION: GLP1-GDF15 Fusion Protein 27

<400> SEQUENCE: 59

His Gly Glu Gly Thr Phe Thr Ser Asp Leu Ser Lys Gln Met Glu Glu
1               5                   10                  15

```
Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Gly Gly Gly Ser Gly Gly Gly Ser Gly Gly Gly
50                  55                  60

Gly Ser Gly Gly Gly Ser Gly Gly Gly Ser Gly Gly Gly Gly
65                  70                  75                  80

Ser Asp Ala His Lys Ser Glu Val Ala His Arg Phe Lys Asp Leu Gly
                85                  90                  95

Glu Glu Asn Phe Lys Ala Leu Val Leu Ile Ala Phe Ala Gln Tyr Leu
            100                 105                 110

Gln Gln Ser Pro Phe Glu Asp His Val Lys Leu Val Asn Glu Val Thr
            115                 120                 125

Glu Phe Ala Lys Thr Cys Val Ala Asp Glu Ser Ala Glu Asn Cys Asp
130                 135                 140

Lys Ser Leu His Thr Leu Phe Gly Asp Lys Leu Cys Thr Val Ala Thr
145                 150                 155                 160

Leu Arg Glu Thr Tyr Gly Glu Met Ala Asp Cys Cys Ala Lys Gln Glu
                165                 170                 175

Pro Glu Arg Asn Glu Cys Phe Leu Gln His Lys Asp Asp Asn Pro Asn
            180                 185                 190

Leu Pro Arg Leu Val Arg Pro Glu Val Asp Val Met Cys Thr Ala Phe
            195                 200                 205

His Asp Asn Glu Glu Thr Phe Leu Lys Lys Tyr Leu Tyr Glu Ile Ala
210                 215                 220

Arg Arg His Pro Tyr Phe Tyr Ala Pro Glu Leu Leu Phe Phe Ala Lys
225                 230                 235                 240

Arg Tyr Lys Ala Ala Phe Thr Glu Cys Cys Gln Ala Ala Asp Lys Ala
                245                 250                 255

Ala Cys Leu Leu Pro Lys Leu Asp Glu Leu Arg Asp Glu Gly Lys Ala
            260                 265                 270

Ser Ser Ala Lys Gln Arg Leu Lys Cys Ala Ser Leu Gln Lys Phe Gly
            275                 280                 285

Glu Arg Ala Phe Lys Ala Trp Ala Val Ala Arg Leu Ser Gln Arg Phe
290                 295                 300

Pro Lys Ala Glu Phe Ala Glu Val Ser Lys Leu Val Thr Asp Leu Thr
305                 310                 315                 320

Lys Val His Thr Glu Cys Cys His Gly Asp Leu Leu Glu Cys Ala Asp
                325                 330                 335

Asp Arg Ala Asp Leu Ala Lys Tyr Ile Cys Glu Asn Gln Asp Ser Ile
            340                 345                 350

Ser Ser Lys Leu Lys Glu Cys Cys Glu Lys Pro Leu Leu Glu Lys Ser
            355                 360                 365

His Cys Ile Ala Glu Val Glu Asn Asp Glu Met Pro Ala Asp Leu Pro
370                 375                 380

Ser Leu Ala Ala Asp Phe Val Glu Ser Lys Asp Val Cys Lys Asn Tyr
385                 390                 395                 400

Ala Glu Ala Lys Asp Val Phe Leu Gly Met Phe Leu Tyr Glu Tyr Ala
                405                 410                 415

Arg Arg His Pro Asp Tyr Ser Val Val Leu Leu Leu Arg Leu Ala Lys
            420                 425                 430
```

Thr Tyr Glu Thr Thr Leu Glu Lys Cys Cys Ala Ala Ala Asp Pro His
            435                 440                 445

Glu Cys Tyr Ala Lys Val Phe Asp Glu Phe Lys Pro Leu Val Glu Glu
450                 455                 460

Pro Gln Asn Leu Ile Lys Gln Asn Cys Glu Leu Phe Glu Gln Leu Gly
465                 470                 475                 480

Glu Tyr Lys Phe Gln Asn Ala Leu Leu Val Arg Tyr Thr Lys Lys Val
                485                 490                 495

Pro Gln Val Ser Thr Pro Thr Leu Val Glu Val Ser Arg Asn Leu Gly
            500                 505                 510

Lys Val Gly Ser Lys Cys Cys Lys His Pro Glu Ala Lys Arg Met Pro
        515                 520                 525

Cys Ala Glu Asp Tyr Leu Ser Val Val Leu Asn Gln Leu Cys Val Leu
530                 535                 540

His Glu Lys Thr Pro Val Ser Asp Arg Val Thr Lys Cys Cys Thr Glu
545                 550                 555                 560

Ser Leu Val Asn Arg Arg Pro Cys Phe Ser Ala Leu Glu Val Asp Glu
                565                 570                 575

Thr Tyr Val Pro Lys Glu Phe Asn Ala Glu Thr Phe Thr Phe His Ala
            580                 585                 590

Asp Ile Cys Thr Leu Ser Glu Lys Glu Arg Gln Ile Lys Lys Gln Thr
        595                 600                 605

Ala Leu Val Glu Leu Val Lys His Lys Pro Lys Ala Thr Lys Glu Gln
            610                 615                 620

Leu Lys Ala Val Met Asp Asp Phe Ala Ala Phe Val Glu Lys Cys Cys
625                 630                 635                 640

Lys Ala Asp Asp Lys Glu Thr Cys Phe Ala Glu Glu Gly Lys Lys Leu
                645                 650                 655

Val Ala Ala Ser Gln Ala Ala Leu Gly Leu Gly Ser Gly Gly Gly Gly
            660                 665                 670

Ser Gly Gly Gly Gly Ser Gly Gly Gly Ser Gly Gly Gly Gly Gly Ser
        675                 680                 685

Gly Gly Gly Gly Ser Gly Gly Gly Ser Gly Gly Gly Gly Gly Ser Gly
690                 695                 700

Gly Gly Gly Ser Asp His Cys Pro Leu Gly Pro Gly Arg Cys Cys Arg
705                 710                 715                 720

Leu His Thr Val Arg Ala Ser Leu Glu Asp Leu Gly Trp Ala Asp Trp
                725                 730                 735

Val Leu Ser Pro Arg Glu Val Gln Val Thr Met Cys Ile Gly Ala Cys
            740                 745                 750

Pro Ser Gln Phe Arg Ala Ala Asn Met His Ala Gln Ile Lys Thr Ser
        755                 760                 765

Leu His Arg Leu Lys Pro Asp Thr Val Pro Ala Pro Cys Cys Val Pro
770                 775                 780

Ala Ser Tyr Asn Pro Met Val Leu Ile Gln Lys Thr Asp Thr Gly Val
785                 790                 795                 800

Ser Leu Gln Thr Tyr Asp Asp Leu Leu Ala Lys Asp Cys His Cys Ile
                805                 810                 815

<210> SEQ ID NO 60
<211> LENGTH: 798
<212> TYPE: PRT
<213> ORGANISM: Artificial Sequence
<220> FEATURE:
<223> OTHER INFORMATION: GLP1-GDF15 Fusion Protein 28

```
<400> SEQUENCE: 60

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Ala Pro Ala Pro Ala Pro Ala
        35                  40                  45

Pro Ala Pro Ala Pro Ala Pro Ala Pro Ala Pro Gly Ser Asp
    50                  55                  60

Ala His Lys Ser Glu Val Ala His Arg Phe Lys Asp Leu Gly Glu Glu
65                  70                  75                  80

Asn Phe Lys Ala Leu Val Leu Ile Ala Phe Ala Gln Tyr Leu Gln Gln
                85                  90                  95

Ser Pro Phe Glu Asp His Val Lys Leu Val Asn Glu Val Thr Glu Phe
            100                 105                 110

Ala Lys Thr Cys Val Ala Asp Glu Ser Ala Glu Asn Cys Asp Lys Ser
        115                 120                 125

Leu His Thr Leu Phe Gly Asp Lys Leu Cys Thr Val Ala Thr Leu Arg
    130                 135                 140

Glu Thr Tyr Gly Glu Met Ala Asp Cys Cys Ala Lys Gln Glu Pro Glu
145                 150                 155                 160

Arg Asn Glu Cys Phe Leu Gln His Lys Asp Asp Asn Pro Asn Leu Pro
                165                 170                 175

Arg Leu Val Arg Pro Glu Val Asp Val Met Cys Thr Ala Phe His Asp
            180                 185                 190

Asn Glu Glu Thr Phe Leu Lys Lys Tyr Leu Tyr Glu Ile Ala Arg Arg
        195                 200                 205

His Pro Tyr Phe Tyr Ala Pro Glu Leu Leu Phe Phe Ala Lys Arg Tyr
    210                 215                 220

Lys Ala Ala Phe Thr Glu Cys Cys Gln Ala Ala Asp Lys Ala Ala Cys
225                 230                 235                 240

Leu Leu Pro Lys Leu Asp Glu Leu Arg Asp Glu Gly Lys Ala Ser Ser
                245                 250                 255

Ala Lys Gln Arg Leu Lys Cys Ala Ser Leu Gln Lys Phe Gly Glu Arg
            260                 265                 270

Ala Phe Lys Ala Trp Ala Val Ala Arg Leu Ser Gln Arg Phe Pro Lys
        275                 280                 285

Ala Glu Phe Ala Glu Val Ser Lys Leu Val Thr Asp Leu Thr Lys Val
    290                 295                 300

His Thr Glu Cys Cys His Gly Asp Leu Leu Glu Cys Ala Asp Asp Arg
305                 310                 315                 320

Ala Asp Leu Ala Lys Tyr Ile Cys Glu Asn Gln Asp Ser Ile Ser Ser
                325                 330                 335

Lys Leu Lys Glu Cys Cys Glu Lys Pro Leu Leu Glu Lys Ser His Cys
            340                 345                 350

Ile Ala Glu Val Glu Asn Asp Glu Met Pro Ala Asp Leu Pro Ser Leu
        355                 360                 365

Ala Ala Asp Phe Val Glu Ser Lys Asp Val Cys Lys Asn Tyr Ala Glu
    370                 375                 380

Ala Lys Asp Val Phe Leu Gly Met Phe Leu Tyr Glu Tyr Ala Arg Arg
385                 390                 395                 400

His Pro Asp Tyr Ser Val Val Leu Leu Leu Arg Leu Ala Lys Thr Tyr
```

```
            405                 410                 415
Glu Thr Thr Leu Glu Lys Cys Cys Ala Ala Ala Asp Pro His Glu Cys
            420                 425                 430

Tyr Ala Lys Val Phe Asp Glu Phe Lys Pro Leu Val Glu Glu Pro Gln
            435                 440                 445

Asn Leu Ile Lys Gln Asn Cys Glu Leu Phe Glu Gln Leu Gly Glu Tyr
450                 455                 460

Lys Phe Gln Asn Ala Leu Leu Val Arg Tyr Thr Lys Lys Val Pro Gln
465                 470                 475                 480

Val Ser Thr Pro Thr Leu Val Glu Val Ser Arg Asn Leu Gly Lys Val
            485                 490                 495

Gly Ser Lys Cys Cys Lys His Pro Glu Ala Lys Arg Met Pro Cys Ala
            500                 505                 510

Glu Asp Tyr Leu Ser Val Val Leu Asn Gln Leu Cys Val Leu His Glu
            515                 520                 525

Lys Thr Pro Val Ser Asp Arg Val Thr Lys Cys Cys Thr Glu Ser Leu
530                 535                 540

Val Asn Arg Arg Pro Cys Phe Ser Ala Leu Glu Val Asp Glu Thr Tyr
545                 550                 555                 560

Val Pro Lys Glu Phe Asn Ala Glu Thr Phe Thr Phe His Ala Asp Ile
            565                 570                 575

Cys Thr Leu Ser Glu Lys Glu Arg Gln Ile Lys Lys Gln Thr Ala Leu
            580                 585                 590

Val Glu Leu Val Lys His Lys Pro Lys Ala Thr Lys Glu Gln Leu Lys
            595                 600                 605

Ala Val Met Asp Asp Phe Ala Ala Phe Val Glu Lys Cys Cys Lys Ala
            610                 615                 620

Asp Asp Lys Glu Thr Cys Phe Ala Glu Glu Gly Lys Lys Leu Val Ala
625                 630                 635                 640

Ala Ser Gln Ala Ala Leu Gly Leu Gly Ser Gly Gly Gly Gly Ser Gly
            645                 650                 655

Gly Gly Gly Ser Gly Gly Gly Ser Gly Gly Gly Ser Gly Gly
            660                 665                 670

Gly Gly Ser Gly Gly Gly Ser Gly Gly Gly Ser Gly Gly Gly
            675                 680                 685

Gly Ser Asp His Cys Pro Leu Gly Pro Gly Arg Cys Cys Arg Leu His
            690                 695                 700

Thr Val Arg Ala Ser Leu Glu Asp Leu Gly Trp Ala Asp Trp Val Leu
705                 710                 715                 720

Ser Pro Arg Glu Val Gln Val Thr Met Cys Ile Gly Ala Cys Pro Ser
            725                 730                 735

Gln Phe Arg Ala Ala Asn Met His Ala Gln Ile Lys Thr Ser Leu His
            740                 745                 750

Arg Leu Lys Pro Asp Thr Val Pro Ala Pro Cys Cys Val Pro Ala Ser
            755                 760                 765

Tyr Asn Pro Met Val Leu Ile Gln Lys Thr Asp Thr Gly Val Ser Leu
770                 775                 780

Gln Thr Tyr Asp Asp Leu Leu Ala Lys Asp Cys His Cys Ile
785                 790                 795

<210> SEQ ID NO 61
<211> LENGTH: 789
<212> TYPE: PRT
<213> ORGANISM: Artificial Sequence
```

<220> FEATURE:
<223> OTHER INFORMATION: GLP1-GDF15 Fusion Protein 29

<400> SEQUENCE: 61

```
His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Ala Pro Ala Pro Ala Pro Ala Pro Ala Pro Ala Pro Ala Pro Ala Pro
        35                  40                  45

Ala Pro Ala Pro Gly Ser Asp Ala His Lys Ser Glu Val Ala His Arg
50                  55                  60

Phe Lys Asp Leu Gly Glu Glu Asn Phe Lys Ala Leu Val Leu Ile Ala
65                  70                  75                  80

Phe Ala Gln Tyr Leu Gln Gln Ser Pro Phe Glu Asp His Val Lys Leu
                85                  90                  95

Val Asn Glu Val Thr Glu Phe Ala Lys Thr Cys Val Ala Asp Glu Ser
            100                 105                 110

Ala Glu Asn Cys Asp Lys Ser Leu His Thr Leu Phe Gly Asp Lys Leu
        115                 120                 125

Cys Thr Val Ala Thr Leu Arg Glu Thr Tyr Gly Glu Met Ala Asp Cys
130                 135                 140

Cys Ala Lys Gln Glu Pro Glu Arg Asn Glu Cys Phe Leu Gln His Lys
145                 150                 155                 160

Asp Asp Asn Pro Asn Leu Pro Arg Leu Val Arg Pro Glu Val Asp Val
                165                 170                 175

Met Cys Thr Ala Phe His Asp Asn Glu Glu Thr Phe Leu Lys Lys Tyr
            180                 185                 190

Leu Tyr Glu Ile Ala Arg Arg His Pro Tyr Phe Tyr Ala Pro Glu Leu
        195                 200                 205

Leu Phe Phe Ala Lys Arg Tyr Lys Ala Ala Phe Thr Glu Cys Cys Gln
210                 215                 220

Ala Ala Asp Lys Ala Ala Cys Leu Leu Pro Lys Leu Asp Glu Leu Arg
225                 230                 235                 240

Asp Glu Gly Lys Ala Ser Ser Ala Lys Gln Arg Leu Lys Cys Ala Ser
                245                 250                 255

Leu Gln Lys Phe Gly Glu Arg Ala Phe Lys Ala Trp Ala Val Ala Arg
            260                 265                 270

Leu Ser Gln Arg Phe Pro Lys Ala Glu Phe Ala Glu Val Ser Lys Leu
        275                 280                 285

Val Thr Asp Leu Thr Lys Val His Thr Glu Cys Cys His Gly Asp Leu
290                 295                 300

Leu Glu Cys Ala Asp Asp Arg Ala Asp Leu Ala Lys Tyr Ile Cys Glu
305                 310                 315                 320

Asn Gln Asp Ser Ile Ser Ser Lys Leu Lys Glu Cys Cys Glu Lys Pro
                325                 330                 335

Leu Leu Glu Lys Ser His Cys Ile Ala Glu Val Glu Asn Asp Glu Met
            340                 345                 350

Pro Ala Asp Leu Pro Ser Leu Ala Ala Asp Phe Val Glu Ser Lys Asp
        355                 360                 365

Val Cys Lys Asn Tyr Ala Glu Ala Lys Asp Val Phe Leu Gly Met Phe
370                 375                 380

Leu Tyr Glu Tyr Ala Arg Arg His Pro Asp Tyr Ser Val Val Leu Leu
385                 390                 395                 400
```

Leu Arg Leu Ala Lys Thr Tyr Glu Thr Thr Leu Glu Lys Cys Cys Ala
                405                 410                 415

Ala Ala Asp Pro His Glu Cys Tyr Ala Lys Val Phe Asp Glu Phe Lys
            420                 425                 430

Pro Leu Val Glu Glu Pro Gln Asn Leu Ile Lys Gln Asn Cys Glu Leu
            435                 440                 445

Phe Glu Gln Leu Gly Glu Tyr Lys Phe Gln Asn Ala Leu Leu Val Arg
        450                 455                 460

Tyr Thr Lys Lys Val Pro Gln Val Ser Thr Pro Thr Leu Val Glu Val
465                 470                 475                 480

Ser Arg Asn Leu Gly Lys Val Gly Ser Lys Cys Cys Lys His Pro Glu
                485                 490                 495

Ala Lys Arg Met Pro Cys Ala Glu Asp Tyr Leu Ser Val Val Leu Asn
            500                 505                 510

Gln Leu Cys Val Leu His Glu Lys Thr Pro Val Ser Asp Arg Val Thr
        515                 520                 525

Lys Cys Cys Thr Glu Ser Leu Val Asn Arg Arg Pro Cys Phe Ser Ala
    530                 535                 540

Leu Glu Val Asp Glu Thr Tyr Val Pro Lys Glu Phe Asn Ala Glu Thr
545                 550                 555                 560

Phe Thr Phe His Ala Asp Ile Cys Thr Leu Ser Glu Lys Glu Arg Gln
                565                 570                 575

Ile Lys Lys Gln Thr Ala Leu Val Glu Leu Val Lys His Lys Pro Lys
            580                 585                 590

Ala Thr Lys Glu Gln Leu Lys Ala Val Met Asp Asp Phe Ala Ala Phe
        595                 600                 605

Val Glu Lys Cys Cys Lys Ala Asp Asp Lys Glu Thr Cys Phe Ala Glu
610                 615                 620

Glu Gly Lys Lys Leu Val Ala Ala Ser Gln Ala Ala Leu Gly Leu Gly
625                 630                 635                 640

Ser Gly Gly Gly Gly Ser Gly Gly Gly Ser Gly Gly Gly Gly Ser
                645                 650                 655

Gly Gly Gly Gly Ser Gly Gly Gly Ser Gly Gly Gly Gly Ser Gly
            660                 665                 670

Gly Gly Gly Ser Gly Gly Gly Ser Asp His Cys Pro Leu Gly Pro
        675                 680                 685

Gly Arg Cys Cys Arg Leu His Thr Val Arg Ala Ser Leu Glu Asp Leu
690                 695                 700

Gly Trp Ala Asp Trp Val Leu Ser Pro Arg Glu Val Gln Val Thr Met
705                 710                 715                 720

Cys Ile Gly Ala Cys Pro Ser Gln Phe Arg Ala Ala Asn Met His Ala
                725                 730                 735

Gln Ile Lys Thr Ser Leu His Arg Leu Lys Pro Asp Thr Val Pro Ala
            740                 745                 750

Pro Cys Cys Val Pro Ala Ser Tyr Asn Pro Met Val Leu Ile Gln Lys
        755                 760                 765

Thr Asp Thr Gly Val Ser Leu Gln Thr Tyr Asp Asp Leu Leu Ala Lys
770                 775                 780

Asp Cys His Cys Ile
785

<210> SEQ ID NO 62
<211> LENGTH: 807

```
<212> TYPE: PRT
<213> ORGANISM: Artificial Sequence
<220> FEATURE:
<223> OTHER INFORMATION: GLP1-GDF15 Fusion Protein 30

<400> SEQUENCE: 62
```

| His | Ser | Glu | Gly | Thr | Phe | Thr | Ser | Asp | Val | Ser | Ser | Tyr | Leu | Glu | Gly |
|---|---|---|---|---|---|---|---|---|---|---|---|---|---|---|---|
| 1 | | | | 5 | | | | | 10 | | | | | 15 | |

| Gln | Ala | Ala | Lys | Glu | Phe | Ile | Glu | Trp | Leu | Val | Lys | Gly | Arg | Ala | Ser |
|---|---|---|---|---|---|---|---|---|---|---|---|---|---|---|---|
| | | | 20 | | | | | 25 | | | | | 30 | | |

| Gly | Gly | Gly | Gly | Ser | Gly | Gly | Gly | Ser | Gly | Gly | Gly | Ser | Gly |
|---|---|---|---|---|---|---|---|---|---|---|---|---|---|
| | | 35 | | | | 40 | | | | 45 | | | |

| Gly | Gly | Gly | Ser | Gly | Gly | Gly | Ser | Gly | Gly | Gly | Ser | Gly | Gly |
|---|---|---|---|---|---|---|---|---|---|---|---|---|---|
| | 50 | | | | 55 | | | | 60 | | | | |

| Gly | Gly | Ser | Gly | Gly | Gly | Ser | Asp | Ala | His | Lys | Ser | Glu | Val | Ala |
|---|---|---|---|---|---|---|---|---|---|---|---|---|---|---|
| 65 | | | | 70 | | | | | 75 | | | | | 80 |

| His | Arg | Phe | Lys | Asp | Leu | Gly | Glu | Glu | Asn | Phe | Lys | Ala | Leu | Val | Leu |
|---|---|---|---|---|---|---|---|---|---|---|---|---|---|---|---|
| | | | | 85 | | | | | 90 | | | | | 95 | |

| Ile | Ala | Phe | Ala | Gln | Tyr | Leu | Gln | Gln | Ser | Pro | Phe | Glu | Asp | His | Val |
|---|---|---|---|---|---|---|---|---|---|---|---|---|---|---|---|
| | | | 100 | | | | | 105 | | | | | 110 | | |

| Lys | Leu | Val | Asn | Glu | Val | Thr | Glu | Phe | Ala | Lys | Thr | Cys | Val | Ala | Asp |
|---|---|---|---|---|---|---|---|---|---|---|---|---|---|---|---|
| | | | 115 | | | | | 120 | | | | | 125 | | |

| Glu | Ser | Ala | Glu | Asn | Cys | Asp | Lys | Ser | Leu | His | Thr | Leu | Phe | Gly | Asp |
|---|---|---|---|---|---|---|---|---|---|---|---|---|---|---|---|
| 130 | | | | | 135 | | | | | 140 | | | | | |

| Lys | Leu | Cys | Thr | Val | Ala | Thr | Leu | Arg | Glu | Thr | Tyr | Gly | Glu | Met | Ala |
|---|---|---|---|---|---|---|---|---|---|---|---|---|---|---|---|
| 145 | | | | | 150 | | | | | 155 | | | | | 160 |

| Asp | Cys | Cys | Ala | Lys | Gln | Glu | Pro | Glu | Arg | Asn | Glu | Cys | Phe | Leu | Gln |
|---|---|---|---|---|---|---|---|---|---|---|---|---|---|---|---|
| | | | | 165 | | | | | 170 | | | | | 175 | |

| His | Lys | Asp | Asp | Asn | Pro | Asn | Leu | Pro | Arg | Leu | Val | Arg | Pro | Glu | Val |
|---|---|---|---|---|---|---|---|---|---|---|---|---|---|---|---|
| | | | 180 | | | | | 185 | | | | | 190 | | |

| Asp | Val | Met | Cys | Thr | Ala | Phe | His | Asp | Asn | Glu | Glu | Thr | Phe | Leu | Lys |
|---|---|---|---|---|---|---|---|---|---|---|---|---|---|---|---|
| | | 195 | | | | | 200 | | | | | 205 | | | |

| Lys | Tyr | Leu | Tyr | Glu | Ile | Ala | Arg | Arg | His | Pro | Tyr | Phe | Tyr | Ala | Pro |
|---|---|---|---|---|---|---|---|---|---|---|---|---|---|---|---|
| 210 | | | | | 215 | | | | | 220 | | | | | |

| Glu | Leu | Leu | Phe | Phe | Ala | Lys | Arg | Tyr | Lys | Ala | Ala | Phe | Thr | Glu | Cys |
|---|---|---|---|---|---|---|---|---|---|---|---|---|---|---|---|
| 225 | | | | | 230 | | | | | 235 | | | | | 240 |

| Cys | Gln | Ala | Ala | Asp | Lys | Ala | Ala | Cys | Leu | Leu | Pro | Lys | Leu | Asp | Glu |
|---|---|---|---|---|---|---|---|---|---|---|---|---|---|---|---|
| | | | | 245 | | | | | 250 | | | | | 255 | |

| Leu | Arg | Asp | Glu | Gly | Lys | Ala | Ser | Ser | Ala | Lys | Gln | Arg | Leu | Lys | Cys |
|---|---|---|---|---|---|---|---|---|---|---|---|---|---|---|---|
| | | | 260 | | | | | 265 | | | | | 270 | | |

| Ala | Ser | Leu | Gln | Lys | Phe | Gly | Glu | Arg | Ala | Phe | Lys | Ala | Trp | Ala | Val |
|---|---|---|---|---|---|---|---|---|---|---|---|---|---|---|---|
| | | 275 | | | | | 280 | | | | | 285 | | | |

| Ala | Arg | Leu | Ser | Gln | Arg | Phe | Pro | Lys | Ala | Glu | Phe | Ala | Glu | Val | Ser |
|---|---|---|---|---|---|---|---|---|---|---|---|---|---|---|---|
| | 290 | | | | | 295 | | | | | 300 | | | | |

| Lys | Leu | Val | Thr | Asp | Leu | Thr | Lys | Val | His | Thr | Glu | Cys | Cys | His | Gly |
|---|---|---|---|---|---|---|---|---|---|---|---|---|---|---|---|
| 305 | | | | | 310 | | | | | 315 | | | | | 320 |

| Asp | Leu | Leu | Glu | Cys | Ala | Asp | Asp | Arg | Ala | Asp | Leu | Ala | Lys | Tyr | Ile |
|---|---|---|---|---|---|---|---|---|---|---|---|---|---|---|---|
| | | | | 325 | | | | | 330 | | | | | 335 | |

| Cys | Glu | Asn | Gln | Asp | Ser | Ile | Ser | Ser | Lys | Leu | Lys | Glu | Cys | Cys | Glu |
|---|---|---|---|---|---|---|---|---|---|---|---|---|---|---|---|
| | | | 340 | | | | | 345 | | | | | 350 | | |

| Lys | Pro | Leu | Leu | Glu | Lys | Ser | His | Cys | Ile | Ala | Glu | Val | Glu | Asn | Asp |
|---|---|---|---|---|---|---|---|---|---|---|---|---|---|---|---|
| | | 355 | | | | | 360 | | | | | 365 | | | |

| Glu | Met | Pro | Ala | Asp | Leu | Pro | Ser | Leu | Ala | Ala | Asp | Phe | Val | Glu | Ser |
|---|---|---|---|---|---|---|---|---|---|---|---|---|---|---|---|
| | 370 | | | | | 375 | | | | | 380 | | | | |

```
Lys Asp Val Cys Lys Asn Tyr Ala Glu Ala Lys Asp Val Phe Leu Gly
385                 390                 395                 400

Met Phe Leu Tyr Glu Tyr Ala Arg Arg His Pro Asp Tyr Ser Val Val
            405                 410                 415

Leu Leu Leu Arg Leu Ala Lys Thr Tyr Glu Thr Thr Leu Glu Lys Cys
            420                 425                 430

Cys Ala Ala Ala Asp Pro His Glu Cys Tyr Ala Lys Val Phe Asp Glu
            435                 440                 445

Phe Lys Pro Leu Val Glu Glu Pro Gln Asn Leu Ile Lys Gln Asn Cys
    450                 455                 460

Glu Leu Phe Glu Gln Leu Gly Glu Tyr Lys Phe Gln Asn Ala Leu Leu
465                 470                 475                 480

Val Arg Tyr Thr Lys Lys Val Pro Gln Val Ser Thr Pro Thr Leu Val
            485                 490                 495

Glu Val Ser Arg Asn Leu Gly Lys Val Gly Ser Lys Cys Cys Lys His
            500                 505                 510

Pro Glu Ala Lys Arg Met Pro Cys Ala Glu Asp Tyr Leu Ser Val Val
            515                 520                 525

Leu Asn Gln Leu Cys Val Leu His Glu Lys Thr Pro Val Ser Asp Arg
530                 535                 540

Val Thr Lys Cys Cys Thr Glu Ser Leu Val Asn Arg Arg Pro Cys Phe
545                 550                 555                 560

Ser Ala Leu Glu Val Asp Glu Thr Tyr Val Pro Lys Glu Phe Asn Ala
            565                 570                 575

Glu Thr Phe Thr Phe His Ala Asp Ile Cys Thr Leu Ser Glu Lys Glu
            580                 585                 590

Arg Gln Ile Lys Lys Gln Thr Ala Leu Val Glu Leu Val Lys His Lys
            595                 600                 605

Pro Lys Ala Thr Lys Glu Gln Leu Lys Ala Val Met Asp Asp Phe Ala
610                 615                 620

Ala Phe Val Glu Lys Cys Cys Lys Ala Asp Asp Lys Glu Thr Cys Phe
625                 630                 635                 640

Ala Glu Glu Gly Lys Lys Leu Val Ala Ala Ser Gln Ala Ala Leu Gly
            645                 650                 655

Leu Gly Ser Gly Gly Gly Gly Ser Gly Gly Gly Gly Ser Gly Gly Gly
            660                 665                 670

Gly Ser Gly Gly Gly Gly Ser Gly Gly Gly Gly Ser Gly Gly Gly Gly
            675                 680                 685

Ser Gly Gly Gly Gly Ser Gly Gly Gly Ser Asp His Cys Pro Leu
            690                 695                 700

Gly Pro Gly Arg Cys Cys Arg Leu His Thr Val Arg Ala Ser Leu Glu
705                 710                 715                 720

Asp Leu Gly Trp Ala Asp Trp Val Leu Ser Pro Arg Glu Val Gln Val
            725                 730                 735

Thr Met Cys Ile Gly Ala Cys Pro Ser Gln Phe Arg Ala Ala Asn Met
            740                 745                 750

His Ala Gln Ile Lys Thr Ser Leu His Arg Leu Lys Pro Asp Thr Val
            755                 760                 765

Pro Ala Pro Cys Cys Val Pro Ala Ser Tyr Asn Pro Met Val Leu Ile
            770                 775                 780

Gln Lys Thr Asp Thr Gly Val Ser Leu Gln Thr Tyr Asp Asp Leu Leu
785                 790                 795                 800

Ala Lys Asp Cys His Cys Ile
```

<210> SEQ ID NO 63
<211> LENGTH: 780
<212> TYPE: PRT
<213> ORGANISM: Artificial Sequence
<220> FEATURE:
<223> OTHER INFORMATION: GLP1-GDF15 Fusion Protein 31

<400> SEQUENCE: 63

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Gly Ser Gly Gly Gly Gly Ser Asp Ala His
        35                  40                  45

Lys Ser Glu Val Ala His Arg Phe Lys Asp Leu Gly Glu Glu Asn Phe
    50                  55                  60

Lys Ala Leu Val Leu Ile Ala Phe Ala Gln Tyr Leu Gln Gln Ser Pro
65                  70                  75                  80

Phe Glu Asp His Val Lys Leu Val Asn Glu Val Thr Glu Phe Ala Lys
                85                  90                  95

Thr Cys Val Ala Asp Glu Ser Ala Glu Asn Cys Asp Lys Ser Leu His
            100                 105                 110

Thr Leu Phe Gly Asp Lys Leu Cys Thr Val Ala Thr Leu Arg Glu Thr
        115                 120                 125

Tyr Gly Glu Met Ala Asp Cys Cys Ala Lys Gln Glu Pro Glu Arg Asn
    130                 135                 140

Glu Cys Phe Leu Gln His Lys Asp Asp Asn Pro Asn Leu Pro Arg Leu
145                 150                 155                 160

Val Arg Pro Glu Val Asp Val Met Cys Thr Ala Phe His Asp Asn Glu
                165                 170                 175

Glu Thr Phe Leu Lys Lys Tyr Leu Tyr Glu Ile Ala Arg Arg His Pro
            180                 185                 190

Tyr Phe Tyr Ala Pro Glu Leu Leu Phe Phe Ala Lys Arg Tyr Lys Ala
        195                 200                 205

Ala Phe Thr Glu Cys Cys Gln Ala Ala Asp Lys Ala Ala Cys Leu Leu
    210                 215                 220

Pro Lys Leu Asp Glu Leu Arg Asp Glu Gly Lys Ala Ser Ser Ala Lys
225                 230                 235                 240

Gln Arg Leu Lys Cys Ala Ser Leu Gln Lys Phe Gly Glu Arg Ala Phe
                245                 250                 255

Lys Ala Trp Ala Val Ala Arg Leu Ser Gln Arg Phe Pro Lys Ala Glu
            260                 265                 270

Phe Ala Glu Val Ser Lys Leu Val Thr Asp Leu Thr Lys Val His Thr
        275                 280                 285

Glu Cys Cys His Gly Asp Leu Leu Glu Cys Ala Asp Asp Arg Ala Asp
    290                 295                 300

Leu Ala Lys Tyr Ile Cys Glu Asn Gln Asp Ser Ile Ser Ser Lys Leu
305                 310                 315                 320

Lys Glu Cys Cys Glu Lys Pro Leu Leu Glu Lys Ser His Cys Ile Ala
                325                 330                 335

Glu Val Glu Asn Asp Glu Met Pro Ala Asp Leu Pro Ser Leu Ala Ala
            340                 345                 350

Asp Phe Val Glu Ser Lys Asp Val Cys Lys Asn Tyr Ala Glu Ala Lys
```

```
                355                 360                 365
Asp Val Phe Leu Gly Met Phe Leu Tyr Glu Tyr Ala Arg Arg His Pro
            370                 375                 380
Asp Tyr Ser Val Val Leu Leu Leu Arg Leu Ala Lys Thr Tyr Glu Thr
385                 390                 395                 400
Thr Leu Glu Lys Cys Cys Ala Ala Ala Asp Pro His Glu Cys Tyr Ala
                405                 410                 415
Lys Val Phe Asp Glu Phe Lys Pro Leu Val Glu Glu Pro Gln Asn Leu
            420                 425                 430
Ile Lys Gln Asn Cys Glu Leu Phe Glu Gln Leu Gly Glu Tyr Lys Phe
                435                 440                 445
Gln Asn Ala Leu Leu Val Arg Tyr Thr Lys Lys Val Pro Gln Val Ser
            450                 455                 460
Thr Pro Thr Leu Val Glu Val Ser Arg Asn Leu Gly Lys Val Gly Ser
465                 470                 475                 480
Lys Cys Cys Lys His Pro Glu Ala Lys Arg Met Pro Cys Ala Glu Asp
                485                 490                 495
Tyr Leu Ser Val Val Leu Asn Gln Leu Cys Val Leu His Glu Lys Thr
            500                 505                 510
Pro Val Ser Asp Arg Val Thr Lys Cys Cys Thr Glu Ser Leu Val Asn
            515                 520                 525
Arg Arg Pro Cys Phe Ser Ala Leu Glu Val Asp Glu Thr Tyr Val Pro
            530                 535                 540
Lys Glu Phe Asn Ala Glu Thr Phe Thr Phe His Ala Asp Ile Cys Thr
545                 550                 555                 560
Leu Ser Glu Lys Glu Arg Gln Ile Lys Lys Gln Thr Ala Leu Val Glu
                565                 570                 575
Leu Val Lys His Lys Pro Lys Ala Thr Lys Glu Gln Leu Lys Ala Val
            580                 585                 590
Met Asp Asp Phe Ala Ala Phe Val Glu Lys Cys Cys Lys Ala Asp Asp
            595                 600                 605
Lys Glu Thr Cys Phe Ala Glu Glu Gly Lys Lys Leu Val Ala Ala Ser
            610                 615                 620
Gln Ala Ala Leu Gly Leu Gly Ser Gly Gly Gly Ser Gly Gly Gly
625                 630                 635                 640
Gly Ser Gly Gly Gly Ser Gly Gly Gly Ser Gly Gly Gly Gly
                645                 650                 655
Ser Gly Gly Gly Ser Gly Gly Gly Ser Gly Gly Gly Ser
            660                 665                 670
Asp His Cys Pro Leu Gly Pro Gly Arg Cys Cys Arg Leu His Thr Val
            675                 680                 685
Arg Ala Ser Leu Glu Asp Leu Gly Trp Ala Asp Trp Val Leu Ser Pro
            690                 695                 700
Arg Glu Val Gln Val Thr Met Cys Ile Gly Ala Cys Pro Ser Gln Phe
705                 710                 715                 720
Arg Ala Ala Asn Met His Ala Gln Ile Lys Thr Ser Leu His Arg Leu
                725                 730                 735
Lys Pro Asp Thr Val Pro Ala Pro Cys Cys Val Pro Ala Ser Tyr Asn
            740                 745                 750
Pro Met Val Leu Ile Gln Lys Thr Asp Thr Gly Val Ser Leu Gln Thr
            755                 760                 765
Tyr Asp Asp Leu Leu Ala Lys Asp Cys His Cys Ile
            770                 775                 780
```

<210> SEQ ID NO 64
<211> LENGTH: 789
<212> TYPE: PRT
<213> ORGANISM: Artificial Sequence
<220> FEATURE:
<223> OTHER INFORMATION: GLP1-GDF15 Fusion Protein 32

<400> SEQUENCE: 64

| His | Gly | Glu | Gly | Thr | Phe | Thr | Ser | Asp | Leu | Ser | Lys | Gln | Met | Glu | Glu |
|---|---|---|---|---|---|---|---|---|---|---|---|---|---|---|---|
| 1 | | | | 5 | | | | | 10 | | | | | 15 | |

| Glu | Ala | Val | Arg | Leu | Phe | Ile | Glu | Trp | Leu | Lys | Asn | Gly | Gly | Pro | Ser |
|---|---|---|---|---|---|---|---|---|---|---|---|---|---|---|---|
| | | | 20 | | | | | 25 | | | | | 30 | | |

| Ser | Gly | Ala | Pro | Pro | Ser | Gly | Gly | Gly | Ser | Gly | Gly | Gly | Gly |
|---|---|---|---|---|---|---|---|---|---|---|---|---|---|
| | | 35 | | | | 40 | | | | | 45 | | |

Ser Gly Gly Gly Gly Ser Asp Ala His Lys Ser Glu Val Ala His Arg
                50                  55                  60

Phe Lys Asp Leu Gly Glu Glu Asn Phe Lys Ala Leu Val Leu Ile Ala
65                  70                  75                  80

Phe Ala Gln Tyr Leu Gln Gln Ser Pro Phe Glu Asp His Val Lys Leu
                85                  90                  95

Val Asn Glu Val Thr Glu Phe Ala Lys Thr Cys Val Ala Asp Glu Ser
            100                 105                 110

Ala Glu Asn Cys Asp Lys Ser Leu His Thr Leu Phe Gly Asp Lys Leu
            115                 120                 125

Cys Thr Val Ala Thr Leu Arg Glu Thr Tyr Gly Glu Met Ala Asp Cys
    130                 135                 140

Cys Ala Lys Gln Glu Pro Glu Arg Asn Glu Cys Phe Leu Gln His Lys
145                 150                 155                 160

Asp Asp Asn Pro Asn Leu Pro Arg Leu Val Arg Pro Glu Val Asp Val
                165                 170                 175

Met Cys Thr Ala Phe His Asp Asn Glu Glu Thr Phe Leu Lys Lys Tyr
            180                 185                 190

Leu Tyr Glu Ile Ala Arg Arg His Pro Tyr Phe Tyr Ala Pro Glu Leu
            195                 200                 205

Leu Phe Phe Ala Lys Arg Tyr Lys Ala Ala Phe Thr Glu Cys Cys Gln
    210                 215                 220

Ala Ala Asp Lys Ala Ala Cys Leu Leu Pro Lys Leu Asp Glu Leu Arg
225                 230                 235                 240

Asp Glu Gly Lys Ala Ser Ser Ala Lys Gln Arg Leu Lys Cys Ala Ser
                245                 250                 255

Leu Gln Lys Phe Gly Glu Arg Ala Phe Lys Ala Trp Ala Val Ala Arg
            260                 265                 270

Leu Ser Gln Arg Phe Pro Lys Ala Glu Phe Ala Glu Val Ser Lys Leu
            275                 280                 285

Val Thr Asp Leu Thr Lys Val His Thr Glu Cys Cys His Gly Asp Leu
    290                 295                 300

Leu Glu Cys Ala Asp Asp Arg Ala Asp Leu Ala Lys Tyr Ile Cys Glu
305                 310                 315                 320

Asn Gln Asp Ser Ile Ser Ser Lys Leu Lys Glu Cys Cys Glu Lys Pro
                325                 330                 335

Leu Leu Glu Lys Ser His Cys Ile Ala Glu Val Glu Asn Asp Glu Met
            340                 345                 350

Pro Ala Asp Leu Pro Ser Leu Ala Ala Asp Phe Val Glu Ser Lys Asp
            355                 360                 365

```
Val Cys Lys Asn Tyr Ala Glu Ala Lys Asp Val Phe Leu Gly Met Phe
    370                 375                 380

Leu Tyr Glu Tyr Ala Arg Arg His Pro Asp Tyr Ser Val Val Leu Leu
385                     390                 395                 400

Leu Arg Leu Ala Lys Thr Tyr Glu Thr Thr Leu Glu Lys Cys Cys Ala
                405                 410                 415

Ala Ala Asp Pro His Glu Cys Tyr Ala Lys Val Phe Asp Glu Phe Lys
            420                 425                 430

Pro Leu Val Glu Glu Pro Gln Asn Leu Ile Lys Gln Asn Cys Glu Leu
        435                 440                 445

Phe Glu Gln Leu Gly Glu Tyr Lys Phe Gln Asn Ala Leu Leu Val Arg
450                     455                 460

Tyr Thr Lys Lys Val Pro Gln Val Ser Thr Pro Thr Leu Val Glu Val
465                 470                 475                 480

Ser Arg Asn Leu Gly Lys Val Gly Ser Lys Cys Cys Lys His Pro Glu
                485                 490                 495

Ala Lys Arg Met Pro Cys Ala Glu Asp Tyr Leu Ser Val Val Leu Asn
            500                 505                 510

Gln Leu Cys Val Leu His Glu Lys Thr Pro Val Ser Asp Arg Val Thr
        515                 520                 525

Lys Cys Cys Thr Glu Ser Leu Val Asn Arg Arg Pro Cys Phe Ser Ala
530                     535                 540

Leu Glu Val Asp Glu Thr Tyr Val Pro Lys Glu Phe Asn Ala Glu Thr
545                 550                 555                 560

Phe Thr Phe His Ala Asp Ile Cys Thr Leu Ser Glu Lys Glu Arg Gln
                565                 570                 575

Ile Lys Lys Gln Thr Ala Leu Val Glu Leu Val Lys His Lys Pro Lys
            580                 585                 590

Ala Thr Lys Glu Gln Leu Lys Ala Val Met Asp Asp Phe Ala Ala Phe
        595                 600                 605

Val Glu Lys Cys Cys Lys Ala Asp Asp Lys Glu Thr Cys Phe Ala Glu
610                     615                 620

Glu Gly Lys Lys Leu Val Ala Ala Ser Gln Ala Ala Leu Gly Leu Gly
625                 630                 635                 640

Ser Gly Gly Gly Gly Ser Gly Gly Gly Gly Ser Gly Gly Gly Gly Ser
                645                 650                 655

Gly Gly Gly Gly Ser Gly Gly Gly Ser Gly Gly Gly Gly Ser Gly
            660                 665                 670

Gly Gly Gly Ser Gly Gly Gly Ser Asp His Cys Pro Leu Gly Pro
        675                 680                 685

Gly Arg Cys Cys Arg Leu His Thr Val Arg Ala Ser Leu Glu Asp Leu
690                     695                 700

Gly Trp Ala Asp Trp Val Leu Ser Pro Arg Glu Val Gln Val Thr Met
705                 710                 715                 720

Cys Ile Gly Ala Cys Pro Ser Gln Phe Arg Ala Ala Asn Met His Ala
                725                 730                 735

Gln Ile Lys Thr Ser Leu His Arg Leu Lys Pro Asp Thr Val Pro Ala
            740                 745                 750

Pro Cys Cys Val Pro Ala Ser Tyr Asn Pro Met Val Leu Ile Gln Lys
        755                 760                 765

Thr Asp Thr Gly Val Ser Leu Gln Thr Tyr Asp Asp Leu Leu Ala Lys
770                     775                 780
```

Asp Cys His Cys Ile
785

<210> SEQ ID NO 65
<211> LENGTH: 777
<212> TYPE: PRT
<213> ORGANISM: Artificial Sequence
<220> FEATURE:
<223> OTHER INFORMATION: GLP1-GDF15 Fusion Protein 33

<400> SEQUENCE: 65

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Gly Gly Gly Gly Ser Gly Gly Gly Gly Ser Asp Ala His Lys Ser Glu
        35                  40                  45

Val Ala His Arg Phe Lys Asp Leu Gly Glu Glu Asn Phe Lys Ala Leu
    50                  55                  60

Val Leu Ile Ala Phe Ala Gln Tyr Leu Gln Gln Ser Pro Phe Glu Asp
65                  70                  75                  80

His Val Lys Leu Val Asn Glu Val Thr Glu Phe Ala Lys Thr Cys Val
                85                  90                  95

Ala Asp Glu Ser Ala Glu Asn Cys Asp Lys Ser Leu His Thr Leu Phe
            100                 105                 110

Gly Asp Lys Leu Cys Thr Val Ala Thr Leu Arg Glu Thr Tyr Gly Glu
        115                 120                 125

Met Ala Asp Cys Cys Ala Lys Gln Glu Pro Glu Arg Asn Glu Cys Phe
130                 135                 140

Leu Gln His Lys Asp Asp Asn Pro Asn Leu Pro Arg Leu Val Arg Pro
145                 150                 155                 160

Glu Val Asp Val Met Cys Thr Ala Phe His Asp Asn Glu Glu Thr Phe
                165                 170                 175

Leu Lys Lys Tyr Leu Tyr Glu Ile Ala Arg Arg His Pro Tyr Phe Tyr
            180                 185                 190

Ala Pro Glu Leu Leu Phe Phe Ala Lys Arg Tyr Lys Ala Ala Phe Thr
        195                 200                 205

Glu Cys Cys Gln Ala Ala Asp Lys Ala Ala Cys Leu Leu Pro Lys Leu
210                 215                 220

Asp Glu Leu Arg Asp Glu Gly Lys Ala Ser Ser Ala Lys Gln Arg Leu
225                 230                 235                 240

Lys Cys Ala Ser Leu Gln Lys Phe Gly Glu Arg Ala Phe Lys Ala Trp
                245                 250                 255

Ala Val Ala Arg Leu Ser Gln Arg Phe Pro Lys Ala Glu Phe Ala Glu
            260                 265                 270

Val Ser Lys Leu Val Thr Asp Leu Thr Lys Val His Thr Glu Cys Cys
        275                 280                 285

His Gly Asp Leu Leu Glu Cys Ala Asp Asp Arg Ala Asp Leu Ala Lys
290                 295                 300

Tyr Ile Cys Glu Asn Gln Asp Ser Ile Ser Ser Lys Leu Lys Glu Cys
305                 310                 315                 320

Cys Glu Lys Pro Leu Leu Glu Lys Ser His Cys Ile Ala Glu Val Glu
                325                 330                 335

Asn Asp Glu Met Pro Ala Asp Leu Pro Ser Leu Ala Ala Asp Phe Val
            340                 345                 350

```
Glu Ser Lys Asp Val Cys Lys Asn Tyr Ala Glu Ala Lys Asp Val Phe
            355                 360                 365

Leu Gly Met Phe Leu Tyr Glu Tyr Ala Arg Arg His Pro Asp Tyr Ser
        370                 375                 380

Val Val Leu Leu Leu Arg Leu Ala Lys Thr Tyr Glu Thr Thr Leu Glu
385                 390                 395                 400

Lys Cys Cys Ala Ala Ala Asp Pro His Glu Cys Tyr Ala Lys Val Phe
                405                 410                 415

Asp Glu Phe Lys Pro Leu Val Glu Glu Pro Gln Asn Leu Ile Lys Gln
            420                 425                 430

Asn Cys Glu Leu Phe Glu Gln Leu Gly Glu Tyr Lys Phe Gln Asn Ala
        435                 440                 445

Leu Leu Val Arg Tyr Thr Lys Lys Val Pro Gln Val Ser Thr Pro Thr
    450                 455                 460

Leu Val Glu Val Ser Arg Asn Leu Gly Lys Val Gly Ser Lys Cys Cys
465                 470                 475                 480

Lys His Pro Glu Ala Lys Arg Met Pro Cys Ala Glu Asp Tyr Leu Ser
                485                 490                 495

Val Val Leu Asn Gln Leu Cys Val Leu His Glu Lys Thr Pro Val Ser
            500                 505                 510

Asp Arg Val Thr Lys Cys Cys Thr Glu Ser Leu Val Asn Arg Arg Pro
        515                 520                 525

Cys Phe Ser Ala Leu Glu Val Asp Glu Thr Tyr Val Pro Lys Glu Phe
    530                 535                 540

Asn Ala Glu Thr Phe Thr Phe His Ala Asp Ile Cys Thr Leu Ser Glu
545                 550                 555                 560

Lys Glu Arg Gln Ile Lys Lys Gln Thr Ala Leu Val Glu Leu Val Lys
                565                 570                 575

His Lys Pro Lys Ala Thr Lys Glu Gln Leu Lys Ala Val Met Asp Asp
            580                 585                 590

Phe Ala Ala Phe Val Glu Lys Cys Cys Lys Ala Asp Asp Lys Glu Thr
        595                 600                 605

Cys Phe Ala Glu Glu Gly Lys Lys Leu Val Ala Ala Ser Gln Ala Ala
    610                 615                 620

Leu Gly Leu Gly Ser Gly Gly Gly Gly Ser Gly Gly Gly Gly Ser Gly
625                 630                 635                 640

Gly Gly Gly Ser Gly Gly Gly Gly Ser Gly Gly Gly Gly Ser Gly Gly
                645                 650                 655

Gly Gly Ser Gly Gly Gly Gly Ser Gly Gly Gly Ser Asp His Cys
            660                 665                 670

Pro Leu Gly Pro Gly Arg Cys Cys Arg Leu His Thr Val Arg Ala Ser
        675                 680                 685

Leu Glu Asp Leu Gly Trp Ala Asp Trp Val Leu Ser Pro Arg Glu Val
    690                 695                 700

Gln Val Thr Met Cys Ile Gly Ala Cys Pro Ser Gln Phe Arg Ala Ala
705                 710                 715                 720

Asn Met His Ala Gln Ile Lys Thr Ser Leu His Arg Leu Lys Pro Asp
                725                 730                 735

Thr Val Pro Ala Pro Cys Cys Val Pro Ala Ser Tyr Asn Pro Met Val
            740                 745                 750

Leu Ile Gln Lys Thr Asp Thr Gly Val Ser Leu Gln Thr Tyr Asp Asp
        755                 760                 765

Leu Leu Ala Lys Asp Cys His Cys Ile
```

```
            770                 775
```

<210> SEQ ID NO 66
<211> LENGTH: 779
<212> TYPE: PRT
<213> ORGANISM: Artificial Sequence
<220> FEATURE:
<223> OTHER INFORMATION: GLP1-GDF15 Fusion Protein 34

<400> SEQUENCE: 66

```
His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Ala Ser
            20                  25                  30

Ala Pro Ala Pro Ala Pro Ala Pro Ala Pro Gly Ser Asp Ala His Lys
        35                  40                  45

Ser Glu Val Ala His Arg Phe Lys Asp Leu Gly Glu Glu Asn Phe Lys
    50                  55                  60

Ala Leu Val Leu Ile Ala Phe Ala Gln Tyr Leu Gln Gln Ser Pro Phe
65                  70                  75                  80

Glu Asp His Val Lys Leu Val Asn Glu Val Thr Glu Phe Ala Lys Thr
                85                  90                  95

Cys Val Ala Asp Glu Ser Ala Glu Asn Cys Asp Lys Ser Leu His Thr
            100                 105                 110

Leu Phe Gly Asp Lys Leu Cys Thr Val Ala Thr Leu Arg Glu Thr Tyr
        115                 120                 125

Gly Glu Met Ala Asp Cys Cys Ala Lys Gln Glu Pro Glu Arg Asn Glu
    130                 135                 140

Cys Phe Leu Gln His Lys Asp Asp Asn Pro Asn Leu Pro Arg Leu Val
145                 150                 155                 160

Arg Pro Glu Val Asp Val Met Cys Thr Ala Phe His Asp Asn Glu Glu
                165                 170                 175

Thr Phe Leu Lys Lys Tyr Leu Tyr Glu Ile Ala Arg Arg His Pro Tyr
            180                 185                 190

Phe Tyr Ala Pro Glu Leu Leu Phe Phe Ala Lys Arg Tyr Lys Ala Ala
        195                 200                 205

Phe Thr Glu Cys Cys Gln Ala Ala Asp Lys Ala Ala Cys Leu Leu Pro
    210                 215                 220

Lys Leu Asp Glu Leu Arg Asp Glu Gly Lys Ala Ser Ser Ala Lys Gln
225                 230                 235                 240

Arg Leu Lys Cys Ala Ser Leu Gln Lys Phe Gly Glu Arg Ala Phe Lys
                245                 250                 255

Ala Trp Ala Val Ala Arg Leu Ser Gln Arg Phe Pro Lys Ala Glu Phe
            260                 265                 270

Ala Glu Val Ser Lys Leu Val Thr Asp Leu Thr Lys Val His Thr Glu
        275                 280                 285

Cys Cys His Gly Asp Leu Leu Glu Cys Ala Asp Asp Arg Ala Asp Leu
    290                 295                 300

Ala Lys Tyr Ile Cys Glu Asn Gln Asp Ser Ile Ser Ser Lys Leu Lys
305                 310                 315                 320

Glu Cys Cys Glu Lys Pro Leu Leu Glu Lys Ser His Cys Ile Ala Glu
                325                 330                 335

Val Glu Asn Asp Glu Met Pro Ala Asp Leu Pro Ser Leu Ala Ala Asp
            340                 345                 350

Phe Val Glu Ser Lys Asp Val Cys Lys Asn Tyr Ala Glu Ala Lys Asp
```

```
                355                 360                 365
Val Phe Leu Gly Met Phe Leu Tyr Glu Tyr Ala Arg Arg His Pro Asp
370                 375                 380

Tyr Ser Val Val Leu Leu Leu Arg Leu Ala Lys Thr Tyr Glu Thr Thr
385                 390                 395                 400

Leu Glu Lys Cys Cys Ala Ala Ala Asp Pro His Glu Cys Tyr Ala Lys
                405                 410                 415

Val Phe Asp Glu Phe Lys Pro Leu Val Glu Glu Pro Gln Asn Leu Ile
                420                 425                 430

Lys Gln Asn Cys Glu Leu Phe Glu Gln Leu Gly Glu Tyr Lys Phe Gln
                435                 440                 445

Asn Ala Leu Leu Val Arg Tyr Thr Lys Lys Val Pro Gln Val Ser Thr
450                 455                 460

Pro Thr Leu Val Glu Val Ser Arg Asn Leu Gly Lys Val Gly Ser Lys
465                 470                 475                 480

Cys Cys Lys His Pro Glu Ala Lys Arg Met Pro Cys Ala Glu Asp Tyr
                485                 490                 495

Leu Ser Val Val Leu Asn Gln Leu Cys Val Leu His Glu Lys Thr Pro
                500                 505                 510

Val Ser Asp Arg Val Thr Lys Cys Cys Thr Glu Ser Leu Val Asn Arg
                515                 520                 525

Arg Pro Cys Phe Ser Ala Leu Glu Val Asp Glu Thr Tyr Val Pro Lys
                530                 535                 540

Glu Phe Asn Ala Glu Thr Phe Thr Phe His Ala Asp Ile Cys Thr Leu
545                 550                 555                 560

Ser Glu Lys Glu Arg Gln Ile Lys Lys Gln Thr Ala Leu Val Glu Leu
                565                 570                 575

Val Lys His Lys Pro Lys Ala Thr Lys Glu Gln Leu Lys Ala Val Met
                580                 585                 590

Asp Asp Phe Ala Ala Phe Val Glu Lys Cys Cys Lys Ala Asp Asp Lys
                595                 600                 605

Glu Thr Cys Phe Ala Glu Glu Gly Lys Lys Leu Val Ala Ala Ser Gln
610                 615                 620

Ala Ala Leu Gly Leu Gly Ser Gly Gly Gly Ser Gly Gly Gly Gly Gly
625                 630                 635                 640

Ser Gly Gly Gly Ser Gly Gly Gly Ser Gly Gly Gly Gly Gly Ser
                645                 650                 655

Gly Gly Gly Gly Ser Gly Gly Gly Ser Gly Gly Gly Gly Ser Asp
                660                 665                 670

His Cys Pro Leu Gly Pro Gly Arg Cys Cys Arg Leu His Thr Val Arg
                675                 680                 685

Ala Ser Leu Glu Asp Leu Gly Trp Ala Asp Trp Val Leu Ser Pro Arg
                690                 695                 700

Glu Val Gln Val Thr Met Cys Ile Gly Ala Cys Pro Ser Gln Phe Arg
705                 710                 715                 720

Ala Ala Asn Met His Ala Gln Ile Lys Thr Ser Leu His Arg Leu Lys
                725                 730                 735

Pro Asp Thr Val Pro Ala Pro Cys Cys Val Pro Ala Ser Tyr Asn Pro
                740                 745                 750

Met Val Leu Ile Gln Lys Thr Asp Thr Gly Val Ser Leu Gln Thr Tyr
                755                 760                 765

Asp Asp Leu Leu Ala Lys Asp Cys His Cys Ile
770                 775
```

<210> SEQ ID NO 67
<211> LENGTH: 786
<212> TYPE: PRT
<213> ORGANISM: Artificial Sequence
<220> FEATURE:
<223> OTHER INFORMATION: GLP1-GDF15 Fusion Protein 35

<400> SEQUENCE: 67

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Gly Gly Gly Ser Gly Gly
        35                  40                  45

Gly Gly Ser Asp Ala His Lys Ser Glu Val Ala His Arg Phe Lys Asp
    50                  55                  60

Leu Gly Glu Glu Asn Phe Lys Ala Leu Val Leu Ile Ala Phe Ala Gln
65                  70                  75                  80

Tyr Leu Gln Gln Ser Pro Phe Glu Asp His Val Lys Leu Val Asn Glu
                85                  90                  95

Val Thr Glu Phe Ala Lys Thr Cys Val Ala Asp Glu Ser Ala Glu Asn
            100                 105                 110

Cys Asp Lys Ser Leu His Thr Leu Phe Gly Asp Lys Leu Cys Thr Val
        115                 120                 125

Ala Thr Leu Arg Glu Thr Tyr Gly Glu Met Ala Asp Cys Cys Ala Lys
    130                 135                 140

Gln Glu Pro Glu Arg Asn Glu Cys Phe Leu Gln His Lys Asp Asp Asn
145                 150                 155                 160

Pro Asn Leu Pro Arg Leu Val Arg Pro Glu Val Asp Val Met Cys Thr
                165                 170                 175

Ala Phe His Asp Asn Glu Glu Thr Phe Leu Lys Lys Tyr Leu Tyr Glu
            180                 185                 190

Ile Ala Arg Arg His Pro Tyr Phe Tyr Ala Pro Glu Leu Leu Phe Phe
        195                 200                 205

Ala Lys Arg Tyr Lys Ala Ala Phe Thr Glu Cys Cys Gln Ala Ala Asp
    210                 215                 220

Lys Ala Ala Cys Leu Leu Pro Lys Leu Asp Glu Leu Arg Asp Glu Gly
225                 230                 235                 240

Lys Ala Ser Ser Ala Lys Gln Arg Leu Lys Cys Ala Ser Leu Gln Lys
                245                 250                 255

Phe Gly Glu Arg Ala Phe Lys Ala Trp Ala Val Ala Arg Leu Ser Gln
            260                 265                 270

Arg Phe Pro Lys Ala Glu Phe Ala Glu Val Ser Lys Leu Val Thr Asp
        275                 280                 285

Leu Thr Lys Val His Thr Glu Cys Cys His Gly Asp Leu Leu Glu Cys
    290                 295                 300

Ala Asp Asp Arg Ala Asp Leu Ala Lys Tyr Ile Cys Glu Asn Gln Asp
305                 310                 315                 320

Ser Ile Ser Ser Lys Leu Lys Glu Cys Cys Glu Lys Pro Leu Leu Glu
                325                 330                 335

Lys Ser His Cys Ile Ala Glu Val Glu Asn Asp Glu Met Pro Ala Asp
            340                 345                 350

Leu Pro Ser Leu Ala Ala Asp Phe Val Glu Ser Lys Asp Val Cys Lys
        355                 360                 365
```

```
Asn Tyr Ala Glu Ala Lys Asp Val Phe Leu Gly Met Phe Leu Tyr Glu
        370                 375                 380

Tyr Ala Arg Arg His Pro Asp Tyr Ser Val Val Leu Leu Leu Arg Leu
385                 390                 395                 400

Ala Lys Thr Tyr Glu Thr Thr Leu Glu Lys Cys Cys Ala Ala Ala Asp
                405                 410                 415

Pro His Glu Cys Tyr Ala Lys Val Phe Asp Glu Phe Lys Pro Leu Val
            420                 425                 430

Glu Glu Pro Gln Asn Leu Ile Lys Gln Asn Cys Glu Leu Phe Glu Gln
                435                 440                 445

Leu Gly Glu Tyr Lys Phe Gln Asn Ala Leu Leu Val Arg Tyr Thr Lys
        450                 455                 460

Lys Val Pro Gln Val Ser Thr Pro Thr Leu Val Glu Val Ser Arg Asn
465                 470                 475                 480

Leu Gly Lys Val Gly Ser Lys Cys Cys Lys His Pro Glu Ala Lys Arg
                485                 490                 495

Met Pro Cys Ala Glu Asp Tyr Leu Ser Val Val Leu Asn Gln Leu Cys
            500                 505                 510

Val Leu His Glu Lys Thr Pro Val Ser Asp Arg Val Thr Lys Cys Cys
        515                 520                 525

Thr Glu Ser Leu Val Asn Arg Arg Pro Cys Phe Ser Ala Leu Glu Val
530                 535                 540

Asp Glu Thr Tyr Val Pro Lys Glu Phe Asn Ala Glu Thr Phe Thr Phe
545                 550                 555                 560

His Ala Asp Ile Cys Thr Leu Ser Glu Lys Glu Arg Gln Ile Lys Lys
                565                 570                 575

Gln Thr Ala Leu Val Glu Leu Val Lys His Lys Pro Lys Ala Thr Lys
            580                 585                 590

Glu Gln Leu Lys Ala Val Met Asp Asp Phe Ala Ala Phe Val Glu Lys
        595                 600                 605

Cys Cys Lys Ala Asp Asp Lys Glu Thr Cys Phe Ala Glu Glu Gly Lys
    610                 615                 620

Lys Leu Val Ala Ala Ser Gln Ala Ala Leu Gly Leu Gly Ser Gly Gly
625                 630                 635                 640

Gly Gly Ser Gly Gly Gly Gly Ser Gly Gly Gly Gly Ser Gly Gly Gly
                645                 650                 655

Gly Ser Gly Gly Gly Gly Ser Gly Gly Gly Gly Ser Gly Gly Gly Gly
            660                 665                 670

Ser Gly Gly Gly Ser Asp His Cys Pro Leu Gly Pro Gly Arg Cys
        675                 680                 685

Cys Arg Leu His Thr Val Arg Ala Ser Leu Glu Asp Leu Gly Trp Ala
    690                 695                 700

Asp Trp Val Leu Ser Pro Arg Glu Val Gln Val Thr Met Cys Ile Gly
705                 710                 715                 720

Ala Cys Pro Ser Gln Phe Arg Ala Ala Asn Met His Ala Gln Ile Lys
                725                 730                 735

Thr Ser Leu His Arg Leu Lys Pro Asp Thr Val Pro Ala Pro Cys Cys
            740                 745                 750

Val Pro Ala Ser Tyr Asn Pro Met Val Leu Ile Gln Lys Thr Asp Thr
        755                 760                 765

Gly Val Ser Leu Gln Thr Tyr Asp Asp Leu Leu Ala Lys Asp Cys His
770                 775                 780
```

```
Cys Ile
785
```

<210> SEQ ID NO 68
<211> LENGTH: 788
<212> TYPE: PRT
<213> ORGANISM: Artificial Sequence
<220> FEATURE:
<223> OTHER INFORMATION: GLP1-GDF15 Fusion Protein 36

<400> SEQUENCE: 68

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Ser Ala Pro Ala Pro Ala Pro Ala
        35                  40                  45

Pro Ala Pro Gly Ser Asp Ala His Lys Ser Glu Val Ala His Arg Phe
    50                  55                  60

Lys Asp Leu Gly Glu Glu Asn Phe Lys Ala Leu Val Leu Ile Ala Phe
65                  70                  75                  80

Ala Gln Tyr Leu Gln Gln Ser Pro Phe Glu Asp His Val Lys Leu Val
                85                  90                  95

Asn Glu Val Thr Glu Phe Ala Lys Thr Cys Val Ala Asp Glu Ser Ala
            100                 105                 110

Glu Asn Cys Asp Lys Ser Leu His Thr Leu Phe Gly Asp Lys Leu Cys
        115                 120                 125

Thr Val Ala Thr Leu Arg Glu Thr Tyr Gly Glu Met Ala Asp Cys Cys
130                 135                 140

Ala Lys Gln Glu Pro Glu Arg Asn Glu Cys Phe Leu Gln His Lys Asp
145                 150                 155                 160

Asp Asn Pro Asn Leu Pro Arg Leu Val Arg Pro Glu Val Asp Val Met
                165                 170                 175

Cys Thr Ala Phe His Asp Asn Glu Glu Thr Phe Leu Lys Lys Tyr Leu
            180                 185                 190

Tyr Glu Ile Ala Arg Arg His Pro Tyr Phe Tyr Ala Pro Glu Leu Leu
        195                 200                 205

Phe Phe Ala Lys Arg Tyr Lys Ala Ala Phe Thr Glu Cys Cys Gln Ala
    210                 215                 220

Ala Asp Lys Ala Ala Cys Leu Leu Pro Lys Leu Asp Glu Leu Arg Asp
225                 230                 235                 240

Glu Gly Lys Ala Ser Ser Ala Lys Gln Arg Leu Lys Cys Ala Ser Leu
                245                 250                 255

Gln Lys Phe Gly Glu Arg Ala Phe Lys Ala Trp Ala Val Ala Arg Leu
            260                 265                 270

Ser Gln Arg Phe Pro Lys Ala Glu Phe Ala Glu Val Ser Lys Leu Val
        275                 280                 285

Thr Asp Leu Thr Lys Val His Thr Glu Cys Cys His Gly Asp Leu Leu
    290                 295                 300

Glu Cys Ala Asp Asp Arg Ala Asp Leu Ala Lys Tyr Ile Cys Glu Asn
305                 310                 315                 320

Gln Asp Ser Ile Ser Ser Lys Leu Lys Glu Cys Cys Glu Lys Pro Leu
                325                 330                 335

Leu Glu Lys Ser His Cys Ile Ala Glu Val Glu Asn Asp Glu Met Pro
            340                 345                 350
```

```
Ala Asp Leu Pro Ser Leu Ala Ala Asp Phe Val Glu Ser Lys Asp Val
            355                 360                 365

Cys Lys Asn Tyr Ala Glu Ala Lys Asp Val Phe Leu Gly Met Phe Leu
        370                 375                 380

Tyr Glu Tyr Ala Arg Arg His Pro Asp Tyr Ser Val Val Leu Leu Leu
385                 390                 395                 400

Arg Leu Ala Lys Thr Tyr Glu Thr Thr Leu Glu Lys Cys Cys Ala Ala
                405                 410                 415

Ala Asp Pro His Glu Cys Tyr Ala Lys Val Phe Asp Glu Phe Lys Pro
            420                 425                 430

Leu Val Glu Glu Pro Gln Asn Leu Ile Lys Gln Asn Cys Glu Leu Phe
        435                 440                 445

Glu Gln Leu Gly Glu Tyr Lys Phe Gln Asn Ala Leu Leu Val Arg Tyr
    450                 455                 460

Thr Lys Lys Val Pro Gln Val Ser Thr Pro Thr Leu Val Glu Val Ser
465                 470                 475                 480

Arg Asn Leu Gly Lys Val Gly Ser Lys Cys Cys Lys His Pro Glu Ala
                485                 490                 495

Lys Arg Met Pro Cys Ala Glu Asp Tyr Leu Ser Val Val Leu Asn Gln
            500                 505                 510

Leu Cys Val Leu His Glu Lys Thr Pro Val Ser Asp Arg Val Thr Lys
        515                 520                 525

Cys Cys Thr Glu Ser Leu Val Asn Arg Arg Pro Cys Phe Ser Ala Leu
        530                 535                 540

Glu Val Asp Glu Thr Tyr Val Pro Lys Glu Phe Asn Ala Glu Thr Phe
545                 550                 555                 560

Thr Phe His Ala Asp Ile Cys Thr Leu Ser Glu Lys Glu Arg Gln Ile
            565                 570                 575

Lys Lys Gln Thr Ala Leu Val Glu Leu Val Lys His Lys Pro Lys Ala
            580                 585                 590

Thr Lys Glu Gln Leu Lys Ala Val Met Asp Asp Phe Ala Ala Phe Val
        595                 600                 605

Glu Lys Cys Cys Lys Ala Asp Asp Lys Glu Thr Cys Phe Ala Glu Glu
    610                 615                 620

Gly Lys Lys Leu Val Ala Ala Ser Gln Ala Ala Leu Gly Leu Gly Ser
625                 630                 635                 640

Gly Gly Gly Gly Ser Gly Gly Gly Ser Gly Gly Gly Gly Ser Gly
                645                 650                 655

Gly Gly Gly Ser Gly Gly Gly Ser Gly Gly Gly Gly Ser Gly Gly
            660                 665                 670

Gly Gly Ser Gly Gly Gly Gly Ser Asp His Cys Pro Leu Gly Pro Gly
        675                 680                 685

Arg Cys Cys Arg Leu His Thr Val Arg Ala Ser Leu Glu Asp Leu Gly
        690                 695                 700

Trp Ala Asp Trp Val Leu Ser Pro Arg Glu Val Gln Val Thr Met Cys
705                 710                 715                 720

Ile Gly Ala Cys Pro Ser Gln Phe Arg Ala Ala Asn Met His Ala Gln
            725                 730                 735

Ile Lys Thr Ser Leu His Arg Leu Lys Pro Asp Thr Val Pro Ala Pro
                740                 745                 750

Cys Cys Val Pro Ala Ser Tyr Asn Pro Met Val Leu Ile Gln Lys Thr
        755                 760                 765

Asp Thr Gly Val Ser Leu Gln Thr Tyr Asp Asp Leu Leu Ala Lys Asp
```

-continued

```
             770                 775                 780

Cys His Cys Ile
785

<210> SEQ ID NO 69
<211> LENGTH: 777
<212> TYPE: PRT
<213> ORGANISM: Artificial Sequence
<220> FEATURE:
<223> OTHER INFORMATION: GLP1-GDF15 Fusion Protein 37

<400> SEQUENCE: 69

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Ser
                20                  25                  30

Gly Gly Gly Gly Ser Gly Gly Gly Ser Asp Ala His Lys Ser Glu
                35                  40                  45

Val Ala His Arg Phe Lys Asp Leu Gly Glu Glu Asn Phe Lys Ala Leu
    50                  55                  60

Val Leu Ile Ala Phe Ala Gln Tyr Leu Gln Gln Ser Pro Phe Glu Asp
65                  70                  75                  80

His Val Lys Leu Val Asn Glu Val Thr Glu Phe Ala Lys Thr Cys Val
                85                  90                  95

Ala Asp Glu Ser Ala Glu Asn Cys Asp Lys Ser Leu His Thr Leu Phe
                100                 105                 110

Gly Asp Lys Leu Cys Thr Val Ala Thr Leu Arg Glu Thr Tyr Gly Glu
                115                 120                 125

Met Ala Asp Cys Cys Ala Lys Gln Glu Pro Glu Arg Asn Glu Cys Phe
            130                 135                 140

Leu Gln His Lys Asp Asp Asn Pro Asn Leu Pro Arg Leu Val Arg Pro
145                 150                 155                 160

Glu Val Asp Val Met Cys Thr Ala Phe His Asp Asn Glu Glu Thr Phe
                165                 170                 175

Leu Lys Lys Tyr Leu Tyr Glu Ile Ala Arg Arg His Pro Tyr Phe Tyr
                180                 185                 190

Ala Pro Glu Leu Leu Phe Phe Ala Lys Arg Tyr Lys Ala Ala Phe Thr
            195                 200                 205

Glu Cys Cys Gln Ala Ala Asp Lys Ala Ala Cys Leu Leu Pro Lys Leu
        210                 215                 220

Asp Glu Leu Arg Asp Glu Gly Lys Ala Ser Ser Ala Lys Gln Arg Leu
225                 230                 235                 240

Lys Cys Ala Ser Leu Gln Lys Phe Gly Glu Arg Ala Phe Lys Ala Trp
                245                 250                 255

Ala Val Ala Arg Leu Ser Gln Arg Phe Pro Lys Ala Glu Phe Ala Glu
                260                 265                 270

Val Ser Lys Leu Val Thr Asp Leu Thr Lys Val His Thr Glu Cys Cys
            275                 280                 285

His Gly Asp Leu Leu Glu Cys Ala Asp Asp Arg Ala Asp Leu Ala Lys
        290                 295                 300

Tyr Ile Cys Glu Asn Gln Asp Ser Ile Ser Lys Leu Lys Glu Cys
305                 310                 315                 320

Cys Glu Lys Pro Leu Leu Glu Lys Ser His Cys Ile Ala Glu Val Glu
                325                 330                 335

Asn Asp Glu Met Pro Ala Asp Leu Pro Ser Leu Ala Ala Asp Phe Val
```

-continued

```
                340                 345                 350
Glu Ser Lys Asp Val Cys Lys Asn Tyr Ala Glu Ala Lys Asp Val Phe
        355                 360                 365
Leu Gly Met Phe Leu Tyr Glu Tyr Ala Arg Arg His Pro Asp Tyr Ser
        370                 375                 380
Val Val Leu Leu Leu Arg Leu Ala Lys Thr Tyr Glu Thr Thr Leu Glu
385                 390                 395                 400
Lys Cys Cys Ala Ala Ala Asp Pro His Glu Cys Tyr Ala Lys Val Phe
                405                 410                 415
Asp Glu Phe Lys Pro Leu Val Glu Glu Pro Gln Asn Leu Ile Lys Gln
        420                 425                 430
Asn Cys Glu Leu Phe Glu Gln Leu Gly Glu Tyr Lys Phe Gln Asn Ala
        435                 440                 445
Leu Leu Val Arg Tyr Thr Lys Lys Val Pro Gln Val Ser Thr Pro Thr
        450                 455                 460
Leu Val Glu Val Ser Arg Asn Leu Gly Lys Val Gly Ser Lys Cys Cys
465                 470                 475                 480
Lys His Pro Glu Ala Lys Arg Met Pro Cys Ala Glu Asp Tyr Leu Ser
                485                 490                 495
Val Val Leu Asn Gln Leu Cys Val Leu His Glu Lys Thr Pro Val Ser
                500                 505                 510
Asp Arg Val Thr Lys Cys Cys Thr Glu Ser Leu Val Asn Arg Arg Pro
        515                 520                 525
Cys Phe Ser Ala Leu Glu Val Asp Glu Thr Tyr Val Pro Lys Glu Phe
        530                 535                 540
Asn Ala Glu Thr Phe Thr Phe His Ala Asp Ile Cys Thr Leu Ser Glu
545                 550                 555                 560
Lys Glu Arg Gln Ile Lys Lys Gln Thr Ala Leu Val Glu Leu Val Lys
                565                 570                 575
His Lys Pro Lys Ala Thr Lys Glu Gln Leu Lys Ala Val Met Asp Asp
                580                 585                 590
Phe Ala Ala Phe Val Glu Lys Cys Cys Lys Ala Asp Asp Lys Glu Thr
        595                 600                 605
Cys Phe Ala Glu Glu Gly Lys Lys Leu Val Ala Ala Ser Gln Ala Ala
        610                 615                 620
Leu Gly Leu Gly Ser Gly Gly Gly Gly Ser Gly Gly Gly Gly Ser Gly
625                 630                 635                 640
Gly Gly Gly Ser Gly Gly Gly Gly Ser Gly Gly Gly Gly Ser Gly Gly
                645                 650                 655
Gly Gly Ser Gly Gly Gly Gly Ser Gly Gly Gly Gly Ser Asp His Cys
                660                 665                 670
Pro Leu Gly Pro Gly Arg Cys Cys Arg Leu His Thr Val Arg Ala Ser
        675                 680                 685
Leu Glu Asp Leu Gly Trp Ala Asp Trp Val Leu Ser Pro Arg Glu Val
        690                 695                 700
Gln Val Thr Met Cys Ile Gly Ala Cys Pro Ser Gln Phe Arg Ala Ala
705                 710                 715                 720
Asn Met His Ala Gln Ile Lys Thr Ser Leu His Arg Leu Lys Pro Asp
                725                 730                 735
Thr Val Pro Ala Pro Cys Cys Val Pro Ala Ser Tyr Asn Pro Met Val
        740                 745                 750
Leu Ile Gln Lys Thr Asp Thr Gly Val Ser Leu Gln Thr Tyr Asp Asp
        755                 760                 765
```

```
Leu Leu Ala Lys Asp Cys His Cys Ile
        770             775
```

<210> SEQ ID NO 70
<211> LENGTH: 779
<212> TYPE: PRT
<213> ORGANISM: Artificial Sequence
<220> FEATURE:
<223> OTHER INFORMATION: GLP1-GDF15 Fusion Protein 38

<400> SEQUENCE: 70

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Ala Ser
            20                  25                  30

Ala Pro Ala Pro Ala Pro Ala Pro Ala Pro Gly Ser Asp Ala His Lys
        35                  40                  45

Ser Glu Val Ala His Arg Phe Lys Asp Leu Gly Glu Glu Asn Phe Lys
    50                  55                  60

Ala Leu Val Leu Ile Ala Phe Ala Gln Tyr Leu Gln Gln Ser Pro Phe
65                  70                  75                  80

Glu Asp His Val Lys Leu Val Asn Glu Val Thr Glu Phe Ala Lys Thr
                85                  90                  95

Cys Val Ala Asp Glu Ser Ala Glu Asn Cys Asp Lys Ser Leu His Thr
            100                 105                 110

Leu Phe Gly Asp Lys Leu Cys Thr Val Ala Thr Leu Arg Glu Thr Tyr
        115                 120                 125

Gly Glu Met Ala Asp Cys Cys Ala Lys Gln Glu Pro Glu Arg Asn Glu
    130                 135                 140

Cys Phe Leu Gln His Lys Asp Asp Asn Pro Asn Leu Pro Arg Leu Val
145                 150                 155                 160

Arg Pro Glu Val Asp Val Met Cys Thr Ala Phe His Asp Asn Glu Glu
                165                 170                 175

Thr Phe Leu Lys Lys Tyr Leu Tyr Glu Ile Ala Arg Arg His Pro Tyr
            180                 185                 190

Phe Tyr Ala Pro Glu Leu Leu Phe Phe Ala Lys Arg Tyr Lys Ala Ala
        195                 200                 205

Phe Thr Glu Cys Cys Gln Ala Ala Asp Lys Ala Ala Cys Leu Leu Pro
    210                 215                 220

Lys Leu Asp Glu Leu Arg Asp Glu Gly Lys Ala Ser Ser Ala Lys Gln
225                 230                 235                 240

Arg Leu Lys Cys Ala Ser Leu Gln Lys Phe Gly Glu Arg Ala Phe Lys
                245                 250                 255

Ala Trp Ala Val Ala Arg Leu Ser Gln Arg Phe Pro Lys Ala Glu Phe
            260                 265                 270

Ala Glu Val Ser Lys Leu Val Thr Asp Leu Thr Lys Val His Thr Glu
        275                 280                 285

Cys Cys His Gly Asp Leu Leu Glu Cys Ala Asp Asp Arg Ala Asp Leu
    290                 295                 300

Ala Lys Tyr Ile Cys Glu Asn Gln Asp Ser Ile Ser Ser Lys Leu Lys
305                 310                 315                 320

Glu Cys Cys Glu Lys Pro Leu Leu Glu Lys Ser His Cys Ile Ala Glu
                325                 330                 335

Val Glu Asn Asp Glu Met Pro Ala Asp Leu Pro Ser Leu Ala Ala Asp
            340                 345                 350
```

```
Phe Val Glu Ser Lys Asp Val Cys Lys Asn Tyr Ala Glu Ala Lys Asp
            355                 360                 365
Val Phe Leu Gly Met Phe Leu Tyr Glu Tyr Ala Arg Arg His Pro Asp
    370                 375                 380
Tyr Ser Val Val Leu Leu Leu Arg Leu Ala Lys Thr Tyr Glu Thr Thr
385                 390                 395                 400
Leu Glu Lys Cys Cys Ala Ala Ala Asp Pro His Glu Cys Tyr Ala Lys
                405                 410                 415
Val Phe Asp Glu Phe Lys Pro Leu Val Glu Glu Pro Gln Asn Leu Ile
            420                 425                 430
Lys Gln Asn Cys Glu Leu Phe Glu Gln Leu Gly Glu Tyr Lys Phe Gln
            435                 440                 445
Asn Ala Leu Leu Val Arg Tyr Thr Lys Lys Val Pro Gln Val Ser Thr
            450                 455                 460
Pro Thr Leu Val Glu Val Ser Arg Asn Leu Gly Lys Val Gly Ser Lys
465                 470                 475                 480
Cys Cys Lys His Pro Glu Ala Lys Arg Met Pro Cys Ala Glu Asp Tyr
                485                 490                 495
Leu Ser Val Val Leu Asn Gln Leu Cys Val Leu His Glu Lys Thr Pro
            500                 505                 510
Val Ser Asp Arg Val Thr Lys Cys Cys Thr Glu Ser Leu Val Asn Arg
            515                 520                 525
Arg Pro Cys Phe Ser Ala Leu Glu Val Asp Glu Thr Tyr Val Pro Lys
            530                 535                 540
Glu Phe Asn Ala Glu Thr Phe Thr Phe His Ala Asp Ile Cys Thr Leu
545                 550                 555                 560
Ser Glu Lys Glu Arg Gln Ile Lys Lys Gln Thr Ala Leu Val Glu Leu
                565                 570                 575
Val Lys His Lys Pro Lys Ala Thr Lys Glu Gln Leu Lys Ala Val Met
            580                 585                 590
Asp Asp Phe Ala Ala Phe Val Glu Lys Cys Cys Lys Ala Asp Asp Lys
            595                 600                 605
Glu Thr Cys Phe Ala Glu Glu Gly Lys Lys Leu Val Ala Ala Ser Gln
            610                 615                 620
Ala Ala Leu Gly Leu Gly Ser Gly Gly Gly Gly Ser Gly Gly Gly Gly
625                 630                 635                 640
Ser Gly Gly Gly Gly Ser Gly Gly Gly Ser Gly Gly Gly Gly Ser
                645                 650                 655
Gly Gly Gly Gly Ser Gly Gly Gly Gly Ser Gly Gly Gly Gly Ser Asp
            660                 665                 670
His Cys Pro Leu Gly Pro Gly Arg Cys Cys Arg Leu His Thr Val Arg
            675                 680                 685
Ala Ser Leu Glu Asp Leu Gly Trp Ala Asp Trp Val Leu Ser Pro Arg
            690                 695                 700
Glu Val Gln Val Thr Met Cys Ile Gly Ala Cys Pro Ser Gln Phe Arg
705                 710                 715                 720
Ala Ala Asn Met His Ala Gln Ile Lys Thr Ser Leu His Arg Leu Lys
                725                 730                 735
Pro Asp Thr Val Pro Ala Pro Cys Cys Val Pro Ala Ser Tyr Asn Pro
            740                 745                 750
Met Val Leu Ile Gln Lys Thr Asp Thr Gly Val Ser Leu Gln Thr Tyr
            755                 760                 765
```

Asp Asp Leu Leu Ala Lys Asp Cys His Cys Ile
        770                 775

<210> SEQ ID NO 71
<211> LENGTH: 780
<212> TYPE: PRT
<213> ORGANISM: Artificial Sequence
<220> FEATURE:
<223> OTHER INFORMATION: GLP1-GDF15 Fusion Protein 39

<400> SEQUENCE: 71

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Gly Ser Gly Gly Gly Gly Ser Gly Gly Gly Gly Ser Asp Ala His
        35                  40                  45

Lys Ser Glu Val Ala His Arg Phe Lys Asp Leu Gly Glu Glu Asn Phe
    50                  55                  60

Lys Ala Leu Val Leu Ile Ala Phe Ala Gln Tyr Leu Gln Gln Ser Pro
65                  70                  75                  80

Phe Glu Asp His Val Lys Leu Val Asn Glu Val Thr Glu Phe Ala Lys
                85                  90                  95

Thr Cys Val Ala Asp Glu Ser Ala Glu Asn Cys Asp Lys Ser Leu His
            100                 105                 110

Thr Leu Phe Gly Asp Lys Leu Cys Thr Val Ala Thr Leu Arg Glu Thr
        115                 120                 125

Tyr Gly Glu Met Ala Asp Cys Cys Ala Lys Gln Glu Pro Glu Arg Asn
    130                 135                 140

Glu Cys Phe Leu Gln His Lys Asp Asp Asn Pro Asn Leu Pro Arg Leu
145                 150                 155                 160

Val Arg Pro Glu Val Asp Val Met Cys Thr Ala Phe His Asp Asn Glu
                165                 170                 175

Glu Thr Phe Leu Lys Lys Tyr Leu Tyr Glu Ile Ala Arg Arg His Pro
            180                 185                 190

Tyr Phe Tyr Ala Pro Glu Leu Leu Phe Phe Ala Lys Arg Tyr Lys Ala
        195                 200                 205

Ala Phe Thr Glu Cys Cys Gln Ala Ala Asp Lys Ala Ala Cys Leu Leu
    210                 215                 220

Pro Lys Leu Asp Glu Leu Arg Asp Glu Gly Lys Ala Ser Ser Ala Lys
225                 230                 235                 240

Gln Arg Leu Lys Cys Ala Ser Leu Gln Lys Phe Gly Glu Arg Ala Phe
                245                 250                 255

Lys Ala Trp Ala Val Ala Arg Leu Ser Gln Arg Phe Pro Lys Ala Glu
            260                 265                 270

Phe Ala Glu Val Ser Lys Leu Val Thr Asp Leu Thr Lys Val His Thr
        275                 280                 285

Glu Cys Cys His Gly Asp Leu Leu Glu Cys Ala Asp Asp Arg Ala Asp
    290                 295                 300

Leu Ala Lys Tyr Ile Cys Glu Asn Gln Asp Ser Ile Ser Ser Lys Leu
305                 310                 315                 320

Lys Glu Cys Cys Glu Lys Pro Leu Leu Glu Lys Ser His Cys Ile Ala
                325                 330                 335

Glu Val Glu Asn Asp Glu Met Pro Ala Asp Leu Pro Ser Leu Ala Ala
            340                 345                 350

```
Asp Phe Val Glu Ser Lys Asp Val Cys Lys Asn Tyr Ala Glu Ala Lys
            355                 360                 365
Asp Val Phe Leu Gly Met Phe Leu Tyr Glu Tyr Ala Arg Arg His Pro
    370                 375                 380
Asp Tyr Ser Val Val Leu Leu Leu Arg Leu Ala Lys Thr Tyr Glu Thr
385                 390                 395                 400
Thr Leu Glu Lys Cys Cys Ala Ala Ala Asp Pro His Glu Cys Tyr Ala
                405                 410                 415
Lys Val Phe Asp Glu Phe Lys Pro Leu Val Glu Glu Pro Gln Asn Leu
            420                 425                 430
Ile Lys Gln Asn Cys Glu Leu Phe Glu Gln Leu Gly Glu Tyr Lys Phe
        435                 440                 445
Gln Asn Ala Leu Leu Val Arg Tyr Thr Lys Lys Val Pro Gln Val Ser
    450                 455                 460
Thr Pro Thr Leu Val Glu Val Ser Arg Asn Leu Gly Lys Val Gly Ser
465                 470                 475                 480
Lys Cys Cys Lys His Pro Glu Ala Lys Arg Met Pro Cys Ala Glu Asp
                485                 490                 495
Tyr Leu Ser Val Val Leu Asn Gln Leu Cys Val Leu His Glu Lys Thr
            500                 505                 510
Pro Val Ser Asp Arg Val Thr Lys Cys Cys Thr Glu Ser Leu Val Asn
        515                 520                 525
Arg Arg Pro Cys Phe Ser Ala Leu Glu Val Asp Glu Thr Tyr Val Pro
    530                 535                 540
Lys Glu Phe Asn Ala Glu Thr Phe Thr Phe His Ala Asp Ile Cys Thr
545                 550                 555                 560
Leu Ser Glu Lys Glu Arg Gln Ile Lys Lys Gln Thr Ala Leu Val Glu
                565                 570                 575
Leu Val Lys His Lys Pro Lys Ala Thr Lys Glu Gln Leu Lys Ala Val
            580                 585                 590
Met Asp Asp Phe Ala Ala Phe Val Glu Lys Cys Cys Lys Ala Asp Asp
        595                 600                 605
Lys Glu Thr Cys Phe Ala Glu Glu Gly Lys Lys Leu Val Ala Ala Ser
    610                 615                 620
Gln Ala Ala Leu Gly Leu Gly Ser Gly Gly Gly Ser Gly Gly Gly Gly
625                 630                 635                 640
Gly Ser Gly Gly Gly Ser Gly Gly Gly Ser Gly Gly Gly Ser Gly Gly
                645                 650                 655
Ser Gly Gly Gly Ser Gly Gly Gly Ser Gly Gly Gly Gly Gly Gly Ser
            660                 665                 670
Asp His Cys Pro Leu Gly Pro Gly Arg Cys Cys Arg Leu His Thr Val
        675                 680                 685
Arg Ala Ser Leu Glu Asp Leu Gly Trp Ala Asp Trp Val Leu Ser Pro
    690                 695                 700
Arg Glu Val Gln Val Thr Met Cys Ile Gly Ala Cys Pro Ser Gln Phe
705                 710                 715                 720
Arg Ala Ala Asn Met His Ala Gln Ile Lys Thr Ser Leu His Arg Leu
                725                 730                 735
Lys Pro Asp Thr Val Pro Ala Pro Cys Cys Val Pro Ala Ser Tyr Asn
            740                 745                 750
Pro Met Val Leu Ile Gln Lys Thr Asp Thr Gly Val Ser Leu Gln Thr
        755                 760                 765
Tyr Asp Asp Leu Leu Ala Lys Asp Cys His Cys Ile
```

<210> SEQ ID NO 72
<211> LENGTH: 780
<212> TYPE: PRT
<213> ORGANISM: Artificial Sequence
<220> FEATURE:
<223> OTHER INFORMATION: GLP1-GDF15 Fusion Protein 40

<400> SEQUENCE: 72

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Gly Ser Gly Gly Gly Gly Ser Asp Ala His
        35                  40                  45

Lys Ser Glu Val Ala His Arg Phe Lys Asp Leu Gly Glu Glu Thr Phe
50                  55                  60

Lys Ala Leu Val Leu Val Ala Phe Ala Gln Tyr Leu Gln Gln Ser Pro
65                  70                  75                  80

Phe Glu Asp His Val Lys Leu Val Asn Glu Val Thr Glu Phe Ala Lys
                85                  90                  95

Thr Cys Val Ala Asp Glu Ser Ala Glu Asn Cys Asp Lys Ser Leu His
            100                 105                 110

Thr Leu Phe Gly Asp Lys Leu Cys Thr Val Ala Thr Leu Arg Glu Thr
        115                 120                 125

Tyr Gly Glu Met Ala Asp Cys Cys Ala Lys Gln Glu Pro Glu Arg Asn
    130                 135                 140

Glu Cys Phe Leu Gln His Lys Asp Asp Asn Pro Asn Leu Pro Arg Leu
145                 150                 155                 160

Val Arg Pro Glu Val Asp Val Met Cys Thr Ala Phe His Asp Asn Glu
                165                 170                 175

Glu Thr Phe Leu Lys Lys Tyr Leu Tyr Glu Ile Ala Arg Arg His Pro
            180                 185                 190

Tyr Phe Tyr Ala Pro Glu Leu Leu Phe Phe Ala Ala Arg Tyr Lys Ala
        195                 200                 205

Ala Phe Thr Glu Cys Cys Gln Ala Ala Asp Lys Ala Ala Cys Leu Leu
    210                 215                 220

Pro Lys Leu Asp Glu Leu Arg Asp Glu Gly Lys Ala Ser Ser Ala Lys
225                 230                 235                 240

Gln Arg Leu Lys Cys Ala Ser Leu Gln Lys Phe Gly Glu Arg Ala Phe
                245                 250                 255

Lys Ala Trp Ala Val Ala Arg Leu Ser Gln Arg Phe Pro Lys Ala Glu
            260                 265                 270

Phe Ala Glu Val Ser Lys Leu Val Thr Asp Leu Thr Lys Val His Thr
        275                 280                 285

Glu Cys Cys His Gly Asp Leu Leu Glu Cys Ala Asp Asp Arg Ala Asp
    290                 295                 300

Leu Ala Lys Tyr Ile Cys Glu Asn Gln Asp Ser Ile Ser Ser Lys Leu
305                 310                 315                 320

Lys Glu Cys Cys Glu Lys Pro Leu Leu Glu Lys Ser His Cys Leu Ala
                325                 330                 335

Glu Val Glu Asn Asp Glu Met Pro Ala Asp Leu Pro Ser Leu Ala Ala
            340                 345                 350

Asp Phe Val Glu Ser Lys Asp Val Cys Lys Asn Tyr Ala Glu Ala Lys
```

```
                  355                 360                 365
Asp Val Phe Leu Gly Met Phe Leu Tyr Glu Tyr Ala Arg Arg His Pro
                  370                 375                 380
Asp Tyr Ser Val Val Leu Leu Arg Leu Ala Lys Thr Tyr Glu Thr
385                 390                 395                 400
Thr Leu Glu Lys Cys Cys Ala Ala Ala Asp Pro His Glu Cys Tyr Ala
                  405                 410                 415
Lys Val Phe Asp Glu Phe Lys Pro Leu Val Glu Glu Pro Gln Asn Leu
                  420                 425                 430
Ile Lys Gln Asn Cys Glu Leu Phe Glu Gln Leu Gly Glu Tyr Lys Phe
                  435                 440                 445
Gln Asn Ala Leu Leu Val Arg Tyr Thr Lys Lys Val Pro Gln Val Ser
                  450                 455                 460
Thr Pro Thr Leu Val Glu Val Ser Arg Asn Leu Gly Lys Val Gly Ser
465                 470                 475                 480
Lys Cys Cys Lys His Pro Glu Ala Lys Arg Met Pro Cys Ala Glu Asp
                  485                 490                 495
Tyr Leu Ser Val Val Leu Asn Gln Leu Cys Val Leu His Glu Lys Thr
                  500                 505                 510
Pro Val Ser Asp Arg Val Thr Lys Cys Cys Thr Glu Ser Leu Val Asn
                  515                 520                 525
Arg Arg Pro Cys Phe Ser Ala Leu Glu Val Asp Glu Thr Tyr Val Pro
                  530                 535                 540
Lys Glu Phe Asn Ala Glu Thr Phe Thr Phe His Ala Asp Ile Cys Thr
545                 550                 555                 560
Leu Ser Glu Lys Glu Arg Gln Ile Lys Lys Gln Thr Ala Leu Ala Glu
                  565                 570                 575
Leu Val Lys His Lys Pro Lys Ala Thr Lys Glu Gln Leu Lys Thr Val
                  580                 585                 590
Met Asp Asp Phe Ala Ala Phe Val Glu Lys Cys Cys Lys Ala Asp Asp
                  595                 600                 605
Lys Glu Thr Cys Phe Ala Glu Glu Gly Lys Lys Leu Val Ala Ala Ser
                  610                 615                 620
Gln Ala Ala Leu Gly Leu Gly Ser Gly Gly Gly Ser Gly Gly Gly
625                 630                 635                 640
Gly Ser Gly Gly Gly Gly Ser Gly Gly Gly Gly Ser Gly Gly Gly Gly
                  645                 650                 655
Ser Gly Gly Gly Gly Ser Gly Gly Gly Ser Gly Gly Gly Gly Ser
                  660                 665                 670
Asp His Cys Pro Leu Gly Pro Gly Arg Cys Cys Arg Leu His Thr Val
                  675                 680                 685
Arg Ala Ser Leu Glu Asp Leu Gly Trp Ala Asp Trp Val Leu Ser Pro
                  690                 695                 700
Arg Glu Val Gln Val Thr Met Cys Ile Gly Ala Cys Pro Ser Gln Phe
705                 710                 715                 720
Arg Ala Ala Asn Met His Ala Gln Ile Lys Thr Ser Leu His Arg Leu
                  725                 730                 735
Lys Pro Asp Thr Val Pro Ala Pro Cys Cys Val Pro Ala Ser Tyr Asn
                  740                 745                 750
Pro Met Val Leu Ile Gln Lys Thr Asp Thr Gly Val Ser Leu Gln Thr
                  755                 760                 765
Tyr Asp Asp Leu Leu Ala Lys Asp Cys His Cys Ile
                  770                 775                 780
```

<210> SEQ ID NO 73
<211> LENGTH: 780
<212> TYPE: PRT
<213> ORGANISM: Artificial Sequence
<220> FEATURE:
<223> OTHER INFORMATION: GLP1-GDF15 Fusion Protein 41

<400> SEQUENCE: 73

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Ser Gly Gly Gly Ser Gly Gly Gly Ser Asp Ala His
            35                  40                  45

Lys Ser Glu Val Ala His Arg Phe Lys Asp Leu Gly Glu Glu Thr Phe
 50                  55                  60

Lys Ala Leu Val Leu Val Ala Phe Ala Gln Tyr Leu Gln Gln Ser Pro
65                   70                  75                  80

Phe Glu Asp His Val Lys Leu Val Asn Glu Val Thr Glu Phe Ala Lys
                85                  90                  95

Thr Cys Val Ala Asp Glu Ser Ala Glu Asn Cys Asp Lys Ser Leu His
                100                 105                 110

Thr Leu Phe Gly Asp Lys Leu Cys Thr Val Ala Thr Leu Arg Glu Thr
            115                 120                 125

Tyr Gly Glu Met Ala Asp Cys Cys Ala Lys Gln Glu Pro Glu Arg Asn
130                 135                 140

Glu Cys Phe Leu Gln His Lys Asp Asp Asn Pro Asn Leu Pro Arg Leu
145                 150                 155                 160

Val Arg Pro Glu Val Asp Val Met Cys Thr Ala Phe His Asp Asn Glu
                165                 170                 175

Glu Thr Phe Leu Lys Lys Tyr Leu Tyr Glu Ile Ala Arg Arg His Pro
            180                 185                 190

Tyr Phe Tyr Ala Pro Glu Leu Leu Phe Phe Ala Ala Arg Tyr Lys Ala
        195                 200                 205

Ala Phe Thr Glu Cys Cys Gln Ala Ala Asp Lys Ala Ala Cys Leu Leu
210                 215                 220

Pro Lys Leu Asp Glu Leu Arg Asp Glu Gly Lys Ala Ser Ser Ala Lys
225                 230                 235                 240

Gln Arg Leu Lys Cys Ala Ser Leu Gln Lys Phe Gly Glu Arg Ala Phe
                245                 250                 255

Lys Ala Trp Ala Val Ala Arg Leu Ser Gln Arg Phe Pro Lys Ala Glu
            260                 265                 270

Phe Ala Glu Val Ser Lys Leu Val Thr Asp Leu Thr Lys Val His Thr
        275                 280                 285

Glu Cys Cys His Gly Asp Leu Leu Glu Cys Ala Asp Asp Arg Ala Asp
290                 295                 300

Leu Ala Lys Tyr Ile Cys Glu Asn Gln Asp Ser Ile Ser Ser Lys Leu
305                 310                 315                 320

Lys Glu Cys Cys Glu Lys Pro Leu Leu Glu Lys Ser His Cys Leu Ala
                325                 330                 335

Glu Val Glu Asn Asp Glu Met Pro Ala Asp Leu Pro Ser Leu Ala Ala
            340                 345                 350

Asp Phe Val Glu Ser Lys Asp Val Cys Lys Asn Tyr Ala Glu Ala Lys
        355                 360                 365
```

```
Asp Val Phe Leu Gly Met Phe Leu Tyr Glu Tyr Ala Arg Arg His Pro
    370                 375                 380

Asp Tyr Ser Val Val Leu Leu Arg Leu Ala Lys Thr Tyr Glu Thr
385                 390                 395                 400

Thr Leu Glu Lys Cys Cys Ala Ala Ala Asp Pro His Glu Cys Tyr Ala
                405                 410                 415

Lys Val Phe Asp Glu Phe Lys Pro Leu Val Glu Glu Pro Gln Asn Leu
                420                 425                 430

Ile Lys Gln Asn Cys Glu Leu Phe Glu Gln Leu Gly Glu Tyr Lys Phe
                435                 440                 445

Gln Asn Ala Leu Leu Val Arg Tyr Thr Lys Lys Val Pro Gln Val Ser
    450                 455                 460

Thr Pro Thr Leu Val Glu Val Ser Arg Asn Leu Gly Lys Val Gly Ser
465                 470                 475                 480

Lys Cys Cys Lys His Pro Glu Ala Lys Arg Met Pro Cys Ala Glu Asp
                485                 490                 495

Tyr Leu Ser Val Val Leu Asn Gln Leu Cys Val Leu His Glu Lys Thr
                500                 505                 510

Pro Val Ser Asp Arg Val Thr Lys Cys Cys Thr Glu Ser Leu Val Asn
    515                 520                 525

Arg Arg Pro Cys Phe Ser Ala Leu Glu Val Asp Glu Thr Tyr Val Pro
    530                 535                 540

Lys Glu Phe Asn Ala Glu Thr Phe Thr Phe His Ala Asp Ile Cys Thr
545                 550                 555                 560

Leu Ser Glu Lys Glu Arg Gln Ile Lys Lys Gln Thr Ala Leu Ala Glu
                565                 570                 575

Leu Val Lys His Lys Pro Lys Ala Thr Lys Glu Gln Leu Lys Thr Val
                580                 585                 590

Met Asp Asp Phe Ala Ala Phe Val Glu Lys Cys Cys Lys Ala Asp Asp
                595                 600                 605

Lys Glu Thr Cys Phe Ala Glu Glu Gly Lys Lys Leu Val Ala Ala Ser
    610                 615                 620

Gln Ala Ala Leu Gly Leu Gly Ser Gly Gly Gly Gly Ser Gly Gly Gly
625                 630                 635                 640

Gly Ser Gly Gly Gly Gly Ser Gly Gly Gly Gly Ser Gly Gly Gly Gly
                645                 650                 655

Ser Gly Gly Gly Gly Ser Gly Gly Gly Ser Gly Gly Gly Gly Ser
                660                 665                 670

Asp His Cys Pro Leu Gly Pro Gly Arg Cys Cys Arg Leu His Thr Val
    675                 680                 685

Arg Ala Ser Leu Glu Asp Leu Gly Trp Ala Asp Trp Val Leu Ser Pro
    690                 695                 700

Arg Glu Val Gln Val Thr Met Cys Ile Gly Ala Cys Pro Ser Gln Phe
705                 710                 715                 720

Arg Ala Ala Asn Met His Ala Gln Ile Lys Thr Ser Leu His Arg Leu
                725                 730                 735

Lys Pro Asp Thr Val Pro Ala Pro Cys Cys Val Pro Ala Ser Tyr Asn
                740                 745                 750

Pro Met Val Leu Arg Gln Lys Thr Asp Thr Gly Val Ser Leu Gln Thr
    755                 760                 765

Tyr Asp Asp Leu Leu Ala Lys Asp Cys His Cys Ile
    770                 775                 780
```

<210> SEQ ID NO 74
<211> LENGTH: 778
<212> TYPE: PRT
<213> ORGANISM: Artificial Sequence
<220> FEATURE:
<223> OTHER INFORMATION: GLP1-GDF15 Fusion Protein 42

<400> SEQUENCE: 74

```
Glu Gly Thr Phe Thr Ser Asp Val Ser Ser Tyr Leu Glu Gln Ala
1               5                   10                  15

Ala Lys Glu Phe Ile Ala Trp Leu Val Lys Gly Gly Gly Gly Gly
                20                  25                  30

Ser Gly Gly Gly Ser Gly Gly Gly Ser Asp Ala His Lys Ser
            35                  40                  45

Glu Val Ala His Arg Phe Lys Asp Leu Gly Glu Glu Thr Phe Lys Ala
    50                  55                  60

Leu Val Leu Val Ala Phe Ala Gln Tyr Leu Gln Gln Ser Pro Phe Glu
65                  70                  75                  80

Asp His Val Lys Leu Val Asn Glu Val Thr Glu Phe Ala Lys Thr Cys
                85                  90                  95

Val Ala Asp Glu Ser Ala Glu Asn Cys Asp Lys Ser Leu His Thr Leu
            100                 105                 110

Phe Gly Asp Lys Leu Cys Thr Val Ala Thr Leu Arg Glu Thr Tyr Gly
        115                 120                 125

Glu Met Ala Asp Cys Cys Ala Lys Gln Glu Pro Glu Arg Asn Glu Cys
130                 135                 140

Phe Leu Gln His Lys Asp Asp Asn Pro Asn Leu Pro Arg Leu Val Arg
145                 150                 155                 160

Pro Glu Val Asp Val Met Cys Thr Ala Phe His Asp Asn Glu Glu Thr
                165                 170                 175

Phe Leu Lys Lys Tyr Leu Tyr Glu Ile Ala Arg Arg His Pro Tyr Phe
            180                 185                 190

Tyr Ala Pro Glu Leu Leu Phe Phe Ala Ala Arg Tyr Lys Ala Ala Phe
        195                 200                 205

Thr Glu Cys Cys Gln Ala Ala Asp Lys Ala Ala Cys Leu Leu Pro Lys
210                 215                 220

Leu Asp Glu Leu Arg Asp Glu Gly Lys Ala Ser Ser Ala Lys Gln Arg
225                 230                 235                 240

Leu Lys Cys Ala Ser Leu Gln Lys Phe Gly Glu Arg Ala Phe Lys Ala
                245                 250                 255

Trp Ala Val Ala Arg Leu Ser Gln Arg Phe Pro Lys Ala Glu Phe Ala
            260                 265                 270

Glu Val Ser Lys Leu Val Thr Asp Leu Thr Lys Val His Thr Glu Cys
        275                 280                 285

Cys His Gly Asp Leu Leu Glu Cys Ala Asp Asp Arg Ala Asp Leu Ala
290                 295                 300

Lys Tyr Ile Cys Glu Asn Gln Asp Ser Ile Ser Ser Lys Leu Lys Glu
305                 310                 315                 320

Cys Cys Glu Lys Pro Leu Leu Glu Lys Ser His Cys Leu Ala Glu Val
                325                 330                 335

Glu Asn Asp Glu Met Pro Ala Asp Leu Pro Ser Leu Ala Ala Asp Phe
            340                 345                 350

Val Glu Ser Lys Asp Val Cys Lys Asn Tyr Ala Glu Ala Lys Asp Val
        355                 360                 365
```

```
Phe Leu Gly Met Phe Leu Tyr Glu Tyr Ala Arg Arg His Pro Asp Tyr
    370                 375                 380

Ser Val Val Leu Leu Arg Leu Ala Lys Thr Tyr Glu Thr Thr Leu
385                 390                 395                 400

Glu Lys Cys Cys Ala Ala Asp Pro His Glu Cys Tyr Ala Lys Val
                405                 410                 415

Phe Asp Glu Phe Lys Pro Leu Val Glu Glu Pro Gln Asn Leu Ile Lys
                420                 425                 430

Gln Asn Cys Glu Leu Phe Glu Gln Leu Gly Glu Tyr Lys Phe Gln Asn
                435                 440                 445

Ala Leu Leu Val Arg Tyr Thr Lys Lys Val Pro Gln Val Ser Thr Pro
    450                 455                 460

Thr Leu Val Glu Val Ser Arg Asn Leu Gly Lys Val Gly Ser Lys Cys
465                 470                 475                 480

Cys Lys His Pro Glu Ala Lys Arg Met Pro Cys Ala Glu Asp Tyr Leu
                485                 490                 495

Ser Val Val Leu Asn Gln Leu Cys Val Leu His Glu Lys Thr Pro Val
                500                 505                 510

Ser Asp Arg Val Thr Lys Cys Cys Thr Glu Ser Leu Val Asn Arg Arg
    515                 520                 525

Pro Cys Phe Ser Ala Leu Glu Val Asp Glu Thr Tyr Val Pro Lys Glu
    530                 535                 540

Phe Asn Ala Glu Thr Phe Thr Phe His Ala Asp Ile Cys Thr Leu Ser
545                 550                 555                 560

Glu Lys Glu Arg Gln Ile Lys Lys Gln Thr Ala Leu Ala Glu Leu Val
                565                 570                 575

Lys His Lys Pro Lys Ala Thr Lys Glu Gln Leu Lys Thr Val Met Asp
                580                 585                 590

Asp Phe Ala Ala Phe Val Glu Lys Cys Cys Lys Ala Asp Asp Lys Glu
                595                 600                 605

Thr Cys Phe Ala Glu Glu Gly Lys Lys Leu Val Ala Ala Ser Gln Ala
    610                 615                 620

Ala Leu Gly Leu Gly Ser Gly Gly Gly Ser Gly Gly Gly Ser
625                 630                 635                 640

Gly Gly Gly Gly Ser Gly Gly Gly Ser Gly Gly Gly Ser Gly
                645                 650                 655

Gly Gly Ser Gly Gly Gly Ser Gly Gly Gly Ser Asp His
                660                 665                 670

Cys Pro Leu Gly Pro Gly Arg Cys Cys Arg Leu His Thr Val Arg Ala
    675                 680                 685

Ser Leu Glu Asp Leu Gly Trp Ala Asp Trp Val Leu Ser Pro Arg Glu
    690                 695                 700

Val Gln Val Thr Met Cys Ile Gly Ala Cys Pro Ser Gln Phe Arg Ala
705                 710                 715                 720

Ala Asn Met His Ala Gln Ile Lys Thr Ser Leu His Arg Leu Lys Pro
                725                 730                 735

Asp Thr Val Pro Ala Pro Cys Cys Val Pro Ala Ser Tyr Asn Pro Met
                740                 745                 750

Val Leu Ile Gln Lys Thr Asp Thr Gly Val Ser Leu Gln Thr Tyr Asp
                755                 760                 765

Asp Leu Leu Ala Lys Asp Cys His Cys Ile
    770                 775
```

<210> SEQ ID NO 75
<211> LENGTH: 735
<212> TYPE: PRT
<213> ORGANISM: Artificial Sequence
<220> FEATURE:
<223> OTHER INFORMATION: GSA-GDF15 fusion protein

<400> SEQUENCE: 75

```
Asp Ala His Lys Ser Glu Val Ala His Arg Phe Lys Asp Leu Gly Glu
1               5                   10                  15

Glu Thr Phe Lys Ala Leu Val Leu Val Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Ala Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Leu Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
```

```
            370                 375                 380
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Ala Glu Leu Val Lys His Lys Pro Lys Ala Thr Lys Glu Gln Leu
    530                 535                 540

Lys Thr Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Gly Gly Ser
            580                 585                 590

Gly Gly Gly Gly Ser Gly Gly Gly Ser Gly Gly Gly Gly Ser Gly Gly
        595                 600                 605

Gly Gly Gly Ser Gly Gly Gly Ser Gly Gly Gly Gly Ser Gly Gly Gly
    610                 615                 620

Gly Gly Ser Asp His Cys Pro Leu Gly Pro Gly Arg Cys Cys Arg Leu
625                 630                 635                 640

His Thr Val Arg Ala Ser Leu Glu Asp Leu Gly Trp Ala Asp Trp Val
                645                 650                 655

Leu Ser Pro Arg Glu Val Gln Val Thr Met Cys Ile Gly Ala Cys Pro
            660                 665                 670

Ser Gln Phe Arg Ala Ala Asn Met His Ala Gln Ile Lys Thr Ser Leu
        675                 680                 685

His Arg Leu Lys Pro Asp Thr Val Pro Ala Pro Cys Cys Val Pro Ala
    690                 695                 700

Ser Tyr Asn Pro Met Val Leu Ile Gln Lys Thr Asp Thr Gly Val Ser
705                 710                 715                 720

Leu Gln Thr Tyr Asp Asp Leu Leu Ala Lys Asp Cys His Cys Ile
                725                 730                 735

<210> SEQ ID NO 76
<211> LENGTH: 20
<212> TYPE: PRT
<213> ORGANISM: Artificial Sequence
<220> FEATURE:
<223> OTHER INFORMATION: HSE peptide

<400> SEQUENCE: 76

His Ser Glu Gly Thr Phe Thr Ser Asp Val Ser Ser Tyr Leu Glu Gly
```

-continued

```
1               5                   10                  15

Gln Ala Ala Lys
            20

<210> SEQ ID NO 77
<211> LENGTH: 20
<212> TYPE: PRT
<213> ORGANISM: Artificial Sequence
<220> FEATURE:
<223> OTHER INFORMATION: HGE-1 peptide

<400> SEQUENCE: 77

His Gly Glu Gly Thr Phe Thr Ser Asp Val Ser Ser Tyr Leu Glu Glu
1               5                   10                  15

Gln Ala Ala Lys
            20

<210> SEQ ID NO 78
<211> LENGTH: 12
<212> TYPE: PRT
<213> ORGANISM: Artificial Sequence
<220> FEATURE:
<223> OTHER INFORMATION: HGE-2 peptide

<400> SEQUENCE: 78

His Gly Glu Gly Thr Phe Thr Ser Asp Leu Ser Lys
1               5                   10

<210> SEQ ID NO 79
<211> LENGTH: 21
<212> TYPE: PRT
<213> ORGANISM: Artificial Sequence
<220> FEATURE:
<223> OTHER INFORMATION: ALV peptide

<400> SEQUENCE: 79

Ala Leu Val Leu Ile Ala Phe Ala Gln Tyr Leu Gln Gln Ser Pro Phe
1               5                   10                  15

Glu Asp His Val Lys
            20

<210> SEQ ID NO 80
<211> LENGTH: 16
<212> TYPE: PRT
<213> ORGANISM: Artificial Sequence
<220> FEATURE:
<223> OTHER INFORMATION: TDT peptide

<400> SEQUENCE: 80

Thr Asp Thr Gly Val Ser Leu Gln Thr Tyr Asp Asp Leu Leu Ala Lys
1               5                   10                  15

<210> SEQ ID NO 81
<211> LENGTH: 727
<212> TYPE: PRT
<213> ORGANISM: Artificial Sequence
<220> FEATURE:
<223> OTHER INFORMATION: HSA-GDF15 fusion protein

<400> SEQUENCE: 81

Glu Phe His His His His His His Asp Ala His Lys Ser Glu Val Ala
1               5                   10                  15

His Arg Phe Lys Asp Leu Gly Glu Glu Asn Phe Lys Ala Leu Val Leu
            20                  25                  30
```

```
Ile Ala Phe Ala Gln Tyr Leu Gln Gln Ser Pro Phe Glu Asp His Val
             35                  40                  45

Lys Leu Val Asn Glu Val Thr Glu Phe Ala Lys Thr Cys Val Ala Asp
 50                  55                  60

Glu Ser Ala Glu Asn Cys Asp Lys Ser Leu His Thr Leu Phe Gly Asp
 65                  70                  75                  80

Lys Leu Cys Thr Val Ala Thr Leu Arg Glu Thr Tyr Gly Glu Met Ala
                 85                  90                  95

Asp Cys Cys Ala Lys Gln Glu Pro Glu Arg Asn Glu Cys Phe Leu Gln
                100                 105                 110

His Lys Asp Asp Asn Pro Asn Leu Pro Arg Leu Val Arg Pro Glu Val
            115                 120                 125

Asp Val Met Cys Thr Ala Phe His Asp Asn Glu Glu Thr Phe Leu Lys
        130                 135                 140

Lys Tyr Leu Tyr Glu Ile Ala Arg Arg His Pro Tyr Phe Tyr Ala Pro
145                 150                 155                 160

Glu Leu Leu Phe Phe Ala Lys Arg Tyr Lys Ala Ala Phe Thr Glu Cys
                165                 170                 175

Cys Gln Ala Ala Asp Lys Ala Ala Cys Leu Leu Pro Lys Leu Asp Glu
            180                 185                 190

Leu Arg Asp Glu Gly Lys Ala Ser Ser Ala Lys Gln Arg Leu Lys Cys
        195                 200                 205

Ala Ser Leu Gln Lys Phe Gly Glu Arg Ala Phe Lys Ala Trp Ala Val
        210                 215                 220

Ala Arg Leu Ser Gln Arg Phe Pro Lys Ala Glu Phe Ala Glu Val Ser
225                 230                 235                 240

Lys Leu Val Thr Asp Leu Thr Lys Val His Thr Glu Cys Cys His Gly
                245                 250                 255

Asp Leu Leu Glu Cys Ala Asp Asp Arg Ala Asp Leu Ala Lys Tyr Ile
            260                 265                 270

Cys Glu Asn Gln Asp Ser Ile Ser Ser Lys Leu Lys Glu Cys Cys Glu
        275                 280                 285

Lys Pro Leu Leu Glu Lys Ser His Cys Ile Ala Glu Val Glu Asn Asp
290                 295                 300

Glu Met Pro Ala Asp Leu Pro Ser Leu Ala Ala Asp Phe Val Glu Ser
305                 310                 315                 320

Lys Asp Val Cys Lys Asn Tyr Ala Glu Ala Lys Asp Val Phe Leu Gly
                325                 330                 335

Met Phe Leu Tyr Glu Tyr Ala Arg Arg His Pro Asp Tyr Ser Val Val
            340                 345                 350

Leu Leu Leu Arg Leu Ala Lys Thr Tyr Glu Thr Thr Leu Glu Lys Cys
        355                 360                 365

Cys Ala Ala Ala Asp Pro His Glu Cys Tyr Ala Lys Val Phe Asp Glu
        370                 375                 380

Phe Lys Pro Leu Val Glu Glu Pro Gln Asn Leu Ile Lys Gln Asn Cys
385                 390                 395                 400

Glu Leu Phe Glu Gln Leu Gly Glu Tyr Lys Phe Gln Asn Ala Leu Leu
                405                 410                 415

Val Arg Tyr Thr Lys Lys Val Pro Gln Val Ser Thr Pro Thr Leu Val
            420                 425                 430

Glu Val Ser Arg Asn Leu Gly Lys Val Gly Ser Lys Cys Cys Lys His
        435                 440                 445

Pro Glu Ala Lys Arg Met Pro Cys Ala Glu Asp Tyr Leu Ser Val Val
```

```
              450                 455                 460
Leu Asn Gln Leu Cys Val Leu His Glu Lys Thr Pro Val Ser Asp Arg
465                 470                 475                 480

Val Thr Lys Cys Cys Thr Glu Ser Leu Val Asn Arg Arg Pro Cys Phe
                485                 490                 495

Ser Ala Leu Glu Val Asp Glu Thr Tyr Val Pro Lys Glu Phe Asn Ala
                500                 505                 510

Glu Thr Phe Thr Phe His Ala Asp Ile Cys Thr Leu Ser Glu Lys Glu
            515                 520                 525

Arg Gln Ile Lys Lys Gln Thr Ala Leu Val Glu Leu Val Lys His Lys
        530                 535                 540

Pro Lys Ala Thr Lys Glu Gln Leu Lys Ala Val Met Asp Asp Phe Ala
545                 550                 555                 560

Ala Phe Val Glu Lys Cys Cys Lys Ala Asp Asp Lys Glu Thr Cys Phe
                565                 570                 575

Ala Glu Glu Gly Lys Lys Leu Val Ala Ala Ser Gln Ala Ala Leu Gly
                580                 585                 590

Leu Gly Ser Gly Gly Gly Gly Ser Gly Gly Gly Ser Gly Gly Gly
            595                 600                 605

Gly Ser Gly Gly Gly Gly Ser Ala Arg Asn Gly Asp His Cys Pro Leu
610                 615                 620

Gly Pro Gly Arg Cys Cys Arg Leu His Thr Val Arg Ala Ser Leu Glu
625                 630                 635                 640

Asp Leu Gly Trp Ala Asp Trp Val Leu Ser Pro Arg Glu Val Gln Val
                645                 650                 655

Thr Met Cys Ile Gly Ala Cys Pro Ser Gln Phe Arg Ala Ala Asn Met
            660                 665                 670

His Ala Gln Ile Lys Thr Ser Leu His Arg Leu Lys Pro Asp Thr Val
        675                 680                 685

Pro Ala Pro Cys Cys Val Pro Ala Ser Tyr Asn Pro Met Val Leu Ile
                690                 695                 700

Gln Lys Thr Asp Thr Gly Val Ser Leu Gln Thr Tyr Asp Asp Leu Leu
705                 710                 715                 720

Ala Lys Asp Cys His Cys Ile
            725

<210> SEQ ID NO 82
<211> LENGTH: 16
<212> TYPE: PRT
<213> ORGANISM: Artificial Sequence
<220> FEATURE:
<223> OTHER INFORMATION: VVS peptide

<400> SEQUENCE: 82

Val Val Ser Val Leu Thr Val Leu His Gln Asp Trp Leu Asn Gly Lys
1               5                   10                  15

<210> SEQ ID NO 83
<211> LENGTH: 713
<212> TYPE: PRT
<213> ORGANISM: Artificial Sequence
<220> FEATURE:
<223> OTHER INFORMATION: HSA-GDF15 fusion peptide

<400> SEQUENCE: 83

Asp Ala His Lys Ser Glu Val Ala His Arg Phe Lys Asp Leu Gly Glu
1               5                   10                  15
```

```
Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
```

```
                435                 440                 445
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Pro Ala Pro Ala Pro Asp His Cys
        595                 600                 605

Pro Leu Gly Pro Gly Arg Cys Cys Arg Leu His Thr Val Arg Ala Ser
    610                 615                 620

Leu Glu Asp Leu Gly Trp Ala Asp Trp Val Leu Ser Pro Arg Glu Val
625                 630                 635                 640

Gln Val Thr Met Cys Ile Gly Ala Cys Pro Ser Gln Phe Arg Ala Ala
                645                 650                 655

Asn Met His Ala Gln Ile Lys Thr Ser Leu His Arg Leu Lys Pro Asp
            660                 665                 670

Thr Val Pro Ala Pro Cys Cys Val Pro Ala Ser Tyr Asn Pro Met Val
        675                 680                 685

Leu Ile Gln Lys Thr Asp Thr Gly Val Ser Leu Gln Thr Tyr Asp Asp
    690                 695                 700

Leu Leu Ala Lys Asp Cys His Cys Ile
705                 710
```

<210> SEQ ID NO 84
<211> LENGTH: 762
<212> TYPE: PRT
<213> ORGANISM: Artificial Sequence
<220> FEATURE:
<223> OTHER INFORMATION: GLP1-GDF15 (I89R) fusion peptide

<400> SEQUENCE: 84

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ala Pro Ala Pro Ala Pro Ala Pro Ala Pro
        35                  40                  45

Pro Asp Ala His Lys Ser Glu Val Ala His Arg Phe Lys Asp Leu Gly
    50                  55                  60

Glu Glu Asn Phe Lys Ala Leu Val Leu Ile Ala Phe Ala Gln Tyr Leu
65                  70                  75                  80

Gln Gln Ser Pro Phe Glu Asp His Val Lys Leu Val Asn Glu Val Thr
```

```
                          85                  90                  95
Glu Phe Ala Lys Thr Cys Val Ala Asp Glu Ser Ala Glu Asn Cys Asp
                100                 105                 110

Lys Ser Leu His Thr Leu Phe Gly Asp Lys Leu Cys Thr Val Ala Thr
            115                 120                 125

Leu Arg Glu Thr Tyr Gly Met Ala Asp Cys Cys Ala Lys Gln Glu
        130                 135                 140

Pro Glu Arg Asn Glu Cys Phe Leu Gln His Lys Asp Asp Asn Pro Asn
145                 150                 155                 160

Leu Pro Arg Leu Val Arg Pro Glu Val Asp Val Met Cys Thr Ala Phe
                165                 170                 175

His Asp Asn Glu Glu Thr Phe Leu Lys Lys Tyr Leu Tyr Glu Ile Ala
            180                 185                 190

Arg Arg His Pro Tyr Phe Tyr Ala Pro Glu Leu Leu Phe Phe Ala Lys
                195                 200                 205

Arg Tyr Lys Ala Ala Phe Thr Glu Cys Cys Gln Ala Ala Asp Lys Ala
        210                 215                 220

Ala Cys Leu Leu Pro Lys Leu Asp Glu Leu Arg Asp Glu Gly Lys Ala
225                 230                 235                 240

Ser Ser Ala Lys Gln Arg Leu Lys Cys Ala Ser Leu Gln Lys Phe Gly
                245                 250                 255

Glu Arg Ala Phe Lys Ala Trp Ala Val Ala Arg Leu Ser Gln Arg Phe
            260                 265                 270

Pro Lys Ala Glu Phe Ala Glu Val Ser Lys Leu Val Thr Asp Leu Thr
        275                 280                 285

Lys Val His Thr Glu Cys Cys His Gly Asp Leu Leu Glu Cys Ala Asp
290                 295                 300

Asp Arg Ala Asp Leu Ala Lys Tyr Ile Cys Glu Asn Gln Asp Ser Ile
305                 310                 315                 320

Ser Ser Lys Leu Lys Glu Cys Cys Glu Lys Pro Leu Leu Glu Lys Ser
                325                 330                 335

His Cys Ile Ala Glu Val Glu Asn Asp Glu Met Pro Ala Asp Leu Pro
            340                 345                 350

Ser Leu Ala Ala Asp Phe Val Glu Ser Lys Asp Val Cys Lys Asn Tyr
        355                 360                 365

Ala Glu Ala Lys Asp Val Phe Leu Gly Met Phe Leu Tyr Glu Tyr Ala
        370                 375                 380

Arg Arg His Pro Asp Tyr Ser Val Val Leu Leu Leu Arg Leu Ala Lys
385                 390                 395                 400

Thr Tyr Glu Thr Thr Leu Glu Lys Cys Cys Ala Ala Ala Asp Pro His
                405                 410                 415

Glu Cys Tyr Ala Lys Val Phe Asp Glu Phe Lys Pro Leu Val Glu Glu
            420                 425                 430

Pro Gln Asn Leu Ile Lys Gln Asn Cys Glu Leu Phe Glu Gln Leu Gly
        435                 440                 445

Glu Tyr Lys Phe Gln Asn Ala Leu Leu Val Arg Tyr Thr Lys Lys Val
        450                 455                 460

Pro Gln Val Ser Thr Pro Thr Leu Val Glu Val Ser Arg Asn Leu Gly
465                 470                 475                 480

Lys Val Gly Ser Lys Cys Cys Lys His Pro Glu Ala Lys Arg Met Pro
                485                 490                 495

Cys Ala Glu Asp Tyr Leu Ser Val Val Leu Asn Gln Leu Cys Val Leu
            500                 505                 510
```

```
His Glu Lys Thr Pro Val Ser Asp Arg Val Thr Lys Cys Cys Thr Glu
    515                 520                 525

Ser Leu Val Asn Arg Arg Pro Cys Phe Ser Ala Leu Glu Val Asp Glu
    530                 535                 540

Thr Tyr Val Pro Lys Glu Phe Asn Ala Glu Thr Phe Thr Phe His Ala
545                 550                 555                 560

Asp Ile Cys Thr Leu Ser Glu Lys Glu Arg Gln Ile Lys Lys Gln Thr
                565                 570                 575

Ala Leu Val Glu Leu Val Lys His Lys Pro Lys Ala Thr Lys Glu Gln
                580                 585                 590

Leu Lys Ala Val Met Asp Asp Phe Ala Ala Phe Val Glu Lys Cys Cys
            595                 600                 605

Lys Ala Asp Asp Lys Glu Thr Cys Phe Ala Glu Glu Gly Lys Lys Leu
    610                 615                 620

Val Ala Ala Ser Gln Ala Ala Leu Gly Leu Ala Pro Ala Pro Ala Pro
625                 630                 635                 640

Ala Pro Ala Pro Ala Pro Ala Pro Ala Pro Ala Pro Ala Pro Asp His
                645                 650                 655

Cys Pro Leu Gly Pro Gly Arg Cys Cys Arg Leu His Thr Val Arg Ala
            660                 665                 670

Ser Leu Glu Asp Leu Gly Trp Ala Asp Trp Val Leu Ser Pro Arg Glu
    675                 680                 685

Val Gln Val Thr Met Cys Ile Gly Ala Cys Pro Ser Gln Phe Arg Ala
    690                 695                 700

Ala Asn Met His Ala Gln Ile Lys Thr Ser Leu His Arg Leu Lys Pro
705                 710                 715                 720

Asp Thr Val Pro Ala Pro Cys Cys Val Pro Ala Ser Tyr Asn Pro Met
                725                 730                 735

Val Leu Arg Gln Lys Thr Asp Thr Gly Val Ser Leu Gln Thr Tyr Asp
            740                 745                 750

Asp Leu Leu Ala Lys Asp Cys His Cys Ile
    755                 760
```

GLUCAGON LIKE PEPTIDE 1 (GLP1)-GROWTH DIFFERENTIATION FACTOR 15 (GDF15) FUSION PROTEINS AND USES THEREOF

CROSS REFERENCE TO RELATED APPLICATIONS

This application is a Section 371 of International Application No. PCT/IB2019/059029, filed on Oct. 22, 2019, which was published in the English language on Apr. 30, 2020, under International Publication No. WO2020084496 A1, which claims priority to U.S. Provisional Application No. 62/784,603, filed Oct. 22, 2018. Each disclosure is incorporated herein by reference in its entirety.

FIELD OF THE INVENTION

The present invention is directed generally to novel glucagon like peptide-1 (GLP1)-growth differentiation factor 15 (GDF15) fusion proteins. The GLP1-GDF15 fusion proteins modulate the GLP1R and/or the GDF15R. The invention also relates to pharmaceutical compositions and methods for use thereof. The novel GLP1-GDF15 fusion proteins are useful for preventing, treating or ameliorating diseases and disorders, such as obesity, type 2 diabetes, the metabolic syndrome, insulin resistance, and dyslipidemia, among others.

REFERENCE TO SEQUENCE LISTING SUBMITTED ELECTRONICALLY

This application contains a sequence listing, which is submitted electronically via EFS-Web as an ASCII formatted sequence listing with a file name "004852_181US1_Sequence_Listing" and a creation date of Apr. 26, 2021 and having a size of 328 kb. The sequence listing submitted via EFS-Web is part of the specification and is herein incorporated by reference in its entirety.

BACKGROUND OF THE INVENTION

GDF15, a member of the TGFβ family, is a secreted protein that circulates in plasma as a 25 kDa homodimer and elicits its biological function through interaction with the brainstem expressed receptor GFRAL (Mullican et al., Nat Med. 23:1150-7 (2017), Yang et al., Nat Med. 23:1158-66 (2017), Hsu et al., Nature 550:255-9 (2017), Emmerson et al., Nat Med 23:1215-9 (2017)). Plasma levels of GDF15 range between 150 and 1150 pg/ml in most individuals (Tsai et al., J Cachexia Sarcopenia Muscle 3:239-43 (2012)). Elevated plasma levels of GDF15 are associated with weight loss due to anorexia and cachexia in cancer, and in renal and heart failure. Furthermore, GDF15 is increased in patients experiencing weight loss after Roux-en-Y gastric bypass (RYGB) surgery (Vila et al., Clin Chem 57:309-16 (2011)).

The correlation between weight loss and GDF15 is conserved in rodents. Overexpression of GDF15 results in decreased food intake, lower body weight and protects mice from obesity, liver steatosis and glucose intolerance upon high fat diet feeding (Baek et al., Gastroenterology 131: 1553-60 (2006), Johnen et al., Nat Med 13:1333-40 (2007), Chrysovergis et al., Int J Obesity 38:1555-64 (2014), Macia et al., PloS One 7:e34868 (2012), Jones et al., Cell Reports 22:1522-30 (2018), Xiong et al., Sci Trans Med 9:412 (2017)). Xenografts of prostate tumor cells transfected with GDF15 also decrease food intake and body weight (Johnen et al., Nat Med 13:1333-40 (2007)). Conversely, numerous investigators have reported that mice lacking GDF15 gain more weight and have greater fat mass than wildtype animals (Strelau et al., J Neurosci 29:13640-8 (2009), Casanovas et al., Haematologica 98:444-7 (2013), Bonaterra et al., J Amer Heart Assoc 1:e002550 (2012), Tsai et al., PloS one. 8:e55174 (2013)).

The potential of pharmacologically administered GDF15 to decrease energy intake and thereby elicit weight loss has been demonstrated in mice, rats and monkeys. Lean mice treated with recombinant GDF15 eat less and lose weight (Johnen et al., Nat Med 13:1333-40 (2007), Hsu et al., Nature 550:255-9 (2017), Mullican et al., Nat Med 23:1150-7 (2017), Tsai et al., Int J Obesity 42:561-71 (2018)). Decreased food intake and body weight is also observed in genetic and diet induced rat and mouse models of obesity after administration of GDF15 (Johnen et al., Nat Med 13:1333-40 (2007), Hsu et al., Nature 550:255-9 (2017), Mullican et al., Nat Med 23:1150-7 (2017), Yang et al., Nat Med 23:1158-66 (2017), Tsai et al., Int J Obesity 42:561-71 (2018), Xiong et al., Sci Trans Med 9:412 (2017)). GDF15 treatment mediated weight loss in diet induced obese mice leads to metabolic improvements including enhanced glucose homeostasis and lower plasma triglycerides and cholesterol. These effects translate to higher species as a six-week daily treatment regimen with recombinant human GDF15 in spontaneously obese non-human primates reduced food intake, body weight, and plasma triglyceride concentrations and improved glucose tolerance (Xiong et al., Sci Trans Med 9:412 (2017)). Furthermore, the half-life of recombinant GDF15 was previously demonstrated to be extended by fusion to human serum albumin (HSA) and is predicted to be a therapeutic suitable for once-weekly dosing in human (Mullican et al., Nat Med 23:1150-7 (2017) and U.S. Patent Publication No. 2017/0327560.

GLP1 is a peptide hormone derived from the enteroendocrine cells of the gut that also reduces food intake leading to weight loss. This function is mediated by interaction with the GLP1 receptor (GLP1R) within the central nervous system and this ligand/receptor interaction in peripheral tissues has additional biological effects including enhancement of glucose stimulated insulin secretion, suppression of glucagon release and slowing of gastric emptying (Druker et al. Cell Met 27:740-56 (2018)). Harnessing all of these biological effects, GLP1R agonists improve glucose homeostasis and drive weight loss in humans. In addition, treatment with GLP1R agonists is reported to significantly improve cardiovascular outcomes in diabetic patients although the exact mechanism is yet to be determined (Lim et al. Trends Endocrinol Metab. 29:238-48 (2018)). GLP1R agonist therapeutics are peptide sequences based on either native human GLP1 or exendin-4 (a peptide isolated from the saliva of the Gila monster lizard) with modifications to prevent enzymatic cleavage. The GLP1R agonists can be delivered via platforms that extend half-life such as lipidation, antibody Fc or human serum albumin (HSA) (Cheang and Moyle, Chem Med Chem 13:662-71 (2018)).

Thus, it is desirable to obtain a GLP1 analogue or derivative thereof and/or a GDF15 analogue or derivative thereof with an improved metabolic stability and pharmacokinetic profile relative to GLP1 or GDF15, respectively. Such derivatives would provide GLP1 receptor and GDF15 receptor modulation with greater duration of action, making them suitable as therapeutic agents for subjects in need of such modulation.

SUMMARY OF THE INVENTION

In one general aspect, the invention relates to novel glucagon-like peptide-1 (GLP1)-growth differentiation factor 15 (GDF15) fusion proteins. The GLP1-GDF15 fusion proteins modulate the GLP1R and/or the GDF15R (GFRAL).

Provided herein are glucagon-like peptide-1 (GLP1)-growth differentiation factor 15 (GDF15) fusion proteins. The GLP1-GDF15 fusion proteins comprise a GLP1 peptide, a first linker peptide, a serum albumin protein, a second linker peptide, and a GDF15 protein.

In certain embodiments, GLP1 peptide comprises an amino acid sequence selected from the group consisting of SEQ ID NOs:1-4.

In certain embodiments, the first linker peptide comprises an amino acid sequence selected from the group consisting of SEQ ID NOs:5-25.

In certain embodiments, the serum albumin protein comprises an amino acid sequence selected from SEQ ID NO:26 or SEQ ID NO:27.

In certain embodiments, the second linker peptide comprises an amino acid sequence selected from the group consisting of SEQ ID NOs:28-30.

In certain embodiments, the GDF15 protein comprises an amino acid sequence selected from SEQ ID NO:31 or SEQ ID NO:32.

In certain embodiments, the GLP1-GDF15 fusion protein comprises an amino acid sequence selected from the group consisting of SEQ ID NOs:33-74 and 84.

Also provided are isolated nucleic acids encoding the GLP1-GDF15 fusion proteins of the invention. Also provided are vectors comprising the isolated nucleic acids of the invention. Also provided are host cells comprising the isolated nucleic acids of the invention or the vectors of the invention.

Also provided are pharmaceutical compositions comprising the GLP1-GDF15 fusion proteins of the invention and a pharmaceutically acceptable carrier.

Also provided are methods for treating or preventing a disease or disorder in a subject in need thereof, wherein said disease or disorder is selected from the group consisting of obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the method comprising administering to the subject in need thereof an effective amount of the pharmaceutical composition of the invention.

Also provided are methods of reducing food intake in a subject in need thereof, the method comprising administering to the subject in need thereof an effective amount of the pharmaceutical composition of the invention.

Also provided are methods of modulating GLP1 receptor activity in a subject in need thereof, the method comprising administering to the subject in need thereof an effective amount of the pharmaceutical composition of the invention.

Also provided are methods of modulating GDF15 receptor (GFRAL) activity in a subject in need thereof, the method comprising administering to the subject in need thereof an effective amount of the pharmaceutical composition of the invention.

In certain embodiments, the pharmaceutical composition is administered via an injection.

Also provided are kits comprising the GLP1-GDF15 fusion proteins of the invention, the isolated nucleic acids of the invention, and/or the vectors of the invention. The kit can, for example, further comprise a device for injection.

Also provided are methods of producing a pharmaceutical composition comprising the GLP1-GDF15 fusion proteins of the invention. The methods comprise combining the GLP1-GDF15 fusion proteins with a pharmaceutically acceptable carrier to obtain the pharmaceutical composition.

Also provided are methods of producing the GLP1-GDF15 fusion proteins of the invention. The methods comprise culturing a cell comprising a nucleic acid encoding the GLP1-GDF15 fusion protein under conditions to produce the GLP1-GDF15 fusion protein and recovering the GLP1-GDF15 fusion protein from the cell or culture.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1:
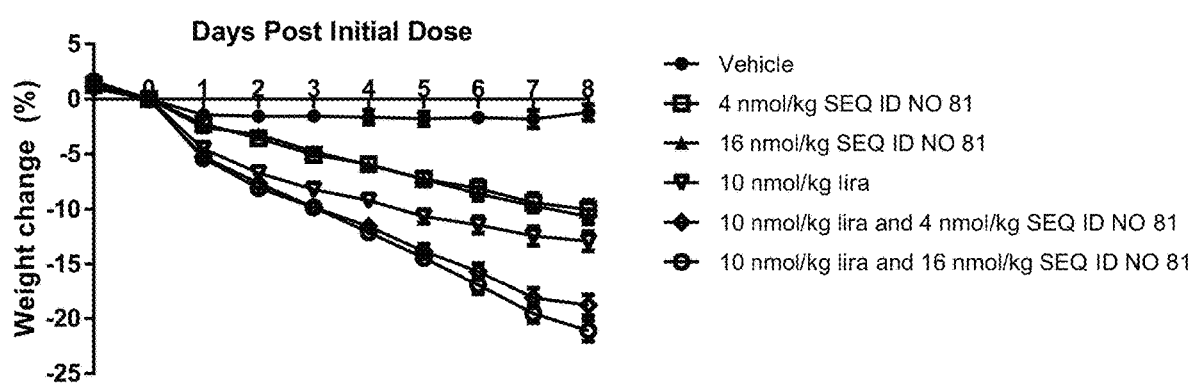
FIG. 1 shows a graph demonstrating percent weight change (from day 0) in DIO mice receiving daily administration of liraglutide (lira) and/or every other day administration of HSA-GDF15 (SEQ ID NO: 81).

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., GLP1 peptide, linker peptides, serum albumin proteins, GDF15 proteins and polynucleotides that encode the peptides), refer to two or more sequences or subsequences that are the same or have a specified percentage of amino acid residues or nucleotides that are the same, when compared and aligned for maximum correspondence, as measured using one of the following sequence comparison algorithms or by visual inspection using methods known in the art in view of the present disclosure.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The term "administering" with respect to the methods of the invention, means a method for therapeutically or prophylactically preventing, treating or ameliorating a syndrome, disorder or disease as described herein by using a conjugate or compound of the invention or a form, composition or medicament thereof. Such methods include administering an effective amount of said conjugate, compound, a form, composition or medicament thereof at different times during the course of a therapy or concurrently in a combination form. The methods of the invention are to be understood as embracing all known therapeutic treatment regimens.

The term "effective amount" means that amount of active conjugate, compound or pharmaceutical agent that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed polypeptide can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The convention one-letter or three-letter code for amino acid residues is used herein. The terms "peptide," "polypeptide," and "protein" can be used interchangeably herein to refer to polymers of amino acids of any length, including those comprising linked (e.g., fused) peptides/polypeptide (e.g., fusion proteins). The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Glucagon-Like Peptide-1 (GLP1)-Growth Differentiation Factor 15 (GDF15) Fusion Proteins Although both GDF15 and GLP1 signaling can reduce food intake, these effects appear to be independent of one another. For example, GDF15 effects are maintained in the absence of GLP1R in mice and conversely, GLP1 treatment still leads to food intake effects in the absence of GFRAL (Hsu et al., Nature 550:255-9 (2017), Mullican et al., Nat Med 23:1150-7 (2017)). Therefore, it is hypothesized that targeting both mechanisms simultaneously could lead to greater food intake reductions and weight loss than either mechanism alone. Combining the independent yet complementary pharmacology of GDF15 and GLP1 agonists through fusion to human serum albumin will deliver benefits on weight loss, insulin sensitivity, insulin secretion and cardiovascular outcomes with a single fully recombinant molecule suitable for once-weekly administration. A major challenge to this approach will be to deliver each agonist within the molecule in a balanced manner that engages the corresponding receptor at the desired level, enough to achieve all desired effects but that avoids on-target adverse effects. This balance can be fine-tuned by adjusting potency and/or pharmacokinetic properties of either agonist arm of the molecule.

In one general aspect, the invention relates to glucagon-like peptide-1 (GLP1)-growth differentiation factor 15 (GDF15) fusion proteins. The GLP1-GDF15 fusion proteins comprise a GLP1 or GLP1 variant peptide, a first linker peptide (e.g., an amino (N)-terminal linker), a human serum albumin (HSA) protein, a second linker peptide (e.g., a carboxy (C)-terminal linker), and a GDF15 or GDF15 variant protein.

Glucagon-Like Peptide-1 (GLP1) or GLP1 Variant Peptide

Glucagon-like peptide 1 (GLP1) is an insulin secretagogue synthesized in the intestine and released in response to the intake of food. It is secreted primarily in two forms, GLP1-(7-37) and GLP1-(7-36)$NH_2$, both of which bind to a specific GLP1 receptor (GLP1R) found in many tissues including the pancreatic beta-cell where it augments glucose-stimulated insulin secretion and in the brainstem where it controls satiety and meal size.

Numerous GLP1 analogs and derivatives are known and can be referred to herein as "GLP1 variants." These GLP1 variant peptides can include the Exendins, which are peptides found in the venom of the Gila monster. These Exendins have sequence homology to native GLP1 and can bind the GLP1 receptor and initiate the signal transduction cascade response.

GLP1 and GLP1 variant peptides have been shown to act in a variety of manners, which can include, but are not limited to, decreasing food intake, stimulating insulin release, lowering glucagon secretion, inhibiting gastric emptying, and enhancing glucose utilization.

GLP1R belongs to the class B family of 7-transmembrane-spanning, heterotrimeric G-protein-coupled receptors and is expressed in a wide range of tissues including, but not limited to, α-, β-, and δ-cells of the pancreatic islets, heart, kidney, stomach, intestine, nodose ganglion neurons of the vagus nerve, and several regions of the central nervous system (CNS) including the hypothalamus and brainstem. The GLP1R can couple to $G\alpha_s$, $G\alpha_q$, $G\alpha_i$, and $G\alpha_o$ (Montrose-Rafizadeh et al., Endocrinology 140:1132-40 (1999); Hallbrink et al., Biochim Biophys Acta 1546:79-86 (2001)) leading to increases in intracellular calcium, adenylate cyclase, and phospholipase C, and activation of PKA, PKC, PI-3K, Epac2, and MAPK signal transduction pathways (Drucker et al., PNAS 84:3434-8 (1987); Wheeler et al., Endrocrinology 133:57-62 (1993); and Holz et al., JBC 270:17749-57 (1995)).

Provided herein are GLP1-GDF15 fusion proteins that comprise a first component, wherein the first component is a GLP1 or GLP1 variant peptide. As used herein, the terms "GLP1 peptide," "GLP1 variant peptide," "GLP1 peptide variant," and "GLP1 or GLP1 variant peptide" are used interchangeably. The GLP1 or GLP1 variant peptide can comprise one of the sequences provided in Table 1. The GLP1 or GLP1 variant peptide can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 1. The GLP1 or GLP1 variant peptide sequence can be chosen based on at least one of the following criteria: (i) expression yield and purity, (ii) in vitro stability, (iii) in vitro potency, (iv) the retention of in vitro potency in combination with the GDF15 or GDF15 variant protein, (v) lack of serine xylosylation or potential for serine xylosylation, and (vi) properties of the GLP1-GDF15 fusion proteins (e.g., in vitro stability, in vivo potency (i.e., whether the GLP1 or GLP1 variant peptide and GDF15 or GDF15 variant protein are capable of having agonist activity on GLP1R and GDF15R (GFRAL) receptor, respectively)).

The GLP1 or GLP1 variant peptides that make up the first component of the GLP1 fusion peptide are intended to encompass peptides that have sufficient homology and functionality to the native GLP1. The GLP1 or GLP1 variant peptides are designed to be capable of binding to the GLP1 receptor in tissues including the pancreas and brainstem resulting in the same signaling pathway and exhibiting the same or similar physiological activity as when the native GLP1 binds the GLP1 receptor in these tissues.

TABLE 1

Glucagon-like peptide-1 and variants thereof

| GLP1 or GLP1 Variant Peptide | Peptide Sequence | SEQ ID NO: |
|---|---|---|
| (A8S, A30E) GLP1 (7-36) | HSEGTFTSDVSSYLEGQAAKEFIEWLVKGR | 1 |
| (A8G, G22E, R36G) GLP1 (7-36) | HGEGTFTSDVSSYLEEQAAKEFIAWLVKGG | 2 |
| Exendin 4 (1-39) | HGEGTFTSDLSKQMEEEAVRLFIEWLKNGGPSSGAPPPS | 3 |
| Exendin 4 (1-28) | HGEGTFTSDLSKQMEEEAVRLFIEWLKN | 4 |

First Linker Peptide: Amino-Terminal Liker (N-Terminal Linker)

Provided herein are GLP1-GDF15 fusion proteins that comprise a second component, wherein the second component is a first linker peptide (i.e., an amino-terminal linker peptide). The first linker peptide can comprise one of the sequences provided in Table 2. The first linker peptide can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 2.

The first linker peptide can, for example, comprise about 5 to about 60 amino acid residues, about 10 to about 50 amino acid residues, about 10 to about 60 amino acid residues, about 5 to about 50 amino acid residues, about 15 to about 40 amino acid residues, about 12 to about 30 amino acid residues, about 12 to about 42 amino acid residues, about 20 to about 25 amino acid residues, about 8 to about 48 amino acid residues, about 10 to about 46 amino acid residues, about 12 to about 44 amino acid residues, about 14 to about 42 amino acid residues, about 16 to about 40 amino acid residues, about 18 to about 38 amino acid residues, about 20 to about 36 amino acid residues, about 20 to about 42 amino acid residues, about 22 to about 34 amino acid residues, about 24 to about 32 amino acid residues, about 26 to about 30 amino acid residues, or any value in between. The first linker peptide can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acid residues.

In certain embodiments, the first linker peptide can contain an alanine-proline repeat (i.e., an AP repeat), wherein an AP dipeptide can be referred to as an AP unit. The AP repeat can comprise 2, 3, 4, 5, 6, 7, 8, 9, 10, 11, 12, 13, 14, 15, 16, 17, 18, 19, 20, 21, 22, 23, 24, 25, 26, or 27 AP units. In certain embodiments, the first linker peptide can, for example, comprise 2 to 25 AP units, 5 to 25 units, 4 to 23 AP units, 6 to 21 AP units, 8 to 19 AP units, 10 to 17 AP units, 12 to 15 AP units, 5 to 10 AP units, 5 to 15 AP units, 10 to 25 AP units, 15 to 25 AP units, 20 to 25 AP units, or any value in between. In certain embodiments, the AP repeat can be internal to an alanine-serine dipeptide (i.e., an AS unit) and a glycine-serine dipeptide (i.e., a GS unit). The AS unit can, for example, be at the amino terminal end of the first linker peptide. The GS unit can, for example, be at the carboxyl terminal end of the first linker peptide.

In certain embodiments, the first linker peptide can contain a glycine-glycine-glycine-glycine-serine repeat (i.e., a $G_4S$ repeat), wherein a $G_4S$ pentapeptide can be referred to as a $G_4S$ unit. The $G_4S$ repeat can comprise 2, 3, 4, 5, 6, 7, 8, 9, 10, 11, 12, 13, 14, or 15 $G_4S$ units. In certain embodiments, the first linker peptide can, for example, comprise 2 to 15 $G_4S$ units, 4 to 13 $G_4S$ units, 6 to 11 $G_4S$ units, 8 to 9 $G_4S$ units, 2 to 8 $G_4S$ units, 2 to 6 $G_4S$ units, 6 to 8 $G_4S$ units, 7 to 8 $G_4S$ units, 7 to 9 $G_4S$ units, 7 to 10 $G_4S$ units, or any value in between. In certain embodiments, an AS or a GS unit can, for example be at the amino terminal end of the first linker peptide.

In certain embodiments, the first linker peptide can contain a glycine-glycine-glycine-glycine-alanine repeat (i.e., a $G_4A$ repeat), wherein a $G_4A$ pentapeptide can be referred to as a $G_4A$ unit. The $G_4A$ repeat can comprise 2, 3, 4, 5, 6, 7, 8, 9, 10, 11, 12, 13, 14, or 15 $G_4A$ units. In certain embodiments, the first linker peptide can, for example, comprise 2 to 15 $G_4A$ units, 4 to 13 $G_4A$ units, 6 to 11 $G_4A$ units, 8 to 9 $G_4A$ units, 2 to 8 $G_4A$ units, 2 to 4 $G_4A$ units, 2 to 6 $G_4A$ units, 4 to 6 $G_4A$ units, 4 to 8 $G_4A$ units, 6 to 8 $G_4A$ units, 6 to 9 $G_4A$ units, 6 to 10 $G_4A$ units or any value in between. In certain embodiments, a glycine-alanine dipeptide (i.e., a GA unit) unit can, for example be at the amino terminal end of the first linker peptide.

In certain embodiments, the first linker peptide can be a poly-glycine peptide. The poly-glycine peptide can comprise about 6 to about 50 glycine residues, about 10 to about 45 glycine residues, about 15 to about 40 glycine residues, about 20 to about 35 glycine residues, about 25 to about 30 glycine residues, about 20 to about 25 glycine residues, or any number in between. The poly-glycine first linker peptide can comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 glycine residues.

The first linker peptide sequence can be chosen based on at least one of the following criteria: (i) expression yield and purity, (ii) in vitro potency, (iii) in vitro stability, (iv) lack of serine xylosylation or potential for serine xylosylation, and (v) properties of the GLP1-GDF15 fusion protein (e.g., in vivo stability, in vivo potency (i.e., whether GLP1 or GLP1 variant peptide and GDF15 or GDF15 variant protein are capable of having agonist activity on GLP1R and GDF15R (GFRAL), respectively)).

TABLE 2

First linker peptides (N-terminal linker peptide)

| First Linker Peptide | Peptide Sequence | SEQ ID NO: |
|---|---|---|
| 1-1 | APAPAPAPAP | 5 |
| 1-2 | APAPAPAPAPAPAPAPAP | 6 |
| 1-3 | APAPAPAPAPAPAPAPAPAPAPAPAP | 7 |
| 1-4 | APAPAPAPAPAPAPAPAPAPAPAPAPAPAPAPAP | 8 |
| 1-5 | APAPAPAPAPAPAPAPAPAPAPAPAPAPAPAPAPAPAPAP | 9 |
| 1-6 | ASAPAPAPAPAPAPAPAPAPGS | 10 |
| 1-7 | ASAPAPAPAPAPGS | 11 |
| 1-8 | ASGGGGSGGGGS | 12 |
| 1-9 | ASGGGGSGGGGSGGGGSGGGGSGGGGSGGGGSGGGGS | 13 |
| 1-10 | GAGGGGAGGGGA | 14 |
| 1-11 | GAGGGGAGGGGAGGGGAGGGGAGGGGAGGGGAGGGGA | 15 |
| 1-12 | GGGGAGGGGAGGGGA | 16 |
| 1-13 | GGGGAGGGGAGGGGAGGGGA | 17 |
| 1-14 | GGGGAGGGGAGGGGAGGGGAGGGGA | 18 |
| 1-15 | GGGGAGGGGAGGGGAGGGGAGGGGAGGGGA | 19 |
| 1-16 | GGGGAGGGGAGGGGAGGGGAGGGGAGGGGAGGGGA | 20 |
| 1-17 | GGGGGGGGGGGGGGGGGG | 21 |
| 1-18 | GGGGGGGGGGGGGGGGGGGGGGGG | 22 |
| 1-19 | GGGGSGGGGSGGGGS | 23 |
| 1-20 | GGGGSGGGGSGGGGSGGGGSGGGGS | 24 |
| 1-21 | GGGGSGGGGSGGGGSGGGGSGGGGSGGGGS | 25 |

Serum Albumin Protein

Provided herein are GLP1-GDF15 fusion proteins that comprise a third component, wherein the third component is a serum albumin protein (e.g., a human serum albumin (HSA) protein or a gorilla serum albumin (GSA) protein). Native human serum albumin protein contains 35 cysteine (Cys, C) residues that form 17 disulfide bonds, with the Cys-34 residue being the only free cysteine in the molecule. This free Cys-34 has been shown to function as a free radical scavenger, by trapping multiple reactive oxygen species (ROS) and reactive nitrogen species (RNS) (Taverna et al., Ann. Intensive Care 3:4 (2013)). This free Cys was mutated to serine (Ser) to minimize the risk of heterogeneity due to oxidation.

The serum albumin protein can comprise one of the sequences provided in Table 3. The serum albumin protein can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 3. The serum albumin protein sequence can be chosen based on at least one of the following criteria: (i) in vitro stability, (ii) in vitro potency, and (iii) properties of the GLP1-GDF15 fusion protein (e.g., in vivo stability and in vivo potency (i.e., whether the GLP1 or GLP1 variant peptide and GDF15 or GDF15 variant protein are capable of having agonist activity on GLP1R and GDF15R, respectively)).

The second linker peptide can, for example, comprise about 5 to about 60 amino acid residues, about 10 to about 50 amino acid residues, about 10 to about 60 amino acid residues, about 5 to about 50 amino acid residues, about 15 to about 40 amino acid residues, about 12 to about 30 amino acid residues, about 12 to about 42 amino acid residues, about 20 to about 25 amino acid residues, about 8 to about 48 amino acid residues, about 10 to about 46 amino acid residues, about 12 to about 44 amino acid residues, about 14 to about 42 amino acid residues, about 16 to about 40 amino acid residues, about 18 to about 38 amino acid residues, about 20 to about 36 amino acid residues, about 20 to about 42 amino acid residues, about 22 to about 34 amino acid residues, about 24 to about 32 amino acid residues, about 26 to about 30 amino acid residues, or any value in between. The second linker peptide can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 amino acid residues.

In certain embodiments, the second linker peptide can contain an alanine-proline repeat (i.e., an AP repeat), wherein an AP dipeptide can be referred to as an AP unit. The AP repeat can comprise 2, 3, 4, 5, 6, 7, 8, 9, 10, 11, 12, 13, 14, 15, 16, 17, 18, 19, 20, 21, 22, 23, 24, 25, 26 or 27 AP units. In certain embodiments, the second linker peptide can, for example, comprise 2 to 25 AP units, 5 to 25 units,

TABLE 3

Serum Albumin protein

| Half-life extension protein | Protein Sequence | SEQ ID NO: |
|---|---|---|
| HSA (C34S) | DAHKSEVAHRFKDLGEENFKALVLIAFAQYLQQSPFEDHVKLVNEVTEFAKTCV ADESAENCDKSLHTLFGDKLCTVATLRETYGEMADCCAKQEPERNECFLQHKDD NPNLPRLVRPEVDVMCTAFHDNEETFLKKYLYEIARRHPYFYAPELLFFAKRYKA AFTECCQAADKAACLLPKLDELRDEGKASSAKQRLKCASLQKFGERAFKAWAV ARLSQRFPKAEFAEVSKLVTDLTKVHTECCHGDLLECADDRADLAKYICENQDSI SSKLKECCEKPLLEKSHCIAEVENDEMPADLPSLAADFVESKDVCKNYAEAKDVF LGMFLYEYARRHPDYSVVLLLRLAKTYETTLEKCCAAADPHECYAKVFDEFKPL VEEPQNLIKQNCELFEQLGEYKFQNALLVRYTKKVPQVSTPTLVEVSRNLGKVGS KCCKHPEAKRMPCAEDYLSVVLNQLCVLHEKTPVSDRVTKCCTESLVNRRPCFS ALEVDETYVPKEFNAETFTFHADICTLSEKERQIKKQTALVELVKHKPKATKEQL KAVMDDFAAFVEKCCKADDKETCFAEEGKKLVAASQAALGL | 26 |
| GSA (C34S) | DAHKSEVAHRFKDLGEETFKALVLVAFAQYLQQSPFEDHVKLVNEVTEFAKTCV ADESAENCDKSLHTLFGDKLCTVATLRETYGEMADCCAKQEPERNECFLQHKDD NPNLPRLVRPEVDVMCTAFHDNEETFLKKYLYEIARRHPYFYAPELLFFAARYKA AFTECCQAADKAACLLPKLDELRDEGKASSAKQRLKCASLQKFGERAFKAWAV ARLSQRFPKAEFAEVSKLVTDLTKVHTECCHGDLLECADDRADLAKYICENQDSI SSKLKECCEKPLLEKSHCLAEVENDEMPADLPSLAADFVESKDVCKNYAEAKDV FLGMFLYEYARRHPDYSVVLLLRLAKTYETTLEKCCAAADPHECYAKVFDEFKP LVEEPQNLIKQNCELFEQLGEYKFQNALLVRYTKKVPQVSTPTLVEVSRNLGKVG SKCCKHPEAKRMPCAEDYLSVVLNQLCVLHEKTPVSDRVTKCCTESLVNRRPCF SALEVDETYVPKEFNAETFTFHADICTLSEKERQIKKQTALAELVKHKPKATKEQ LKTVMDDFAAFVEKCCKADDKETCFAEEGKKLVAASQAALGL | 27 |

Second Linker Peptide: Carboxy-Terminal Linker (C-Terminal Linker)

Provided herein are GLP1-GDF15 fusion proteins that comprise a fourth component, wherein the fourth component is a second linker peptide (i.e., a carboxy-terminal linker peptide). The second linker peptide can comprise one of the sequences provided in Table 4. The second linker peptide can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 4.

4 to 23 AP units, 6 to 21 AP units, 8 to 19 AP units, 10 to 17 AP units, 12 to 15 AP units, 5 to 10 units, 5 to 15 units, 10 to 25 units, 15 to 25 units, 20 to 25 units, or any value in between. In certain embodiments, the AP repeat can be internal to an alanine-serine dipeptide (i.e., an AS unit) and a glycine-serine dipeptide (i.e., a GS unit). The AS unit can, for example, be at the amino terminal end of the second linker peptide. The GS unit can, for example, be at the carboxyl terminal end of the second linker peptide.

In certain embodiments, the second linker peptide can contain a glycine-glycine-glycine-glycine-serine repeat (i.e., a $G_4S$ repeat), wherein a $G_4S$ pentapeptide can be referred to as a $G_4S$ unit. The $G_4S$ repeat can comprise 2, 3, 4, 5, 6, 7, 8, 9, 10, 11, 12, 13, 14, or 15 $G_4S$ units. In certain embodiments, the second linker peptide can, for example, comprise 2 to 15 $G_4S$ units, 4 to 13 $G_4S$ units, 6 to 11 $G_4S$ units, 8 to 9 $G_4S$ units, 2 to 8 $G_4S$ units, 2 to 6 $G_4S$ units, 6 to 8 $G_4S$ units, 7 to 8 $G_4S$ units, 7 to 9 $G_4S$ units, 7 to 10 $G_4S$ units, or any value in between. In certain embodiments, an AS or a GS unit can, for example be at the amino terminal end of the second linker peptide.

In certain embodiments, the second linker peptide can contain a glycine-glycine-glycine-glycine-alanine repeat (i.e., a $G_4A$ repeat), wherein a $G_4A$ pentapeptide can be referred to as a $G_4A$ unit. The $G_4A$ repeat can comprise 2, 3, 4, 5, 6, 7, 8, 9, 10, 11, 12, 13, 14, or 15 $G_4A$ units. In certain embodiments, the second linker peptide can, for example, comprise 2 to 15 $G_4A$ units, 4 to 13 $G_4A$ units, 6 to 11 $G_4A$ units, 8 to 9 $G_4A$ units, 2 to 8 $G_4A$ units, 2 to 4 $G_4A$ units, 2 to 6 $G_4A$ units, 4 to 6 $G_4A$ units, 4 to 8 $G_4A$ units, 6 to 8 $G_4A$ units, 6 to 9 $G_4A$ units, 6 to 10 $G_4A$ units, or any value in between. In certain embodiments, a glycine-alanine dipeptide (i.e., a GA unit) unit can, for example be at the amino terminal end of the second linker peptide.

In certain embodiments, the second linker peptide can be a poly-glycine peptide. The poly-glycine peptide can comprise about 6 to about 50 glycine residues, about 10 to about 45 glycine residues, about 15 to about 40 glycine residues, about 20 to about 35 glycine residues, about 25 to about 30 glycine residues, about 20 to about 25 glycine residues, or any number in between. The poly-glycine second linker peptide can comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 glycine residues.

The second linker peptide sequence can be chosen based on at least one of the following criteria: (i) expression yield and purity, (ii) in vitro potency, (iii) in vitro stability, (iv) lack of serine xylosylation or potential for serine xylosylation, and (v) properties of the GLP1-GDF15 fusion protein (e.g., in vivo stability, in vivo potency (i.e., whether the GLP1 or GLP1 variant peptide and GDF15 or GDF15 variant protein are capable of having agonist activity of GLP1R and GDF15R (GFRAL), respectively)).

lation, and cachexia driven by cancer and chronic disease. The potential of pharmacologically administered GDF15 to decrease energy intake and thereby elicit weight loss has been demonstrated in mice, rats and monkeys. (Johnen et al., Nat Med 13:1333-40 (2007), Hsu et al., Nature 550:255-9 (2017), Mullican et al., Nat Med 23:1150-7 (2017), Tsai et al., Int J Obesity 42:561-71 (2018)). GDF15 treatment mediated weight loss leads to metabolic improvements including enhanced glucose homeostasis and lower plasma triglycerides and cholesterol (Xiong et al., Sci Trans Med 9:412 (2017)).

GDF15 binds to GDNF Family Receptor Alpha Like (GFRAL), a transmembrane receptor exclusively located in neurons in the brainstem (Mullican et al., Hsu et al, Yang et al., Emmerson et al.). Upon GDF15 binding, GFRAL complexes with RET, a tyrosine kinase that stimulates a downstream intracellular phosphorylation cascade including the post-translational modification of AKT, ERK and PLCγ. While the additional molecular and cellular components of this cascade remain to be elucidated, the ultimate effect of GDF15/GFRAL signaling is decreased food intake and weight loss (Mullican and Rangwala, 2018).

Provided herein are GLP1-GDF15 fusion proteins that comprise a fifth component, wherein the fifth component is a GDF15 or GDF15 variant protein. The GDF15 protein can comprise the sequence provided in Table 5, and a GDF15 variant protein can comprise a variant of the sequence provided in Table 5. The GDF15 or GDF15 variant protein can comprise at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to one of the sequences provided in Table 5. The GDF15 and/or GDF15 variant protein sequence can be chosen based on at least one of the following criteria: (i) expression yield and purity, (ii) in vitro stability, (iii) in vitro potency, (iv) the retention of in vitro potency in combination with the GLP1 or GLP1 variant protein, (v) lack of serine xylosylation or potential for serine xylosylation, and (vi) properties of the GLP1-GDF15 fusion protein (e.g., in vivo stability, in vivo potency (i.e., whether GLP1 or GLP1 variant peptide and GDF15 or GDF15 variant protein are

TABLE 4

Second linker peptide (C-terminal linker peptide)

| Second linker peptide | Peptide Sequence | SEQ ID NO: |
|---|---|---|
| 2-1 | APAPAPAPAPAPAPAPAPAP | 28 |
| 2-2 | GAGGGGAGGGGAGGGGAGGGGAGGGGAGGGGAGGGGAGGGGA | 29 |
| 2-3 | GSGGGGSGGGGSGGGGSGGGGSGGGGSGGGGSGGGGSGGGGS | 30 |

GDF15 or GDF15 Variant Protein

Growth differentiation factor 15 (GDF15) is a protein belonging to the transforming growth factor beta (TGF-β) superfamily. GDF15 is a secreted protein that circulates as a 25-kDa dimer. GDF15 is also referred to as prostate derived factor (PDF), macrophage inhibitory cytokine-1 (MIC-1), NSAID (nonsteroidal anti-inflammatory drugs)-activated gene (NAG-1) and placental TGF-beta (PTGFβ).

GDF15 function has yet to be fully elucidated, but has been implicated in multiple biological processes including, but not limited to, energy homeostasis, body weight regucapable of having agonist activity on GLP1R and/or GDF15R (GFRAL) receptor, respectively)).

The GDF15 or GDF15 variant proteins that make up the fifth component of the GLP1-GDF15 fusion proteins are intended to encompass proteins that have sufficient homology and functionality to activate the native GDF15R (GFRAL). The GDF15 or GDF15 variant proteins are designed to be capable of binding to GFRAL in the brainstem resulting in the same signaling pathway and exhibiting the same impact on food intake as when the native GDF15 binds GFRAL in these neurons.

TABLE 5

GDF15 or GDF15 variant protein

| GDF15 or GDF15 variant protein | Protein Sequence | SEQ ID NO: |
|---|---|---|
| GDF15 valiant 1 | DHCPLGPGRCCRLHTVRASLEDLGWADWVLSPREVQVTMCIGACPSQFR AANMHAQIKTSLHRLKPDTVPAPCCVPASYNPMVLIQKTDTGVSLQTYD DLLAKDCHCI | 31 |
| GDF15 WT mature | ARNGDHCPLGPGRCCRLHTVRASLEDLGWADWVLSPREVQVTMCIGACP SQFRAANMHAQIKTSLHRLKPDTVPAPCCVPASYNPMVLIQKTDTGVSLQ TYDDLLAKDCHCI | 32 |

GLP1-GDF15 Fusion Proteins

Provided herein are GLP1-GDF15 fusion proteins that comprise a first, a second, a third, a fourth, and a fifth component as described previously. The first component is a GLP1 or GLP1 variant peptide, the second component is a first linker peptide, the third component is a serum albumin protein, the fourth component is a second linker peptide, and the fifth component is a GDF15 or GDF15 variant protein. The GLP1-GDF15 fusion proteins can comprise one of the sequences provided in Table 6. The GLP1-GDF15 fusion protein can comprise at least 85%, 86%, 87%, 88%, 89%, 90%, 91%, 92%, 93%, 94%, 95%, 96%, 97%, 98%, or 99% identity to one of the sequences provided in Table 6. The GLP1-GDF15 fusion protein can be chosen based on at least one of the following criteria: (i) expression yield and purity, (ii) in vitro potency, (iii) in vitro stability, (iv) lack of serine xylosylation, and (v) physical properties of the GLP1-GDF15 fusion protein (e.g., in vivo stability, in vivo potency (i.e., whether the GLP1 or GLP1 variant peptide and GDF15 or GDF15 variant protein are capable of having agonist activity on GLP1R and GDF15R, respectively)), and (vi) desired balance of dual agonism pharmacology in vivo.

For a fusion protein therapeutic that delivers dual pharmacology in one molecule, it is important to properly adjust the pharmacokinetic/pharmacodynamic (PK/PD) properties of each moiety so that both agonists are in the therapeutic range with the intended dosing. Extensive investigation of various glucagon-like peptide-1 (GLP1)-growth differentiation factor 15 (GDF15) fusion proteins comprising various combinations of a GLP1 peptide or GLP1 variant peptide sequence, a first linker peptide sequence, a serum albumin protein sequence, a second linker peptide sequence, and a GDF15 or GDF15 variant protein sequence resulted in the discovery of novel molecules possessing the unique property of delivering optimal balanced doses of both GLP1 and GDF15 agonists. These novel GLP1-GDF15 fusion proteins were demonstrated to be as efficacious in engaging the GDF15R (GFRAL) in vivo as HSA-GDF15, when used at a specific dose range (see Example 11). Furthermore, the GLP1-GDF15 fusion proteins, used at the same dose range (see Example 11), were unexpectedly as efficacious in engaging the GLP1R as dulaglutide (GLP1-Fc), and without adverse side effects, despite having a GLP1 moiety exposure 10-30 times greater than that in dulaglutide. The delivery of GLP1 peptides as fusions with HSA-GDF15 unexpectedly altered the in vivo potency of the GLP1 moiety yet enabled novel glucagon-like peptide-1 (GLP1)-growth differentiation factor 15 (GDF15) fusion proteins to have an optimal balance of both agonists.

TABLE 6

GLP1-GDF15 fusion proteins

| GLP1-GDF15 fusion proteins | Protein Sequence | SEQ ID NO: |
|---|---|---|
| 1 | HGEGTFTSDVSSYLEEQAAKEFIAWLVKGGGGGGAGGGGAGGGGAGGGGAGGGGA DAHKSEVAHRFKDLGEENFKALVLIAFAQYLQQSPFEDHVKLVNEVTEFAKTCVADE SAENCDKSLHTLFGDKLCTVATLRETYGEMADCCAKQEPERNECFLQHKDDNPNLPR LVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAE FAEVSKLVTDLTKVHTECCHGDLLECADDRADLAKYICENQDSISSKLKECCEKPLLE KSHCIAEVENDEMPADLPSLAADFVESKDVCKNYAEAKDVFLGMFLYEYARRHPDY SVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSV VLNQLCVLHEKTPVSDRVTKCCTESLVNRRPCFSALEVDETYVPKEFNAETFTFHADI CTLSEKERQIKKQTALVELVKHKPKATKEQLKAVMDDFAAFVEKCCKADDKETCFA EEGKKLVAASQAALGLAPAPAPAPAPAPAPAPAPAPAPDHCPLGPGRCCRLHTVRASLE DLGWADWVLSPREVQVTMCIGACPSQFRAANMHAQIKTSLHRLKPDTVPAPCCVPA SYNPMVLIQKTDTGVSLQTYDDLLAKDCHCI | 33 |
| 2 | HGEGTFTSDVSSYLEEQAAKEFIAWLVKGGGGGGAGGGGAGGGGADAHKSEVAHR FKDLGEENFKALVLIAFAQYLQQSPFEDHVKLVNEVTEFAKTCVADESAENCDKSLH TLFGDKLCTVATLRETYGEMADCCAKQEPERNECFLQHKDDNPNLPRLVRPEVDVM CTAFHDNEETFLKKYLYEIARRHPYFYAPELLFFAKRYKAAFTECCQAADKAACLLP KLDELRDEGKASSAKQRLKCASLQKFGERAFKAWAVARLSQRFPKAEFAEVSKLVT DLTKVHTECCHGDLLECADDRADLAKYICENQDSISSKLKECCEKPLLEKSHCIAEVE NDEMPADLPSLAADFVESKDVCKNYAEAKDVFLGMFLYEYARRHPDYSVVLLLRLA KTYETTLEKCCAAADPHECYAKVFDEFKPLVEEPQNLIKQNCELFEQLGEYKFQNAL LVRYTKKVPQVSTPTLVEVSRNLGKVGSKCCKHPEAKRMPCAEDYLSVVLNQLCVL | 34 |

TABLE 6-continued

GLP1-GDF15 fusion proteins

| GLP1-GDF15 fusion proteins | Protein Sequence | SEQ ID NO: |
|---|---|---|
|  | HEKTPVSDRVTKCCTESLVNRRPCFSALEVDETYVPKEFNAETFTFHADICTLSEKERQ IKKQTALVELVKHKPKATKEQLKAVMDDFAAFVEKCCKADDKETCFAEEGKKLVAA SQAALGLAPAPAPAPAPAPAPAPAPDHCPLGPGRCCRLHTVRASLEDLGWADVVL SPREVQVTMCIGACPSQFRAANMHAQIKTSLHRLKPDTVPAPCCVPASYNPMVLIQKT DTGVSLQTYDDLLAKDCHCI |  |
| 3 | HGEGTFTSDVSSYLEEQAAKEFIAWLVKGGAPAPAPAPAPAPAPAPAPAPAPAPAP APAPAPAPAPAPAPAPAPAPAPAPDAHKSEVAHRFKDLGEENFKALVLIAFAQYLQQSPF EDHVKLVNEVTEFAKTCVADESAENCDKSLHTLFGDKLCTVATLRETYGEMADCCA KQEPERNECFLQHKDDNPNLPRLVRPEVDVMCTAFHDNEETFLKKYLYEIARRHPYF YAPELLFFAKRYKAAFTECCQAADKAACLLPKLDELRDEGKASSAKQRLKCASLQKF GERAFKAWAVARLSQRFPKAEFAEVSKLVTDLTKVHTECCHGDLLECADDRADLAK YICENQDSISSKLKECCEKPLLEKSHCIAEVENDEMPADLPSLAADFVESKDVCKNYA EAKDVFLGMFLYEYARRHPDYSVVLLLRLAKTYETTLEKCCAAADPHECYAKVFDE FKPLVEEPQNLIKQNCELFEQLGEYKFQNALLVRYTKKVPQVSTPTLVEVSRNLGKVG SKCCKHPEAKRMPCAEDYLSVVLNQLCVLHEKTPVSDRVTKCCTESLVNRRPCFSAL EVDETYVPKEFNAETFTFHADICTLSEKERQIKKQTALVELVKHKPKATKEQLKAVM DDFAAFVEKCCKADDKETCFAEEGKKLVAASQAALGLAPAPAPAPAPAPAPAPAPAP DHCPLGPGRCCRLHTVRASLEDLGWADVVLSPREVQVTMCIGACPSQFRAANMHAQ IKTSLHRLKPDTVPAPCCVPASYNPMVLIQKTDTGVSLQTYDDLLAKDCHCI | 35 |
| 4 | HGEGTFTSDVSSYLEEQAAKEFIAWLVKGGAPAPAPAPAPAPAPAPAPAPAPAPAP APAPAPAPAPAPDAHKSEVAHRFKDLGEENFKALVLIAFAQYLQQSPFEDHVKLVNE VTEFAKTCVADESAENCDKSLHTLFGDKLCTVATLRETYGEMADCCAKQEPERNECF LQHKDDNPNLPRLVRPEVDVMCTAFHDNEETFLKKYLYEIARRHPYFYAPELLFFAK RYKAAFTECCQAADKAACLLPKLDELRDEGKASSAKQRLKCASLQKFGERAFKAWA VARLSQRFPKAEFAEVSKLVTDLTKVHTECCHGDLLECADDRADLAKYICENQDSISS KLKECCEKPLLEKSHCIAEVENDEMPADLPSLAADFVESKDVCKNYAEAKDVFLGMF LYEYARRHPDYSVVLLLRLAKTYETTLEKCCAAADPHECYAKVFDEFKPLVEEPQNL IKQNCELFEQLGEYKFQNALLVRYTKKVPQVSTPTLVEVSRNLGKVGSKCCKHPEAK RMPCAEDYLSVVLNQLCVLHEKTPVSDRVTKCCTESLVNRRPCFSALEVDETYVPKE FNAETFTFHADICTLSEKERQIKKQTALVELVKHKPKATKEQLKAVMDDFAAFVEKC CKADDKETCFAEEGKKLVAASQAALGLAPAPAPAPAPAPAPAPAPAPDHCPLGPGRC CRLHTVRASLEDLGWADVVLSPREVQVTMCIGACPSQFRAANMHAQIKTSLHRLKP DTVPAPCCVPASYNPMVLIQKTDTGVSLQTYDDLLAKDCHCI | 36 |
| 5 | HGEGTFTSDVSSYLEEQAAKEFIAWLVKGGAPAPAPAPAPAPAPAPAPAPAPAP APDAHKSEVAHRFKDLGEENFKALVLIAFAQYLQQSPFEDHVKLVNEVTEFAKTCVA DESAENCDKSLHTLFGDKLCTVATLRETYGEMADCCAKQEPERNECFLQHKDDNPN LPRLVRPEVDVMCTAFHDNEETFLKKYLYEIARRHPYFYAPELLFFAKRYKAAFTECC QAADKAACLLPKLDELRDEGKASSAKQRLKCASLQKFGERAFKAWAVARLSQRFPK AEFAEVSKLVTDLTKVHTECCHGDLLECADDRADLAKYICENQDSISSKLKECCEKPL LEKSHCIAEVENDEMPADLPSLAADFVESKDVCKNYAEAKDVFLGMFLYEYARRHP DYSVVLLLRLAKTYETTLEKCCAAADPHECYAKVFDEFKPLVEEPQNLIKQNCELFEQ LGEYKFQNALLVRYTKKVPQVSTPTLVEVSRNLGKVGSKCCKHPEAKRMPCAEDYL SVVLNQLCVLHEKTPVSDRVTKCCTESLVNRRPCFSALEVDETYVPKEFNAETFTFHA DICTLSEKERQIKKQTALVELVKHKPKATKEQLKAVMDDFAAFVEKCCKADDKETCF AEEGKKLVAASQAALGLAPAPAPAPAPAPAPAPAPAPDHCPLGPGRCCRLHTVRASL EDLGWADVVLSPREVQVTMCIGACPSQFRAANMHAQIKTSLHRLKPDTVPAPCCVP ASYNPMVLIQKTDTGVSLQTYDDLLAKDCHCI | 37 |
| 6 | HGEGTFTSDVSSYLEEQAAKEFIAWLVKGGGGGGAGGGGAGGGGAGGGGAGGGGA GGGGAGGGGAGGGGADAHKSEVAHRFKDLGEENFKALVLIAFAQYLQQSPFEDHVK LVNEVTEFAKTCVADESAENCDKSLHTLFGDKLCTVATLRETYGEMADCCAKQEPE RNECFLQHKDDNPNLPRLVRPEVDVMCTAFHDNEETFLKKYLYEIARRHPYFYAPEL LFFAKRYKAAFTECCQAADKAACLLPKLDELRDEGKASSAKQRLKCASLQKFGERAF KAWAVARLSQRFPKAEFAEVSKLVTDLTKVHTECCHGDLLECADDRADLAKYICEN QDSISSKLKECCEKPLLEKSHCIAEVENDEMPADLPSLAADFVESKDVCKNYAEAKDV FLGMFLYEYARRHPDYSVVLLLRLAKTYETTLEKCCAAADPHECYAKVFDEFKPLVE EPQNLIKQNCELFEQLGEYKFQNALLVRYTKKVPQVSTPTLVEVSRNLGKVGSKCCK HPEAKRMPCAEDYLSVVLNQLCVLHEKTPVSDRVTKCCTESLVNRRPCFSALEVDET YVPKEFNAETFTFHADICTLSEKERQIKKQTALVELVKHKPKATKEQLKAVMDDFAA FVEKCCKADDKETCFAEEGKKLVAASQAALGLAPAPAPAPAPAPAPAPAPAPDHCPL GPGRCCRLHTVRASLEDLGWADVVLSPREVQVTMCIGACPSQFRAANMHAQIKTSL HRLKPDTVPAPCCVPASYNPMVLIQKTDTGVSLQTYDDLLAKDCHCI | 38 |
| 7 | HGEGTFTSDLSKQMEEEAVRLFIEWLKNGGPSSGAPPPSAPAPAPAPAPAPAPAPAP APAPAPAPAPAPAPAPAPAPAPAPDAHKSEVAHRFKDLGEENFKALVLIAFA QYLQQSPFEDHVKLVNEVTEFAKTCVADESAENCDKSLHTLFGDKLCTVATLRETYG EMADCCAKQEPERNECFLQHKDDNPNLPRLVRPEVDVMCTAFHDNEETFLKKYLYEI ARRHPYFYAPELLFFAKRYKAAFTECCQAADKAACLLPKLDELRDEGKASSAKQRLK CASLQKFGERAFKAWAVARLSQRFPKAEFAEVSKLVTDLTKVHTECCHGDLLECAD DRADLAKYICENQDSISSKLKECCEKPLLEKSHCIAEVENDEMPADLPSLAADFVESK | 39 |

TABLE 6-continued

GLP1-GDF15 fusion proteins

| GLP1-GDF15 fusion proteins | Protein Sequence | SEQ ID NO: |
|---|---|---|
| | DVCKNYAEAKDVFLGMFLYEYARRHPDYSVVLLLRLAKTYETTLEKCCAAADPHEC YAKVFDEFKPLVEEPQNLIKQNCELFEQLGEYKFQNALLVRYTKKVPQVSTPTLVEVS RNLGKVGSKCCKHPEAKRMPCAEDYLSVVLNQLCVLHEKTPVSDRVTKCCTESLVN RRPCFSALEVDETYVPKEFNAETFTFHADICTLSEKERQIKKQTALVELVKHKPKATK EQLKAVMDDFAAFVEKCCKADDKETCFAEEGKKLVAASQAALGLAPAPAPAPAPAP APAPAPAPDHCPLGPGRCCRLHTVRASLEDLGWADWVLSPREVQVTMCIGACPSQFR AANMHAQIKTSLHRLKPDTVPAPCCVPASYNPMVLIQKTDTGVSLQTYDDLLAKDCH CI | |
| 8 | HGEGTFTSDLSKQMEEEAVRLFIEWLKNGGPSSGAPPPSAPAPAPAPAPAPAPAPAP APAPAPAPDAHKSEVAHRFKDLGEENFKALVLIAFAQYLQQSPFEDHVKLVNEVT EFAKTCVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFFAKRY KAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKL KECCEKPLLEKSHCIAEVENDEMPADLPSLAADFVESKDVCKNYAEAKDVFLGMFLY EYARRHPDYSVVLLLRLAKTYETTLEKCCAAADPHECYAKVFDEFKPLVEEPQNLIK QNCELFEQLGEYKFQNALLVRYTKKVPQVSTPTLVEVSRNLGKVGSKCCKHPEAKR MPCAEDYLSVVLNQLCVLHEKTPVSDRVTKCCTESLVNRRPCFSALEVDETYVPKEF NAETFTFHADICTLSEKERQIKKQTALVELVKHKPKATKEQLKAVMDDFAAFVEKCC KADDKETCFAEEGKKLVAASQAALGLAPAPAPAPAPAPAPAPAPDHCPLGPGRCC RLHTVRASLEDLGWADWVLSPREVQVTMCIGACPSQFRAANMHAQIKTSLHRLKPD TVPAPCCVPASYNPMVLIQKTDTGVSLQTYDDLLAKDCHCI | 40 |
| 9 | HGEGTFTSDLSKQMEEEAVRLFIEWLKNGGPSSGAPPPSAPAPAPAPAPAPAPAPAP DAHKSEVAHRFKDLGEENFKALVLIAFAQYLQQSPFEDHVKLVNEVTEFAKTCVADE SAENCDKSLHTLFGDKLCTVATLRETYGEMADCCAKQEPERNECFLQHKDDNPNLPR LVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAE FAEVSKLVTDLTKVHTECCHGDLLECADDRADLAKYICENQDSISSKLKECCEKPLLE KSHCIAEVENDEMPADLPSLAADFVESKDVCKNYAEAKDVFLGMFLYEYARRHPDY SVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSV VLNQLCVLHEKTPVSDRVTKCCTESLVNRRPCFSALEVDETYVPKEFNAETFTFHADI CTLSEKERQIKKQTALVELVKHKPKATKEQLKAVMDDFAAFVEKCCKADDKETCFA EEGKKLVAASQAALGLAPAPAPAPAPAPAPAPAPDHCPLGPGRCCRLHTVRASLE DLGWADWVLSPREVQVTMCIGACPSQFRAANMHAQIKTSLHRLKPDTVPAPCCVPA SYNPMVLIQKTDTGVSLQTYDDLLAKDCHCI | 41 |
| 10 | HGEGTFTSDLSKQMEEEAVRLFIEWLKNGGPSSGAPPPSGGGGAGGGGAGGGGAGG GGAGGGGAGGGGAGGGGADAHKSEVAHRFKDLGEENFKALVLIAFAQYLQ QSPFEDHVKLVNEVTEFAKTCVADESAENCDKSLHTLFGDKLCTVATLRETYGEMAD CCAKQEPERNECFLQHKDDNPNLPRLVRPEVDVMCTAFHDNEETFLKKYLYEIARRH PYFYAPELLFFAKRYKAAFTECCQAADKAACLLPKLDELRDEGKASSAKQRLKCASL QKFGERAFKAWAVARLSQRFPKAEFAEVSKLVTDLTKVHTECCHGDLLECADDRAD LAKYICENQDSISSKLKECCEKPLLEKSHCIAEVENDEMPADLPSLAADFVESKDVCK NYAEAKDVFLGMFLYEYARRHPDYSVVLLLRLAKTYETTLEKCCAAADPHECYAKV FDEFKPLVEEPQNLIKQNCELFEQLGEYKFQNALLVRYTKKVPQVSTPTLVEVSRNLG KVGSKCCKHPEAKRMPCAEDYLSVVLNQLCVLHEKTPVSDRVTKCCTESLVNRRPCF SALEVDETYVPKEFNAETFTFHADICTLSEKERQIKKQTALVELVKHKPKATKEQLKA VMDDFAAFVEKCCKADDKETCFAEEGKKLVAASQAALGLAPAPAPAPAPAPAPAPA PAPDHCPLGPGRCCRLHTVRASLEDLGWADWVLSPREVQVTMCIGACPSQFRAANM HAQIKTSLHRLKPDTVPAPCCVPASYNPMVLIQKTDTGVSLQTYDDLLAKDCHCI | 42 |
| 11 | HGEGTFTSDLSKQMEEEAVRLFIEWLKNGGPSSGAPPPSGGGGAGGGGAGGGGAGG GGAGGGGADAHKSEVAHRFKDLGEENFKALVLIAFAQYLQQSPFEDHVKLVNEVTE FAKTCVADESAENCDKSLHTLFGDKLCTVATLRETYGEMADCCAKQEPERNECFLQ HKDDNPNLPRLVRPEVDVMCTAFHDNEETFLKKYLYEIARRHPYFYAPELLFFAKRY KAAFTECCQAADKAACLLPKLDELRDEGKASSAKQRLKCASLQKFGERAFKAWAVA RLSQRFPKAEFAEVSKLVTDLTKVHTECCHGDLLECADDRADLAKYICENQDSISSKL KECCEKPLLEKSHCIAEVENDEMPADLPSLAADFVESKDVCKNYAEAKDVFLGMFLY EYARRHPDYSVVLLLRLAKTYETTLEKCCAAADPHECYAKVFDEFKPLVEEPQNLIK QNCELFEQLGEYKFQNALLVRYTKKVPQVSTPTLVEVSRNLGKVGSKCCKHPEAKR MPCAEDYLSVVLNQLCVLHEKTPVSDRVTKCCTESLVNRRPCFSALEVDETYVPKEF NAETFTFHADICTLSEKERQIKKQTALVELVKHKPKATKEQLKAVMDDFAAFVEKCC KADDKETCFAEEGKKLVAASQAALGLAPAPAPAPAPAPAPAPAPDHCPLGPGRCC RLHTVRASLEDLGWADWVLSPREVQVTMCIGACPSQFRAANMHAQIKTSLHRLKPD TVPAPCCVPASYNPMVLIQKTDTGVSLQTYDDLLAKDCHCI | 43 |
| 12 | HGEGTFTSDLSKQMEEEAVRLFIEWLKNGGPSSGAPPPSAPAPAPAPAPDAHKSEVAH RFKDLGEENFKALVLIAFAQYLQQSPFEDHVKLVNEVTEFAKTCVADESAENCDKSL HTLFGDKLCTVATLRETYGEMADCCAKQEPERNECFLQHKDDNPNLPRLVRPEVDV MCTAFHDNEETFLKKYLYEIARRHPYFYAPELLFFAKRYKAAFTECCQAADKAACLL | 44 |

TABLE 6-continued

GLP1-GDF15 fusion proteins

| GLP1-GDF15 fusion proteins | Protein Sequence | SEQ ID NO: |
|---|---|---|
|  | PKLDELRDEGKASSAKQRLKCASLQKFGERAFKAWAVARLSQRFPKAEFAEVSKLVT DLTKVHTECCHGDLLECADDRADLAKYICENQDSISSKLKECCEKPLLEKSHCIAVE NDEMPADLPSLAADFVESKDVCKNYAEAKDVFLGMFLYEYARRHPDYSVVLLLRLA KTYETTLEKCCAAADPHECYAKVFDEFKPLVEEPQNLIKQNCELFEQLGEYKFQNAL LVRYTKKVPQVSTPTLVEVSRNLGKVGSKCCKHPEAKRMPCAEDYLSVVLNQLCVL HEKTPVSDRVTKCCTESLVNRRPCFSALEVDETYVPKEFNAETFTFHADICTLSEKERQ IKKQTALVELVKHKPKATKEQLKAVMDDFAAFVEKCCKADDKETCFAEEGKKLVAA SQAALGLAPAPAPAPAPAPAPAPAPAPDHCPLGPGRCCRLHTVRASLEDLGWADWVL SPREVQVTMCIGACPSQFRAANMHAQIKTSLHRLKPDTVPAPCCVPASYNPMVLIQKT DTGVSLQTYDDLLAKDCHCI |  |
| 13 | HGEGTFTSDVSSYLEEQAAKEFIAWLVKGGAPAPAPAPAPAPAPAPAPAPDAHKSEV AHRFKDLGEENFKALVLIAFAQYLQQSPFEDHVKLVNEVTEFAKTCVADESAENCDK SLHTLFGDKLCTVATLRETYGEMADCCAKQEPERNECFLQHKDDNPNLPRLVRPEVD VMCTAFHDNEETFLKKYLYEIARRHPYFYAPELLFFAKRYKAAFTECCQAADKAACL LPKLDELRDEGKASSAKQRLKCASLQKFGERAFKAWAVARLSQRFPKAEFAEVSKLV TDLTKVHTECCHGDLLECADDRADLAKYICENQDSISSKLKECCEKPLLEKSHCIAEV ENDEMPADLPSLAADFVESKDVCKNYAEAKDVFLGMFLYEYARRHPDYSVVLLLRL AKTYETTLEKCCAAADPHECYAKVFDEFKPLVEEPQNLIKQNCELFEQLGEYKFQNA LLVRYTKKVPQVSTPTLVEVSRNLGKVGSKCCKHPEAKRMPCAEDYLSVVLNQLCV LHEKTPVSDRVTKCCTESLVNRRPCFSALEVDETYVPKEFNAETFTFHADICTLSEKER QIKKQTALVELVKHKPKATKEQLKAVMDDFAAFVEKCCKADDKETCFAEEGKKLVA ASQAALGLAPAPAPAPAPAPAPAPAPAPDHCPLGPGRCCRLHTVRASLEDLGWADW VLSPREVQVTMCIGACPSQFRAANMHAQIKTSLHRLKPDTVPAPCCVPASYNPMVLIQ KTDTGVSLQTYDDLLAKDCHCI | 45 |
| 14 | HGEGTFTSDLSKQMEEEAVRLFIEWLKNGGPSSGAPPPSAPAPAPAPAPDAHKSEVAH RFKDLGEENFKALVLIAFAQYLQQSPFEDHVKLVNEVTEFAKTCVADESAENCDKSL HTLFGDKLCTVATLRETYGEMADCCAKQEPERNECFLQHKDDNPNLPRLVRPEVDV MCTAFHDNEETFLKKYLYEIARRHPYFYAPELLFFAKRYKAAFTECCQAADKAACLL PKLDELRDEGKASSAKQRLKCASLQKFGERAFKAWAVARLSQRFPKAEFAEVSKLVT DLTKVHTECCHGDLLECADDRADLAKYICENQDSISSKLKECCEKPLLEKSHCIAVE NDEMPADLPSLAADFVESKDVCKNYAEAKDVFLGMFLYEYARRHPDYSVVLLLRLA KTYETTLEKCCAAADPHECYAKVFDEFKPLVEEPQNLIKQNCELFEQLGEYKFQNAL LVRYTKKVPQVSTPTLVEVSRNLGKVGSKCCKHPEAKRMPCAEDYLSVVLNQLCVL HEKTPVSDRVTKCCTESLVNRRPCFSALEVDETYVPKEFNAETFTFHADICTLSEKERQ IKKQTALVELVKHKPKATKEQLKAVMDDFAAFVEKCCKADDKETCFAEEGKKLVAA SQAALGLGAGGGGAGGGGAGGGGAGGGGAGGGGAGGGGAGGGGADHCP LGPGRCCRLHTVRASLEDLGWADWVLSPREVQVTMCIGACPSQFRAANMHAQIKTS LHRLKPDTVPAPCCVPASYNPMVLIQKTDTGVSLQTYDDLLAKDCHCI | 46 |
| 15 | HGEGTFTSDVSSYLEEQAAKEFIAWLVKGGGGGGGGGGGGGGGGGGGGGGGG DAHKSEVAHRFKDLGEENFKALVLIAFAQYLQQSPFEDHVKLVNEVTEFAKTCVADE SAENCDKSLHTLFGDKLCTVATLRETYGEMADCCAKQEPERNECFLQHKDDNPNLPR LVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAE FAEVSKLVTDLTKVHTECCHGDLLECADDRADLAKYICENQDSISSKLKECCEKPLLE KSHCIAVENDEMPADLPSLAADFVESKDVCKNYAEAKDVFLGMFLYEYARRHPDY SVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSV VLNQLCVLHEKTPVSDRVTKCCTESLVNRRPCFSALEVDETYVPKEFNAETFTFHADI CTLSEKERQIKKQTALVELVKHKPKATKEQLKAVMDDFAAFVEKCCKADDKETCFA EEGKKLVAASQAALGLGAGGGGAGGGGAGGGGAGGGGAGGGGAGGGGA GGGGADHCPLGPGRCCRLHTVRASLEDLGWADWVLSPREVQVTMCIGACPSQFRAA NMHAQIKTSLHRLKPDTVPAPCCVPASYNPMVLIQKTDTGVSLQTYDDLLAKDCHCI | 47 |
| 16 | HGEGTFTSDVSSYLEEQAAKEFIAWLVKGGGGGGGGGGGGGGGGGGGGDAHKS EVAHRFKDLGEENFKALVLIAFAQYLQQSPFEDHVKLVNEVTEFAKTCVADESAENC DKSLHTLFGDKLCTVATLRETYGEMADCCAKQEPERNECFLQHKDDNPNLPRLVRPE VDVMCTAFHDNEETFLKKYLYEIARRHPYFYAPELLFFAKRYKAAFTECCQAADKAA CLLPKLDELRDEGKASSAKQRLKCASLQKFGERAFKAWAVARLSQRFPKAEFAEVSK LVTDLTKVHTECCHGDLLECADDRADLAKYICENQDSISSKLKECCEKPLLEKSHCIA EVENDEMPADLPSLAADFVESKDVCKNYAEAKDVFLGMFLYEYARRHPDYSVVLLL RLAKTYETTLEKCCAAADPHECYAKVFDEFKPLVEEPQNLIKQNCELFEQLGEYKFQ NALLVRYTKKVPQVSTPTLVEVSRNLGKVGSKCCKHPEAKRMPCAEDYLSVVLNQL CVLHEKTPVSDRVTKCCTESLVNRRPCFSALEVDETYVPKEFNAETFTFHADICTLSEK ERQIKKQTALVELVKHKPKATKEQLKAVMDDFAAFVEKCCKADDKETCFAEEGKKL VAASQAALGLGAGGGGAGGGGAGGGGAGGGGAGGGGAGGGGAGGGGA DHCPLGPGRCCRLHTVRASLEDLGWADWVLSPREVQVTMCIGACPSQFRAANMHAQI KTSLHRLKPDTVPAPCCVPASYNPMVLIQKTDTGVSLQTYDDLLAKDCHCI | 48 |
| 17 | HGEGTFTSDVSSYLEEQAAKEFIAWLVKGGGGGGAGGGGAGGGGAGGGGADAHKS EVAHRFKDLGEENFKALVLIAFAQYLQQSPFEDHVKLVNEVTEFAKTCVADESAENC | 49 |

TABLE 6-continued

GLP1-GDF15 fusion proteins

| GLP1-GDF15 fusion proteins | Protein Sequence | SEQ ID NO: |
|---|---|---|
| | DKSLHTLFGDKLCTVATLRETYGEMADCCAKQEPERNECFLQHKDDNPNLPRLVRPE VDVMCTAFHDNEETFLKKYLYEIARRHPYFYAPELLFFAKRYKAAFTECCQAADKAA CLLPKLDELRDEGKASSAKQRLKCASLQKFGERAFKAWAVARLSQRFPKAEFAEVSK LVTDLTKVHTECCHGDLLECADDRADLAKYICENQDSISSKLKECCEKPLLEKSHCIA EVENDEMPADLPSLAADFVESKDVCKNYAEAKDVFLGMFLYEYARRHPDYSVVLLL RLAKTYETTLEKCCAAADPHECYAKVFDEFKPLVEEPQNLIKQNCELFEQLGEYKFQ NALLVRYTKKVPQVSTPTLVEVSRNLGKVGSKCCKHPEAKRMPCAEDYLSVVLNQL CVLHEKTPVSDRVTKCCTESLVNRRPCFSALEVDETYVPKEFNAETFTFHADICTLSEK ERQIKKQTALVELVKHKPKATKEQLKAVMDDFAAFVEKCCKADDKETCFAEEGKKL VAASQAALGLGAGGGGAGGGGAGGGGAGGGGAGGGGAGGGGAGGGGAD HCPLGPGRCCRLHTVRASLEDLGWADWVLSPREVQVTMCIGACPSQFRAANMHAQI KTSLHRLKPDTVPAPCCVPASYNPMVLIQKTDTGVSLQTYDDLLAKDCHCI | |
| 18 | HGEGTFTSDVSSYLEEQAAKEFIAWLVKGGGGGGAGGGGAGGGGAGGGGAGGGGA DAHKSEVAHRFKDLGEENFKALVLIAFAQYLQQSPFEDHVKLVNEVTEFAKTCVADE SAENCDKSLHTLFGDKLCTVATLRETYGEMADCCAKQEPERNECFLQHKDDNPNLPR LVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAE FAEVSKLVTDLTKVHTECCHGDLLECADDRADLAKYICENQDSISSKLKECCEKPLLE KSHCIAEVENDEMPADLPSLAADFVESKDVCKNYAEAKDVFLGMFLYEYARRHPDY SVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSV VLNQLCVLHEKTPVSDRVTKCCTESLVNRRPCFSALEVDETYVPKEFNAETFTFHADI CTLSEKERQIKKQTALVELVKHKPKATKEQLKAVMDDFAAFVEKCCKADDKETCFA EEGKKLVAASQAALGLGAGGGGAGGGGAGGGGAGGGGAGGGGAGGGGAGGGGA GGGGADHCPLGPGRCCRLHTVRASLEDLGWADWVLSPREVQVTMCIGACPSQFRAA NMHAQIKTSLHRLKPDTVPAPCCVPASYNPMVLIQKTDTGVSLQTYDDLLAKDCHCI | 50 |
| 19 | HGEGTFTSDVSSYLEEQAAKEFIAWLVKGGGAGGGGAGGGGAGGGGAGGGGAGGG GAGGGGAGGGGAGGGGADAHKSEVAHRFKDLGEENFKALVLIAFAQYLQQSPFEDH VKLVNEVTEFAKTCVADESAENCDKSLHTLFGDKLCTVATLRETYGEMADCCAKQE PERNECFLQHKDDNPNLPRLVRPEVDVMCTAFHDNEETFLKKYLYEIARRHPYFYAP ELLFFAKRYKAAFTECCQAADKAACLLPKLDELRDEGKASSAKQRLKCASLQKFGER AFKAWAVARLSQRFPKAEFAEVSKLVTDLTKVHTECCHGDLLECADDRADLAKYIC ENQDSISSKLKECCEKPLLEKSHCIAEVENDEMPADLPSLAADFVESKDVCKNYAEAK DVFLGMFLYEYARRHPDYSVVLLLRLAKTYETTLEKCCAAADPHECYAKVFDEFKPL VEEPQNLIKQNCELFEQLGEYKFQNALLVRYTKKVPQVSTPTLVEVSRNLGKVGSKC CKHPEAKRMPCAEDYLSVVLNQLCVLHEKTPVSDRVTKCCTESLVNRRPCFSALEVD ETYVPKEFNAETFTFHADICTLSEKERQIKKQTALVELVKHKPKATKEQLKAVMDDF AAFVEKCCKADDKETCFAEEGKKLVAASQAALGLGSGGGGSGGGGSGGGGSGGGG SGGGGSGGGGSGGGGSGGGGSDHCPLGPGRCCRLHTVRASLEDLGWADWVLSPREV QVTMCIGACPSQFRAANMHAQIKTSLHRLKPDTVPAPCCVPASYNPMVLIQKTDTGV SLQTYDDLLAKDCHCI | 51 |
| 20 | HGEGTFTSDLSKQMEEEAVRLFIEWLKNGGPSSGAPPPSGAGGGGAGGGGADAHKSE VAHRFKDLGEENFKALVLIAFAQYLQQSPFEDHVKLVNEVTEFAKTCVADESAENCD KSLHTLFGDKLCTVATLRETYGEMADCCAKQEPERNECFLQHKDDNPNLPRLVRPEV DVMCTAFHDNEETFLKKYLYEIARRHPYFYAPELLFFAKRYKAAFTECCQAADKAAC LLPKLDELRDEGKASSAKQRLKCASLQKFGERAFKAWAVARLSQRFPKAEFAEVSKL VTDLTKVHTECCHGDLLECADDRADLAKYICENQDSISSKLKECCEKPLLEKSHCIAE VENDEMPADLPSLAADFVESKDVCKNYAEAKDVFLGMFLYEYARRHPDYSVVLLLR LAKTYETTLEKCCAAADPHECYAKVFDEFKPLVEEPQNLIKQNCELFEQLGEYKFQN ALLVRYTKKVPQVSTPTLVEVSRNLGKVGSKCCKHPEAKRMPCAEDYLSVVLNQLC VLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLV AASQAALGLGSGGGGSGGGGSGGGGSGGGGSGGGGSGGGGSGGGGSGGGGSDHCP LGPGRCCRLHTVRASLEDLGWADWVLSPREVQVTMCIGACPSQFRAANMHAQIKTS LHRLKPDTVPAPCCVPASYNPMVLIQKTDTGVSLQTYDDLLAKDCHCI | 52 |
| 21 | HGEGTFTSDVSSYLEEQAAKEFIAWLVKGGGGGGAGGGGAGGGGAGGGGAGGGGA GGGGADAHKSEVAHRFKDLGEENFKALVLIAFAQYLQQSPFEDHVKLVNEVTEFAKT CVADESAENCDKSLHTLFGDKLCTVATLRETYGEMADCCAKQEPERNECFLQHKDD NPNLPRLVRPEVDVMCTAFHDNEETFLKKYLYEIARRHPYFYAPELLFFAKRYKAAFT ECCQAADKAACLLPKLDELRDEGKASSAKQRLKCASLQKFGERAFKAWAVARLSQR FPKAEFAEVSKLVTDLTKVHTECCHGDLLECADDRADLAKYICENQDSISSKLKECCE KPLLEKSHCIAEVENDEMPADLPSLAADFVESKDVCKNYAEAKDVFLGMFLYEYARR HPDYSVVLLLRLAKTYETTLEKCCAAADPHECYAKVFDEFKPLVEEPQNLIKQNCELF EQLGEYKFQNALLVRYTKKVPQVSTPTLVEVSRNLGKVGSKCCKHPEAKRMPCAED YLSVVLNQLCVLHEKTPVSDRVTKCCTESLVNRRPCFSALEVDETYVPKEFNAETFTF HADICTLSEKERQIKKQTALVELVKHKPKATKEQLKAVMDDFAAFVEKCCKADDKE | 53 |

TABLE 6-continued

GLP1-GDF15 fusion proteins

| GLP1-GDF15 fusion proteins | Protein Sequence | SEQ ID NO: |
|---|---|---|
|  | TCFAEEGKKLVAASQAALGLGSGGGGSGGGGSGGGGSGGGGSGGGGSGGGGSGGG GSGGGGSDHCPLGPGRCCRLHTVRASLEDLGWADWVLSPREVQVTMCIGACPSQFR AANMHAQIKTSLHRLKPDTVPAPCCVPASYNPMVLIQKTDTGVSLQTYDDLLAKDCH CI |  |
| 22 | HGEGTFTSDVSSYLEEQAAKEFIAWLVKGGGGGGAGGGGAGGGGAGGGGAGGGGA DAHKSEVAHRFKDLGEENFKALVLIAFAQYLQQSPFEDHVKLVNEVTEFAKTCVADE SAENCDKSLHTLFGDKLCTVATLRETYGEMADCCAKQEPERNECFLQHKDDNPNLPR LVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAE FAEVSKLVTDLTKVHTECCHGDLLECADDRADLAKYICENQDSISSKLKECCEKPLLE KSHCIAEVENDEMPADLPSLAADFVESKDVCKNYAEAKDVFLGMFLYEYARRHPDY SVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSV VLNQLCVLHEKTPVSDRVTKCCTESLVNRRPCFSALEVDETYVPKEFNAETFTFHADI CTLSEKERQIKKQTALVELVKHKPKATKEQLKAVMDDFAAFVEKCCKADDKETCFA EEGKKLVAASQAALGLGSGGGGSGGGGSGGGGSGGGGSGGGGSGGGGSGGGGSGG GGSDHCPLGPGRCCRLHTVRASLEDLGWADWVLSPREVQVTMCIGACPSQFRAANM HAQIKTSLHRLKPDTVPAPCCVPASYNPMVLIQKTDTGVSLQTYDDLLAKDCHCI | 54 |
| 23 | HGEGTFTSDVSSYLEEQAAKEFIAWLVKGGGGGGSGGGGSGGGGSGGGGSGGGGSG GGGSDAHKSEVAHRFKDLGEENFKALVLIAFAQYLQQSPFEDHVKLVNEVTEFAKTC VADESAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYKAAFTE CCQAADKAACLLPKLDELRDEGKASSAKQRLKCASLQKFGERAFKAWAVARLSQRF PKAEFAEVSKLVTDLTKVHTECCHGDLLECADDRADLAKYICENQDSISSKLKECCEK PLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFE QLGEYKFQNALLVRYTKKVPQVSTPTLVEVSRNLGKVGSKCCKHPEAKRMPCAEDY LSVVLNQLCVLHEKTPVSDRVTKCCTESLVNRRPCFSALEVDETYVPKEFNAETFTFH ADICTLSEKERQIKKQTALVELVKHKPKATKEQLKAVMDDFAAFVEKCCKADDKET CFAEEGKKLVAASQAALGLGSGGGGSGGGGSGGGGSGGGGSGGGGSGGGGSGGGG SGGGGSDHCPLGPGRCCRLHTVRASLEDLGWADWVLSPREVQVTMCIGACPSQFRA ANMHAQIKTSLHRLKPDTVPAPCCVPASYNPMVLIQKTDTGVSLQTYDDLLAKDCHC I | 55 |
| 24 | HGEGTFTSDVSSYLEEQAAKEFIAWLVKGGGGGGSGGGGSGGGGSGGGGSGGGGSD AHKSEVAHRFKDLGEENFKALVLIAFAQYLQQSPFEDHVKLVNEVTEFAKTCVADES AENCDKSLHTLFGDKLCTVATLRETYGEMADCCAKQEPERNECFLQHKDDNPNLPR LVRPEVDVMCTAFHDNEETFLKKYLYEIARRHPYFYAPELLFFAKRYKAAFTECCQA ADKAACLLPKLDELRDEGKASSAKQRLKCASLQKFGERAFKAWAVARLSQRFPKAE FAEVSKLVTDLTKVHTECCHGDLLECADDRADLAKYICENQDSISSKLKECCEKPLLE KSHCIAEVENDEMPADLPSLAADFVESKDVCKNYAEAKDVFLGMFLYEYARRHPDY SVVLLLRLAKTYETTLEKCCAAADPHECYAKVFDEFKPLVEEPQNLIKQNCELFEQLG EYKFQNALLVRYTKKVPQVSTPTLVEVSRNLGKVGSKCCKHPEAKRMPCAEDYLSV VLNQLCVLHEKTPVSDRVTKCCTESLVNRRPCFSALEVDETYVPKEFNAETFTFHADI CTLSEKERQIKKQTALVELVKHKPKATKEQLKAVMDDFAAFVEKCCKADDKETCFA EEGKKLVAASQAALGLGSGGGGSGGGGSGGGGSGGGGSGGGGSGGGGSGGGGSGG GGGSDHCPLGPGRCCRLHTVRASLEDLGWADWVLSPREVQVTMCIGACPSQFRAANM HAQIKTSLHRLKPDTVPAPCCVPASYNPMVLIQKTDTGVSLQTYDDLLAKDCHCI | 56 |
| 25 | HGEGTFTSDVSSYLEEQAAKEFIAWLVKGGASAPAPAPAPAPAPAPAPAPGSDAH KSEVAHRFKDLGEENFKALVLIAFAQYLQQSPFEDHVKLVNEVTEFAKTCVADESAE NCDKSLHTLFGDKLCTVATLRETYGEMADCCAKQEPERNECFLQHKDDNPNLPRLV RPEVDVMCTAFHDNEETFLKKYLYEIARRHPYFYAPELLFFAKRYKAAFTECCQAAD KAACLLPKLDELRDEGKASSAKQRLKCASLQKFGERAFKAWAVARLSQRFPKAEFA EVSKLVTDLTKVHTECCHGDLLECADDRADLAKYICENQDSISSKLKECCEKPLLEKS HCIAEVENDEMPADLPSLAADFVESKDVCKNYAEAKDVFLGMFLYEYARRHPDYSV VLLLRLAKTYETTLEKCCAAADPHECYAKVFDEFKPLVEEPQNLIKQNCELFEQLGEY KFQNALLVRYTKKVPQVSTPTLVEVSRNLGKVGSKCCKHPEAKRMPCAEDYLSVVL NQLCVLHEKTPVSDRVTKCCTESLVNRRPCFSALEVDETYVPKEFNAETFTFHADICT LSEKERQIKKQTALVELVKHKPKATKEQLKAVMDDFAAFVEKCCKADDKETCFAEE GKKLVAASQAALGLGSGGGGSGGGGSGGGGSGGGGSGGGGSGGGGSGGGGSGGGG SDHCPLGPGRCCRLHTVRASLEDLGWADWVLSPREVQVTMCIGACPSQFRAANMHA QIKTSLHRLKPDTVPAPCCVPASYNPMVLIQKTDTGVSLQTYDDLLAKDCHCI | 57 |
| 26 | HGEGTFTSDVSSYLEEQAAKEFIAWLVKGGASGGGGSGGGGSGGGGSGGGGSGGGG SGGGGSGGGGSGGGGSDAHKSEVAHRFKDLGEENFKALVLIAFAQYLQQSPFEDHV KLVNEVTEFAKTCVADESAENCDKSLHTLFGDKLCTVATLRETYGEMADCCAKQEP ERNECFLQHKDDNPNLPRLVRPEVDVMCTAFHDNEETFLKKYLYEIARRHPYFYAPE LLFFAKRYKAAFTECCQAADKAACLLPKLDELRDEGKASSAKQRLKCASLQKFGERA FKAWAVARLSQRFPKAEFAEVSKLVTDLTKVHTECCHGDLLECADDRADLAKYICE NQDSISSKLKECCEKPLLEKSHCIAEVENDEMPADLPSLAADFVESKDVCKNYAEAKD | 58 |

TABLE 6-continued

GLP1-GDF15 fusion proteins

| GLP1-GDF15 fusion proteins | Protein Sequence | SEQ ID NO: |
|---|---|---|
| | VFLGMFLYEYARRHPDYSVVLLLRLAKTYETTLEKCCAAADPHECYAKVFDEFKPLV EEPQNLIKQNCELFEQLGEYKFQNALLVRYTKKVPQVSTPTLVEVSRNLGKVGSKCC KHPEAKRMPCAEDYLSVVLNQLCVLHEKTPVSDRVTKCCTESLVNRRPCFSALEVDE TYVPKEFNAETFTFHADICTLSEKERQIKKQTALVELVKHKPKATKEQLKAVMDDFA AFVEKCCKADDKETCFAEEGKKLVAASQAALGLGSGGGGSGGGGSGGGGSGGGGS GGGGSGGGGSGGGGSGGGGSDHCPLGPGRCCRLHTVRASLEDLGWADWVLSPREV QVTMCIGACPSQFRAANMHAQIKTSLHRLKPDTVPAPCCVPASYNPMVLIQKTDTGV SLQTYDDLLAKDCHCI | |
| 27 | HGEGTFTSDLSKQMEEEAVRLFIEWLKNGGPSSGAPPPSASGGGGSGGGGSGGGGSG GGGSGGGGSGGGGSGGGGSGGGGSDAHKSEVAHRFKDLGEENFKALVLIAFAQYLQ QSPFEDHVKLVNEVTEFAKTCVADESAENCDKSLHTLFGDKLCTVATLRETYGEMAD CCAKQEPERNECFLQHKDDNPNLPRLVRPEVDVMCTAFHDNEETFLKKYLYEIARRH PYFYAPELLFFAKRYKAAFTECCQAADKAACLLPKLDELRDEGKASSAKQRLKCASL QKFGERAFKAWAVARLSQRFPKAEFAEVSKLVTDLTKVHTECCHGDLLECADDRAD LAKYICENQDSISSKLKECCEKPLLEKSHCIAEVENDEMPADLPSLAADFVESKDVCK NYAEAKDVFLGMFLYEYARRHPDYSVVLLLRLAKTYETTLEKCCAAADPHECYAKV FDEFKPLVEEPQNLIKQNCELFEQLGEYKFQNALLVRYTKKVPQVSTPTLVEVSRNLG KVGSKCCKHPEAKRMPCAEDYLSVVLNQLCVLHEKTPVSDRVTKCCTESLVNRRPCF SALEVDETYVPKEFNAETFTFHADICTLSEKERQIKKQTALVELVKHKPKATKEQLKA VMDDFAAFVEKCCKADDKETCFAEEGKKLVAASQAALGLGSGGGGSGGGGSGGGG SGGGGSGGGGSGGGGSGGGGSGGGGSDHCPLGPGRCCRLHTVRASLEDLGWADWV LSPREVQVTMCIGACPSQFRAANMHAQIKTSLHRLKPDTVPAPCCVPASYNPMVLIQK TDTGVSLQTYDDLLAKDCHCI | 59 |
| 28 | HGEGTFTSDLSKQMEEEAVRLFIEWLKNGGPSSGAPPPSASAPAPAPAPAPAPAPAP APGSDAHKSEVAHRFKDLGEENFKALVLIAFAQYLQQSPFEDHVKLVNEVTEFAKTC VADESAENCDKSLHTLFGDKLCTVATLRETYGEMADCCAKQEPERNECFLQHKDDN PNLPRLVRPEVDVMCTAFHDNEETFLKKYLYEIARRHPYFYAPELLFFAKRYKAAFTE CCQAADKAACLLPKLDELRDEGKASSAKQRLKCASLQKFGERAFKAWAVARLSQRF PKAEFAEVSKLVTDLTKVHTECCHGDLLECADDRADLAKYICENQDSISSKLKECCEK PLLEKSHCIAEVENDEMPADLPSLAADFVESKDVCKNYAEAKDVFLGMFLYEYARRH PDYSVVLLLRLAKTYETTLEKCCAAADPHECYAKVFDEFKPLVEEPQNLIKQNCELFE QLGEYKFQNALLVRYTKKVPQVSTPTLVEVSRNLGKVGSKCCKHPEAKRMPCAEDY LSVVLNQLCVLHEKTPVSDRVTKCCTESLVNRRPCFSALEVDETYVPKEFNAETFTFH ADICTLSEKERQIKKQTALVELVKHKPKATKEQLKAVMDDFAAFVEKCCKADDKET CFAEEGKKLVAASQAALGLGSGGGGSGGGGSGGGGSGGGGSGGGGSGGGGSGGGG SGGGGSDHCPLGPGRCCRLHTVRASLEDLGWADWVLSPREVQVTMCIGACPSQFRA ANMHAQIKTSLHRLKPDTVPAPCCVPASYNPMVLIQKTDTGVSLQTYDDLLAKDCHC I | 60 |
| 29 | HSEGTFTSDVSSYLEGQAAKEFIEWLVKGRASAPAPAPAPAPAPAPAPAPAPAPGSDAHK SEVAHRFKDLGEENFKALVLIAFAQYLQQSPFEDHVKLVNEVTEFAKTCVADESAEN CDKSLHTLFGDKLCTVATLRETYGEMADCCAKQEPERNECFLQHKDDNPNLPRLVRP EVDVMCTAFHDNEETFLKKYLYEIARRHPYFYAPELLFFAKRYKAAFTECCQAADKA ACLLPKLDELRDEGKASSAKQRLKCASLQKFGERAFKAWAVARLSQRFPKAEFAEVS KLVTDLTKVHTECCHGDLLECADDRADLAKYICENQDSISSKLKECCEKPLLEKSHCI AEVENDEMPADLPSLAADFVESKDVCKNYAEAKDVFLGMFLYEYARRHPDYSVVLL LRLAKTYETTLEKCCAAADPHECYAKVFDEFKPLVEEPQNLIKQNCELFEQLGEYKFQ NALLVRYTKKVPQVSTPTLVEVSRNLGKVGSKCCKHPEAKRMPCAEDYLSVVLNQL CVLHEKTPVSDRVTKCCTESLVNRRPCFSALEVDETYVPKEFNAETFTFHADICTLSEK ERQIKKQTALVELVKHKPKATKEQLKAVMDDFAAFVEKCCKADDKETCFAEEGKKL VAASQAALGLGSGGGGSGGGGSGGGGSGGGGSGGGGSGGGGSGGGGSGGGGSDHC PLGPGRCCRLHTVRASLEDLGWADWVLSPREVQVTMCIGACPSQFRAANMHAQIKT SLHRLKPDTVPAPCCVPASYNPMVLIQKTDTGVSLQTYDDLLAKDCHCI | 61 |
| 30 | HSEGTFTSDVSSYLEGQAAKEFIEWLVKGRASGGGGSGGGGSGGGGSGGGGSGGGG SGGGGSGGGGSGGGGSDAHKSEVAHRFKDLGEENFKALVLIAFAQYLQQSPFEDHV KLVNEVTEFAKTCVADESAENCDKSLHTLFGDKLCTVATLRETYGEMADCCAKQEP ERNECFLQHKDDNPNLPRLVRPEVDVMCTAFHDNEETFLKKYLYEIARRHPYFYAPE LLFFAKRYKAAFTECCQAADKAACLLPKLDELRDEGKASSAKQRLKCASLQKFGERA FKAWAVARLSQRFPKAEFAEVSKLVTDLTKVHTECCHGDLLECADDRADLAKYICE NQDSISSKLKECCEKPLLEKSHCIAEVENDEMPADLPSLAADFVESKDVCKNYAEAKD VFLGMFLYEYARRHPDYSVVLLLRLAKTYETTLEKCCAAADPHECYAKVFDEFKPLV EEPQNLIKQNCELFEQLGEYKFQNALLVRYTKKVPQVSTPTLVEVSRNLGKVGSKCC KHPEAKRMPCAEDYLSVVLNQLCVLHEKTPVSDRVTKCCTESLVNRRPCFSALEVDE TYVPKEFNAETFTFHADICTLSEKERQIKKQTALVELVKHKPKATKEQLKAVMDDFA AFVEKCCKADDKETCFAEEGKKLVAASQAALGLGSGGGGSGGGGSGGGGSGGGGS GGGGSGGGGSGGGGSGGGGSDHCPLGPGRCCRLHTVRASLEDLGWADWVLSPREV QVTMCIGACPSQFRAANMHAQIKTSLHRLKPDTVPAPCCVPASYNPMVLIQKTDTGV SLQTYDDLLAKDCHCI | 62 |

TABLE 6-continued

GLP1-GDF15 fusion proteins

| GLP1-GDF15 fusion proteins | Protein Sequence | SEQ ID NO: |
|---|---|---|
| 31 | HGEGTFTSDVSSYLEEQAAKEFIAWLVKGGGGGSGGGGSGGGGSDAHKSEVAHRF KDLGEENFKALVLIAFAQYLQQSPFEDHVKLVNEVTEFAKTCVADESAENCDKSLHT LFGDKLCTVATLRETYGEMADCCAKQEPERNECFLQHKDDNPNLPRLVRPEVDVMC TAFHDNEETFLKKYLYEIARRHPYFYAPELLFFAKRYKAAFTECCQAADKAACLLPK LDELRDEGKASSAKQRLKCASLQKFGERAFKAWAVARLSQRFPKAEFAEVSKLVTDL TKVHTECCHGDLLECADDRADLAKYICENQDSISSKLKECCEKPLLEKSHCIAEVEND EMPADLPSLAADFVESKDVCKNYAEAKDVFLGMFLYEYARRHPDYSVVLLLRLAKT YETTLEKCCAAADPHECYAKVFDEFKPLVEEPQNLIKQNCELFEQLGEYKFQNALLV RYTKKVPQVSTPTLVEVSRNLGKVGSKCCKHPEAKRMPCAEDYLSVVLNQLCVLHE KTPVSDRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKLVAAS QAALGLGSGGGGSGGGGSGGGGSGGGGSGGGGSGGGGSGGGGSDHCPLGP GRCCRLHTVRASLEDLGWADWVLSPREVQVTMCIGACPSQFRAANMHAQIKTSLHR LKPDTVPAPCCVPASYNPMVLIQKTDTGVSLQTYDDLLAKDCHCI | 63 |
| 32 | HGEGTFTSDLSKQMEEEAVRLFIEWLKNGGPSSGAPPPSGGGGSGGGGSGGGGSDAH KSEVAHRFKDLGEENFKALVLIAFAQYLQQSPFEDHVKLVNEVTEFAKTCVADESAE NCDKSLHTLFGDKLCTVATLRETYGEMADCCAKQEPERNECFLQHKDDNPNLPRLV RPEVDVMCTAFHDNEETFLKKYLYEIARRHPYFYAPELLFFAKRYKAAFTECCQAAD KAACLLPKLDELRDEGKASSAKQRLKCASLQKFGERAFKAWAVARLSQRFPKAEFA EVSKLVTDLTKVHTECCHGDLLECADDRADLAKYICENQDSISSKLKECCEKPLLEKS HCIAEVENDEMPADLPSLAADFVESKDVCKNYAEAKDVFLGMFLYEYARRHPDYSV VLLLRLAKTYETTLEKCCAAADPHECYAKVFDEFKPLVEEPQNLIKQNCELFEQLGEY KFQNALLVRYTKKVPQVSTPTLVEVSRNLGKVGSKCCKHPEAKRMPCAEDYLSVVL NQLCVLHEKTPVSDRVTKCCTESLVNRRPCFSALEVDETYVPKEFNAETFTFHADICT LSEKERQIKKQTALVELVKHKPKATKEQLKAVMDDFAAFVEKCCKADDKETCFAEE GKKLVAASQAALGLGSGGGGSGGGGSGGGGSGGGGSGGGGSGGGGSGGGG SDHCPLGPGRCCRLHTVRASLEDLGWADWVLSPREVQVTMCIGACPSQFRAANMHA QIKTSLHRLKPDTVPAPCCVPASYNPMVLIQKTDTGVSLQTYDDLLAKDCHCI | 64 |
| 33 | HSEGTFTSDVSSYLEGQAAKEFIEWLVKGRASGGGGSGGGGSDAHKSEVAHRFKDLG EENFKALVLIAFAQYLQQSPFEDHVKLVNEVTEFAKTCVADESAENCDKSLHTLFGD KLCTVATLRETYGEMADCCAKQEPERNECFLQHKDDNPNLPRLVRPEVDVMCTAFH DNEETFLKKYLYEIARRHPYFYAPELLFFAKRYKAAFTECCQAADKAACLLPKLDEL RDEGKASSAKQRLKCASLQKFGERAFKAWAVARLSQRFPKAEFAEVSKLVTDLTKV HTECCHGDLLECADDRADLAKYICENQDSISSKLKECCEKPLLEKSHCIAEVENDEMP ADLPSLAADFVESKDVCKNYAEAKDVFLGMFLYEYARRHPDYSVVLLLRLAKTYET TLEKCCAAADPHECYAKVFDEFKPLVEEPQNLIKQNCELFEQLGEYKFQNALLVRYT KKVPQVSTPTLVEVSRNLGKVGSKCCKHPEAKRMPCAEDYLSVVLNQLCVLHEKTP VSDRVTKCCTESLVNRRPCFSALEVDETYVPKEFNAETFTFHADICTLSEKERQIKKQT ALVELVKHKPKATKEQLKAVMDDFAAFVEKCCKADDKETCFAEEGKKLVAASQAA LGLGSGGGGSGGGGSGGGGSGGGGSGGGGSGGGGSGGGGSDHCPLGPGRC CRLHTVRASLEDLGWADWVLSPREVQVTMCIGACPSQFRAANMHAQIKTSLHRLKP DTVPAPCCVPASYNPMVLIQKTDTGVSLQTYDDLLAKDCHCI | 65 |
| 34 | HSEGTFTSDVSSYLEGQAAKEFIEWLVKGRASAPAPAPAPAPGSDAHKSEVAHRFKD LGEENFKALVLIAFAQYLQQSPFEDHVKLVNEVTEFAKTCVADESAENCDKSLHTLF GDKLCTVATLRETYGEMADCCAKQEPERNECFLQHKDDNPNLPRLVRPEVDVMCTA FHDNEETFLKKYLYEIARRHPYFYAPELLFFAKRYKAAFTECCQAADKAACLLPKLD ELRDEGKASSAKQRLKCASLQKFGERAFKAWAVARLSQRFPKAEFAEVSKLVTDLTK VHTECCHGDLLECADDRADLAKYICENQDSISSKLKECCEKPLLEKSHCIAEVENDEM PADLPSLAADFVESKDVCKNYAEAKDVFLGMFLYEYARRHPDYSVVLLLRLAKTYE TTLEKCCAAADPHECYAKVFDEFKPLVEEPQNLIKQNCELFEQLGEYKFQNALLVRY TKKVPQVSTPTLVEVSRNLGKVGSKCCKHPEAKRMPCAEDYLSVVLNQLCVLHEKTP VSDRVTKCCTESLVNRRPCFSALEVDETYVPKEFNAETFTFHADICTLSEKERQIKKQT ALVELVKHKPKATKEQLKAVMDDFAAFVEKCCKADDKETCFAEEGKKLVAASQAA LGLGSGGGGSGGGGSGGGGSGGGGSGGGGSGGGGSGGGGSDHCPLGPGRC CRLHTVRASLEDLGWADWVLSPREVQVTMCIGACPSQFRAANMHAQIKTSLHRLKP DTVPAPCCVPASYNPMVLIQKTDTGVSLQTYDDLLAKDCHCI | 66 |
| 35 | HGEGTFTSDLSKQMEEEAVRLFIEWLKNGGPSSGAPPPSASGGGGSGGGGSDAHKSE VAHRFKDLGEENFKALVLIAFAQYLQQSPFEDHVKLVNEVTEFAKTCVADESAENCD KSLHTLFGDKLCTVATLRETYGEMADCCAKQEPERNECFLQHKDDNPNLPRLVRPEV DVMCTAFHDNEETFLKKYLYEIARRHPYFYAPELLFFAKRYKAAFTECCQAADKAAC LLPKLDELRDEGKASSAKQRLKCASLQKFGERAFKAWAVARLSQRFPKAEFAEVSKL VTDLTKVHTECCHGDLLECADDRADLAKYICENQDSISSKLKECCEKPLLEKSHCIAE VENDEMPADLPSLAADFVESKDVCKNYAEAKDVFLGMFLYEYARRHPDYSVVLLLR LAKTYETTLEKCCAAADPHECYAKVFDEFKPLVEEPQNLIKQNCELFEQLGEYKFQN ALLVRYTKKVPQVSTPTLVEVSRNLGKVGSKCCKHPEAKRMPCAEDYLSVVLNQLC VLHEKTPVSDRVTKCCTESLVNRRPCFSALEVDETYVPKEFNAETFTFHADICTLSEKE RQIKKQTALVELVKHKPKATKEQLKAVMDDFAAFVEKCCKADDKETCFAEEGKKLV AASQAALGLGSGGGGSGGGGSGGGGSGGGGSGGGGSGGGGSGGGGSDHCP | 67 |

TABLE 6-continued

GLP1-GDF15 fusion proteins

| GLP1-GDF15 fusion proteins | Protein Sequence | SEQ ID NO: |
|---|---|---|
| | LGPGRCCRLHTVRASLEDLGWADWVLSPREVQVTMCIGACPSQFRAANMHAQIKTS LHRLKPDTVPAPCCVPASYNPMVLIQKTDTGVSLQTYDDLLAKDCHCI | |
| 36 | HGEGTFTSDLSKQMEEEAVRLFIEWLKNGGPSSGAPPPSASAPAPAPAPAPGSDAHKS EVAHRFKDLGEENFKALVLIAFAQYLQQSPFEDHVKLVNEVTEFAKTCVADESAENC DKSLHTLFGDKLCTVATLRETYGEMADCCAKQEPERNECFLQHKDDNPNLPRLVRPE VDVMCTAFHDNEETFLKKYLYEIARRHPYFYAPELLFFAKRYKAAFTECCQAADKAA CLLPKLDELRDEGKASSAKQRLKCASLQKFGERAFKAWAVARLSQRFPKAEFAEVSK LVTDLTKVHTECCHGDLLECADDRADLAKYICENQDSISSKLKECCEKPLLEKSHCIA EVENDEMPADLPSLAADFVESKDVCKNYAEAKDVFLGMFLYEYARRHPDYSVVLLL RLAKTYETTLEKCCAAADPHECYAKVFDEFKPLVEEPQNLIKQNCELFEQLGEYKFQ NALLVRYTKKVPQVSTPTLVEVSRNLGKVGSKCCKHPEAKRMPCAEDYLSVVLNQL CVLHEKTPVSDRVTKCCTESLVNRRPCFSALEVDETYVPKEFNAETFTFHADICTLSEK ERQIKKQTALVELVKHKPKATKEQLKAVMDDFAAFVEKCCKADDKETCFAEEGKKL VAASSQAALGLGSGGGGSGGGGSGGGGSGGGGSGGGGSGGGGSGGGGSDHC PLGPGRCCRLHTVRASLEDLGWADWVLSPREVQVTMCIGACPSQFRAANMHAQIKT SLHRLKPDTVPAPCCVPASYNPMVLIQKTDTGVSLQTYDDLLAKDCHCI | 68 |
| 37 | HGEGTFTSDVSSYLEEQAAKEFIAWLVKGGASGGGGSGGGGSDAHKSEVAHRFKDL GEENFKALVLIAFAQYLQQSPFEDHVKLVNEVTEFAKTCVADESAENCDKSLHTLFG DKLCTVATLRETYGEMADCCAKQEPERNECFLQHKDDNPNLPRLVRPEVDVMCTAF HDNEETFLKKYLYEIARRHPYFYAPELLFFAKRYKAAFTECCQAADKAACLLPKLD LRDEGKASSAKQRLKCASLQKFGERAFKAWAVARLSQRFPKAEFAEVSKLVTDLTK VHTECCHGDLLECADDRADLAKYICENQDSISSKLKECCEKPLLEKSHCIAEVENDEM PADLPSLAADFVESKDVCKNYAEAKDVFLGMFLYEYARRHPDYSVVLLLRLAKTYE TTLEKCCAAADPHECYAKVFDEFKPLVEEPQNLIKQNCELFEQLGEYKFQNALLVRY TKKVPQVSTPTLVEVSRNLGKVGSKCCKHPEAKRMPCAEDYLSVVLNQLCVLHEKTP VSDRVTKCCTESLVNRRPCFSALEVDETYVPKEFNAETFTFHADICTLSEKERQIKKQT ALVELVKHKPKATKEQLKAVMDDFAAFVEKCCKADDKETCFAEEGKKLVAASQAA LGLGSGGGGSGGGGSGGGGSGGGGSGGGGSGGGGSGGGGSDHCPLGPGRC CRLHTVRASLEDLGWADWVLSPREVQVTMCIGACPSQFRAANMHAQIKTSLHRLKP DTVPAPCCVPASYNPMVLIQKTDTGVSLQTYDDLLAKDCHCI | 69 |
| 38 | HGEGTFTSDVSSYLEEQAAKEFIAWLVKGGASAPAPAPAPAPGSDAHKSEVAHRFKD LGEENFKALVLIAFAQYLQQSPFEDHVKLVNEVTEFAKTCVADESAENCDKSLHTLF GDKLCTVATLRETYGEMADCCAKQEPERNECFLQHKDDNPNLPRLVRPEVDVMCTA FHDNEETFLKKYLYEIARRHPYFYAPELLFFAKRYKAAFTECCQAADKAACLLPKLD ELRDEGKASSAKQRLKCASLQKFGERAFKAWAVARLSQRFPKAEFAEVSKLVTDLTK VHTECCHGDLLECADDRADLAKYICENQDSISSKLKECCEKPLLEKSHCIAEVENDEM PADLPSLAADFVESKDVCKNYAEAKDVFLGMFLYEYARRHPDYSVVLLLRLAKTYE TTLEKCCAAADPHECYAKVFDEFKPLVEEPQNLIKQNCELFEQLGEYKFQNALLVRY TKKVPQVSTPTLVEVSRNLGKVGSKCCKHPEAKRMPCAEDYLSVVLNQLCVLHEKTP VSDRVTKCCTESLVNRRPCFSALEVDETYVPKEFNAETFTFHADICTLSEKERQIKKQT ALVELVKHKPKATKEQLKAVMDDFAAFVEKCCKADDKETCFAEEGKKLVAASQAA LGLGSGGGGSGGGGSGGGGSGGGGSGGGGSGGGGSGGGGSDHCPLGPGRC CRLHTVRASLEDLGWADWVLSPREVQVTMCIGACPSQFRAANMHAQIKTSLHRLKP DTVPAPCCVPASYNPMVLIQKTDTGVSLQTYDDLLAKDCHCI | 70 |
| 39 | HSEGTFTSDVSSYLEGQAAKEFIEWLVKGRGGGGSGGGGSGGGGSDAHKSEVAHRF KDLGEENFKALVLIAFAQYLQQSPFEDHVKLVNEVTEFAKTCVADESAENCDKSLHT LFGDKLCTVATLRETYGEMADCCAKQEPERNECFLQHKDDNPNLPRLVRPEVDVMC TAFHDNEETFLKKYLYEIARRHPYFYAPELLFFAKRYKAAFTECCQAADKAACLLPK LDELRDEGKASSAKQRLKCASLQKFGERAFKAWAVARLSQRFPKAEFAEVSKLVTDL TKVHTECCHGDLLECADDRADLAKYICENQDSISSKLKECCEKPLLEKSHCIAEVEND EMPADLPSLAADFVESKDVCKNYAEAKDVFLGMFLYEYARRHPDYSVVLLLRLAKT YETTLEKCCAAADPHECYAKVFDEFKPLVEEPQNLIKQNCELFEQLGEYKFQNALLV RYTKKVPQVSTPTLVEVSRNLGKVGSKCCKHPEAKRMPCAEDYLSVVLNQLCVLHE KTPVSDRVTKCCTESLVNRRPCFSALEVDETYVPKEFNAETFTFHADICTLSEKERQIK KQTALVELVKHKPKATKEQLKAVMDDFAAFVEKCCKADDKETCFAEEGKKLVAAS QAALGLGSGGGGSGGGGSGGGGSGGGGSGGGGSGGGGSGGGGSDHCPLGP GRCCRLHTVRASLEDLGWADWVLSPREVQVTMCIGACPSQFRAANMHAQIKTSLHR LKPDTVPAPCCVPASYNPMVLIQKTDTGVSLQTYDDLLAKDCHCI | 71 |
| 40 | HGEGTFTSDVSSYLEEQAAKEFIAWLVKGGGGGGSGGGGSGGGGSDAHKSEVAHRF KDLGEETFKALVLVAFAQYLQQSPFEDHVKLVNEVTEFAKTCVADESAENCDKSLHT LFGDKLCTVATLRETYGEMADCCAKQEPERNECFLQHKDDNPNLPRLVRPEVDVMC TAFHDNEETFLKKYLYEIARRHPYFYAPELLFFAARYKAAFTECCQAADKAACLLPK LDELRDEGKASSAKQRLKCASLQKFGERAFKAWAVARLSQRFPKAEFAEVSKLVTDL TKVHTECCHGDLLECADDRADLAKYICENQDSISSKLKECCEKPLLEKSHCIAEVEND EMPADLPSLAADFVESKDVCKNYAEAKDVFLGMFLYEYARRHPDYSVVLLLRLAKT YETTLEKCCAAADPHECYAKVFDEFKPLVEEPQNLIKQNCELFEQLGEYKFQNALLV RYTKKVPQVSTPTLVEVSRNLGKVGSKCCKHPEAKRMPCAEDYLSVVLNQLCVLHE KTPVSDRVTKCCTESLVNRRPCFSALEVDETYVPKEFNAETFTFHADICTLSEKERQIK | 72 |

TABLE 6-continued

GLP1-GDF15 fusion proteins

| GLP1-GDF15 fusion proteins | Protein Sequence | SEQ ID NO: |
|---|---|---|
| | KQTALAELVKHKPKATKEQLKTVMDDFAAFVEKCCKADDKETCFAEEGKKLVAAS<br>QAALGLGSGGGGSGGGGSGGGGSGGGGSGGGGSGGGGSGGGGSGGGGSDHCPLGP<br>GRCCRLHTVRASLEDLGWADWVLSPREVQVTMCIGACPSQFRAANMHAQIKTSLHR<br>LKPDTVPAPCCVPASYNPMVLIQKTDTGVSLQTYDDLLAKDCHCI | |
| 41 | HGEGTFTSDVSSYLEEQAAKEFIAWLVKGGGGGGSGGGGSGGGGSDAHKSEVAHRF<br>KDLGEETFKALVLVAFAQYLQQSPFEDHVKLVNEVTEFAKTCVADESAENCDKSLHT<br>LFGDKLCTVATLRETYGEMADCCAKQEPERNECFLQHKDDNPNLPRLVRPEVDVMC<br>TAFHDNEETFLKKYLYEIARRHPYFYAPELLFFAARYKAAFTECCQAADKAACLLPK<br>LDELRDEGKASSAKQRLKCASLQKFGERAFKAWAVARLSQRFPKAEFAEVSKLVTDL<br>TKVHTECCHGDLLECADDRADLAKYICENQDSISSKLKECCEKPLLEKSHCLAEVEND<br>EMPADLPSLAADFVESKDVCKNYAEAKDVFLGMFLYEYARRHPDYSVVLLLRLAKT<br>YETTLEKCCAAADPHECYAKVFDEFKPLVEEPQNLIKQNCELFEQLGEYKFQNALLV<br>RYTKKVPQVSTPTLVEVSRNLGKVGSKCCKHPEAKRMPCAEDYLSVVLNQLCVLHE<br>KTPVSDRVTKCCTESLVNRRPCFSALEVDETYVPKEFNAETFTFHADICTLSEKERQIK<br>KQTALAELVKHKPKATKEQLKTVMDDFAAFVEKCCKADDKETCFAEEGKKLVAAS<br>QAALGLGSGGGGSGGGGSGGGGSGGGGSGGGGSGGGGSGGGGSDHCPLGP<br>GRCCRLHTVRASLEDLGWADWVLSPREVQVTMCIGACPSQFRAANMHAQIKTSLHR<br>LKPDTVPAPCCVPASYNPMVLRQKTDTGVSLQTYDDLLAKDCHCI | 73 |
| 42 | EGTFTSDVSSYLEEQAAKEFIAWLVKGGGGGGSGGGGSGGGGSDAHKSEVAHRFKD<br>LGEETFKALVLVAFAQYLQQSPFEDHVKLVNEVTEFAKTCVADESAENCDKSLHTLF<br>GDKLCTVATLRETYGEMADCCAKQEPERNECFLQHKDDNPNLPRLVRPEVDVMCTA<br>FHDNEETFLKKYLYEIARRHPYFYAPELLFFAARYKAAFTECCQAADKAACLLPKLD<br>ELRDEGKASSAKQRLKCASLQKFGERAFKAWAVARLSQRFPKAEFAEVSKLVTDLTK<br>VHTECCHGDLLECADDRADLAKYICENQDSISSKLKECCEKPLLEKSHCLAEVENDE<br>MPADLPSLAADFVESKDVCKNYAEAKDVFLGMFLYEYARRHPDYSVVLLLRLAKTY<br>ETTLEKCCAAADPHECYAKVFDEFKPLVEEPQNLIKQNCELFEQLGEYKFQNALLVR<br>YTKKVPQVSTPTLVEVSRNLGKVGSKCCKHPEAKRMPCAEDYLSVVLNQLCVLHEK<br>TPVSDRVTKCCTESLVNRRPCFSALEVDETYVPKEFNAETFTFHADICTLSEKERQIKK<br>QTALAELVKHKPKATKEQLKTVMDDFAAFVEKCCKADDKETCFAEEGKKLVAASQ<br>AALGLGSGGGGSGGGGSGGGGSGGGGSGGGGSGGGGSGGGGSDHCPLGPG<br>RCCRLHTVRASLEDLGWADWVLSPREVQVTMCIGACPSQFRAANMHAQIKTSLHRL<br>KPDTVPAPCCVPASYNPMVLIQKTDTGVSLQTYDDLLAKDCHCI | 74 |

GLP1-GDF15 Fusion Polynucleotides and Vectors

In another general aspect, the invention relates to an isolated nucleic acid encoding the GLP1-GDF15 fusion proteins of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding the fusion proteins of the invention can be altered without changing the amino acid sequences of the proteins.

In another general aspect, the invention relates to a vector comprising an isolated nucleic acid encoding a fusion protein of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of a fusion protein in the cell. Conventional cloning techniques or artificial gene synthesis can be used to generate a recombinant expression vector according to embodiments of the invention.

In another general aspect, the invention relates to a host cell comprising an isolated nucleic acid encoding a fusion protein of the invention. Any host cell known to those skilled in the art in view of the present disclosure can be used for recombinant expression of fusion proteins of the invention. In some embodiments, the host cells are *E. coli* TG1 or BL21 cells, CHO-DG44 or CHO-K1 cells or HEK293 cells. According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a fusion protein of the invention, comprising culturing a cell comprising a nucleic acid encoding the fusion protein under conditions to produce a fusion protein of the invention, and recovering the fusion protein from the cell or cell culture (e.g., from the supernatant). Expressed fusion proteins can be harvested from the cells and purified according to conventional techniques known in the art and as described herein.

Pharmaceutical Compositions

In another general aspect, the invention relates to a pharmaceutical composition, comprising the GLP1-GDF15 fusion proteins and/or GLP1-GDF15 fusion polynucleotides of the invention and a pharmaceutically acceptable carrier. The term "pharmaceutical composition" as used herein means a product comprising a GLP1-GDF15 fusion proteins and/or GLP1-GDF15 fusion polynucleotides of the invention together with a pharmaceutically acceptable carrier. GLP1-GDF15 fusion proteins and/or GLP1-GDF15 fusion polynucleotides of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in a peptide pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl) aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical formulations are provided comprising the GLP1-GDF15 fusion proteins and/or GLP1-GDF15 fusion polynucleotides of the invention in an amount from about 0.001 mg/ml to about 100 mg/ml, from about 0.01 mg/ml to about 50 mg/ml, or from about 0.1 mg/ml to about 25 mg/ml. The pharmaceutical formulation can have a pH from about 3.0 to about 10, for example from about 3 to about 7, or from about 5 to about 9. The formulation can further comprise at least one ingredient selected from the group consisting of a buffer system, preservative(s), tonicity agent(s), chelating agent(s), stabilizer(s) and surfactant(s).

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorhexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention can comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid can be present either in its free base form or in its salt form. Any stereoisomer (i.e., L, D, or a mixture thereof) of the amino acid base can be present. The amino acid base can be present individually or in the combination with other amino acid bases, in a concentration from about 0.01 mg/ml to about 50 mg/ml, for example from about 0.1 mg/ml to about 20 mg/ml. Pharmaceutical compositions comprising each one of these specific amino acid bases constitute alternative embodiments of the invention.

The pharmaceutically-acceptable salts of the GLP1-GDF15 fusion proteins and/or GLP1-GDF15 fusion polynucleotides of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups can be quaternized with, for example, alkyl halides.

The pharmaceutical compositions of the invention can be administered by any means that accomplish their intended purpose. Examples include administration by parenteral, subcutaneous, intravenous, intramuscular, intraperitoneal, transdermal, buccal or ocular routes. Administration can be by the oral route. Suitable formulations for parenteral administration include aqueous solutions of the active conjugates in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the GLP1-GDF15 fusion proteins and/or GLP1-GDF15 fusion polynucleotides of the present invention. Additionally, the present invention includes pharmaceutical compositions made by mixing one or more pharmaceutically acceptable carriers with any of the GLP1-GDF15 fusion proteins and/or GLP1-GDF15 polynucleotides of the present invention.

Furthermore, the GLP1-GDF15 fusion proteins and/or GLP1-GDF15 fusion polynucleotides of the present invention can have one or more polymorph or amorphous crystalline forms and as such are intended to be included in the scope of the invention. In addition, the GLP1-GDF15 fusion proteins and/or GLP1-GDF15 fusion polynucleotides can form solvates, for example with water (i.e., hydrates) or common organic solvents. As used herein, the term "solvate" means a physical association of the GLP1-GDF15 fusion proteins and/or GLP1-GDF15 fusion polynucleotides of the present invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the GLP1-GDF15 fusion proteins and/or GLP1-GDF15 fusion polynucleotides of the present invention. Thus, in the methods of treatment of the present invention, the term "administering" shall encompass the means for treating, ameliorating or preventing a syndrome, disorder or disease described herein with the GLP1-GDF15 fusion proteins and/or GLP1-GDF15 fusion polynucleotides of the present invention or a polymorph or solvate thereof, which would obviously be included within the scope of the invention albeit not specifically disclosed.

In another embodiment, the invention relates to the GLP1-GDF15 fusion proteins and/or GLP1-GDF15 fusion polynucleotides of the invention for use as a medicament.

The present invention includes within its scope prodrugs of the GLP1-GDF15 fusion proteins and/or GLP1-GDF15 fusion polynucleotides of this invention. In general, such prodrugs will be functional derivatives of the GLP1-GDF15 fusion proteins and/or GLP1-GDF15 fusion polynucleotides, which are readily convertible in vivo into the required GLP1-GDF15 fusion proteins and/or GLP1-GDF15 fusion polynucleotides. Thus, in the methods of treatment of the present invention, the term "administering" shall encompass the treatment of the various disorders described with the GLP1-GDF15 fusion proteins and/or GLP1-GDF15 fusion polynucleotides specifically disclosed or with a GLP1-GDF15 fusion proteins and/or GLP1-GDF15 fusion polynucleotides, which may not be specifically disclosed, but which converts to the specified GLP1-GDF15 fusion proteins and/or GLP1-GDF15 fusion polynucleotides in vivo after administration to the patient. Conventional procedures for the selection and preparation of suitable prodrug derivatives are described, for example, in "Design of Prodrugs", Ed. H. Bundgaard, Elsevier, 1985.

During any of the processes for preparation of the GLP1-GDF15 fusion proteins and/or GLP1-GDF15 fusion polynucleotides of the present invention, it can be necessary and/or desirable to protect sensitive or reactive groups on any of the molecules concerned. This can be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, each of which is herein incorporated by reference in its entirety for all purposes. The protecting groups can be removed at a convenient subsequent stage using methods known from the art.

Methods of Use

The present invention is directed to a method for preventing, treating or ameliorating a GDF15 receptor (GDF15R, GFRAL) mediated syndrome and/or a GLP1 receptor mediated syndrome, disorder or disease in a subject in need thereof comprising administering to the subject in need thereof an effective amount of a GLP1-GDF15 fusion protein, GLP1-GDF15 fusion polynucleotide, and/or pharmaceutical composition of the invention.

The present invention also provides a method for preventing, treating, delaying the onset of, or ameliorating a disorder, disease, or condition or any one or more symptoms of said disorder, disease, or condition in a subject in need thereof, comprising administering to the subject in need thereof an effective amount of a GLP1-GDF15 fusion protein, GLP1-GDF15 fusion polynucleotide, and/or pharmaceutical composition of the invention.

According to particular embodiments, the disease disorder, or condition is selected from the group consisting of obesity, type I or II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, eczema, sleep apnea, osteoarthritis, polycystic ovarian syndrome, chronic kidney syndrome, depression, and/or cancer.

According to particular embodiments, a therapeutically effective amount refers to the amount of therapy which is sufficient to achieve one, two, three, four, or more of the following effects: (i) reduce or ameliorate the severity of the disease, disorder, or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; (xii) enhance or improve the prophylactic or therapeutic effect(s) of another therapy; and/or (xiii) improve quality of life of a subject with the disease, disorder or condition to be treated.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related the disease, disorder, or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In one embodiment, the invention provides a method for preventing, treating, delaying the onset of, or ameliorating obesity, or any one or more symptoms of obesity in a subject in need thereof, the method comprising administering to the subject in need thereof an effective amount of a GLP1-GDF15 fusion protein, GLP1-GDF15 fusion polynucleotide, and/or pharmaceutical composition of the invention. In some embodiments, the body weight of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to the body weight of a subject prior to administration of any of the GLP1-GDF15 fusion proteins, GLP1-GDF15 fusion polynucleotides, pharmaceutical compositions, forms, or medicaments of the invention described herein, or compared to control subjects not receiving any of the GLP1-GDF15 fusion proteins, GLP1-GDF15 fusion polynucleotides, compositions, forms, medicaments, or combinations of the invention described herein.

In some embodiments, the reduction in body weight is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of preventing, treating, delaying the onset of, or ameliorating a syndrome, disorder or disease, or any one or more symptoms of said syndrome, disorder, or disease in a subject in need thereof, wherein said syndrome, disorder or disease is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, comprising administering to the subject in need thereof an effective amount of a GLP1-GDF15 fusion protein, GLP1-GDF15 fusion polynucleotide, and/or pharmaceutical composition of the invention.

As used herein, metabolic syndrome refers to a subject having any one or more of the following: high blood sugar (e.g., high fasting blood sugar), high blood pressure, abnormal cholesterol levels (e.g., low HDL levels), abnormal triglyceride levels (e.g., high triglycerides), a large waistline (i.e., waist circumference), increased fat in the abdominal area, insulin resistance, glucose intolerance, elevated C-reactive protein levels (i.e., a proinflammatory state), and increased plasma plasminogen activator inhibitor-1 and fibrinogen levels (i.e., a prothrombotic state).

The present invention provides a method of reducing food intake in a subject in need thereof, the method comprising administering to the subject in need thereof an effective amount of a GLP1-GDF15 fusion protein, GLP1-GDF15 fusion polynucleotide, and/or pharmaceutical composition of the invention. In some embodiments, food intake of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to food intake of a subject prior to administration of any of the GLP1-GDF15 fusion proteins, GLP1-GDF15 fusion polynucleotides, compositions, forms, medicaments, or combinations of the invention described herein, or compared to control subjects not receiving any of the GLP1-GDF15 fusion proteins, GLP1-GDF15 fusion polynucleotides, compositions, forms, medicaments, or combinations of the invention described herein.

In some embodiments, the reduction in food intake is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of reducing glycated hemoglobin (A1C) in a subject in need thereof, the method comprising administering to the subject in need thereof an effective amount of a GLP1-GDF15 fusion protein, GLP1-GDF15 fusion polynucleotide, and/or pharmaceutical composition of the invention. In some embodiments, A1C of a subject is reduced, for example, by between about 0.001% and about 0.01%, between about 0.01% and about 0.1%, between about 0.1% and about 0.2%, between about 0.2% and about 0.3%, between about 0.3% and about 0.4%, between about 0.4% and about 0.5%, between about 0.5% and about 1%, between about 1% and about 1.5%, between about 1.5% and about 2%, between about 2% and about 2.5%, between about 2.5% and about 3%, between about 3% and about 4%, between about 4% and about 5%, between about 5% and about 6%, between about 6% and about 7%, between about 7% and about 8%, between about 8% and about 9%, or between about 9% and about 10% relative to the A1C of a subject prior to administration of any of the GLP1-GDF15 fusion proteins, GLP1-GDF15 fusion polynucleotides, compositions, forms, medicaments, or combinations of the invention described herein, or compared to control subjects not receiving any of the GLP1-GDF15 fusion proteins, GLP1-GDF15 fusion polynucleotides, compositions, forms, medicaments, or combinations of the invention described herein.

In other embodiments, methods are provided for reducing fasting blood glucose levels in a subject in need thereof, the methods comprising administering to the subject in need thereof an effective amount of a GLP1-GDF15 fusion protein, GLP1-GDF15 fusion polynucleotide, and/or pharmaceutical composition of the invention. Fasting blood glucose levels may be reduced to less than about 140 to about 150 mg/dL, less than about 140 to about 130 mg/dL, less than about 130 to about 120 mg/dL, less than about 120 to about 110 mg/dL, less than about 110 to about 100 mg/dL, less than about 100 to about 90 mg/dL, or less than about 90 to about 80 mg/dL, relative to the fasting blood glucose levels of a subject prior to administration of any of the GLP1-GDF15 fusion proteins, GLP1-GDF15 fusion polynucleotides, compositions, forms, medicaments, or combinations of the invention described herein, or compared to control subjects not receiving any of the GLP1-GDF15 fusion proteins, GLP1-GDF15 fusion polynucleotides, compositions, forms, medicaments, or combinations of the invention described herein.

The present invention provides a method of modulating GLP1 receptor activity and GDF15 receptor activity in a subject in need thereof, the method comprising administering to the subject in need thereof an effective amount of a GLP1-GDF15 fusion protein, GLP1-GDF15 fusion polynucleotide, and/or pharmaceutical composition of the invention. As used herein, "modulating" refers to increasing or decreasing receptor activity.

In some embodiments, an effective amount of a GLP1-GDF15 fusion protein and/or GLP1-GDF15 fusion polynucleotide of the invention or a form, composition or medicament thereof is administered to a subject in need thereof once daily, twice daily, three times daily, four times daily, five times daily, six times daily, seven times daily, or eight times daily. In other embodiments, an effective amount of a GLP1-GDF15 fusion protein and/or GLP1-GDF15 fusion polynucleotide of the invention or a form, composition or medicament thereof is administered to a subject in need thereof once every other day, once per week, twice per week, three times per week, four times per week, five times per week, six times per week, two times per month, three times per month, or four times per month.

Another embodiment of the invention comprises a method of preventing, treating, delaying the onset of, or ameliorating a disease, disorder or syndrome, or one or more symptoms of any of said diseases, disorders, or syndromes in a subject in need thereof, the method comprising administering to the subject in need thereof an effective amount of a GLP1-GDF15 fusion protein, GLP1-GDF15 fusion polynucleotide, and/or pharmaceutical composition of the invention in a combination therapy. In certain embodiments, the combination therapy is a second therapeutic agent. In certain embodiments, the combination therapy is a surgical therapy.

As used herein, the term "in combination," in the context of the administration of two or more therapies to a subject, refers to the use of more than one therapy.

As used herein, combination therapy refers to administering to a subject in need thereof one or more additional therapeutic agents, or one or more surgical therapies, concurrently with an effective amount of a GLP1-GDF15 fusion protein and/or GLP1-GDF15 fusion polynucleotide of the invention or a form, composition or medicament thereof. In some embodiments, the one or more additional therapeutic agents or surgical therapies can be administered on the same day as an effective amount of a GLP1-GDF15 fusion protein and/or GLP1-GDF15 fusion polynucleotide of the invention, and in other embodiments, the one or more additional therapeutic agents or surgical therapies may be administered in the same week or the same month as an effective amount of a GLP1-GDF15 fusion protein and/or GLP1-GDF15 fusion polynucleotide of the invention.

The present invention also contemplates preventing, treating, delaying the onset of, or ameliorating any of the diseases, disorders, syndromes, or symptoms described herein in a subject in need thereof with a combination therapy that comprises administering to the subject in need thereof an effective amount of a GLP1-GDF15 fusion protein, GLP1-GDF15 fusion polynucleotide, and/or pharmaceutical composition of the invention, in combination with any one or more of the following therapeutic agents: a dipeptidyl peptidase-4 (DPP-4) inhibitor (e.g., sitagliptin, saxagliptin, linagliptin, alogliptin, etc.); a GLP1 receptor agonist (e.g., short-acting GLP1 receptor agonists such as exenatide and lixisenatide; intermediate-acting GLP1 receptor agonists such as liraglutide; long-acting GLP1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); dopamine receptor agonists (e.g., bromocriptine quick-release); biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g; pioglitazone, rosiglitazone, lobeglitazone, ciglitazone, darglitazone, englitazone, netoglitazone, rivoglitazone, troglitazone, etc.). In some embodiments, the dose of the additional therapeutic agent(s) is reduced when given in combination with a GLP1-GDF15 fusion protein and/or GLP1-GDF15 fusion polynucleotide of the invention. In some embodiments, when used in combination with a GLP1-GDF15 fusion protein and/or GLP1-GDF15 fusion polynucleotide of the invention, the additional therapeutic agent(s) may be used in lower doses than when each is used singly.

The present invention contemplates preventing, treating, delaying the onset of, or ameliorating any of the diseases, disorders, syndromes, or symptoms described herein in a subject in need thereof, with a combination therapy that comprises administering to the subject in need thereof an effective amount of a GLP1-GDF15 fusion protein, GLP1-GDF15 fusion polynucleotide, and/or pharmaceutical composition of the invention in combination with a surgical therapy. In certain embodiments, the surgical therapy can be bariatric surgery (e.g., gastric bypass surgery, such as Roux-en-Y gastric bypass surgery; sleeve gastrectomy; adjustable gastric band surgery; biliopancreatic diversion with duodenal switch; intragastric balloon; gastric plication; and combinations thereof).

In embodiments in which the one or more additional therapeutic agents or surgical therapies is administered on the same day as an effective amount of a GLP1-GDF15 fusion protein and/or GLP1-GDF15 fusion polynucleotide of the invention, the GLP1-GDF15 fusion protein and/or GLP1-GDF15 fusion polynucleotide of the invention may be administered prior to, after, or simultaneously with the additional therapeutic agent or surgical therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Embodiments

The invention provides also the following non-limiting embodiments.

Embodiment 1 is a glucagon-like peptide-1 (GLP1)/growth differentiation factor 15 (GDF15) fusion protein, wherein the GLP1-GDF15 fusion protein comprises a GLP1 peptide, a first linker peptide, a serum albumin protein, a second linker peptide, and a GDF15 protein.

Embodiment 2 is the GLP1-GDF15 fusion protein of embodiment 1, wherein GLP1 peptide comprises an amino acid sequence selected from the group consisting of SEQ ID NOs:1-4.

Embodiment 3 is the GLP1-GDF15 fusion protein of embodiment 1 or 2, wherein the first linker peptide comprises an amino acid sequence selected from the group consisting of SEQ ID NOs:5-25.

Embodiment 4 is the GLP1-GDF15 fusion protein of any one of embodiments 1-3, wherein the serum albumin protein comprises an amino acid sequence selected from SEQ ID NO:26 or SEQ ID NO:27.

Embodiment 5 is the GLP1-GDF15 fusion protein of any one of embodiments 1-4, wherein the second linker peptide comprises an amino acid sequence selected from the group consisting of SEQ ID NOs:28-30.

Embodiment 6 is the GLP1-GDF15 fusion protein of any one of embodiments 1-5, wherein the GDF15 protein comprises an amino acid sequence selected from SEQ ID NO:31 or SEQ ID NO:32.

Embodiment 7 is a GLP1-GDF15 fusion protein, wherein the GLP1-GDF15 fusion protein comprises an amino acid sequence selected from the group consisting of SEQ ID NOs:33-74 and 84.

Embodiment 8 is an isolated nucleic acid encoding the GLP1-GDF15 fusion protein of any one of embodiments 1-7.

Embodiment 9 is a vector comprising the isolated nucleic acid of embodiment 8.

Embodiment 10 is a host cell comprising the isolated nucleic acid of embodiment 8 or the vector of claim 9.

Embodiment 11 is a pharmaceutical composition comprising the GLP1-GDF15 fusion protein of any one of embodiments 1-7 and a pharmaceutically acceptable carrier.

Embodiment 12 is a method for treating or preventing obesity in a subject in need thereof, comprising administering to the subject in need thereof an effective amount of the pharmaceutical composition of embodiment 11.

Embodiment 13 is the method of embodiment 12, wherein administration of the effective amount of the pharmaceutical composition to the subject in need thereof results in a reduction in body weight of about 5% to about 10%, about 10% to about 15%, about 15% to about 20%, or about 20% to about 25% as compared to the body weight of the subject prior to administration of the pharmaceutical composition.

Embodiment 14 is a method for treating or preventing a disease or disorder in a subject in need thereof, wherein said disease or disorder is selected from the group consisting of obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the method comprising administering to the subject in need thereof an effective amount of the pharmaceutical composition of embodiment 11.

Embodiment 15 is the method of embodiment 14, wherein said disease or disorder is obesity.

Embodiment 16 is the method of embodiment 14, wherein said disease or disorder is type I diabetes.

Embodiment 17 is the method of embodiment 14, wherein said disease or disorder is type II diabetes.

Embodiment 18 is the method of embodiment 14, wherein said disease or disorder is a metabolic syndrome.

Embodiment 19 is the method of embodiment 14, wherein said disease or disorder is a renal disease.

Embodiment 20 is the method of embodiment 14, wherein said disease or disorder is non-alcoholic steatohepatitis (NASH).

Embodiment 21 is the method of embodiment 14, wherein said disease or disorder is non-alcoholic fatty liver disease (NAFLD).

Embodiment 22 is a method of reducing food intake in a subject in need thereof, the method comprising administering to the subject in need thereof an effective amount of the pharmaceutical composition of embodiment 11.

Embodiment 23 is the method of embodiment 22, wherein administration of the effective amount of the pharmaceutical composition to the subject in need thereof results in a reduction in food intake of about 5% to about 10%, about 10% to about 15%, about 15% to about 20%, about 20% to about 25%, about 25% to about 30%, about 30% to about 35%, about 35% to about 40%, about 40% to about 45%, or about 45% to about 50% as compared to the food intake of the subject prior to administration of the pharmaceutical composition.

Embodiment 24 is a method of modulating GLP1 receptor activity in a subject in need thereof, the method comprising administering to the subject in need thereof an effective amount of the pharmaceutical composition of embodiment 11.

Embodiment 25 is a method of modulating GDF15 receptor activity in a subject in need thereof, the method comprising administering to the subject in need thereof an effective amount of the pharmaceutical composition of embodiment 11.

Embodiment 26 is the method of any one of embodiments 11-25, wherein the pharmaceutical composition is administered via an injection.

Embodiment 27 is the method of embodiment 26, wherein the injection is delivered subcutaneously, intramuscularly, intraperitoneally, or intravenously.

Embodiment 28 is the method of any one of embodiments 11-27, wherein the pharmaceutical composition is administered in combination with a second therapeutic agent.

Embodiment 29 is the method of any one of embodiments 11-28, wherein the pharmaceutical composition is administered daily, weekly, or monthly to the subject in need thereof.

Embodiment 30 is the method of embodiment 29, wherein the pharmaceutical composition is administered once, twice, three, four, five, or six times per day.

Embodiment 31 is the method of embodiment 29, wherein the pharmaceutical composition is administered once, twice, three, four, five, or six times per week.

Embodiment 32 is the method of embodiment 29, wherein the pharmaceutical composition is administered once, twice, three, or four times per month.

Embodiment 33 is a kit comprising the GLP1-GDF15 fusion protein of any one of embodiments 1-7, the isolated nucleic acid of embodiment 8, and/or the vector of embodiment 9.

Embodiment 34 is the kit of embodiment 33, wherein the kit further comprises a device for injection.

Embodiment 35 is a method of producing a pharmaceutical composition comprising the GLP1-GDF15 fusion protein of any one of embodiments 1-7, comprising combining the GLP1-GDF15 fusion protein with a pharmaceutically acceptable carrier to obtain the pharmaceutical composition.

Embodiment 36 is a method of producing the GLP1-GDF15 fusion protein of any one of embodiments 1-7, comprising culturing a cell comprising a nucleic acid encoding the GLP1-GDF15 fusion protein under conditions to produce the GLP1-GDF15 fusion protein, and recovering the GLP1-GDF15 fusion protein from the cell or culture.

EXAMPLES

Example 1: Combination of GLP1 and GDF15 Agonists

The potential additive weight loss effects of combining GLP1 and GDF15 agonists were tested in diet induced obese (DIO) mice. Liraglutide, a GLP1 agonist, was administered alone or in combination with an HSA-GDF15 (SEQ ID NO:81) molecule for 8 days. Liraglutide was subcutaneously administered daily while HSA-GDF15 was given every two days. Body weight loss was greater in the animals receiving both agonists compared to either single agent demonstrating the potential for additivity when combining these independent mechanisms (FIG. 1).

Example 2: Design of the GLP1-GDF15 Fusion Proteins

Figure 3:
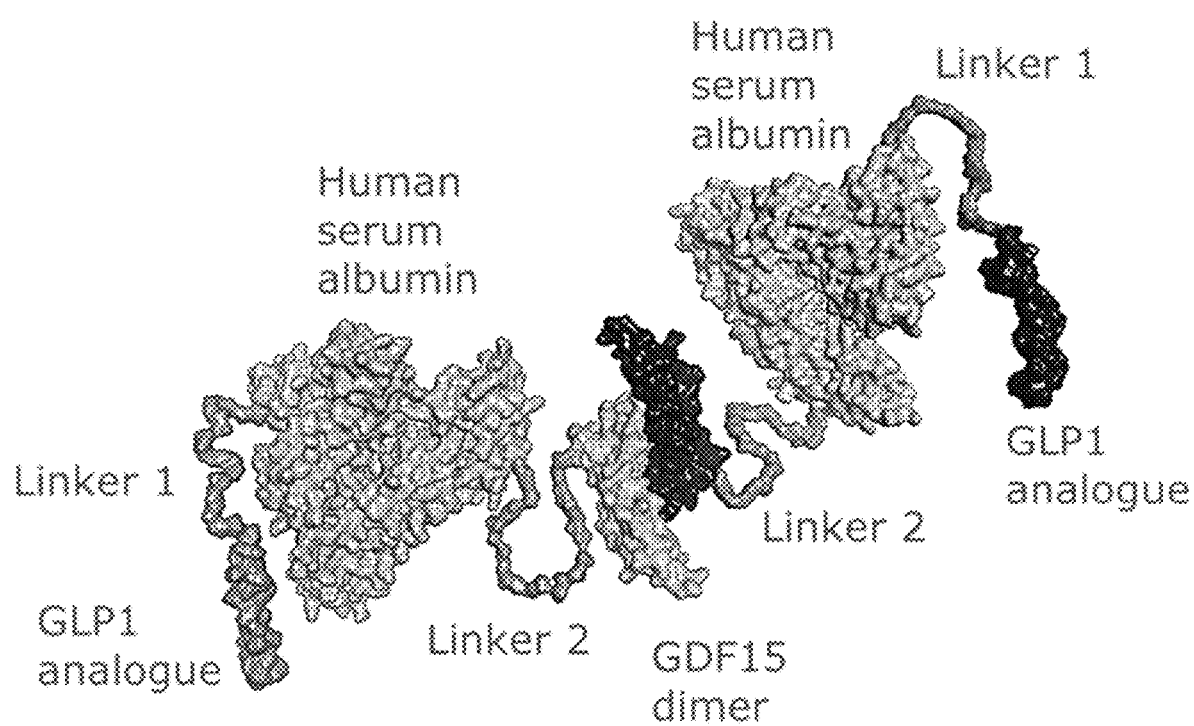
FIG. 3 shows a schematic of a GLP1-GDF15 fusion protein.

Recombinant fusion proteins comprised of a GLP1 peptide or GLP1 variant peptide, serum albumin protein, and GDF15 protein or GDF15 variant protein were designed as follows: GLP1 peptide or GLP1 variant peptides were connected via a first linker peptide at the C-terminus of the GLP1 peptide or GLP1 variant peptide to the N-terminus of human serum albumin. The human serum albumin is connected at the C-terminus to the N-terminus of the GDF15 protein or GDF15 protein variant via a second linker peptide. The design aims to leave the GDF15 dimerization interface unperturbed and allow for formation of the native inter-chain disulfide, resulting in a homodimer of approximately 170 KDa. The entire molecules were designed to be made recombinantly, needing only one gene (FIG. 3).

GLP1 peptides or GLP1 variant peptides include either human GLP1(7-36) peptide with mutations or Exendin 4(9-39) peptide, a venom peptide from Gila monster that agonizes the human GLP1 receptor. SEQ ID NO:1 contains (A8S, A30E) mutations (numbering for mutation positions refer to GLP1 peptide mutations in Table 1, not from the starting of fusion protein) and SEQ ID NO:2 contains (A8G, G22E, R36G) mutations from human GLP1 peptide (UniProtKB—P01275 98-127). SEQ ID NO:3 contains the Exendin 4 peptide (UniProtKB—P26349 48-86).

Native human serum albumin (UniProtKB—P02768 25-609) contains 35 cysteine (Cys, C) residues which form 17 intramolecular disulfide bonds, leaving Cys-34 as the only free cysteine. This free Cys-34 has been shown to function as a free radical scavenger, by trapping multiple reactive oxygen species (ROS) and reactive nitrogen species (RNS) (Taverna et. al, Ann Intensive Care, 3:4 (2013)). This free Cys was therefore mutated to Ser to create SEQ ID NO:26 to minimize chemical reactivity and the risk of heterogeneity due to oxidation.

The N terminus of mature GDF15 (UniProtKB—Q99988 197-308) contains a proteolytic liability site (R198) and a deamidation liability site (N199). Therefore, the fusion proteins contain GDF15(201-308) (SEQ ID NO:31) with those liability sites deleted.

Example 3: Expression and Purification Methods

GLP1-GDF15 fusion proteins, GLP1-first linker-serum albumin (e.g., HSA, GSA) proteins, serum albumin (e.g., HSA, GSA)-second linker-GDF15 proteins, and/or GDF15 proteins utilized in the examples above were expressed either in HEK Expi293F™ (ThermoFisher Scientific, Cat #A14527) or ExpiCHO-S™ (ThermoFisher Scientific, Cat #A29127; Waltham, Mass.). For expression in HEK Expi293F™, a plasmid encoding the GLP1-GDF15 fusion protein was transfected into cells by transient transfection following the manufacturer's recommendations. Briefly, Expi293F cells were maintained in suspension in Expi293™ expression medium (ThermoFisher Scientific) in a shaking incubator set at 37° C., 8% $CO_2$ and 125 RPM. The cells were passaged so that on the day of transfection, dilution down to $2.5 \times 10^6$ cells per ml could be achieved, maintaining cell viability at 95% or better. Transient transfections were performed using the ExpiFectamine™ 293 transfection kit (ThermoFisher Scientific). For each ml of diluted cells to be transfected, one microgram of plasmid DNA was diluted into OptiMEM™ SFM complexation medium. ExpiFectamine™ 293 reagent was used at a 1:2.6 ratio (v/v, DNA:reagent) and also diluted into OptiMEM™ and allowed to incubate for 5 minutes at room temperature. The diluted DNA and transfection reagent were combined for twenty minutes, allowing DNA/lipid complex formation, and then added to the cells. After overnight incubation, Expi293™ feed and ExpiFectamine™ 293 enhancer were added to the cells. Cells were cultured with shaking at 37° C. for four days prior to harvesting the culture supernatants.

ExpiCHO-S™ cells were maintained in suspension in ExpiCHO™ expression medium (ThermoFisher Scientific) in a shaking incubator set at 37° C., 8% $CO_2$ and 125 RPM. The cells were passaged so that on the day of transfection, dilution down to $6.0 \times 10^6$ cells per ml could be achieved, maintaining cell viability at 98% or better. Transient transfections were done using the ExpiFectamine™ CHO transfection kit (ThermoFisher Scientific). For each ml of diluted cells to be transfected, one microgram of plasmid DNA is diluted into OptiPRO™ SFM complexation medium. ExpiFectamine™ CHO reagent is used at a 1:3 ratio (v/v, DNA:reagent) and also diluted into OptiPRO™. The diluted DNA and transfection reagent were combined for one minute, allowing DNA/lipid complex formation, and then added to the cells. After overnight incubation, ExpiCHO™ feed and ExpiFectamine™ CHO enhancer were added to the cells. Cells were cultured with shaking at 32° C. for five days prior to harvesting the culture supernatants.

GLP1-GDF15 fusion proteins were purified from harvested culture supernatant either by single-step affinity capture or a two-step process using affinity capture followed by a preparative size exclusion chromatography (SEC) polishing step. Cell supernatants from transiently transfected ExpiCHO™ cells were loaded onto a pre-equilibrated (dPBS, pH 7.2) HSA CaptureSelect column (CaptureSelect Human Albumin Affinity Matrix from ThermoFisher Scientific) at an approximate capacity of 10 mg protein per ml of resin. After loading, unbound proteins and impurities were removed by washing the column with up to 12 column volumes (CV) of dPBS pH 7.2 followed by 3 CV of 1M NaCl in 50 mM Sodium phosphate, pH 7.4. The GLP1-GDF15 fusion protein which bound to the column was eluted with up to 10 CV of 0.1M Sodium Acetate, pH 3.5, into fraction tubes containing 10 percent (by volume) of 1M Tris (untitrated). Peak fractions were pooled and filtered over a 0.2 μm membrane, then either buffer exchanged into dPBS pH 7.2 or continued to SEC step at 4° C.

For SEC step, the protein from the capture step was concentrated to an appropriate volume before loading onto a 26/60 superdex 200 column (GE Healthcare; Little Chalfont, United Kingdom). Protein fractions eluted from SEC column with high purity (determined by SDS-PAGE) were pooled. The concentration of protein (from either method) was determined by the absorbance at 280 nm on a BioTek Synergy HTTM spectrophotometer. The quality of the purified proteins was assessed by SDS-PAGE and analytical size exclusion HPLC (SE-HPLC, Dionex HPLC system). Endotoxin levels were measured using a LAL assay (Pyrotell®-T, Associates of Cape Cod; East Falmouth, Mass.).

Figure 2:
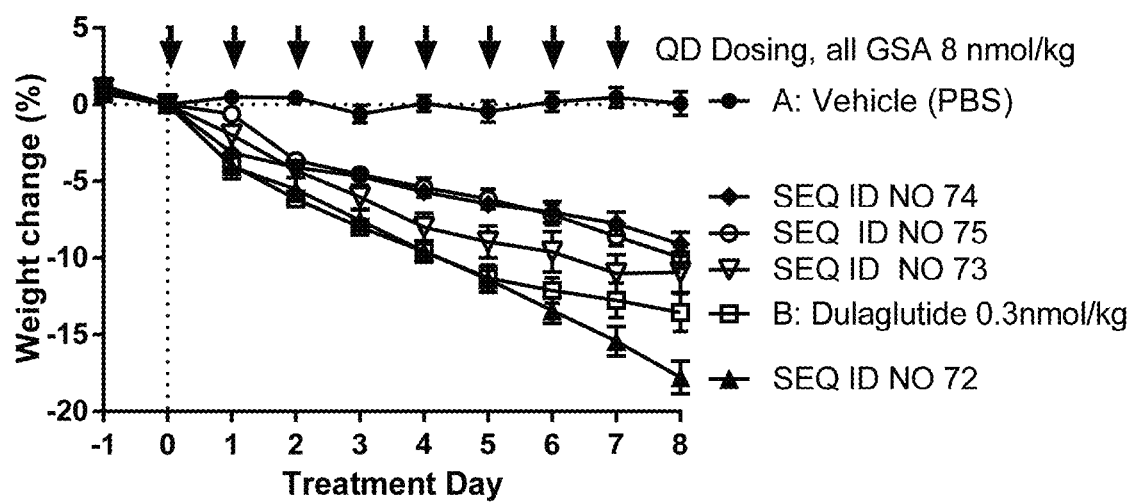
FIG. 2 shows a graph demonstrating average percent weight change (from day 0) in DIO mice receiving daily administration of GLP1-GSA-GDF15 (SEQ ID NO:72), GLP1-GSA-GDF15(I89R) (SEQ ID NO:73, I89R mutation abolishes GDF15 activity), GLP1(9-39)-GSA-GDF15 (SEQ ID NO:74, abolishes GLP1 activity), or GSA-GDF15 (SEQ ID NO:75). Dulaglutide treatment served as a positive control, while vehicle treatment served as a negative control. ±SEM, n=8.

Example 4: Dual Target Engagement and Additive Effects with Delivery of Both GLP1 and GDF15 Agonists on One Molecule The potential to achieve additive effects through delivering both GLP1 and GDF15 agonists on one molecule was tested by assessing weight loss in DIO mice over eight days of treatment with fusions of the agonists with gorilla serum albumin (GSA). GSA was used as a surrogate for HSA in these tool molecules. Mice received subcutaneous administration of 8 nmol/kg of GLP1-GSA-GDF15 (SEQ ID NO:72), GLP1-GSA-GDF15(I89R) (SEQ ID NO:73, I89R mutation abolishes GDF15 activity), GLP1(9-36)-GSA-GDF15 (SEQ ID NO:74, or GSA-GDF15 (SEQ ID NO:75), the latter two both designed to represent degraded GLP1. Two additional groups of animals served as controls and references, one receiving vehicle alone or another that was administered the GLP1 agonist dulaglutide. Mice treated with GLP1-GSA-GDF15 (SEQ ID NO:72) had greater weight loss than those treated with GLP1(9-36)-GSA-GDF15 (SEQ ID NO:74), GLP1-GSA-GDF15(I89R) (SEQ ID NO:73), and GSA-GDF15 (SEQ ID NO:75), providing proof of concept that both GLP1R and GFRAL can be agonized with a single molecule resulting in additive efficacy (FIG. 2).

Example 5: Effect of GLP1 Peptide or GLP1 Peptide Variants and First Linker Peptides on In Vitro Human GLP1R Potency, Ex Vivo Human, and In Vivo Mouse Plasma Stability Different GLP1 peptide or GLP1 peptide variants and different first linker peptides have different effects on in vitro hGLP1 receptor potency in an assay measuring cyclic adenosine monophosphate (cAMP) levels in hGLP1-overexpressing HEK cells. Fusions were screened for in vitro GLP1R potency in cell-based assays measuring intracellular cAMP production using the Lance competitive cAMP immunoassay (Perkin Elmer, Waltham, Mass.) according to the kit instructions. Clonal HEK293 cells stably expressing mouse or human GLP1R were used in the assays. Resulting data was used to calculate compound $EC_{50}$ values using Prism statistical software (GraphPad Software, San Diego, Calif.). In general, GLP1 variant (SEQ ID NO:1) is less potent than the other two GLP1 variants (SEQ ID NO:2 and SEQ ID NO:3) in the in vitro hGLP1R assay.

Ex vivo stability in human plasma was assessed. In brief, fresh, non-frozen human plasma was generated from heparinized blood by centrifugation. Fusion proteins were incubated in this matrix at 37° C. with gentle mixing for 0, 4, 24, 48, 72, and 96 hours. The stability of the GLP1 region of the fusion molecules over time in human plasma was monitored by immuno-affinity capture-trypsin digestion-LC-MS/MS analysis. Selected tryptic peptides, namely HSE (HSEGTFTSDVSSYLEGQAAK) (SEQ ID NO:76), HGE-1 (HGEGTFTSDVSSYLEEQAAK) (SEQ ID NO:77), and HGE-2 (HGEGTFTSDLSK) (SEQ ID NO:78), are located at the N-terminus of the GLP1 peptide or GLP1 variant peptides (SEQ ID NOs:1, 2, and 3), respectively. These selected tryptic peptides were monitored by LC-MS/MS after anti-GDF15 immuno-affinity capture and trypsin digestion which served as a surrogate measure of the concentration of fusion molecule with an intact GLP1 containing N-terminus. With this methodology, all the molecules tested demonstrated reasonable GLP1 stability over time in human plasma.

In vivo stability in mice was assessed. The fusion proteins were subcutaneously administered to male C57Bl/6 mice at a dose of 2 mg/kg in PBS, pH 7. Blood samples were collected into K3E Sarstedt blood collection tubes with protease inhibitors at 0, 4, 24 and 48 hours post administration. Plasma was prepared by centrifugation. The stability of the GLP1 region of the fusion proteins over time in vivo in mice was monitored by immuno-affinity capture-trypsin digestion-LC-MS/MS analysis. Selected tryptic peptides, namely HSE (HSEGTFTSDVSSYLEGQAAK) (SEQ ID NO:76), HGE-1 (HGEGTFTSDVSSYLEEQAAK) (SEQ ID NO:77), and HGE-2 (HGEGTFTSDLSK) (SEQ ID NO:78), are located at the N-terminus of SEQ ID NOs:1, 2, and 3 containing fusion proteins, respectively. These selected tryptic peptides were monitored by LC-MS/MS after anti-GDF15 immuno-affinity capture and trypsin digestion which served as a surrogate measure of the concentration of fusion protein with an intact GLP1 containing N-terminus. With this methodology, all the molecules tested demonstrated reasonable GLP1 stability over time in vivo in mice.

Table 7 provides results for in vitro GLP1 receptor potency measuring cAMP levels of GLP1R over-expressing cells, ex vivo human plasma stability and in vivo mouse plasma stability, both assessed by mass spectrometry, for the indicated GLP1-GDF15 fusion proteins.

TABLE 7

In vitro hGLP1R potency, ex vivo human, and in vivo mouse plasma stability of GLP1-GDF15 fusion proteins

| Molecule | | | In vitro | | Ex vivo human plasma stability by MS (% intact GLP1 relative to t = 0) | | | | | In vivo mouse plasma stability by MS (% intact GLP1 relative to HSA on the same molecule) | | |
|---|---|---|---|---|---|---|---|---|---|---|---|---|
| | | | hGLP1R potency | | | | | | | | | |
| Seq ID | GLP1 (SEQ ID NO) | First Linker Peptide (SEQ ID NO) | (nM) | +/−error | 4 h | 24 h | 48 h | 72 h | 96 h | 4 h | 24 h | 48 h |
| 68 | 3 | 1-7 (11) | 0.09 | 0.04 | 90.8 | 94 | 89.5 | 74.4 | 70.1 | 93.4 | 57.6 | 31.5 |
| 60 | 3 | 1-6 (10) | 0.09 | 0.03 | Not tested | | | | | Not tested | | |
| 59 | 3 | 1-9 (13) | 0.1 | 0.05 | | | | | | | | |
| 64 | 3 | 1-19 (23) | 0.12 | 0.03 | 87.4 | 80 | 75.7 | 62.2 | 56.9 | 80.3 | 51.7 | 32.9 |
| 67 | 3 | 1-8 (12) | 0.13 | 0.02 | 86.5 | 89.8 | 76 | 68.2 | 64.7 | 88.8 | 55 | 34.1 |
| 70 | 2 | 1-7 (11) | 0.26 | 0.1 | 122.7 | 125.8 | 122.1 | 102.9 | 99.5 | 93.1 | 71.2 | 44.8 |
| 62 | 1 | 1-9 (13) | 0.35 | 0.1 | | | | | | Not tested | | |
| 69 | 2 | 1-8 (12) | 0.38 | 0.03 | 102.3 | 100.1 | 102.7 | 84.7 | 91.3 | 81.5 | 69.6 | 64.9 |
| 63 | 2 | 1-19 (23) | 0.39 | 0.15 | 92.5 | 88.7 | 82.2 | 77.8 | 77.3 | 109 | 95 | 74.6 |
| 61 | 1 | 1-6 (10) | 0.39 | 0.09 | Not tested | | | | | Not tested | | |
| 66 | 1 | 1-7 (11) | 0.6 | 0.14 | 107.5 | 99 | 91.2 | 80.5 | 70.7 | 112 | 55.9 | 37.3 |
| 71 | 1 | 1-19 (23) | 1.5 | 0.13 | 100.2 | 93.6 | 84.9 | 62.6 | 60.6 | 87 | 52 | 30 |
| 65 | 1 | 1-8 (12) | 2.98 | 0.74 | 100.7 | 84.9 | 84.8 | 69.4 | 65.4 | 102 | 59.3 | 45.8 |

Example 6: Removing O-Linked Xylosylation by Eliminating Serine Residues in First and Second Linker Peptides Molecules containing glycine-serine linkers were tested for O-linked xylose levels since xylose glycans were reported to attach to glycine-serine linkers (Spahr et. al, mAbs 6 (4): 904-914). Briefly, samples were prepared by dilution into Guanidine-HCl buffered at pH 8.0 for denaturation, followed by adding DTT for reduction and incubating for 1 hour at 37° C. After reduction, the samples were alkylated using freshly prepared iodoacetamide for 60 minutes at room temperature in the dark. Then, DTT was added to the sample to chelate unreacted iodoacetamide. Next, samples were desalted using Zeba Spin Desalting columns according to the manufacturer's protocol in 50 mM Tris, 1 mM $CaCl_2$), pH 8.0 and digested with trypsin (Promega) for 4 hr at 37° C. Following digestion, TFA was added to each sample in order to quench the digestion reaction. Digested samples were kept at 4° C. and injected into LC/MS within 24 hours.

Digested samples were injected into an Agilent AdvanceBio Peptide Map Micro Bore Rapid Resolution Column using an Agilent Infinity 1290 UHPLC (Agilent Technologies) at a flow rate of 0.1 mL/min. The column temperature was maintained at 65° C. Mass spectrometry grade HPLC solvents (0.1% Formic acid and B: 100% ACN in 0.1% Formic acid) were purchased from VWR. The proteolytic peptides were eluted from the column using a 50 min gradient of 2 to 40% ACN in 0.1% FA. The column effluent was introduced into a Thermo Orbitrap Q-Exactive Mass spectrometer via heated electrospray ionization probe (HESI) using a spray voltage of 3.5 kV, sheath gas 20, aux gas 7, ion transfer tube at 299° C. and vaporizer at 100° C.

A top 2 data dependent experiment was performed with the precursor scan set to Orbitrap detection, 70,000 resolution, mass range 150-2000 m/z, AGC Target 1.0e6, maximum injection time 50 ms, 1 microscan, positive polarity. The precursor decision criteria were monoisotopic precursor selection—peptides, charge state: 2-7, dynamic exclusion: 6.0 seconds and precursor intensity threshold of 5e4. Precursor peptides were isolated by the quadrupole with an isolation window of 1.6 m/z and sent to the collision cell. A collision energy of 28 resulted in high energy collisional dissociation (HCD) of the peptide. These fragments were then transferred to the orbitrap for mass measurement. The orbitrap settings were 17,500 resolution, 200-2000 m/z range, AGC target 5e5, maximum injection time 100 ms, 1 microscan, and spectra acquired in centroid mode.

Peptide mapping data is processed using Byonic (Protein Metrics Inc) search algorithm. Custom library of core xylose glycosoaminoglycans and their monoisotopic mass was added to the search parameters as a Ser specific modification. Byonic search results were imported into Byologic (Protein Metrics Inc) for quantification based on extracted ion chromatograms (XIC) areas of the modified and unmodified peptide species.

GLP1-GDF15 fusion proteins containing $G_4S$ first and second linker peptides showed various levels of O-linked xylosylation on the serine residues of the first and second linker peptides. Table 8 shows the results of three such molecules expressed transiently from ExpiCHO cells. The level of xylose was protein context-dependent and ranged from 'not detected' to 1% in first linker peptides, which connect the GLP1 peptide or GLP1 peptide variants to the HSA protein, and from 11.61% to 56.2% in second linker peptides, which connect the HSA protein to the GDF15 protein or GDF15 protein variant. To avoid potential O-linked xylosylation risk on linker peptides, GLP1-GDF15 fusion proteins that do not contain serine residues in the first and/or second linker peptides were designed and generated. These GLP1-GDF15 fusion proteins contained linkers that comprise AP repeats, $G_4A$ repeats or poly-glycine repeats.

TABLE 8

Levels of xylose detected on serine residues in first or second linker peptide of GLP1-GDF15 fusion proteins comprising $G_4S$ linker peptides.

| Sequence ID | Linker motif | | Total Xyl % relative abundance by peptide mapping |
|---|---|---|---|
| 64 | Frist linker peptide (1-9) connecting GLP1 to HSA | SEQ ID NO:13 AS-8x($G_4S$) | Not detected |
| | Second linker peptide (2-3) connecting HSA to GDF15 | SEQ ID NO:30 GS-8x($G_4S$) | 11.61 |

TABLE 8-continued

Levels of xylose detected on serine residues in first or second linker peptide of GLP1-GDF15 fusion proteins comprising G4S linker peptides.

| Sequence ID | Linker motif | | Total Xyl % relative abundance by peptide mapping |
|---|---|---|---|
| 67 | Frist linker peptide (1-8) connecting GLP1 to HSA | SEQ ID NO:12 AS-2x(G4S) | 1.0 |
| | Second linker peptide (2-3) connecting HSA to GDF15 | SEQ ID NO:30 GS-8x(G4S) | 56.2 |
| 63 | Frist linker peptide (1-19) connecting GLP1 to HSA | SEQ ID NO:23 3x(G4S) | 0.5 |
| | Second linker peptide (2-3) connecting HSA to GDF15 | SEQ ID NO:30 GS-8x(G4S) | 23.1 |

Example 7: In Vitro Potency on GLP1R and GDF15R

In vitro activity of GLP1-GDF15 fusion proteins were tested for both GLP1R and GDF15R potency in cell based assays. GDF15R (GFRAL) activity was determined by measuring phospho-AKT (Ser473) level in SK-N-AS human neuroblastoma cells stably transfected to overexpress either human or cynomolgus monkey GFRAL. Phosphorylation of AKT after treating the GFRAL expressing cells with various concentrations of fusion molecules was measured using the Phospho-AKT (Ser473) Assay kit (Cisbio, Beford, Mass.) according to manufacturer's instructions. Resulting data was used to calculate compound $EC_{50}$ values using Prism statistical software (GraphPad Software San Diego). GLP1-GDF15 fusion proteins tested in Table 9 have similar GDF15R potency, with $EC_{50}$ in the 4.6-6.9 nM range.

GLP1R potency of the fusions was determined by measuring cAMP levels in clonal HEK293 cells stably transfected to overexpress human, mouse, or cynomolgus monkey GLP1R. Intracellular cAMP production after treating the cells with varying concentrations of the fusion molecules was measured using the Lance competitive cAMP immunoassay (Perkin Elmer, Waltham, Mass.) according to the kit instructions. Resulting data was used to calculate compound $EC_{50}$ values using Prism statistical software (GraphPad Software San Diego).

When serine residues in the first linker peptide, which connects the GLP1 peptide or GLP1 peptide variant to the HSA protein, were replaced with alanine or removed (switching from G4S to G4A or poly-G linker with similar length), GLP1 activity was not impacted when tested in a human or mouse GLP1R assay. In addition, changing the second linker peptide, which connects the HSA protein to the GDF15 protein or GDF15 protein variant, from GS-8x(G4S) to GA-8x(G4A) or 10x(AP) did not impact GLP1R potency. In addition, fusion proteins with increasing numbers of repeats in first linker (5x(G4A), 8x(G4A), 5x(AP), 10x(AP), 20x(AP), 25x(AP) were made and tested in the human GLP1R assay. Results demonstrated that these fusion proteins activated GLP1R signaling with varying potency.

TABLE 9 in vitro potency of GLP1-GDF15 fusion proteins on GLP1R and GDF15R

| | cAMP induction | | | | | | | | |
|---|---|---|---|---|---|---|---|---|---|
| | hGLP1R | | | mGLP1R | | | cGLP1R | | |
| SEQ ID NO: | EC50 (nM) | STD | n | EC50 (nM) | STD | n | EC50 (nM) | STD | n |
| 45 | 0.070 | 0.012 | 2 | 0.023 | 0.003 | 2 | 0.155 | 0.125 | 4 |
| 47 | 0.081 | 0.038 | 2 | 0.029 | 0.007 | 2 | 0.156 | 0.074 | 4 |
| 48 | 0.092 | 0.040 | 2 | 0.037 | 0.006 | 2 | 0.163 | 0.038 | 4 |
| 49 | 0.127 | 0.058 | 2 | 0.040 | 0.001 | 2 | 0.170 | 0.031 | 4 |
| 50 | 0.095 | 0.050 | 2 | 0.029 | 0.004 | 2 | 0.154 | 0.029 | 4 |
| 33 | 0.120 | 0.051 | 2 | 0.034 | 0.000 | 2 | 0.190 | 0.140 | 4 |
| 46 | 0.065 | 0.008 | 2 | 0.030 | 0.001 | 2 | 0.117 | 0.003 | 2 |
| 44 | 0.076 | 0.037 | 2 | 0.032 | 0.004 | 2 | 0.109 | 0.039 | 2 |
| GLP1 | 0.011 | 0.004 | 25 | 0.012 | 0.004 | 21 | 0.013 | 0.003 | 8 |
| Dulaglutide | 0.038 | 0.010 | 27 | 0.020 | 0.004 | 23 | 0.045 | 0.014 | 8 |
| Liraglutide | 0.057 | 0.025 | 18 | 0.052 | 0.022 | 14 | 0.079 | 0.022 | 2 |
| Albiglutide | 0.981 | 0.438 | 23 | 1.486 | 0.624 | 19 | 1.759 | 0.735 | 6 |

| | Phosphor-AKT (Ser473) | | | | | |
|---|---|---|---|---|---|---|
| | hGDF15R | | | cGDF15R | | |
| SEQ ID NO: | EC50 (nM) | 95% CI | n | EC50 (nM) | 95% CI | n |
| 45 | 4.561 | 3.975-5.258 | 1 | 1.031 | 0.6679-1.4 | 1 |
| 47 | 5.899 | 5.146-6.813 | 1 | 0.937 | 0.7413-1.137 | 1 |
| 48 | 6.283 | 5.479-7.281 | 1 | 1.585 | 1.374-1.819 | 1 |
| 49 | 4.825 | 4.11-5.726 | 1 | 1.157 | 0.7357-1.62 | 1 |
| 50 | 5.983 | 5.333-6.731 | 1 | 1.225 | 0.9865-1.473 | 1 |
| 33 | 5.251 | 4.523-6.113 | 1 | 1.004 | 0.7745-1.243 | 1 |
| 46 | 6.917 | 6.3-7.623 | 1 | 1.521 | 1.267-1.805 | 1 |
| 44 | 4.945 | 4.393-5.572 | 1 | 1.350 | 1.102-1.614 | 1 |

Example 8: Effect of First and Second Linker Peptides on Protein Purity and Stability Size exclusion high-performance liquid chromatography (SE-HPLC) was used to examine the purity and stability of the molecules by quantifying the percentage of main species as well as both high molecular weight (HMW) species that represent aggregates and low molecular weight (LMW) species that represent fragments. Briefly, to determine protein purity, 20 μg of protein was injected onto Tosoh TSKgel BioAssist G3SWXL (Cat #20026) column with a 1xDPBS, pH7.2 (Gibco Cat #14190-136) mobile phase. The protein species were eluted at a flow rate of 1 mL/min at room temperature, and the UV-280 nm absorbance values were monitored using a Dionex Ultimate3000 HPLC system equipped with a variable wavelength detector. To determine protein stability, 100 μg of protein was injected onto Tosoh TSKgel BioAssist G3SWXL (Cat #20026) column with a 0.2 M sodium phosphate pH 7.0 mobile phase. The protein species were eluted at a flow rate of 0.7 mL/min at room temperature, and the UV-280 nm absorbance values were monitored using a Dionex Ultimate3000 HPLC system equipped with a variable wavelength detector. Data is analyzed using Chromeleon software.

When GLP1-GDF15 fusion proteins were made from transient expression in ExpiCHO cells and purified by affinity capture following the methods described in Example 2, the GLP1-GDF15 fusion proteins with 10x(AP) second linker peptides (SEQ ID NO:28) (connecting the HSA protein to the GDF15 protein or GDF15 protein variant) consistently resulted in a lower percentage of low molecular weight (LMW) species compared with molecules containing GA-8x(G4A) second linker peptides (SEQ ID NO:29)

(Table 10). The LMW species were removed by polishing steps during purification and the resulting final GLP1-GDF15 fusion proteins were greater than 97% pure by SE-HPLC.

These GLP1-GDF15 fusion proteins were tested for stability under defined stressed conditions. To force chemical induced oxidation stress, the samples were exposed to a final concentration of 0.1% hydrogen peroxide and incubated for 6 hours in the dark prior to adding catalase to stop the reaction. In the metal induced oxidation condition, a final concentration of 30 µM ferrous iron was added to the samples. After incubation for two weeks in the dark, EDTA was added to stop the reaction. To test stability at low pH, the samples were dialyzed into 50 mM acetate pH 3.5 buffer, kept for 6 hours and dialyzed back to 0.1M sodium phosphate pH 7.4. To test sample stability under thermal stress, they were concentrated to approximately 10 mg/ml using ultra centrifugal filter with a molecular weight cut-off of 30 KDal and were held at 40° C. for two weeks in PBS. These samples that undergo the abovementioned chemical- or metal-induced oxidation, as well as low pH condition or thermal stress condition were analyzed under analytical size-exclusion chromatography (TOSOH column) with flow rate of 1 ml/min for a 20-minute run at room temperature. Signals are collected for UV-280 nm (Agilent 1100 LC system) and data analysis is done with Chemstation (Agilent).

Table 11 shows the influence of second linker on the stability of GLP1-GDF15 fusion proteins under thermal stress (40° C. for 2 weeks). The GLP1-GDF15 fusion proteins that contained a 10×(AP) second linker peptide (SEQ ID NO:28) resulted in a lower level of LMW species formed compared with GLP1-GDF15 fusion proteins containing a GA-8×($G_4$A) second linker peptide (SEQ ID NO:29), indicating that a AP second linker peptide is more thermally stable compared with a $G_4$A second linker peptide. Under other tested stress conditions (low pH, metal- or chemical-induced oxidation), the level of LMW species of the samples remain at minimal levels, similar to the non-stressed samples.

Differential Scanning calorimetry (DSC) was performed to determine the thermal stability of the GLP1-HSA-GDF15 proteins. Samples were evaluated at approximately 0.5-1 mg/ml in PBS pH7.4 buffer using an automated MicroCal VP-Capillary DSC instrument. The thermal scans span from 25° C. to 95° C. at a linear rate of 1° C./min. A pre-scan time of 15 minutes and a filtering period of 10 seconds were used for each run. The data were processed using non-2 state fitting function in Origin7 software package. DSC results demonstrated that these GLP1-GDF15 fusion proteins have melting temperature (Tm) in the 63-72° C. range (Table 12), similar to an HSA-GDF15 fusion protein that does not contain a GLP1 peptide or GLP1 peptide variant.

TABLE 10

GLP1-GDF15 fusion proteins with different first and second linker peptides show various levels of low molecular weight species by SE-HPLC after affinity purification.

| SEQ ID NO: | First linker peptide (SEQ ID NO) | Second linker peptide (SEQ ID NO) | SE-HPLC after affinity purification | | |
|---|---|---|---|---|---|
| | | | % HMW | % main | % LMW |
| 45 | 10x(AP) (6) | 10x(AP) (28) | 0-1.32 | 98.68-100 | 0 |
| 33 | 5x($G_4$A) (18) | 10x(AP) (28) | 0 | 100 | 0 |
| 44 | 5x(AP) (5) | 10x(AP) (28) | 0 | 100 | 0 |
| 47 | 25x(G) (22) | GA-8x($G_4$A) (29) | 2.3 | 86.64 | 11.06 |
| 48 | 20x(G) (21) | GA-8x($G_4$A) (29) | 5.56 | 83.77 | 10.67 |
| 49 | 4x($G_4$A) (17) | GA-8x($G_4$A) (29) | 2.93 | 94.64 | 2.43 |
| 46 | 5x(AP) (5) | GA-8x($G_4$A) (29) | 0 | 92.33 | 7.67 |
| 50 | 5x($G_4$A) (18) | GA-8x($G_4$A) (29) | 0.77-3 | 89.71-91.00 | 7.29-8.22 |

TABLE 11

GLP1-GDF15 fusion proteins with different first and second linker peptides show various levels of low molecular weight species under thermal stress (40° C. for 2 weeks).

| SEQ ID NO: | GLP1 peptide or GLP1 peptide variant | First linker peptide (SEQ ID NO:) | Second linker peptide (SEQ ID NO:) | SE-HPLC after all-step purification % main | SE-HPLC after 40° C. for 2 weeks | | |
|---|---|---|---|---|---|---|---|
| | | | | | % HMW | % main | % LMW |
| 45 | GLP1-based | 10x(AP) (6) | 10x(AP) (28) | 98.68-100 | 5.32 | 92.6 | 2.13 |
| 33 | GLP1-based | 5x($G_4$A) (18) | 10x(AP) (28) | 100 | 2.5 | 95.4 | 2.1 |
| 44 | Exendin4-based | 5x(AP) (5) | 10x(AP) (28) | 100 | 7.3 | 90.8 | 2.6 |
| 47 | GLP1-based | 25x(G) (22) | GA-8x($G_4$A) (29) | 100 | 0.91 | 93.9 | 5.19 |
| 48 | GLP1-based | 10x(G) (21) | GA-8x($G_4$A) (29) | 97.13 | 5.22 | 86.97 | 7.81 |
| 49 | GLP1-based | 4x($G_4$A) (17) | GA-8x($G_4$A) (29) | 100 | 0.42 | 93.56 | 6.02 |
| 50 | GLP1-based | 5x($G_4$A) (18) | GA-8x($G_4$A) (29) | 100 | 0.49 | 92.17 | 7.34 |
| 46 | Exendin4-based | 5x(AP) (5) | GA-8x($G_4$A) (29) | 100 | 5.9 | 74.5 | 19.6 |

TABLE 12

Tm for GLP1-GDF15 fusion proteins by differential scanning calorimetry (DSC).

| SEQ ID NO: | GLP1 peptide or GLP1 peptide variant | First linker peptide (SEQ ID NO:) | Second linker peptide (SEQ ID NO:) | Tm by DSC (° C.) | | | |
|---|---|---|---|---|---|---|---|
| | | | | Tm1 | Tm2 | Tm3 | Tm4 |
| 45 | GLP1-based | 10x(AP) (6) | 10x(AP) (28) | 64.88 | 68.79 | 73.38 | 76.59 |
| 33 | GLP1-based | 5x(G$_4$A) (18) | 10x(AP) (28) | 63.96 | 68.38 | 73.37 | 76.44 |
| 47 | GLP1-based | 25x(G) (22) | GA-8x(G$_4$A) (29) | 68.31 | 74.55 | 77.98 | na |
| 48 | GLP1-based | 20x(G) (21) | GA-8x(G$_4$A) (29) | 64.74 | 69.28 | 74.27 | 77.15 |
| 49 | GLP1-based | 4x(G$_4$A) (17) | GA-8x(G$_4$A) (29) | 64.64 | 69.58 | 74.29 | 77.04 |
| 50 | GLP1-based | 5x(G$_4$A) (18) | GA-8x(G$_4$A) (29) | 63.39 | 67.78 | 72.8 | 75.99 |
| 46 | Exendin4-based | 5x(AP) (5) | GA-8x(G$_4$A) (29) | 72.07 | 74.81 | 77.02 | na |
| 44 | Exendin4-based | 5x(AP) (5) | 10x(AP) (29) | 69.79 | 73.82 | 76.23 | na |

Example 9: Ex Vivo Human Plasma Study

The stability of the GLP1-GDF15 fusion proteins was assessed ex vivo in human plasma. In brief, fresh, non-frozen human plasma was generated from heparinized blood by centrifugation. Fusion proteins were incubated in this matrix at 37° C. with gentle mixing for 0, 4, 24, 48, 72 and 96 hours. The concentration of the fusion molecules over time in human plasma was monitored by immuno-affinity capture with an anti-GDF15 antibody and immuno-detection with either an anti-HSA antibody ("total format") or anti-GLP1 N-terminal specific antibody ("GLP1 active format"). Table 13 and 14 demonstrate the results from these two immunoassays.

TABLE 13 ex vivo human plasma stability by immunoassay measured by an anti-GDF15 capture antibody and an anti-HSA detection antibody.

| | Concentration (μg/mL) | | | | | | | Normalized % recovery to 0 hr | | | | | | |
|---|---|---|---|---|---|---|---|---|---|---|---|---|---|---|
| Time point (hr) | SEQ ID: 50 | SEQ ID: 33 | SEQ ID: 49 | SEQ ID: 48 | SEQ ID: 47 | SEQ ID: 45 | SEQ ID: 44 | SEQ ID: 50 | SEQ ID: 33 | SEQ ID: 49 | SEQ ID: 48 | SEQ ID: 47 | SEQ ID: 45 | SEQ ID: 44 |
| 0 | 13.69 | 13.13 | 13.14 | 12.69 | 13.32 | 12.79 | 13.77 | 100.0 | 100.0 | 100.0 | 100.0 | 100.0 | 100.0 | 100.0 |
| 4 | 14.14 | 13.56 | 12.83 | 13.20 | 12.53 | 12.89 | 13.30 | 103.3 | 103.3 | 97.6 | 104.0 | 94.0 | 100.8 | 96.6 |
| 24 | 13.84 | 13.49 | 12.16 | 13.21 | 13.31 | 12.76 | 12.53 | 101.1 | 102.8 | 92.5 | 104.0 | 99.9 | 99.8 | 91.0 |
| 48 | 12.84 | 13.57 | 12.21 | 12.56 | 12.48 | 11.88 | 11.55 | 93.8 | 103.4 | 92.9 | 98.9 | 93.7 | 92.9 | 83.9 |
| 72 | 13.18 | 14.00 | 11.21 | 12.12 | 12.35 | 12.18 | 12.93 | 96.3 | 106.7 | 85.3 | 95.5 | 92.7 | 95.2 | 93.9 |
| 96 | 12.92 | 13.01 | 11.23 | 12.09 | 12.16 | 12.32 | 12.34 | 94.4 | 99.1 | 85.4 | 95.2 | 91.3 | 96.3 | 89.6 |

TABLE 14 ex vivo human plasma stability by immunoassay by an anti-GDF15 capture antibody and an anti-GLP1 detection antibody (recognizing the N-terminal GLP1, specific to the active form of GLP1).

| | Concentration (μg/mL) | | | | | | | Normalized % recovery to 0 hr | | | | | | |
|---|---|---|---|---|---|---|---|---|---|---|---|---|---|---|
| Time point (hr) | SEQ ID: 50 | SEQ ID: 33 | SEQ ID: 49 | SEQ ID: 48 | SEQ ID: 47 | SEQ ID: 45 | SEQ ID: 44 | SEQ ID: 50 | SEQ ID: 33 | SEQ ID: 49 | SEQ ID: 48 | SEQ ID: 47 | SEQ ID: 45 | SEQ ID: 44 |
| 0 | 11.45 | 10.93 | 11.28 | 11.54 | 11.50 | 11.99 | 12.04 | 100.0 | 100.0 | 100.0 | 100.0 | 100.0 | 100.0 | 100.0 |
| 4 | 11.60 | 10.86 | 10.85 | 11.44 | 11.00 | 11.35 | 10.88 | 101.3 | 99.4 | 96.2 | 99.1 | 95.7 | 94.6 | 90.4 |
| 24 | 10.32 | 10.50 | 10.17 | 10.43 | 10.08 | 10.64 | 9.73 | 90.2 | 96.1 | 90.2 | 90.4 | 87.7 | 88.7 | 80.8 |
| 48 | 9.07 | 9.66 | 9.47 | 9.40 | 8.28 | 10.26 | 8.95 | 79.2 | 88.4 | 83.9 | 81.5 | 72.0 | 85.6 | 74.3 |
| 72 | 8.68 | 9.22 | 8.71 | 8.76 | 6.30 | 9.17 | 9.13 | 75.8 | 84.4 | 77.3 | 75.9 | 54.8 | 76.4 | 75.9 |
| 96 | 8.37 | 9.71 | 7.94 | 8.24 | 6.62 | 9.14 | 8.21 | 73.1 | 88.8 | 70.4 | 71.4 | 57.6 | 76.2 | 68.2 |

Example 10: Multispecies Pharmacokinetics

Mouse Pharmacokinetics

GLP1-GDF15 fusion proteins derived from SEQ ID NOs: 50, 45, 46, and 44 were administered to female C57Bl/6 mice at a dose of 5 mg/kg IV and SC in PBS, pH 7. Blood samples were collected, plasma was processed and drug concentrations were measured up to 4 days following both routes of administration. The concentration of analytes in plasma after IV and SC administration was measured by immuno-affinity capture-trypsin digestion-LC-MS/MS analysis. Selected tryptic peptides, namely, ALV (ALVLIAFAQYLQQSPFEDHVK) (SEQ ID NO:79), HGE-1 (HGEGTFTSDVSSYLEEQAAK) (SEQ ID NO:77), and HGE-2 (HGEGTFTSDLSK) (SEQ ID NO:78), and TDT (TDTGVSLQTYDDLLAK) (SEQ ID NO:80), which are located near the N-terminus of the HSA protein, the N-terminus of the GLP1 peptide or GLP1 peptide variant, and the C-terminus of the GDF15 protein or GDF15 protein variant, respectively. Monitoring these surrogate peptides enabled pharmacokinetic assessment of each region (GLP1, HSA, GDF15) of the GLP1-GDF15 fusion proteins. The plasma drug concentration-time profiles are summarized in Tables 15-22.

TABLE 15

Plasma concentration (µg/mL) and standard error of the mean (SEM, n = 3) of SEQ ID NO:50 over time following a single subcutaneous (SC) administration in C57BL/6 female mice.

| | Concentration (µg/mL) | | | SEM | | |
|---|---|---|---|---|---|---|
| SC Time (h) | HGE (GLP1) | ALV (HSA) | TDT (GDF15) | HGE (GLP1) | ALV (HSA) | TDT (GDF15) |
| 2 | 14.780 | 15.140 | 16.360 | 0.905 | 1.014 | 1.063 |
| 6 | 26.700 | 37.300 | 30.180 | 1.248 | 5.012 | 1.563 |
| 24 | 19.980 | 36.780 | 28.880 | 0.691 | 2.956 | 0.944 |
| 48 | 10.716 | 22.940 | 19.640 | 0.330 | 1.677 | 0.458 |
| 72 | 5.034 | 10.790 | 12.960 | 0.286 | 0.525 | 0.631 |
| 96 | 2.450 | 7.218 | 8.444 | 0.244 | 0.844 | 0.699 |

TABLE 16

Plasma concentration (µg/mL) and standard error of the mean (SEM, n = 3) of SEQ ID NO:50 over time following a single intravenous (IV) administration in C57BL/6 female mice.

| | Concentration (µg/mL) | | | SEM | | |
|---|---|---|---|---|---|---|
| IV Time (h) | HGE (GLP1) | ALV (HSA) | TDT (GDF15) | HGE (GLP1) | ALV (HSA) | TDT (GDF15) |
| 0.5 | 68.320 | 71.760 | 82.860 | 4.188 | 6.659 | 5.408 |
| 6 | 45.020 | 48.560 | 60.660 | 1.427 | 1.487 | 1.707 |
| 24 | 16.900 | 23.820 | 28.340 | 0.991 | 0.913 | 1.646 |
| 48 | 9.472 | 20.620 | 20.540 | 0.510 | 0.843 | 1.365 |
| 72 | 5.048 | 12.118 | 14.440 | 0.303 | 0.996 | 0.842 |
| 96 | 2.144 | 5.404 | 7.926 | 0.103 | 0.365 | 0.445 |

TABLE 17

Plasma concentration (µg/mL) and standard error of the mean (SEM, n = 3) of SEQ ID NO:45 over time following a single subcutaneous (SC) administration in C57BL/6 female mice.

| | Concentration (µg/mL) | | | SEM | | |
|---|---|---|---|---|---|---|
| SC Time (h) | HGE (GLP1) | ALV (HSA) | TDT (GDF15) | HGE (GLP1) | ALV (HSA) | TDT (GDF15) |
| 2 | 13.536 | 12.032 | 12.512 | 3.674 | 3.373 | 3.499 |
| 6 | 21.780 | 20.540 | 22.120 | 3.155 | 2.770 | 3.161 |
| 24 | 18.020 | 27.580 | 26.520 | 1.712 | 3.014 | 2.732 |
| 48 | 8.856 | 20.060 | 18.980 | 0.469 | 1.183 | 1.248 |
| 72 | 4.348 | 18.180 | 15.260 | 0.329 | 1.697 | 1.065 |
| 96 | 1.786 | 9.866 | 9.676 | 0.164 | 0.907 | 0.854 |

TABLE 18

Plasma concentration (µg/mL) and standard error of the mean (SEM, n = 3) of SEQ ID NO:45 over time following a single intravenous (IV) administration in C57BL/6 female mice.

| | Concentration (µg/mL) | | | SEM | | |
|---|---|---|---|---|---|---|
| IV Time (h) | HGE (GLP1) | ALV (HSA) | TDT (GDF15) | HGE (GLP1) | ALV (HSA) | TDT (GDF15) |
| 0.5 | 76.800 | 69.080 | 69.560 | 7.469 | 7.052 | 7.981 |
| 6 | 56.180 | 57.040 | 59.460 | 5.162 | 5.781 | 5.527 |
| 24 | 21.120 | 30.860 | 30.680 | 1.668 | 2.444 | 2.480 |
| 48 | 10.398 | 22.560 | 21.500 | 0.855 | 2.104 | 2.152 |
| 72 | 4.794 | 18.800 | 16.180 | 0.368 | 1.880 | 1.030 |
| 96 | 1.986 | 10.854 | 10.284 | 0.134 | 0.837 | 0.707 |

TABLE 19

Plasma concentration (µg/mL) and standard error of the mean (SEM, n = 3) of SEQ ID NO:46 over time following a single subcutaneous (SC) administration in C57BL/6 female mice.

| | Concentration (µg/mL) | | | SEM | | |
|---|---|---|---|---|---|---|
| SC Time (h) | HGE (GLP1) | ALV (HSA) | TDT (GDF15) | HGE (GLP1) | ALV (HSA) | TDT (GDF15) |
| 2 | 3.420 | 2.850 | 3.720 | 0.376 | 0.311 | 0.337 |
| 6 | 5.718 | 6.522 | 7.516 | 0.730 | 0.704 | 0.609 |
| 24 | 4.792 | 8.504 | 9.154 | 0.398 | 0.708 | 0.858 |
| 48 | 2.146 | 5.766 | 6.910 | 0.389 | 0.541 | 0.455 |
| 72 | 0.689 | 2.818 | 3.286 | 0.061 | 0.260 | 0.336 |
| 96 | 0.205 | 1.270 | 1.516 | 0.026 | 0.137 | 0.186 |

TABLE 20

Plasma concentration (µg/mL) and standard error of the mean (SEM, n = 3) of SEQ ID NO:46 following a single intravenous (IV) administration in C57BL/6 female mice.

| | Concentration (µg/mL) | | | SEM | | |
|---|---|---|---|---|---|---|
| IV Time (h) | HGE (GLP1) | ALV (HSA) | TDT (GDF15) | HGE (GLP1) | ALV (HSA) | TDT (GDF15) |
| 0.5 | 55.525 | 42.525 | 57.875 | 15.521 | 10.592 | 15.368 |
| 6 | 27.125 | 24.750 | 34.950 | 5.185 | 4.660 | 6.461 |
| 24 | 4.933 | 9.423 | 11.280 | 0.255 | 0.893 | 0.879 |
| 48 | 1.355 | 5.023 | 5.893 | 0.125 | 0.278 | 0.702 |
| 72 | 0.510 | 2.623 | 2.968 | 0.049 | 0.269 | 0.329 |
| 96 | 0.196 | 1.345 | 1.593 | 0.020 | 0.155 | 0.171 |

TABLE 21

Plasma concentration (μg/mL) and standard error of the mean (SEM, n = 3) of SEQ ID NO:44 following a single subcutaneous (SC) administration in C57BL/6 female mice.

| SC Time (h) | Concentration (μg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 2 | 6.340 | 6.124 | 6.792 | 2.029 | 1.845 | 2.289 |
| 6 | 8.534 | 10.310 | 10.672 | 1.697 | 1.721 | 1.876 |
| 24 | 4.646 | 10.098 | 10.018 | 0.969 | 1.801 | 1.874 |
| 48 | 1.879 | 6.264 | 6.480 | 0.486 | 1.171 | 1.162 |
| 72 | 0.691 | 3.678 | 3.694 | 0.153 | 0.766 | 0.760 |
| 96 | 0.194 | 1.758 | 1.860 | 0.048 | 0.304 | 0.331 |

TABLE 22

Plasma concentration (μg/mL) and standard error of the mean (SEM, n = 3) of SEQ ID NO:44 following a single intravenous (IV) administration in C57BL/6 female mice.

| IV Time (h) | Concentration (mg/mL) | | | SEM | | |
|---|---|---|---|---|---|---|
| | HGE (GLP1) | ALV (HSA) | TDT (GDF15) | HGE (GLP1) | ALV (HSA) | TDT (GDF15) |
| 0.5 | 57.920 | 53.300 | 60.760 | 4.648 | 3.971 | 4.489 |
| 6 | 29.560 | 33.360 | 37.400 | 2.266 | 2.199 | 2.176 |
| 24 | 4.564 | 10.420 | 10.684 | 0.424 | 0.393 | 0.560 |
| 48 | 1.300 | 6.276 | 6.022 | 0.217 | 0.312 | 0.250 |
| 72 | 0.540 | 3.396 | 3.562 | 0.040 | 0.257 | 0.195 |
| 96 | 0.159 | 1.784 | 1.804 | 0.025 | 0.180 | 0.123 |

Noncompartmental pharmacokinetic analysis (NCA) using the data in Tables 15-22 revealed a terminal half-life of 14-23 hours for the GLP1 peptide or GLP1 peptide variant, 22-49 hours for the GDF15 protein or GDF15 protein variant, and 22-47 hours for the HSA protein following SC and IV administration of the four GLP1-GDF15 fusion proteins tested in C57BL/6 mice (Table 23).

TABLE 23

Estimated terminal half-life of GLP1-GDF15 fusion proteins upon 5 mg/kg IV and SC administration in female C57BL/6 mice.

| SEQ ID NO: | Region | Half-life (hour) NCA SC Dosing | Half-life (hour) NCA IV Dosing |
|---|---|---|---|
| 50 | GDF15 | 39.4 | 39.8 |
| 50 | GLP1 | 22.5 | 24.4 |
| 50 | HSA | 29.5 | 24.8 |
| 45 | GDF15 | 49.4 | 46.7 |
| 45 | GLP1 | 21.8 | 20.1 |
| 45 | HSA | 46.9 | 38.3 |
| 46 | GDF15 | 21.9 | 25.4 |
| 46 | GLP1 | 14.2 | 17.2 |
| 46 | HSA | 22.0 | 25.3 |
| 44 | GDF15 | 26.7 | 28.4 |
| 44 | GLP1 | 15.8 | 15.2 |
| 44 | HSA | 28.8 | 26.5 |

Monkey Pharmacokinetics

GLP1-GDF15 fusion proteins derived from SEQ ID NOs: 33, 50, 45, 46, and 44 were administered to naïve male cynomolgus monkeys (*Macaca fascicularis*) at a dose of 0.5 mg/kg SC in PBS, pH 7. Blood samples were collected, plasma was processed and drug concentrations were measured up to 21 days using immunoassay bioanalysis. Immunoassay strategy included an anti-GDF15 capture antibody and detection with either an antibody recognizing intact GLP1 ("Active") or an antibody recognizing HSA ("Total"). The plasma drug concentration-time profile is summarized in Tables 24 and 25.

TABLE 24

Average (Avg, n = 3) plasma concentration (ng/mL) of active SEQ ID NOs:33, 50, 45, 46, and 44 over time following a single SC administration in cynomolgus monkeys as determined by immunoassay.

| | Time point | SEQ ID NO:46 | SEQ ID NO:44 | SEQ ID NO:45 | SEQ ID NO:50 | SEQ ID NO:33 |
|---|---|---|---|---|---|---|
| Active GLP1 (ng/mL) | Predose | <2.50 | <2.50 | <2.50 | <2.50 | <1.25 |
| | 6-hr | 1747.72 | 2530.81 | 2457.83 | 1667.36 | 1880.02 |
| | 24-hr | 3057.60 | 3492.18 | 3946.41 | 3191.24 | 3151.63 |
| | 48-hr | 3177.96 | 3416.86 | 3655.95 | 3643.12 | 3448.62 |
| | 72-hr | 2689.49 | 3013.14 | 3015.11 | 2991.62 | 2949.14 |
| | 120-hr | 1501.85 | 1669.39 | 1402.39 | 2029.62 | 1991.88 |
| | 168-hr | 813.84 | 1020.04 | 725.75 | 1208.07 | 1246.28 |
| | 240-hr | 378.81 | 471.08 | 265.28 | 564.57 | 583.56 |
| | 336-hr | 137.73 | 192.90 | 81.18 | 197.74 | 211.92 |
| | 432-hr | 53.16 | 61.11 | 25.47 | 70.28 | 79.78 |
| | 528-hr | 23.10 | 35.96 | 10.60 | 25.70 | 36.59 |

TABLE 25

Average (Avg, n = 3) plasma concentration (ng/mL) of Total SEQ ID NOs:33, 50, 45, 46, and 44 over time following a single SC administration in cynomolgus monkeys as determined by immunoassay.

| | Time point | SEQ ID NO:46 | SEQ ID NO:44 | SEQ ID NO:45 | SEQ ID NO:50 | SEQ ID NO:33 |
|---|---|---|---|---|---|---|
| Total (ng/mL) | Predose | <5.00 | <5.00 | <5.00 | <5.00 | <5.00 |
| | 6-hr | 1628.27 | 2299.98 | 2139.00 | 1427.28 | 1726.39 |
| | 24-hr | 3350.99 | 3873.18 | 4639.00 | 3430.23 | 3451.14 |
| | 48-hr | 3956.92 | 4427.70 | 5607.40 | 4892.71 | 4542.34 |
| | 72-hr | 3672.20 | 4399.17 | 5310.44 | 4303.43 | 4514.28 |
| | 120-hr | 2699.22 | 3612.21 | 4616.56 | 4133.96 | 4114.96 |
| | 168-hr | 1930.94 | 2745.57 | 3902.73 | 3237.20 | 3431.95 |
| | 240-hr | 1261.95 | 1964.84 | 2820.20 | 2353.01 | 2504.95 |
| | 336-hr | 719.72 | 1357.09 | 2005.69 | 1597.70 | 1682.87 |
| | 432-hr | 442.57 | 806.98 | 1399.11 | 964.85 | 1096.51 |
| | 528-hr | 328.35 | 532.75 | 961.88 | 708.00 | 879.52 |

Pharmacokinetic analysis of the data in Tables 24 and 25 revealed a terminal half-life of 2-3 days for the active molecule and 5-8 days for the total molecule in cynomolgus monkeys following SC administration (Table 26).

TABLE 26

Terminal half-life of SEQ ID NOs:50, 33, 45, 46, and 44 following 0.5 mg/kg SC administration in cynomolgus monkeys.

| SEQ ID NO: | Detection | half-life (d) |
|---|---|---|
| 44 | Active | 3.2 |
| | Total | 6.6 |
| 46 | Active | 2.6 |
| | Total | 4.6 |
| 50 | Active | 2.9 |
| | Total | 6.6 |
| 45 | Active | 2.3 |
| | Total | 7.6 |
| 33 | Active | 3.0 |
| | Total | 7.8 |

Example 11: In Vivo Potency of GLP1-GDF15 Fusion Proteins

Figure 4:
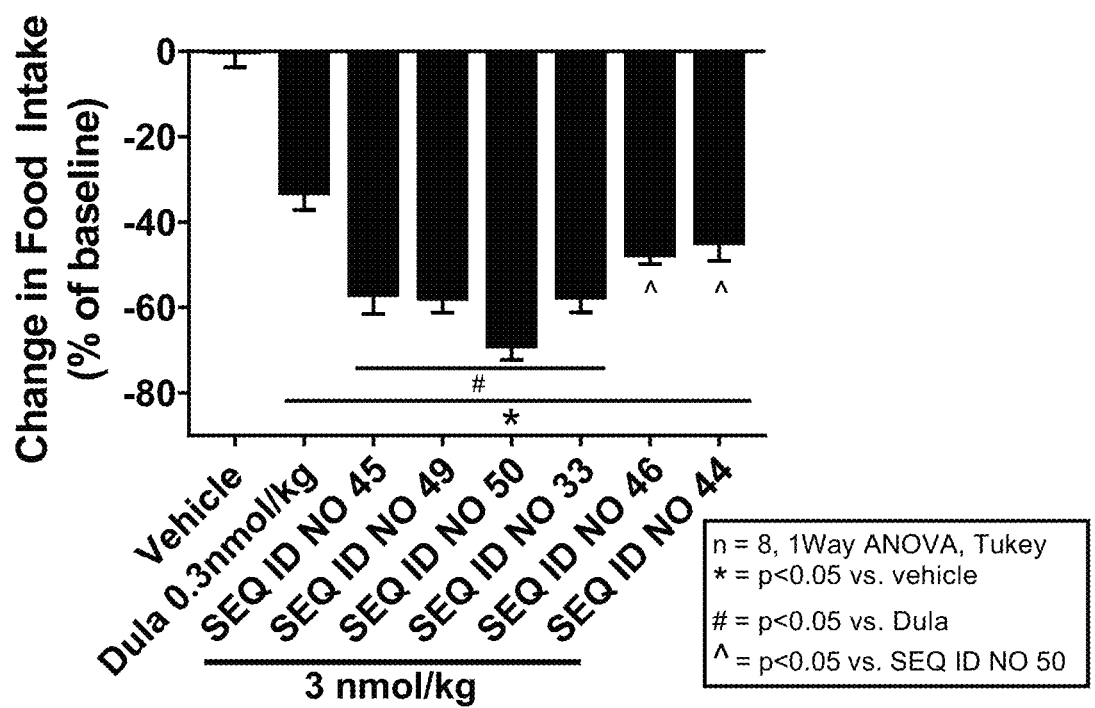
FIG. 4 shows a graph demonstrating the effects of subcutaneous administration of SEQ ID NOs:45, 49, 50, 33, 46, and 44 on food intake in C57BL/6 mice. Data is presented as percent change in food intake as compared to food intake prior to treatment at 24 hours.
Figure 5:
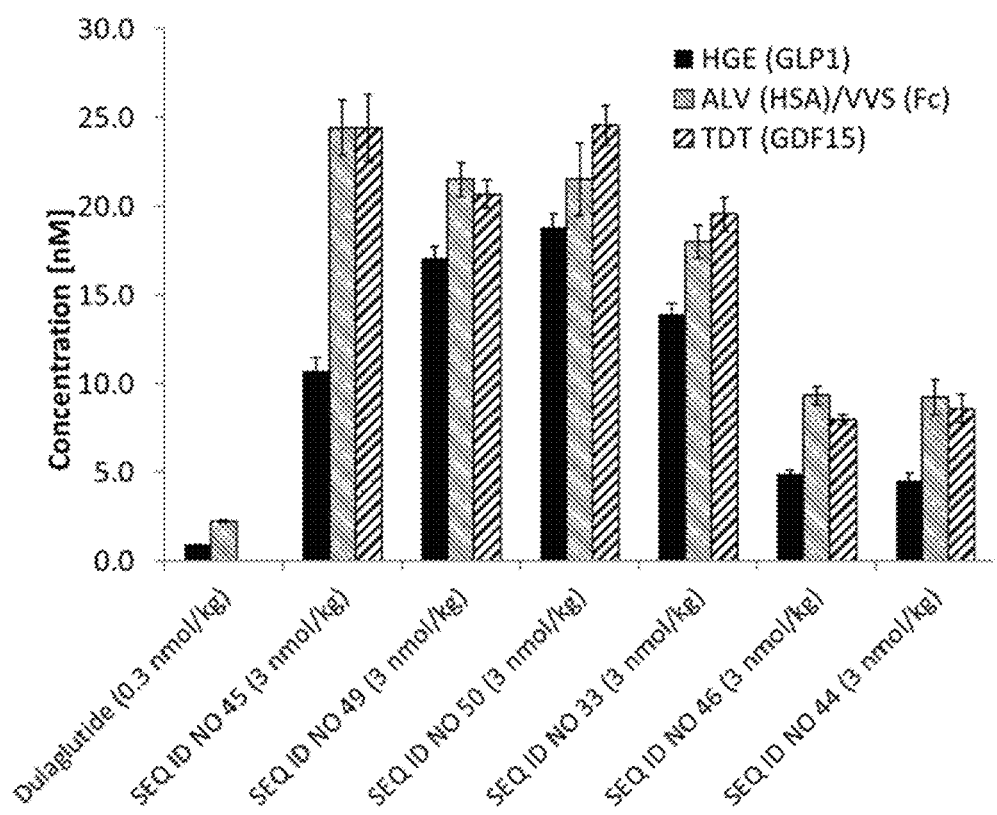
FIG. 5 shows a graph demonstrating the plasma concentration of GLP1-GDF15 fusion proteins (SEQ ID NOs:45, 49, 50, 33, 46, and 44) at 24 hours after administration in mice as determined by immune-affinity capture-trypsin digestion-LC-MS/MS analysis.

Assessment of food intake in C57BL/6 male mice: The purpose of this experiment was to demonstrate the in vivo pharmacodynamic effect of molecules corresponding to SEQ ID NOs:50, 33, 49, 45, 46, and 44 on the inhibition of food intake in C57BL/6 mice. 24-hour food intake was measured before and after subcutaneous administration of GLP1-GDF15 fusion proteins (test articles) or controls (PBS vehicle or dulaglutide) between 4:00 and 5:00 pm. The change in food weight for each cage was recorded every 24 hours. The results are expressed as the percent change in food intake compared to the 24 hours prior to treatment and are partially dependent on the circulating concentration of each test article used in the study (FIG. 4). Circulating concentration of test articles was determined 24 hours after administration by immuno-affinity capture-trypsin digestion-LC-MS/MS analysis. Selected tryptic peptides were monitored, namely, ALV (ALVLIAFAQYLQQSPFEDHVK) (SEQ ID NO:79), HGE-1 (HGEGTFTSDVSSYLEEQAAK) (SEQ ID NO:77), and HGE-2 (HGEGTFTSDLSK) (SEQ ID NO:78), and TDT (TDTGVSLQTYDDLLAK) (SEQ ID NO:80), which are located near the N-terminus of the HSA protein, the N-terminus of the GLP1 peptide or GLP1 peptide variant, and the C-terminus of the GDF15 protein or GDF15 protein variant, respectively. The VVS peptide (VVSVLTVLHQDWLNGK) (SEQ ID NO:82) is located in the Fc portion of dulaglutide. Monitoring these surrogate peptides enabled pharmacokinetic assessment of each region (GLP1, HSA, GDF15) of the GLP1-GDF15 fusion proteins. The plasma drug concentrations are shown in FIG. 5. The results indicated that subcutaneous administration of SEQ ID NOs:50, 33, 49, 45, 46, and 44 to C57BL/6 mice significantly inhibited food intake relative to vehicle-treated animals.

Figure 6:
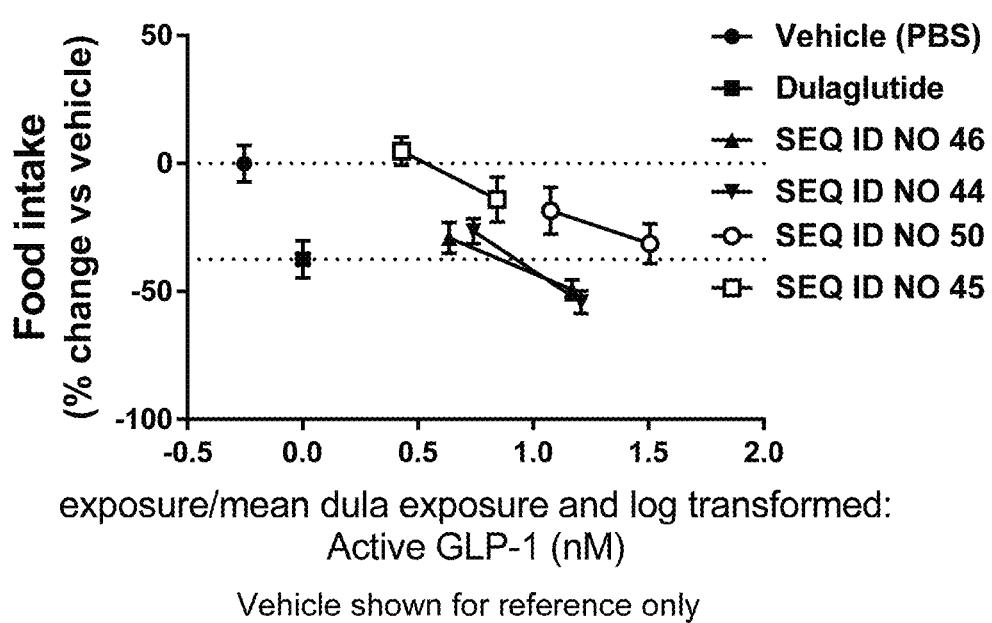
FIG. 6 shows a graph demonstrating the effects of subcutaneous administration of SEQ ID NOs:45, 50, 46, and 44 on food intake in GFRAL-deficient mice. Data is presented as percent change in food intake (compared to vehicle treatment) versus the plasma concentration of the test article with intact GLP1 arms at 24 hours.
Figure 7:
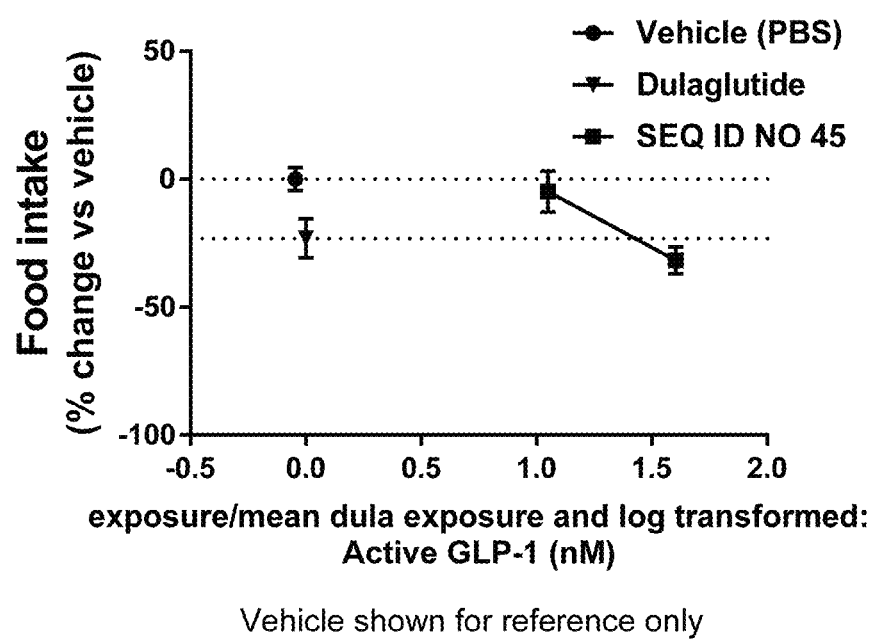
FIG. 7 shows a graph demonstrating the effects of subcutaneous administration of SEQ ID NO:45 on food intake in GFRAL-deficient mice. Data is presented as percent change in food intake (compared to vehicle treatment) versus the plasma concentration of the test article with intact GLP1 arms at 24 hours.
Figure 8:
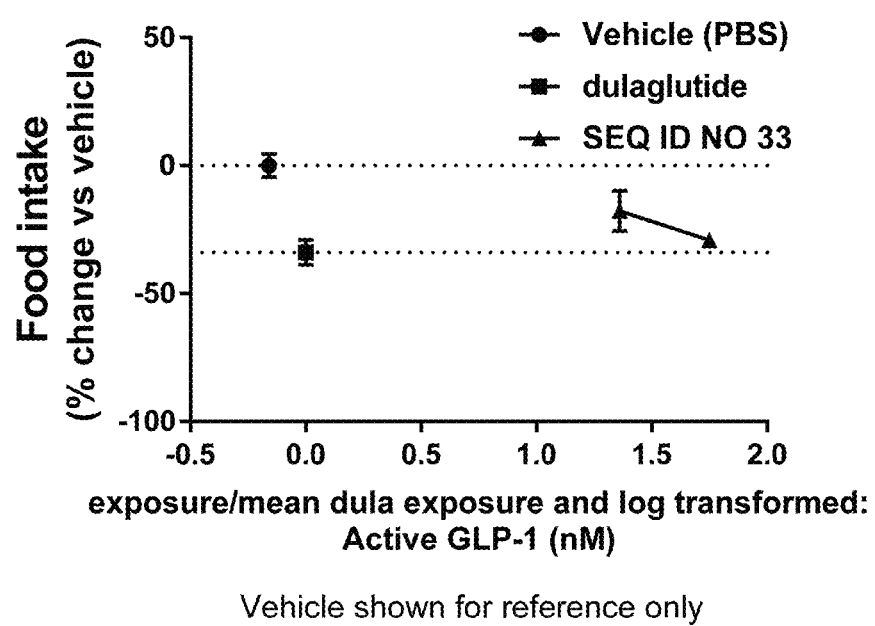
FIG. 8 shows a graph demonstrating the effects of subcutaneous administration of SEQ ID NO:33 on food intake in GFRAL-deficient mice. Data is presented as percent change in food intake (compared to vehicle treatment) versus the plasma concentration of the test article with intact GLP1 arms at 24 hours.
Figure 9:
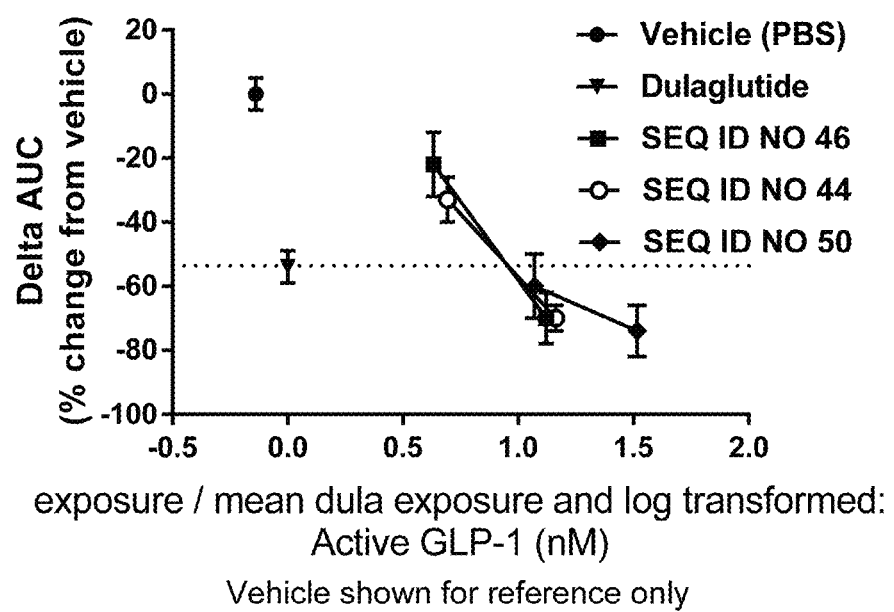
FIG. 9 shows a graph demonstrating the effects of subcutaneous administration of SEQ ID NOs:50, 46, and 44 on glucose tolerance in mice. Data is presented as percent change in delta AUC compared to vehicle treatment versus the plasma concentration of the GLP1-GDF15 fusion proteins with intact GLP1 peptides or GLP1 peptide variants.
Figure 10:
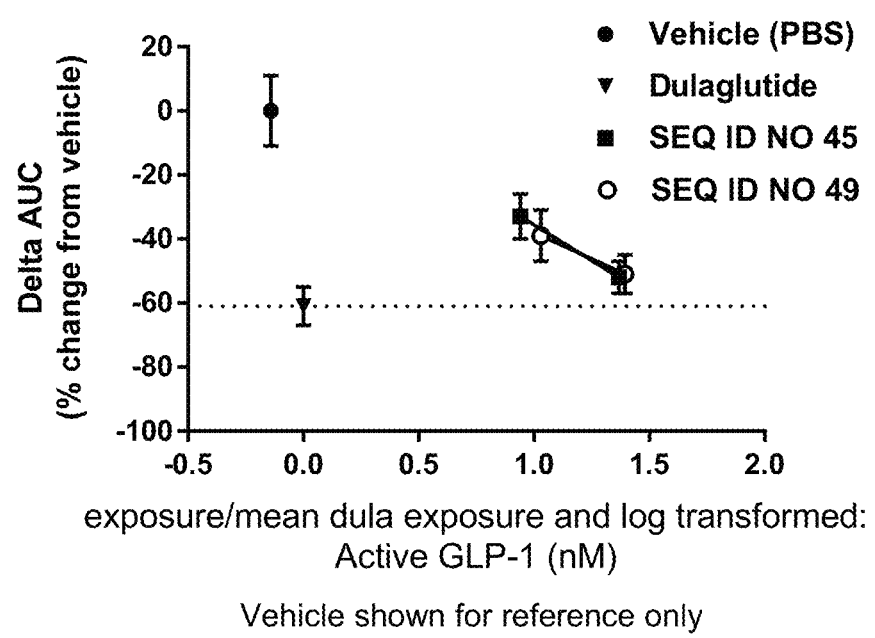
FIG. 10 shows a graph demonstrating the effects of subcutaneous administration of SEQ ID NOs:45 and 49 on glucose tolerance in mice. Data is presented as percent change in delta AUC compared to vehicle treatment versus the plasma concentration of the GLP1-GDF15 fusion proteins with intact GLP1 peptides or GLP1 peptide variants.
Figure 11:
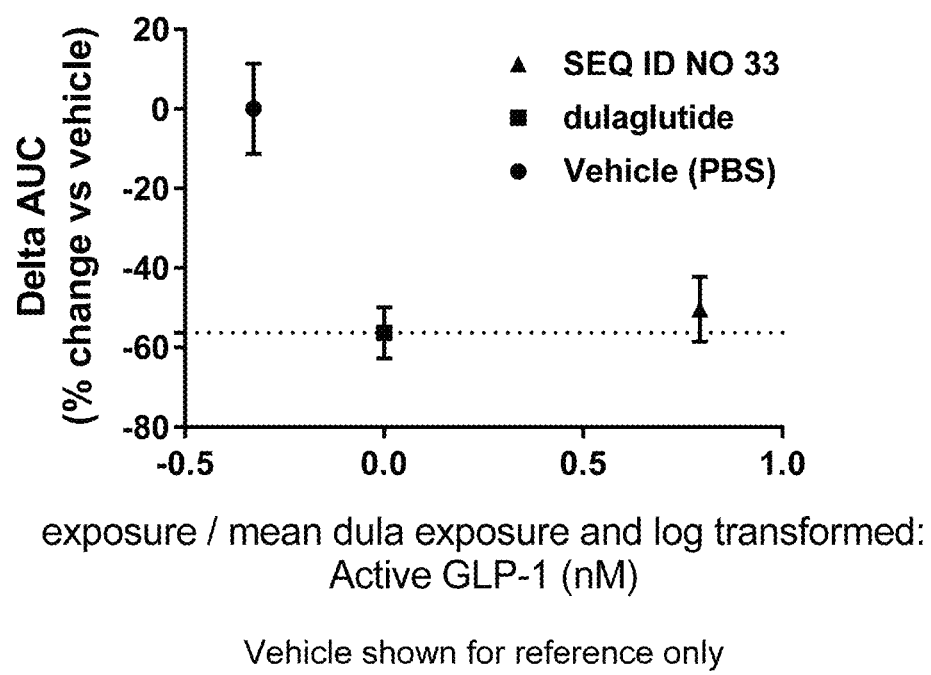
FIG. 11 shows a graph demonstrating the effects of subcutaneous administration of SEQ ID NO:33 on glucose tolerance in mice. Data is presented as percent change in delta AUC compared to vehicle treatment versus the plasma concentration of the GLP1-GDF15 fusion proteins with intact GLP1 peptides or GLP1 peptide variants.
Figure 12:
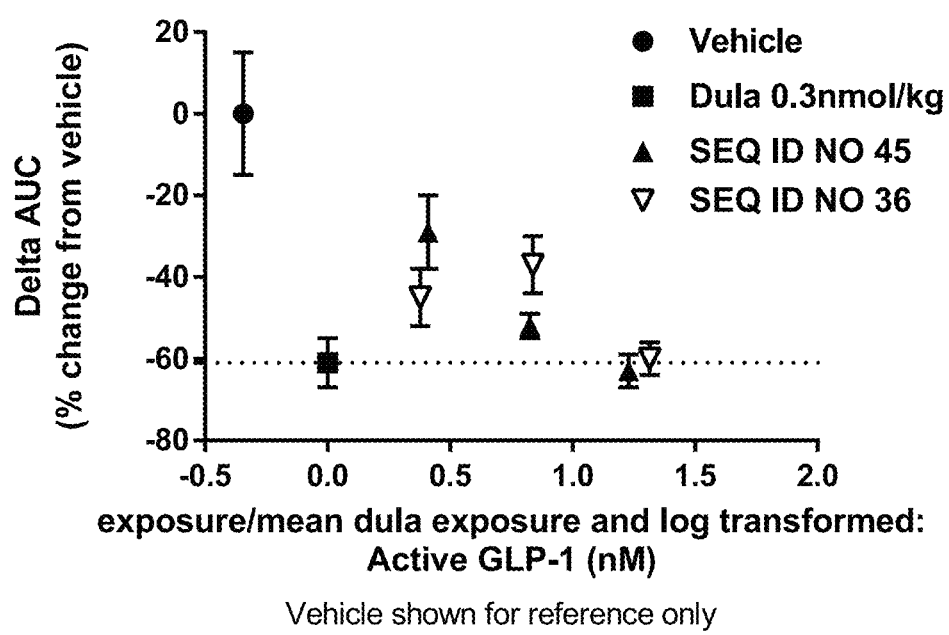
FIG. 12 shows a graph demonstrating the effects of subcutaneous administration of SEQ ID NO:45 and SEQ ID NO:36 on glucose tolerance in mice. Data is presented as percent change in delta AUC compared to vehicle treatment versus the plasma concentration of the GLP1-GDF15 fusion proteins with intact GLP1 peptides or GLP1 peptide variants.

Assessment of GLP1R mediated food intake effects in GFRAL KO mice: Inhibition of food intake in C57BL/6 mice is a result of both GLP1R and GDF15R (GFRAL) engagement. To determine the GLP1R specific effects of SEQ ID NOs:50, 33, 45, 46, and 44 on food intake, mice lacking GFRAL were used. The objective of these experiments was to determine the extent of GLP1R engagement by the fusion proteins when they were administered at a dose predicted to be efficacious for HSA-GDF15 fusions in mice (FIGS. 1 and 2 and US20170327560A1). 24-hour food intake was measured before and after subcutaneous administration of GLP1-GDF15 fusion proteins (test articles: 3 and 10 nmol/kg) or controls (PBS vehicle or dulaglutide) between 4:00 and 5:00 pm. The change in food weight for each cage was recorded every 24 hours. Circulating concentration of fusion molecules containing intact GLP1 peptide or GLP1 peptide variants was determined 24 hours after administration by immuno-affinity capture-trypsin digestion-LC-MS/MS analysis and selective monitoring of tryptic peptides, HGE-1 (HGEGTFTSDVSSYLEEQAAK) (SEQ ID NO:77) or HGE-2 (HGEGTFTSDLSK) (SEQ ID NO:78) which are located near the N-terminus of the GLP1 peptide or GLP1 peptide variant. The results are graphed as the percent change in food intake versus the plasma concentration of the HGE peptide (intact GLP1 peptide or GLP1 peptide variant) (FIGS. 6, 7, and 8). The results indicated that delivery of fusion proteins having SEQ ID NOs: 50, 33, 45, 46, and 44 resulted in GLP1R engagement at doses that were previously demonstrated to be efficacious for HSA-GDF15. Surprisingly, GLP1R engagement elicited a desired pharmacodynamic response similar to the Fc-GLP1 agonist dulaglutide despite having a GLP1 moiety exposure 10-30 times greater than dulaglutide. Had the GLP1 component of the fusion protein been as potent as dulaglutide in vivo, GLP1R engagement would have been much higher than desired, potentially causing predicted adverse events in humans such as nausea and emesis. Therefore, delivery of GLP1 peptides as fusions with HSA-GDF15 impacts in vivo potency at the GLP1R in a way that enables the desired balance of the two agonists.

Assessment of GLP1R mediated glucose tolerance in fasted DIO mice: GLP1R agonism in the pancreas results in enhanced insulin secretion and increased glucose uptake and can be measured using an intraperitoneal glucose tolerance test in diet-induced obese mice. The objective of these experiments was to determine the extent of GLP1R engagement by the fusion proteins when they were administered at a dose predicted to be efficacious for HSA-GDF15 fusions in mice (FIGS. 1 and 2 and US20170327560A1). Male C57BL/6 mice were maintained on Research Diet D12492 from 6 weeks of age until the initiation of dosing at 20 weeks of age to induce obesity. Fed blood glucose and body weight measurements were used to randomize the mice into treatment groups. At 4:00 pm, mice were transferred to clean cages with access to water; food was withheld for the duration of the study. Control (PBS vehicle and dulaglutide) and test articles (SEQ ID NOs:33, 50, 49, 45, 46, 44, and 36) (1, 3, and 10 nmol/kg) were administered subcutaneously at the time of food removal. 17 hours after administration, baseline glucose was collected and 1 g of glucose was administered interperitoneally per kg of body weight. Blood glucose was measured at 10, 30, 60 and 120 minutes following the glucose bolus. Circulating plasma concentration of fusion molecules containing intact GLP1 peptide or GLP1 peptide variants was determined immediately after the 120 minute time point by immuno-affinity capture-trypsin digestion-LC-MS/MS analysis and selective monitoring of tryptic peptides, HGE-1 (HGEGTFTSDVSSYLEEQAAK) (SEQ ID NO:77) or HGE-2 (HGEGTFTSDLSK) (SEQ ID NO:78) which are located near the N-terminus of the GLP1 peptide or GLP1 peptide variant. Glucose was graphed as a function of time and the area under the curve after normalizing to baseline glucose levels (Delta AUC) was calculated for each animal. The results are graphed as the percent change in Delta AUC (compared to vehicle treatment) versus the plasma concentration of the HGE peptide (intact GLP1 agonist) (FIGS. 9, 10, 11, and 12). The results indicated that delivery of fusion proteins having SEQ ID NOs:33, 50, 49, 45, 46, 44, and 36 resulted in GLP1R engagement at doses that were previously demonstrated to be efficacious for HSA-GDF15. Surprisingly, GLP1R engagement elicited a desired pharmacodynamics response similar to the Fc-GLP1 agonist dulaglutide despite having a GLP1 moiety exposure 10-30 times greater than dulaglutide. Had the GLP1 component of the fusion protein been as potent as dulaglutide in vivo, GLP1R engagement would have been much higher than desired, potentially causing predicted adverse events in humans such as nausea and emesis. Therefore, delivery of GLP1 peptides as fusions with HSA-GDF15 impacts in vivo potency at the GLP1R in a way that enables the desired balance of the two agonists.

Figure 13:
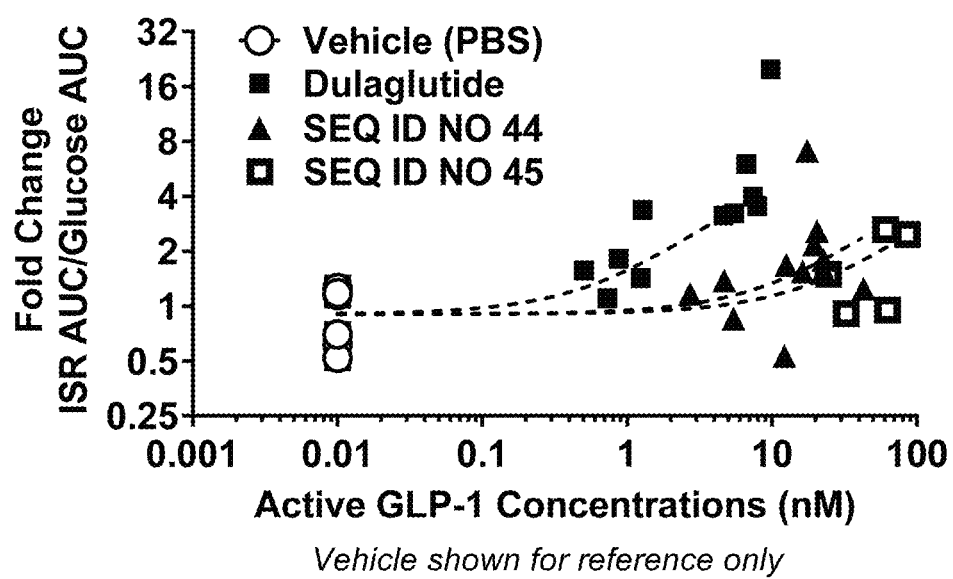
FIG. 13 shows a graph demonstrating the effects of subcutaneous administration of SEQ ID NOs:45 and 44 on insulin secretion during a graded glucose infusion in cynomolgus monkeys. Data is presented as fold change in ISR AUC normalized to glucose AUC (compared to baseline) versus the plasma concentration of the GLP1-GDF15 fusion proteins with intact GLP1 peptides or GLP1 peptide variants.

Assessment of GLP1R engagement in primates with a graded glucose infusion: Insulin secretion upon intravenous graded glucose infusion (GGI) in Non-Human Primates was used to assess GLP1R engagement of SEQ ID NOs:45 and 44. The objective of these experiments was to determine the extent of GLP1R engagement by the fusion proteins when the fusion proteins were administered at a dose predicted to be efficacious for HSA-GDF15 fusions in non-human primates (Mullican et al., 2017 and US20170327560A1). GGI procedures were conducted in sedated cynomolgus monkeys following a 16-hr overnight fast to compare the baseline and treatment responses with a 14-day recovery period between the two GGI procedures. On day 1, animals were dosed with vehicle immediately following food removal. On day 2, animals were anesthetized, and baseline was established with two blood samples collected 10 min apart. GGI1 was initiated at 0 minutes with a glucose infusion rate of 8 mg/kg/min, followed by infusions of 12, 16 and 24 mg/kg/ min. Each infusion rate was administered for a period of 40 minutes. Blood samples were taken at 20-minute intervals for measurement of glucose, insulin, and C-peptide, results were graphed as a function of time and area under the curve (AUC) was determined for each analyte measured in each animal. Animals were then randomized into test article treatment groups based on their baseline insulin secretion rate (ISR) from GGI1. On day 15 animals were dosed with the test article at varying dose concentrations (0.1 to 1.1 mg/kg of fusion proteins and 0.016 to 0.1 dulaglutide) prior to fasting overnight. The second GGI (GGI2) was performed on day 16 as described for day 2. Compound exposure was assessed on plasma samples collected at timepoint 0 prior to glucose infusion by immunoassay specifically designed to monitor test articles with intact GLP1 peptide or peptide variants. Data in FIG. 13 is reported as the treatment induced fold change in ISR AUC normalized to glucose AUC compared to baseline versus the plasma concentration of test article with intact GLP1. Dulaglutide was used as a Fc-GLP1 agonist reference. The results indicated that delivery of fusion proteins having SEQ ID NOs:45 and 44 resulted in GLP1R engagement at doses that were previously demonstrated to be efficacious for HSA-GDF15. Surprisingly, GLP1R engagement elicited a desired pharmacodynamic response similar to Fc-GLP1 agonist dulaglutide despite having a GLP1 moiety exposure 10-30 times greater than dulaglutide. Had the GLP1 component of the fusion protein been as potent as dulaglutide in vivo, GLP1R engagement would have been much higher than desired, potentially causing predicted adverse events in humans such as nausea and emesis. Therefore, delivery of GLP1 peptides as fusions with HSA-GDF15 impacts in vivo potency at the GLP1R in a way that enables the desired balance of the two agonists.

The results shown in FIGS. 6-13 demonstrate that GLP1 in vivo activity or potency in preclinical species is reduced in the homodimeric GLP1-GDF15 dual agonists compared with the Fc fused GLP1 peptide of dulaglutide. This enables balance of both agonists (GLP1 peptide or GLP1 peptide variant and GDF15 protein or GDF15 protein variant) on one molecule; therefore, allowing delivery of a GLP1 peptide or GLP1 peptide variant at an efficacious concentration that also achieves GDF15 protein or GDF15 protein variant exposure within the predicted therapeutic range.

Figure 14:
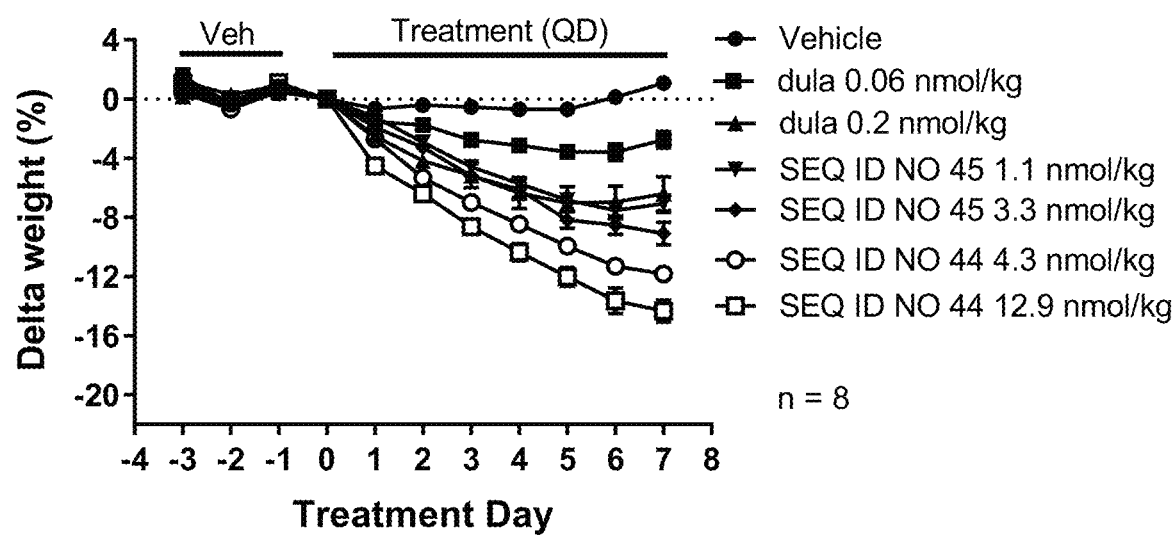
FIG. 14 shows a graph demonstrating the weight loss efficacy of daily subcutaneous administration of GLP1-GDF15 fusion proteins (SEQ ID NOs:45 and 44) in diet induced obese mice. Data is presented as percent change in body weight from Day 0.
Figure 15:
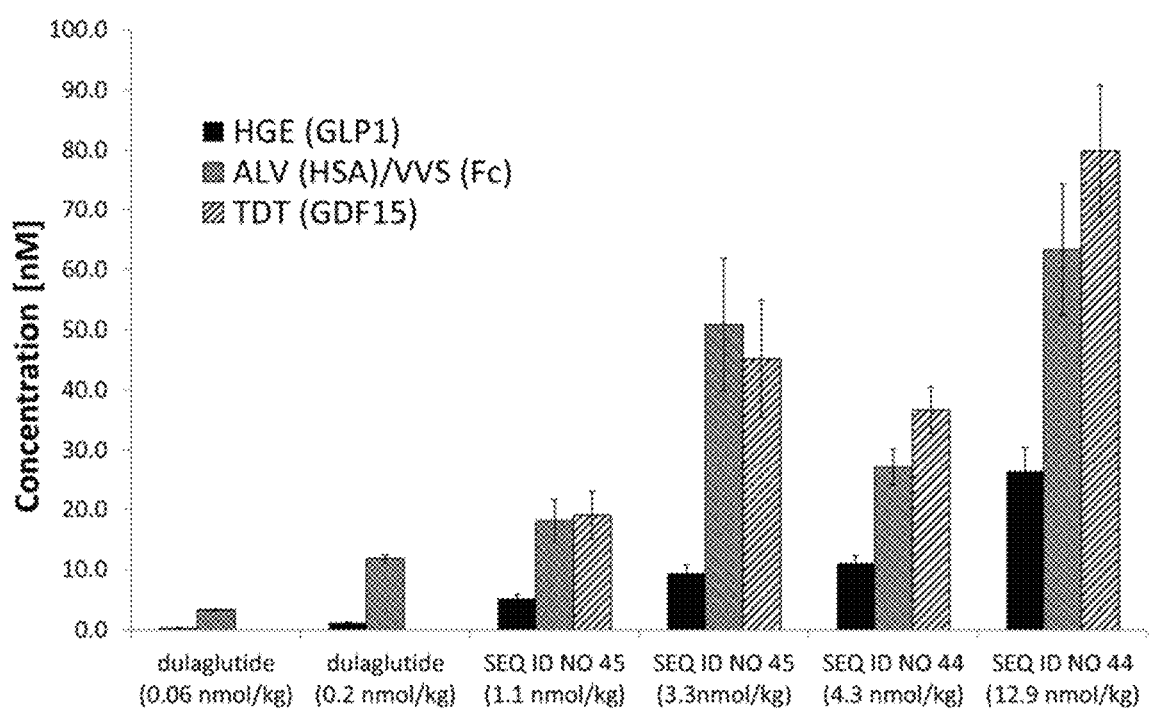
FIG. 15 shows a graph demonstrating the plasma concentration of GLP1-GDF15 fusion proteins (SEQ ID NOs:45 and 44) after 7 days of daily administration in diet induced obese mice as determined by immuno-affinity capture-trypsin digestion-LC-MS/MS analysis.

Assessment of weight loss efficacy of GLP1-GDF15 fusion proteins after repeat dosing in mice: The ability of GLP1-GDF15 fusion proteins to cause weight loss was tested in diet induced obese mice. Mice were subcutaneously administered varying concentrations of test articles (SEQ ID NOS:45 and 44), dulaglutide or a vehicle control daily for seven days. Body weight was monitored throughout the study and FIG. 14 shows the percent change in body weight over time relative to Day 0 (just prior to the first dose). Circulating concentration of test articles was determined after seven days of treatment by immuno-affinity capture-trypsin digestion-LC-MS/MS analysis. Selected tryptic peptides were monitored, namely, ALV (ALVLIA-FAQYLQQSPFEDHVK) (SEQ ID NO:79), HGE-1 (HGEGTFTSDVSSYLEEQAAK) (SEQ ID NO:77), and HGE-2 (HGEGTFTSDLSK) (SEQ ID NO:78), and TDT (TDTGVSLQTYDDLLAK) (SEQ ID NO:80), which are located near the N-terminus of the HSA protein, the N-terminus of the GLP1 peptide or GLP1 peptide variant, and the C-terminus of the GDF15 protein or GDF15 protein variant, respectively. The VVS peptide (VVSVLTVLHQDWLNGK) (SEQ ID NO:82) is located in the Fc portion of dulaglutide. Monitoring these surrogate peptides enabled pharmacokinetic assessment of each region (GLP1, HSA, GDF15) of the GLP1-GDF15 fusion proteins. The plasma drug concentrations are shown in FIG. 15. The results indicated that repeat administration of SEQ ID NOs: 45 and 44 leads to weight loss in diet induced obese mice in a concentration dependent manner.

Assessment of Food Intake Effects of GLP1-GDF15 Fusion Proteins in Nonhuman Primates.

Figure 16:
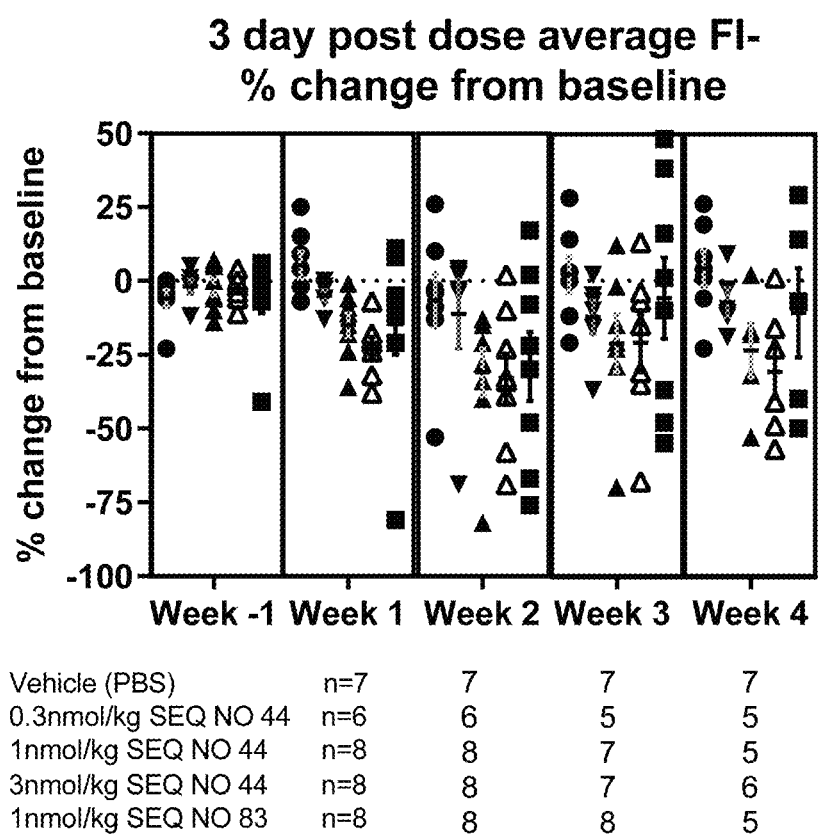
FIG. 16 shows a graph demonstrating the 3-day percent change in food intake at baseline and after each QW subcutaneous administration of GLP1-GDF15 fusion proteins (SEQ ID NOs: 44 and 83) over 4 weeks in spontaneously obese nonhuman primates. Data is presented for individual subjects and those without detectable level of test article in their plasma are not included in the figure as outlined below the x-axis.
Figure 17:
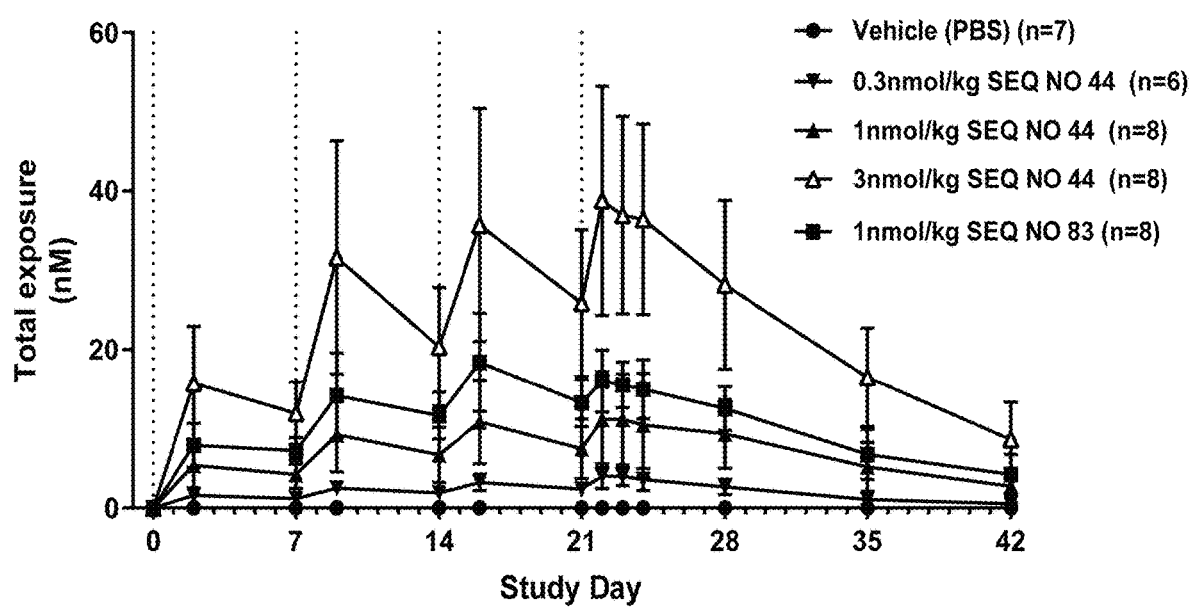
FIG. 17 shows a graph demonstrating the plasma concentration of total test article during a 4-week treatment with varying concentrations of GLP1-GDF15 fusion proteins (SEQ ID NOs: 44 and 83) administered QW in spontaneously obese nonhuman primates as determined by immunoassay. Data is presented as the average (±SEM).
Figure 18:
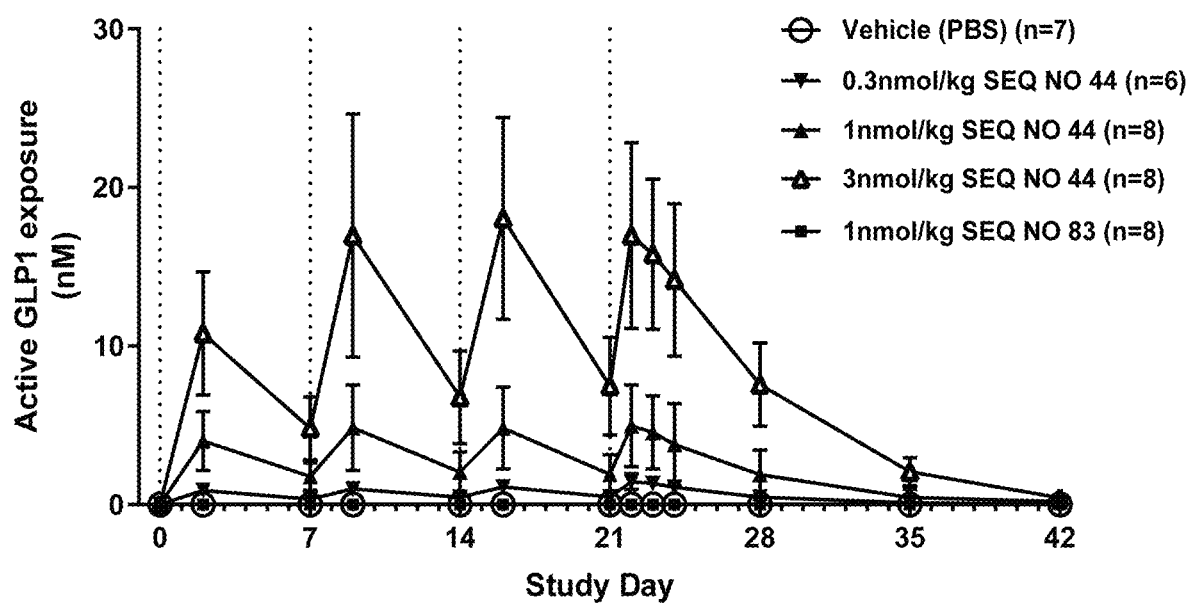
FIG. 18 shows a graph demonstrating the plasma concentration of GLP1 moiety containing test article during a 4-week treatment with varying concentrations of GLP1-GDF15 fusion protein (SEQ ID NO. 44) administered QW in spontaneously obese nonhuman primates as determined by immunoassay. Data is presented as the average (±SEM).

The ability of GLP1-GDF15 fusion proteins to decrease food intake was tested in spontaneously obese cynomolgus monkeys. Subjects were subcutaneously administered varying concentrations of test articles with and without an active GLP1 moiety (SEQ ID NOS: 44 and 83, respectively; SEQ ID NO:83, which comprises a HSA peptide fused to an AP10 linker fused to a GDF15 peptide, was previously disclosed in U.S. Pat. No. 10,336,812) or vehicle QW for a period of 4 weeks. Food intake was monitored prior to dosing and throughout the study. The 3-day percent change in food intake at baseline and after each administration of test article is shown in FIG. 16. The concentration of SEQ ID NOs: 44 and 83 in cynomolgus monkey plasma during the study was determined using two separate immunoassay methods to detect the "total" molecule (HSA detection) and the "active" GLP1 moiety (N-terminal GLP1 peptide detection). The plasma drug concentrations are shown in FIGS. 17 and 18. The results indicated that administration of SEQ ID NOs: 44 and 83 reduces food intake in spontaneously obese nonhuman primates.

Assessment of Food Intake and Body Weight Effects of GLP1-GDF15 Fusion Proteins after a 21-Day Dose Escalation in Nonhuman Primates.

Figure 19:
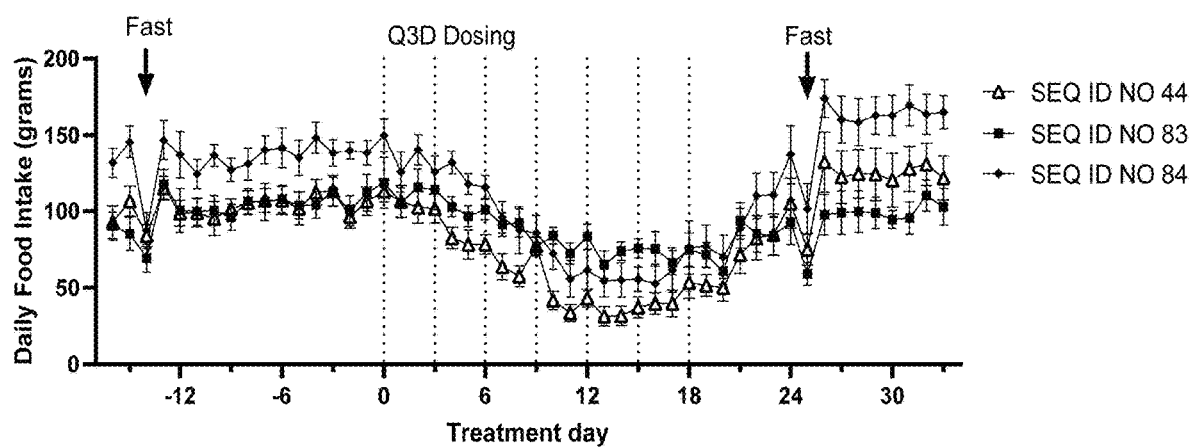
FIG. 19 shows a graph demonstrating the absolute daily food intake before, during and after a 21-day treatment with escalating concentrations of GLP1-GDF15 fusion proteins (SEQ ID NOs: 44, 83 and 84) administered Q3D in spontaneously obese nonhuman primates. Data is presented as the average (±SEM) of ten subjects per group.
Figure 20:
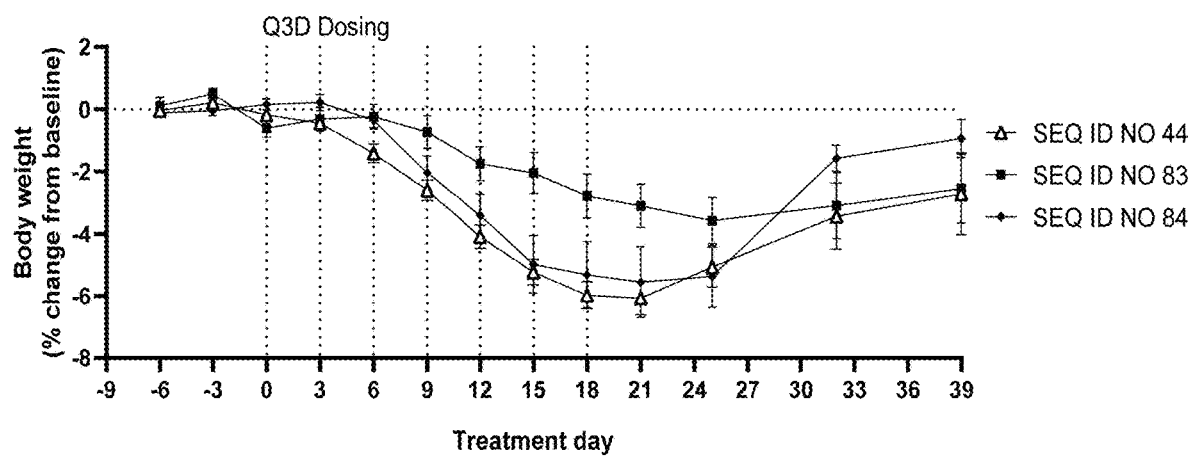
FIG. 20 shows a graph demonstrating body weight change (relative to baseline) after a 21-day treatment with escalating concentrations of GLP1-GDF15 fusion proteins (SEQ ID NOs: 44, 83 and 84) administered Q3D in spontaneously obese nonhuman primates. Data is presented as the average (±SEM) of ten subjects per group.
Figure 21:
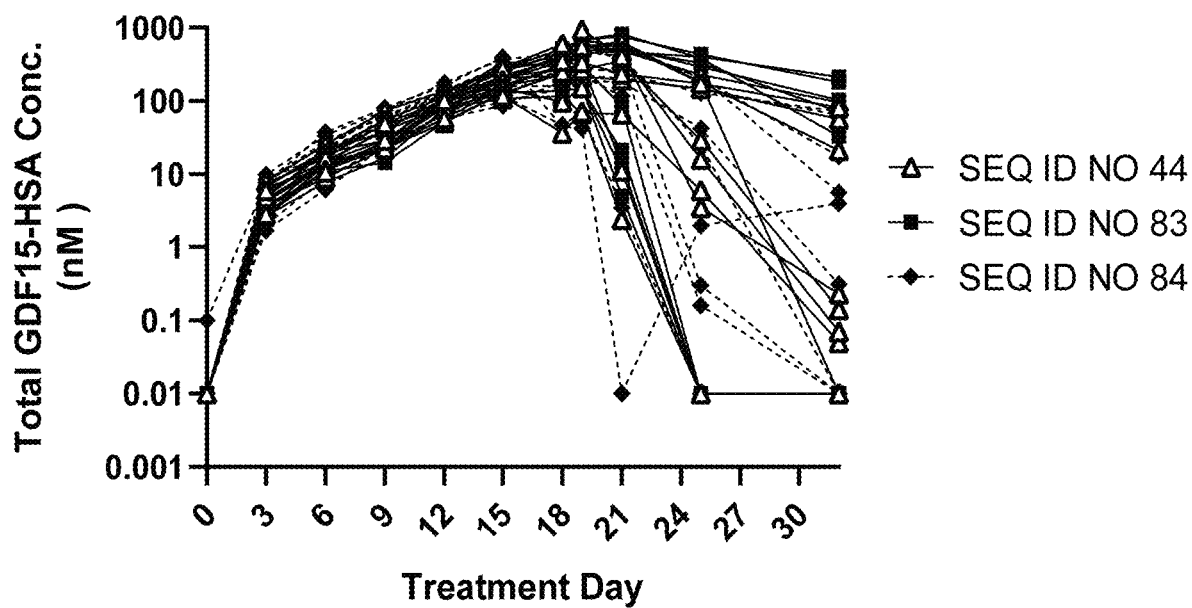
FIG. 21 shows a graph demonstrating the plasma concentration of total test article during and after a 21-day treatment with escalating concentrations of GLP1-GDF15 fusion proteins (SEQ ID NOs: 44, 83 and 84) administered Q3D in spontaneously obese nonhuman primates as determined by immunoassay. Data is presented for individual subjects.
Figure 22:
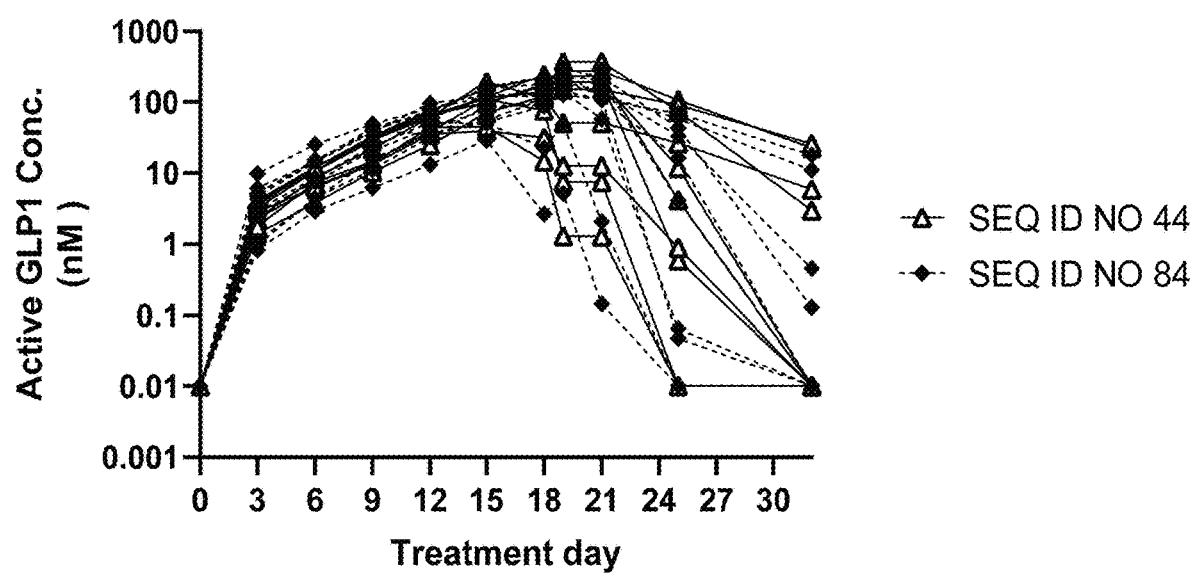
FIG. 22 shows a graph demonstrating the plasma concentration of GLP1 moiety containing test article during and after a 21-day treatment with escalating concentrations of GLP1-GDF15 fusion proteins (SEQ ID NOs: 44 and 84) administered Q3D in spontaneously obese nonhuman primates as determined by immunoassay. Data is presented for individual subjects.

The ability of GLP1-GDF15 fusion proteins to decrease food intake and cause weight loss was tested in spontaneously obese cynomolgus monkeys. Subjects were subcutaneously administered test articles containing both active GDF15 and GLP1, only active GDF15, or only active GLP1 moieties (SEQ ID NOS: 44, 83, 84, respectively; SEQ ID NO:84 comprises a GLP1 peptide fused to an AP5 linker peptide fused to a HSA peptide fused to an AP10 linker peptide fused to a GDF15 peptide with an I89R mutation; the GDF15 peptide with an I89R mutation was previously disclosed in U.S. Pat. No. 10,336,812) every three days for a period of 21 days. The initial dose given at Day 0 was 0.7 nmol/kg and was escalated upon each administration up to 20 nmol/kg. Daily food intake prior to dosing, during the 21-day treatment period and during test article washout is shown in FIG. 19. Body weight was monitored throughout the study and FIG. 20 shows the percent change in body weight over time relative to baseline. The concentration of test articles in cynomolgus monkey plasma during the study was determined using two separate immunoassay methods to detect the "total" molecule (HSA detection; SEQ ID NOS: 44, 83, 84) and the "active" GLP1 moiety (N-terminal GLP1 peptide detection; for SEQ ID NOS: 44 and 84 only). The plasma drug concentrations are shown in FIGS. 21 and 22. The results indicated that repeat administration of SEQ ID NOs: 44, 83, 84 leads to a reduction in food intake and subsequent weight loss in spontaneously obese nonhuman primates.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

All documents cited herein are incorporated by reference.

It is claimed:

1. A glucagon-like peptide-1 (GLP-1)/growth differentiation factor 15 (GDF15) fusion protein, wherein the GLP-1-GDF15 fusion protein comprises a GLP-1 peptide, which is fused to a first linker peptide, which is fused to a serum albumin protein, which is fused to a second linker peptide, which is fused to a GDF15 protein, wherein the GLP-1 peptide comprises an amino acid sequence selected from the group consisting of SEQ ID NOs:1-4, and wherein the GDF15 protein comprises an amino acid sequence selected from SEQ ID NO:31 or SEQ ID NO:32.

2. The GLP-1-GDF15 fusion protein of claim 1, wherein the first linker peptide comprises an amino acid sequence selected from the group consisting of SEQ ID NOs:5-25.

3. The GLP-1-GDF15 fusion protein of claim 1, wherein the serum albumin protein comprises an amino acid sequence selected from SEQ ID NO:26 or SEQ ID NO:27.

4. The GLP-1-GDF15 fusion protein of claim 1, wherein the second linker peptide comprises an amino acid sequence selected from the group consisting of SEQ ID NOs:28-30.

5. The GLP-1-GDF15 fusion protein of claim 1, wherein the GLP-1-GDF15 fusion protein comprises an amino acid sequence selected from the group consisting of SEQ ID NOs:33-72.

6. An isolated nucleic acid encoding the GLP-1-GDF15 fusion protein of claim 1.

7. A vector comprising the isolated nucleic acid of claim 6.

8. A host cell comprising the isolated nucleic acid of claim 6.

9. A pharmaceutical composition comprising the GLP-1-GDF15 fusion protein of claim 1 and a pharmaceutically acceptable carrier.

10. A kit comprising the GLP-1-GDF15 fusion protein of claim 1.

11. The kit of claim 10, wherein the kit further comprises a device for injection.

* * * * *